United States Patent
Bielicki et al.

(10) Patent No.: US 10,774,118 B2
(45) Date of Patent: *Sep. 15, 2020

(54) PEPTIDES HAVING REDUCED TOXICITY THAT STIMULATE CHOLESTEROL EFFLUX

(71) Applicant: THE REGENTS OF THE UNIVERSITY OF CALIFORNIA, Oakland, CA (US)

(72) Inventors: John K. Bielicki, San Ramon, CA (US); Jan Johansson, San Ramon, CA (US); Waleed Danho, Del Mar, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/020,395

(22) Filed: Jun. 27, 2018

(65) Prior Publication Data

US 2018/0298066 A1    Oct. 18, 2018

Related U.S. Application Data

(62) Division of application No. 14/774,682, filed as application No. PCT/US2014/029232 on Mar. 14, 2014, now Pat. No. 10,017,551.

(60) Provisional application No. 61/798,191, filed on Mar. 15, 2013.

(51) Int. Cl.
| | |
|---|---|
| A61K 47/54 | (2017.01) |
| A61K 38/17 | (2006.01) |
| C07K 14/435 | (2006.01) |
| C07K 14/775 | (2006.01) |
| A61K 45/06 | (2006.01) |
| A61K 47/64 | (2017.01) |

(52) U.S. Cl.
CPC ............ *C07K 14/435* (2013.01); *A61K 38/17* (2013.01); *A61K 45/06* (2013.01); *A61K 47/544* (2017.08); *A61K 47/64* (2017.08); *C07K 14/775* (2013.01)

(58) Field of Classification Search
CPC .. A61K 38/17; A61K 45/06; A61K 47/48053; C07K 14/435; C07K 14/775
See application file for complete search history.

(56) References Cited

U.S. PATENT DOCUMENTS

| | | | |
|---|---|---|---|
| 7,601,802 B2 | 10/2009 | Bielicki | |
| 2004/0058869 A1 | 3/2004 | Hayden et al. | |
| 2005/0159362 A1 | 7/2005 | Sircar et al. | |
| 2005/0202532 A1 | 9/2005 | Bielicki et al. | |
| 2005/0250680 A1 | 11/2005 | Walensky et al. | |
| 2008/0096815 A1 | 4/2008 | Fogelman et al. | |
| 2008/0234192 A1 | 9/2008 | Heinecke et al. | |
| 2011/0152112 A1 | 6/2011 | Johansson | |
| 2014/0287994 A1 | 9/2014 | Bielicki et al. | |

FOREIGN PATENT DOCUMENTS

| | | |
|---|---|---|
| WO | 2005/058938 A2 | 6/2005 |
| WO | 2006/020040 A2 | 2/2006 |
| WO | 2008/040111 A1 | 4/2008 |
| WO | 2008/115303 A2 | 9/2008 |
| WO | 2009/155366 A2 | 12/2009 |
| WO | 2011/139819 A2 | 11/2011 |

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
The online medical dictionary, defintion of analog, published online 2000.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
U.S. Appl. No. 14/774,682, "Non-Final Office Action", dated Jan. 11, 2017, 25 pages.
U.S. Appl. No. 14/774,682, "Final Office Action", dated Nov. 2, 2017, 9 pages.
International Search Report and Written Opinion dated Aug. 18, 2014 of International Patent Application No. PCT/US2014/029232, 17 pages.
International Search Report from PCT/US2009/047694, dated Feb. 2, 2010.
Berendsen, "A Glimpse of the Holy Grail?", Science, 282:642-643 (1998).

(Continued)

*Primary Examiner* — Rachael E Bredefeld
*Assistant Examiner* — Erinne R Dabkowski
(74) *Attorney, Agent, or Firm* — Kilpatrick Townsend & Stockton LLP

(57) ABSTRACT

The present invention provides a family of non-naturally occurring polypeptides having cholesterol efflux activity that parallels that of full-length apolipoproteins (e.g., Apo AI and Apo E), and having high selectivity for ABCA1 that parallels that of full-length apolipoproteins. Further, the peptides of the invention have little or no toxicity when administered at therapeutic and higher doses. The invention also provides compositions comprising such polypeptides, methods of identifying, screening and synthesizing such polypeptides, and methods of treating, preventing or diagnosing diseases and disorders associated with dyslipidemia, hypercholesterolemia, or inflammation; or diseases involving abnormal glucose metabolism, e.g., diabetes, metabolic syndrome; or Alzheimer's Disease or frontotemporal dementia.

26 Claims, 56 Drawing Sheets

Specification includes a Sequence Listing.

(56) References Cited

OTHER PUBLICATIONS

Bielicki et al., "A new HDL mimetic peptide that stimulates cellular cholesterol efflux with high efficiency greatly reduces atherosclerosis in mice", *J. Lipid Res.*, 51:1496-1503 (2010).

Bielicki et al.; "A Highly Potent ABCA1 Cholesterol Efflux Peptide (ATI-5261) Greatly Reduces Established Atherosclerosis in Hypercholesterolemic Mouse Models"; Abstract #8080503; 6th annual CardiovascularBiomarker and Surrogate Endpoint Symposium. Retrieved from the Internet Jan. 16, 2010: http://www.cmod.org/2008_Program%20FINAL.pdf] p. 38 of the pdf."Building a Framework for Biomarker Application" Sep. 10-12, 2008.

Bradley et al., "Limits of Cooperativity in a Structurally Modular Protein: Response of the Notch Ankyrin Domain to Analogous Alanine Subsitutions in Each Repeat", *J. Mol. Biol.*, 324:373-386 (2002).

Ngo et al., "Computational Complexity, Protein Structure Protection, and the Levinthal paradox", pp. 491-494 (1994).

On-Line Medical Dictionary Definiation of Anlog, p. 3, http://cancerweb.ncl.ac.uk/omd/about.html(downloaded on Jul. 7, 2005).

Pierce et al., "The complete genome sequence of Moorella thermoacetica (f. *Clostridium thermoaceticum*)", *Environ. Microbiol*, 10:2550-2573 (2008).

Ramprasad et al., "Sustained-delivery of an apolipoprotein E-peptidomimetic using multivesicular liposomes lowers serum cholesterol levels," *Journal of Controlled Release*, 79, 207-218 (2002).

Rudinger, "Characterisitcs of amino acids as componnents of a petpide hormone sequence", *Peptide Hormones*, JA Parsons, ed., pp. 1-7 (1976).

Sigma Genosys, "Design Custom Peptides", pp. 1-2 (2004) http://www.sigma-genosys.com/peptide_design.asp (downloaded Dec. 16, 2004).

Song et al., "Effects of L- or D-Pro incorporation into hydrophobic or hydrophilic helix face of amphipathic alpha-helical model peptide on structure and cell selectivity," *Biochemical and Biophysical Research Communications*, 314, 615-621 (2004).

Sparrow et al., "Apolipoprotein E: phospholipid binding studies with synthetic peptides from the carboxyl terminus," *Biochemistry*, 31, 1065-1068 (1992).

Vedhachalam et al.; "The C-terminal lipid-binding domain of apolipoprotein E is a highly efficient mediator of ABCA1-dependent cholesterol efflux that promotes the assembly of high-density lipoproteins"; Biochemistry; 46:2583-2593 (Mar. 2007) ePub Feb. 17, 2007.

Voet et al., *Biochemistry*, John Wiley & Sons Inc., pp. 235-241 (1995).

Wang et al.; "Regulation and mechanisms of ATP-binding cassette transporter A1-mediated cellular cholesterol efflux"; *Arterioscler. Thromb. Vasc. Biol.*; 23(7):1178-1184 (Jul. 2003) ePub May 2003.

EP14763923.1, "Extended European Search Report", dated Oct. 18, 2016, 7 pages.

Zheng, et al., "The Positional Specificity of EXXK Motifs within an Amphipathic α-Helix Dictates Preferential Lysine Modification by Acrolein: Implications for the Design of High-Density Lipoprotein Mimetic Peptides," *Biochemistry* 51 pp. 6400-6412 (2012).

Zheng, et al., "Retention of α-helical structure by HDLmimetic peptide ATI-5261 upon extension dilution represents an important determinant for stimulating ABCA1 cholesterol efflux with high efficiency," *Biochemical and Biophysical Research Communications*, 441 pp. 71-76 (2013).

Li, et al., "Limitations of Peptide Retro-inverso Isomerization in Molecular Mimicry," J. Biol. Chem., 2010, 285(25), pp. 19572-19581.

\* cited by examiner

Serum lipid concentrations (mg/dl) following treatment (4 versus 6 hours) with peptides

| | triglyceride | | total cholesterol | | free cholesterol | | cholesteryl ester | |
|---|---|---|---|---|---|---|---|---|
| | 4 h | 6 h | 4 h | 6 h | 4 h | 6 h | 4 h | 6 h |
| PBS | 37±7 | 29±6 | 71±21 | 66±4 | 11±2 | 12±4 | 60±21 | 54±5 |
| ATI-5261 | 1951±117 | 1358±161 | 172±25 | 174±18 | 43±15 | 44±8 | 128±36 | 130±15 |
| T5055-13 | 757±500 | 455±28 | 125±39 | 112±32 | 36±19 | 44±29 | 88±23 | 67±18 |
| T5055-14 | 1153±755 | 821±574 | 140±45 | 109±55 | 47±27 | 58±34 | 93±19 | 61±7 |
| T5055-15 | 1393±123 | 1009±64 | 129±24 | 131±11 | 56±16 | 80±6 | 74±25 | 51±14 |
| T5055-16 | 1390±453 | 1011±277 | 103±18 | 130±17 | 52±17 | 65±27 | 51±27 | 66±15 |

Figure 10

LeuATI-5261 — hydrophobic analogs
T4873-7    EVRSKLEEWLAALRELAEELLARLKS    LeuATI-5261
T4883-6    EVRSKLEEWLAALRELAEELLARAKS    L24A
T4883-7    EVRSKLEEWLAALRELAEELLAARLKS   L21A
T4883-12   EVRSKLEEWLAALREAEELAARAKS     L24,21,16A

Serum clinical markers - 4 hour post treatment

|          | ALT (IU/L) | AST (IU/L) | TG (mg/dl) | FC (mg/dl) | NEFA (mg/dl) |
|----------|------------|------------|------------|------------|--------------|
| PBS      | 43±22      | 106±52     |            | 42±6       | 1.2          |
| ATI-5261 | 247±50     | 3368±480   | 1860 162±15| | 1          |
| T4873-7  | 85±3       | 656±183    | 1266 137±23| | 1.9        |
| T4883-6  | 51±9       | 308±28     | 561 111±53 | | 1.7        |
| T4883-7  | 73±47      | 293±56     | 835 156±22 | | 2.7        |
| T4883-12 | 53±12      | 216±74     | 117 52±32  | | 1.3        |

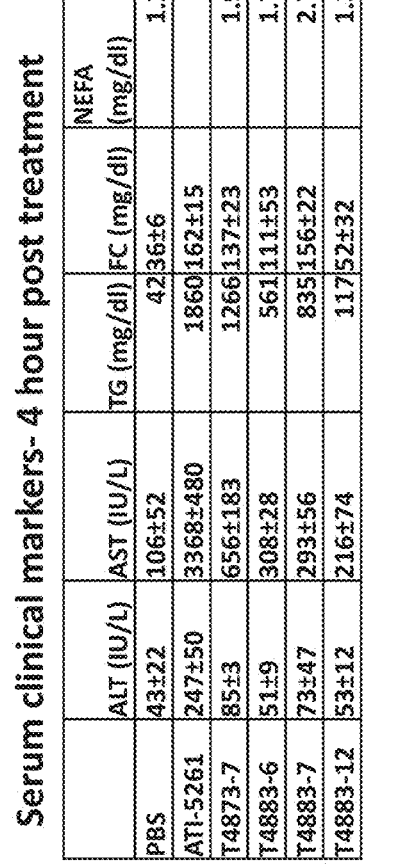

A. Muscle toxicity (CPK activity)

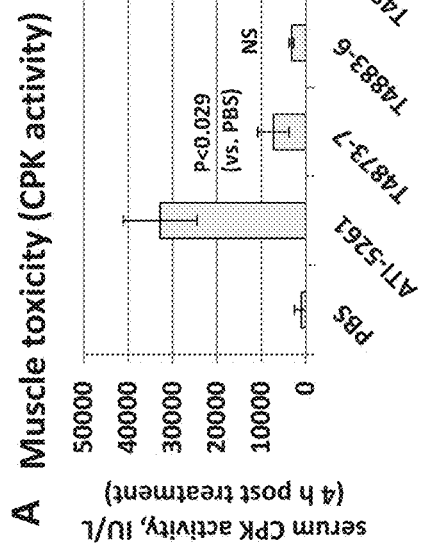

B. ABCA1 dependent cholesterol efflux activity (%/4 h)

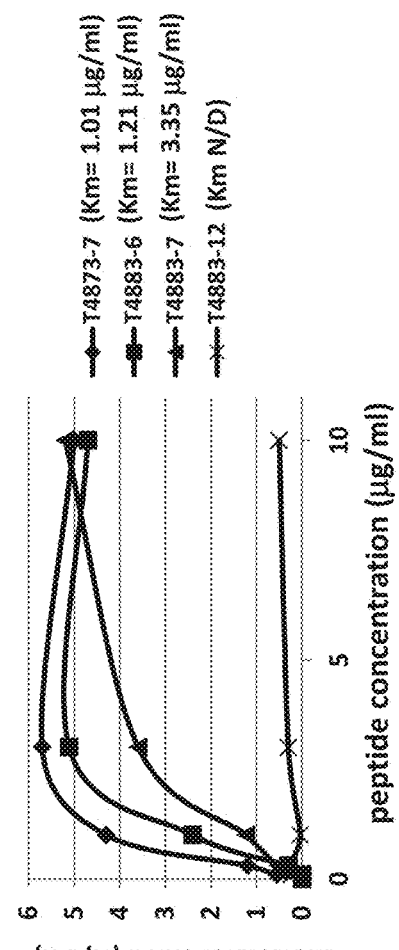

T4873-7 (Km= 1.01 µg/ml)
T4883-6 (Km= 1.21 µg/ml)
T4883-7 (Km= 3.35 µg/ml)
T4883-12 (Km N/D)

C. Cholesterol efflux (%/8 h)

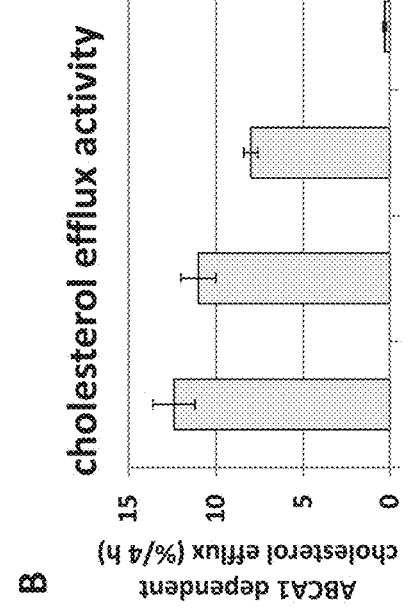

Figure 11

Leu.ATI-5261---- hydrophobic analogs continued
T5505-1    EARSKLEEWLAALRELAEELLARLKS    V2>A
T5505-3    EVRSKLEEWAAALRELAEELLARLKS    L10>A
T5505-9    EVRSKLEELLAALRELAEELLARAKS    L24>A; W9>L
T5505-12   EARSKAEEWLAALRELAEELLARAKS    V2, L6, L24>A

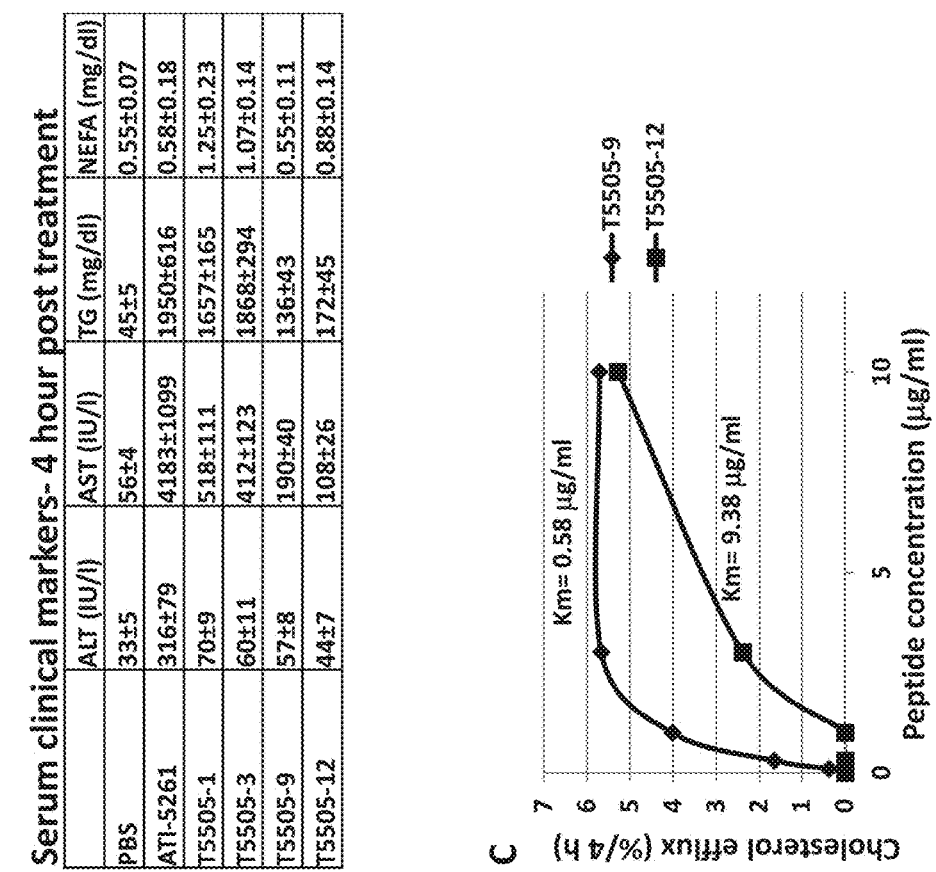

Serum clinical markers- 4 hour post treatment

|          | ALT (IU/l) | AST (IU/l) | TG (mg/dl) | NEFA (mg/dl) |
|----------|------------|------------|------------|--------------|
| PBS      | 33±5       | 56±4       | 45±5       | 0.55±0.07    |
| ATI-5261 | 316±79     | 4183±1099  | 1950±616   | 0.58±0.18    |
| T5505-1  | 70±9       | 518±111    | 1657±165   | 1.25±0.23    |
| T5505-3  | 60±11      | 412±123    | 1868±294   | 1.07±0.14    |
| T5505-9  | 57±8       | 190±40     | 136±43     | 0.55±0.11    |
| T5505-12 | 44±7       | 108±26     | 172±45     | 0.88±0.14    |

A — Muscle toxicity (CPK activity), serum CPK activity, IU/l (4 h post treatment): PBS 143; ATI-5261 33689; T5505-1 4782; T5505-3 5512; T5505-9 864; T5505-12 487

B — Cholesterol efflux activity, ABCA1 dependent cholesterol efflux (%/4 h): ATI-5261, T5505-1, T5505-3, T5505-9, T5505-12

C — Cholesterol efflux (%/4 h) vs Peptide concentration (μg/ml); T5505-9 Km= 0.58 μg/ml; T5505-12 Km= 9.38 μg/ml Figure 12
Leu.ATI-5261 ---- hydrophobic analogs continued
T5325-4   EVRSKLEEALAALRELAEELLARLKS   W9>A
T5325-8   EVRSKLEEVLAALRELAEELLARAKS   L24>A; W9V
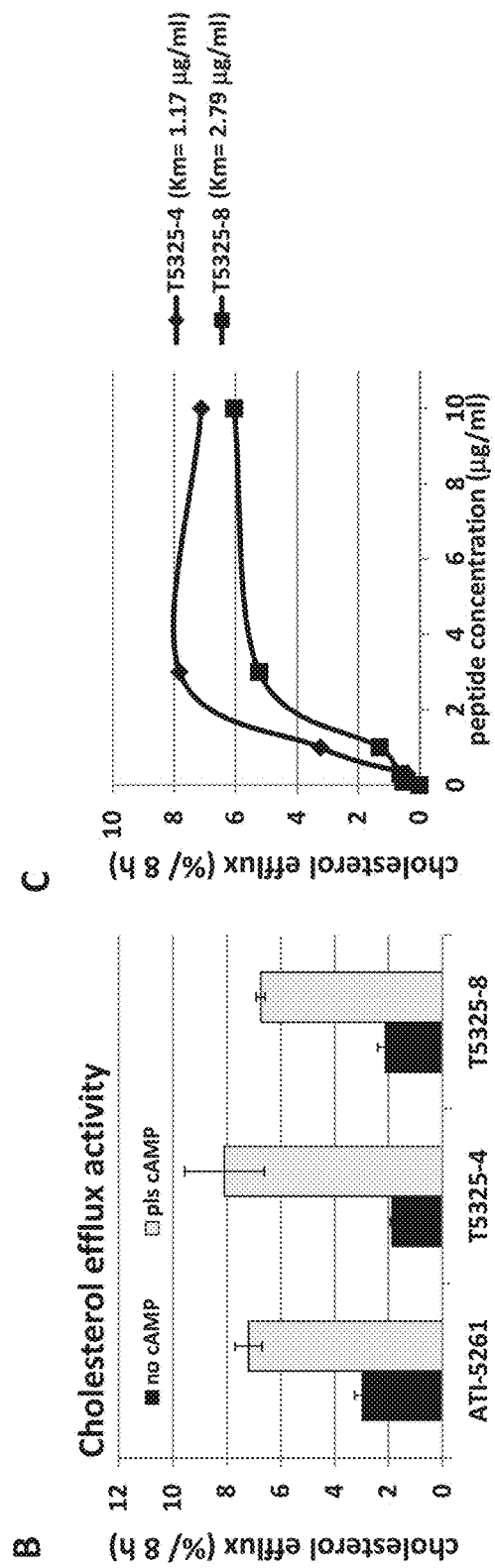
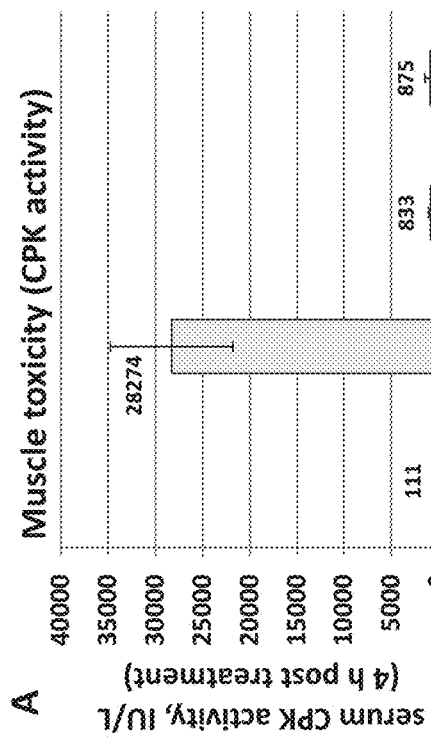

Figure 14

R14L analogs of Leu.ATI-5261 (i.e. T5211-2 analogs)

| | | |
|---|---|---|
| T6023-3 | EARSKAEEWLAALLELAEELLARAKS | T5211-2 |
| T6023-4 | EARSKAEEWLAALLELAEELLARA | T5211-2, (24-mer; no KS) |
| T6023-6 | EVRSKAEEWLAALLELAEELLARA | T5211-2, with A2V (24-mer; no KS) |
| T6023-8 | EVRSKVEEWLAALLELAEELLARA | T5211-2, with A2,6→V(24-mer; no KS) |

A

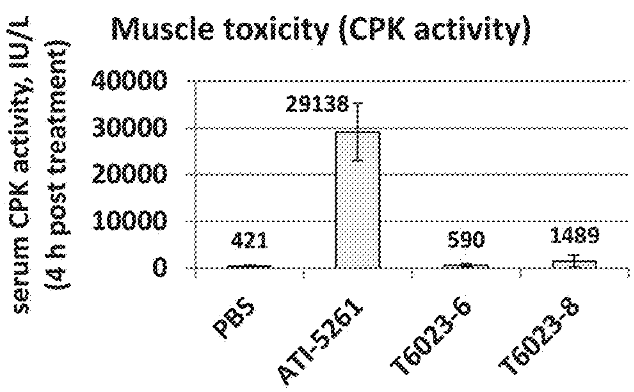

Serum clinical markers- 4 hour post treatment

| | ALT (IU/L) | AST (IU/L) | TG (mg/dl) | TC (mg/dl) | FC (mg/dl) | NEFA (mg/dl) |
|---|---|---|---|---|---|---|
| PBS | 31±8 | 76±27 | 54±9 | 78±9 | 43±1 | 0.94±0.04 |
| ATI-5261 | 210±31 | 2865±725 | 1885±627 | 163±18 | 132±11 | 0.83±0.27 |
| T6023-6 | 76±48 | 170±83 | 1344±429 | 216±24 | 170±16 | 1.85±0.41 |
| T6023-8 | 53±20 | 270±67 | 1317±256 | 176±29 | 152±14 | 1.09±0.44 |

Figure 15

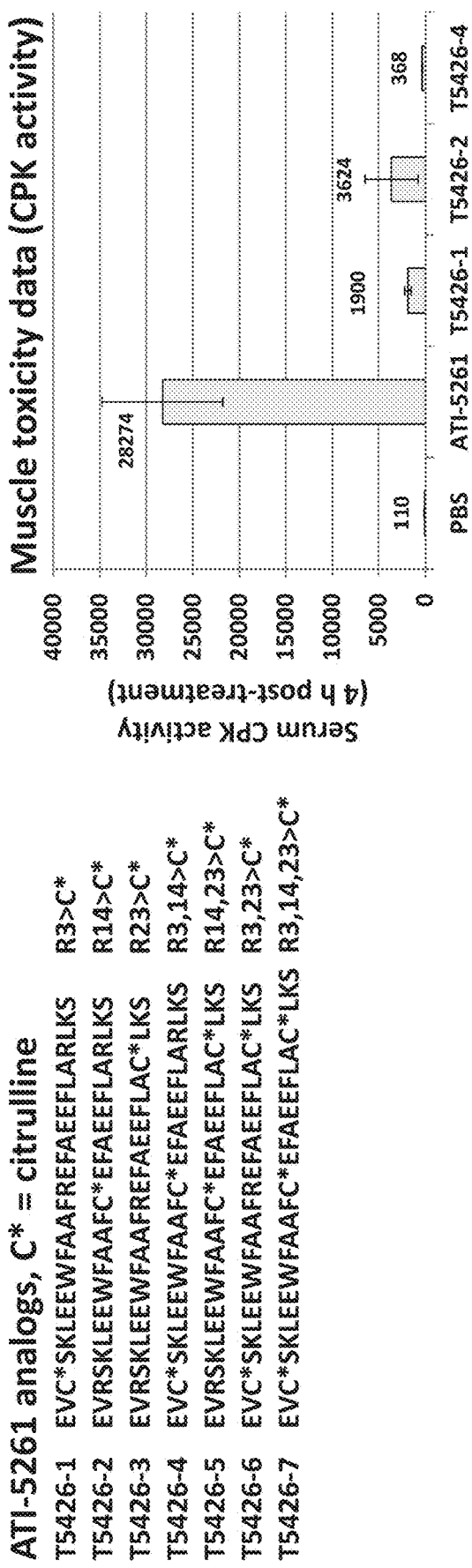

ATI-5261 analogs, C* = citrulline

| | | |
|---|---|---|
| T5426-1 | EVC*SKLEEWFAAFREFAEEFLARLKS | R3>C* |
| T5426-2 | EVRSKLEEWFAAFC*EFAEEFLARLKS | R14>C* |
| T5426-3 | EVRSKLEEWFAAFREFAEEFLAC*LKS | R23>C* |
| T5426-4 | EVC*SKLEEWFAAFC*EFAEEFLARLKS | R3,14>C* |
| T5426-5 | EVRSKLEEWFAAFC*EFAEEFLAC*LKS | R14,23>C* |
| T5426-6 | EVC*SKLEEWFAAFREFAEEFLAC*LKS | R3,23>C* |
| T5426-7 | EVC*SKLEEWFAAFC*EFAEEFLAC*LKS | R3,14,23>C* |

Serum clinical markers- 4 hour post treatment

| | ALT (IU/L) | AST (IU/L) | TG (mg/dl) | FC (mg/dl) | NEFA (mg/dl) |
|---|---|---|---|---|---|
| PBS | 37±11 | 63±11 | 45±6 | 47±11 | 0.43±0.03 |
| ATI-5261 | 226±22 | 3554±629 | 2272±244 | 145±10 | 0.48±0.05 |
| T5426-1 | 49±5 | 241±41 | 1620±150 | 143±10 | 0.62±0.14 |
| T5426-2 | 55±11 | 453±173 | 1434±190 | 138±15 | 0.58±0.03 |
| T5426-4 | 44±12 | 119±18 | 1054±248 | 136±12 | 0.60±0.11 |

Figure 17
Citrulline analogs of ATI-5261; W9→L, A, or V (C* = citrulline)
T5594-1  EVC*SKLEELFAAFC*EFAEEFLARLKS    W9L
T5594-2  EVC*SKLEEAFAAFC*EFAEEFLARLKS    W9A
T5594-3  EVC*SKLEEVFAAFC*EFAEEFLARLKS    W9V
Serum clinical markers - 4 hour post treatment
|         | ALT (IU/L) | AST (IU/L) | TG (mg/dl) | FC (mg/dl) | NEFA (mg/dl) |
|---------|------------|------------|------------|------------|--------------|
| PBS     | 52±36      | 80±33      | 27±2       | 18±2       | 0.44±0.17    |
| ATI-5261| 393±93     | 5269±859   | 1736±338   | 181±50     | 0.50±0.10    |
| T5594-1 | 42±7       | 120±38     | 377±126    | 78±17      | 0.99±0.32    |
| T5594-2 | 32±6       | 89±25      | 150±83     | 40±15      | 0.75±0.24    |
| T5594-3 | 41±13      | 108±17     | 231±114    | 52±19      | 0.87±0.48    |
A  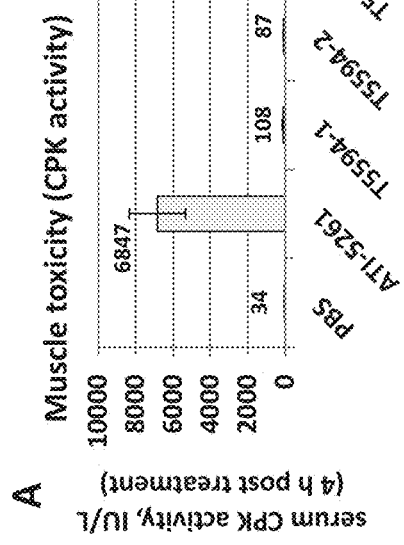
Muscle toxicity (CPK activity)
B  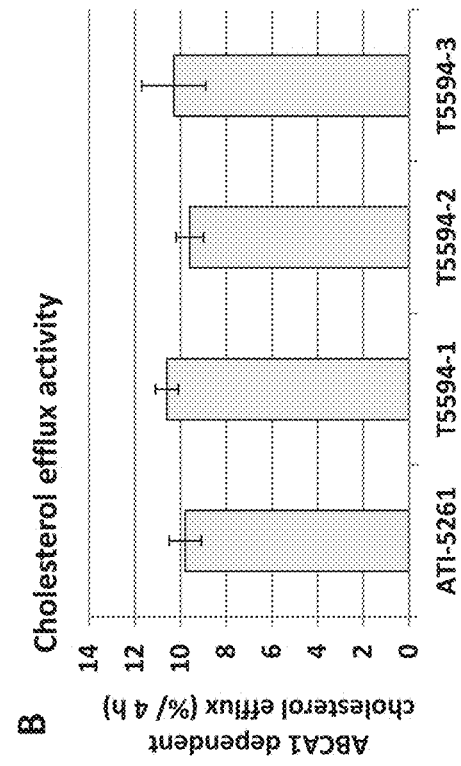
Cholesterol efflux activity

Figure 20

Acidic residue substitutions (E→Q); C* = citrulline

| | | |
|---|---|---|
| T5554-1 | EVRSKLQEWFAAFREFAQEFLARLKS | E7,18→Q |
| T5554-2 | EVRSKLQEWFAAFREFAEEFLARLKS | E7→Q |
| T5554-3 | EVRSKLEEWFAAFREFAQEFLARLKS | E18→Q |
| T5554-4 | EVC*SKLQEWFAAFREFAEEFLARLKS | E7→Q; R3→C* |
| T5554-5 | EVC*SKLQEWFAAFC*EFAQEFLARLKS | E7,18→Q; R3,14→C* |
| T5554-6 | EVC*SKLQEWFAAFC*EFAQQFLAC*LKS | E7,18,19→Q; R3,14,23→C* |
| T5554-7 | EVC*SKLQEWFAAFC*EFAEEFLARLKS | E7→Q; R3,14→C* |
| T5554-8 | EVC*SKLEEWFAAFC*EFAQEFLARLKS | E18→Q; R3,14→C* |
| T5554-9 | EVRSKLQEWLAALRELAEELLARLKS | E7→Q in LeuATI-5261 |
| T5554-10 | EVC*SKLQEWLAALRELAEELLARLKS | E7→Q; R3→C* in LeuATI-5261 |

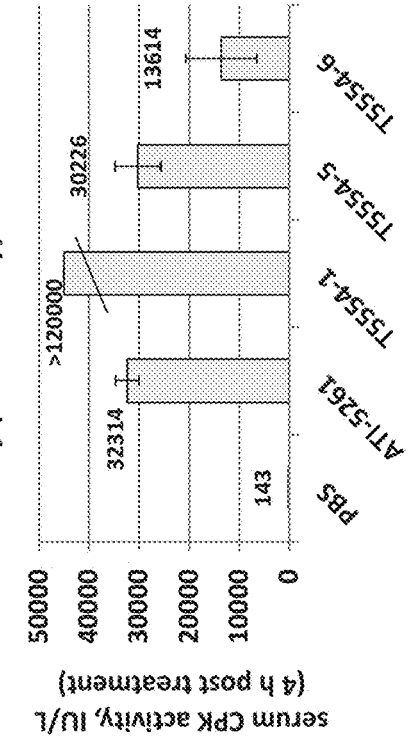

Serum clinical markers - 4 hour post treatment

| | ALT (IU/L) | AST (IU/L) | TG (mg/dl) | FC (mg/dl) | NEFA (mg/dl) |
|---|---|---|---|---|---|
| PBS | 26±6 | 84±21 | 26±5 | 36±3 | 0.49±0.05 |
| ATI-5261 | 233±10 | 4595±933 | 1787±175 | 173±42 | 0.94±0.28 |
| T5554-1 | 1573±226 | 14194±1454 | 726±101 | 128±5 | 0.67±0.06 |
| T5554-5 | 185±47 | 3330±1003 | 1752±380 | 201±97 | 0.36±0.13 |
| T5554-6 | 154±22 | 2095±187 | 1760±174 | 166±31 | 0.56±0.14 |

Figure 22
Cit.LeuATI-5261 analogs, 24-mers, C* = citrulline
T5766-6  EVRSKLEEWLAALRELAEELLARLKS    Leu.ATI-5261 (no KS)
T6023-1  EVC*SKLEEWLAALC*ELAEELLARL    Cit.LeuATI-5261 (no KS)
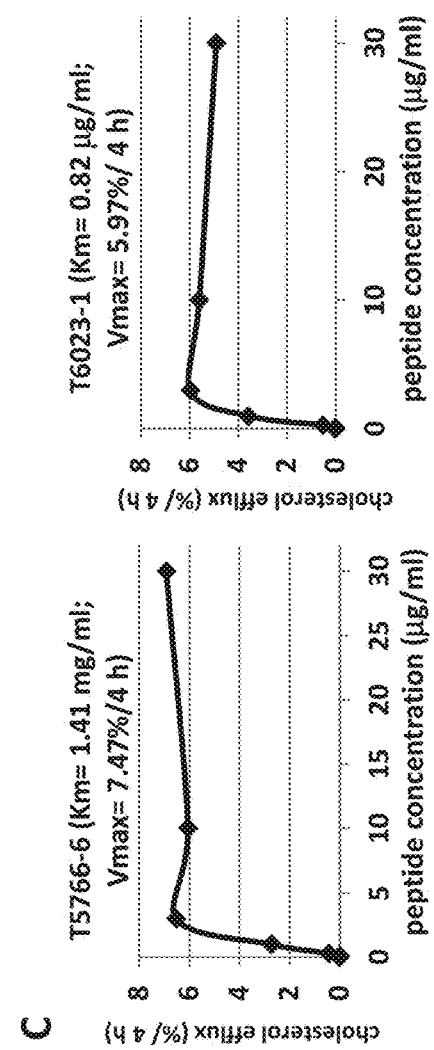
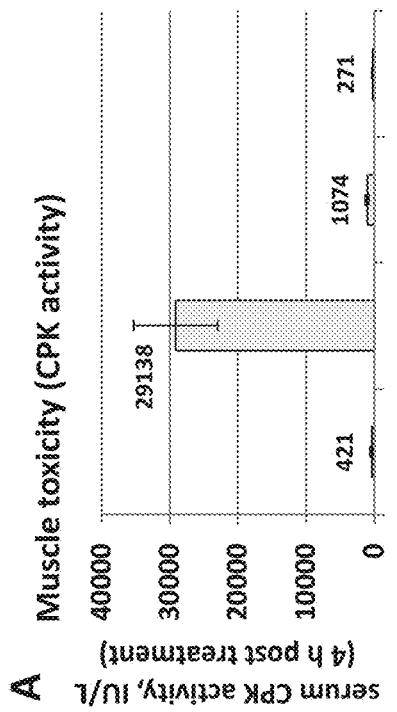
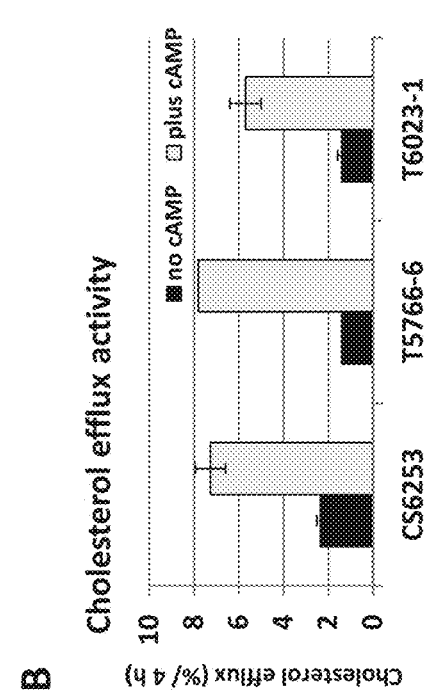

Figure 23
Cit.LeuATI-5261 analogs, C*= citrulline
T6623-2 EVLSKLEEWLAALC*ELAEELLARLKS C*3→L
T6275-3 ELC*SKLEEWLAALC*ELAEELLARLKS V2→L
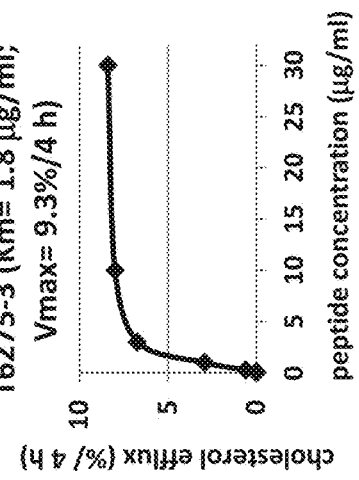
Serum clinical markers- 4 hour post treatment
| | ALT (IU/L) | AST (IU/L) | TG (mg/dl) | FC (mg/dl) | NEFA (mg/dl) |
|---|---|---|---|---|---|
| PBS | 57±3 | 80±8 | 37±1 | 21±3 | 0.69±0.05 |
| ATI-5261 | 242±76 | 3391±1165 | 1671±1092 | 105±8 | 0.77±0.25 |
| T6623-2 | 41±17 | 87±19 | 1540±256 | 103±24 | 1.50±0.09 |
| T6275-3 | 34±4 | 62±10 | 711±337 | 68±17 | 1.40±0.39 |
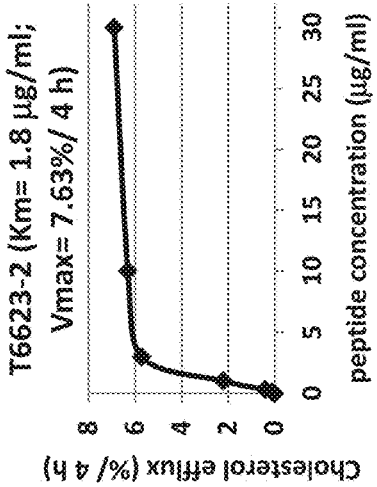
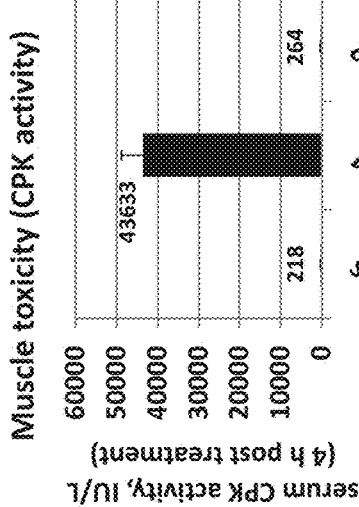
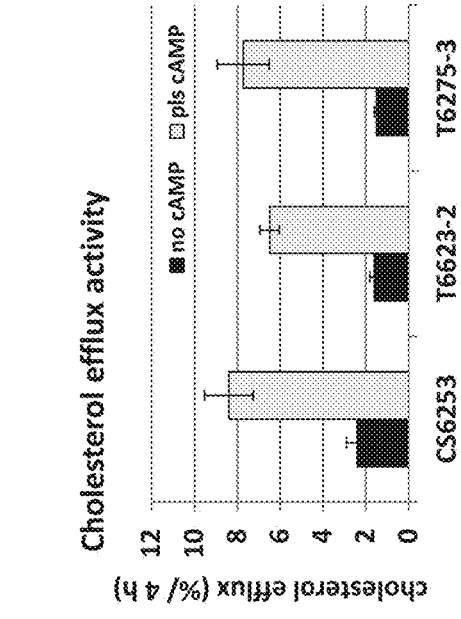

Figure 24

Cit.LeuATI-5261 analogs, C*= citrulline

| | | |
|---|---|---|
| T6275-5 | EVC*SKLEEWLAALLELAEELLARLKS | C*14L |
| T6623-1 | ELC*SKLEEWLAALLELAEELLARLKS | V2L & C*14L |
| T6623-2 | EVLSKLEEWLAALC*ELAEELLARLKS | C*3L |
| T6623-3 | ELLSKLEEWLAALC*ELAEELLARLKS | V2L & C*3L |
| T6623-4 | EVLSKLEEWLAALLELAEELLARLKS | C*3, 14L |
| T6623-5 | ELLSKLEEWLAALLELAEELLARLKS | V2L & C*3, 14L |
| T6623-6 | ELC*SKLEEWLAALLELAEELLARL | V2L & C*14L, no KS |
| T6623-7 | EVLSKLEEWLAALC*ELAEELLARL | C*3L, no KS |
| T6623-8 | ELLSKLEEWLAALC*ELAEELLARL | V2L & C*3L, no KS |
| T6623-9 | EVLSKLEEWLAALLELAEELLARL | C3, 14L, no KS |
| T6623-10 | ELLSKLEEWLAALLELAEELLARL | V2L & C*3, 14L, no KS |
| T6623-11 | ELRSKLEEWLAALLELAEELLARL | V2L & C*14L, with R3 and no KS |
| T6623-12 | ELLSKLEEWLAALRELAEELLARL | V2L & C*3L, with R14 and no KS |

Muscle toxicity (CPK activity)

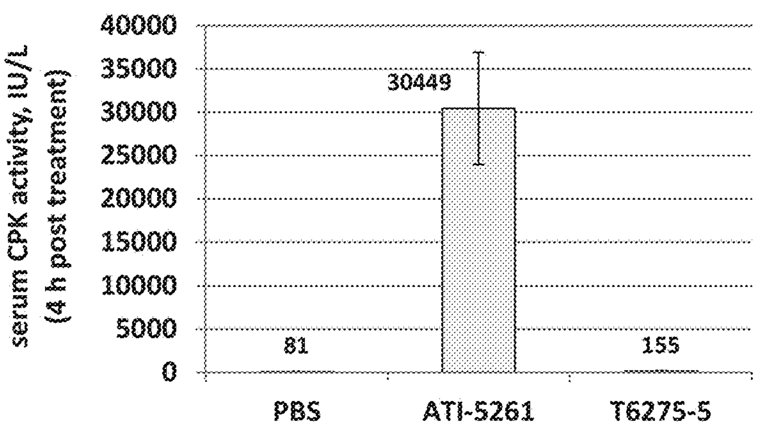

Serum clinical markers- 4 hour post treatment

| | ALT (IU/l) | AST (IU//) | TG (mg/dl) | FC (mg/dl) | NEFA (mg/dl) |
|---|---|---|---|---|---|
| PBS | 33±11 | 49±10 | 51±9 | 29±1 | 0.91±0.15 |
| ATI-5261 | 190±31 | 2611±355 | 2130±37 | 132±23 | 0.68±0.18 |
| T6275-5 | 40±25 | 79±23 | 1232±262 | 135±27 | 1.27±0.22 |

Figure 26

ATI-5261 analogs with citrulline, C* = citrulline

| | | |
|---|---|---|
| T6991-1 | EVRSKLEEWIAAIREIAEEILARLKS | F10,13,16,20→I (F to isoleucine in ATI-5261) |
| T6991-2 | EVC*SKLEEWIAAIC*EIAEEILARLKS | R3, 14→ C* in isoleucine form of ATI-5261 |
| T6991-3 | EVRAKLE Figure 36
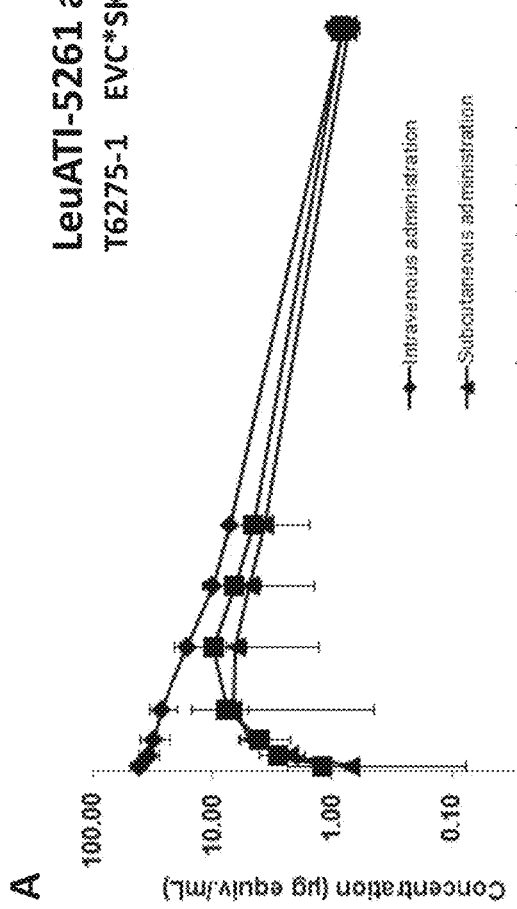
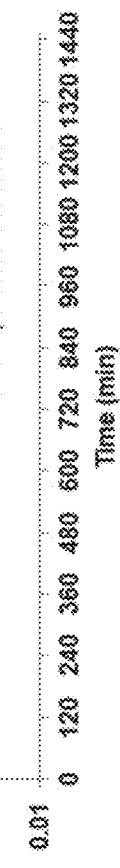
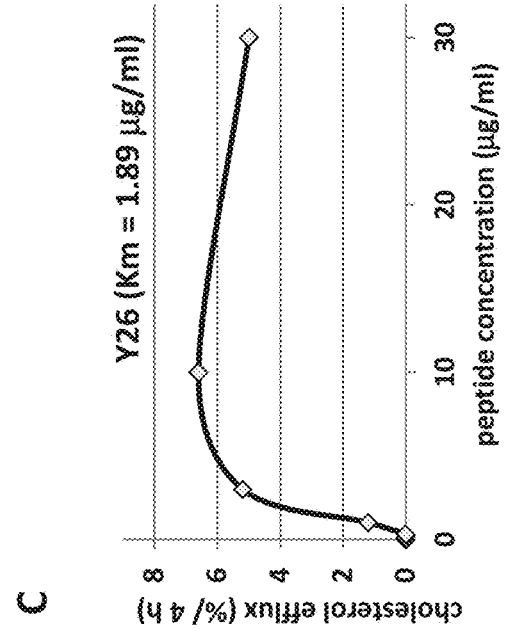
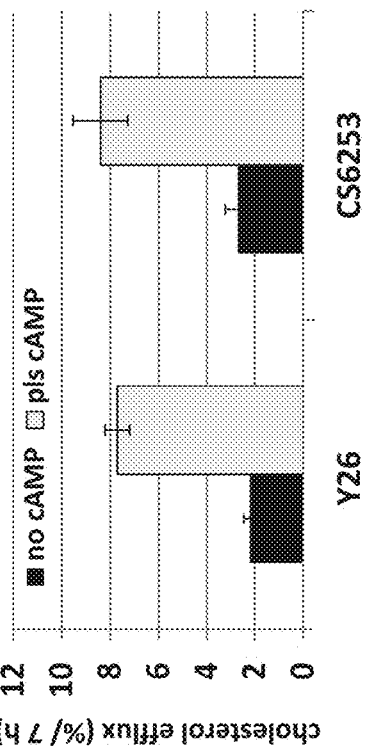

Stapled peptides can be designed to mediate ABCA1 mediated cholesterol efflux from J774 cells CS6257 (ATI-5261, R3,23→A with staple at positions 14 and 21 [S5-R8])
EVASKLEEWFAAF(S5)EFAEEF(R8)AALKS CS6259 (LeuATI-5261, R3,23→Q with staple at positions 14 and 21 [S5-R8])
EVQSKLEEWLAAL(R8)ELAEEL(S5)AQLKS % efflux 4 h (10 ug/ml peptides)
|  | CS6257 | CS6259 | ATI-5261 |
|---|---|---|---|
| no cAMP | 0.45 | 0.67 | 1.4 |
| pls cAMP | 3.06 | 3.28 | 7.81 |

SD values
|  | CS6257 | CS6259 | ATI-5261 |
|---|---|---|---|
|  | 0.05 | 0.04 | 0.22 |
|  | 0.84 | 0.73 | 0.91 |

**CitLeuATI-5261 (CS6253) analogs with Isoleucine, C*= citrulline Figure 47**

| | | |
|---|---|---|
| T7983-1 | EVRSKLEEWIAAIREIAEEILARL | F10,13,16,20→I (all F to isoleucine in 24 mer of ATI-5261) |
| T7983-2 | EVC*SKLEEWIAAIC*EIAEEILARL | R3, 14→ C* in isoleucine form of 24-mer ATI-5261 (24-mer T6991-2) |
| T7983-3 | EVC*SKLEEWLAALC*ELAEEILARLKS | L20→I in CitleuATI-5261 |
| T7983-4 | EVC*SKLEEWIAALC*ELAEEILARLKS | L10, 20→I in CitleuATI-5261 |
| T7983-5 | EVC*SKLEEWLAAIC*EIAEELLARLKS | L13, 16→I in CitLeuATI-5261 |
| T7983-6 | EVC*SKLEEWIAAIC*EIAEELLARLKS | L10,13,16→I in CitLeuATI-5261 |
| T7983-7 | EVC*SKLEEWLAAIC*EIAEEILARLKS | L13,16,20→I in CitLeuATI-5261 |
| T7983-8 | EVISKLEEWLAALC*ELAEELLARLKS | R3→I in Cit14_leuATI-5261 |
| T7983-9 | EVC*SKLEEWLAALIELAEELLARLKS | R14→I in Cit3_leuATI-5261 |
| T7983-10 | EVISKLEEWLAALIELAEELLARLKS | R3,14→I in LeuATI-5261 (i.e. no citrulline) |

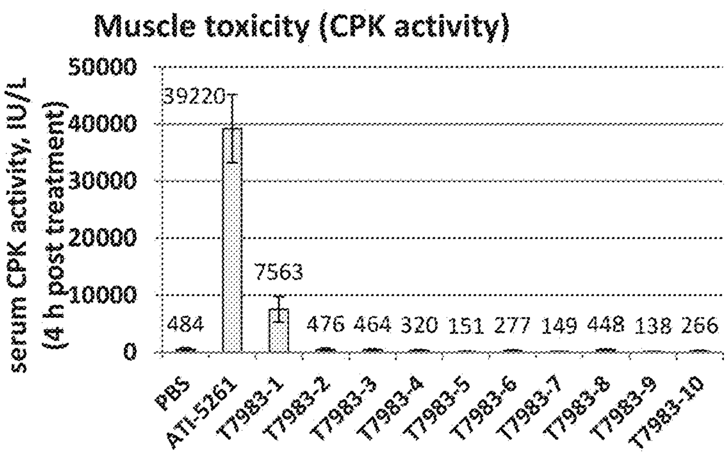

Serum clinical markers- 4 hour post treatment

| | ALT (IU/l) | AST (IU/l) | TG (mg/dl) | TC (mg/dl) | FC (mg/dl) | NEFA (mg/dl) |
|---|---|---|---|---|---|---|
| PBS | 42±6 | 86±28 | 59±7 | 105±20 | 27±3 | 0.85±0.22 |
| ATI-5261 | 230±41 | 3842±747 | 1579±185 | 231±16 | 118±10 | 0.46±0.04 |
| T7983-1 | 115±22 | 1329±131 | 941±34 | 184±20 | 90±6 | 1.41±0.32 |
| T7983-2 | 44±13 | 113±45 | 575±273 | 139±32 | 75±24 | 1.78±1.05 |
| T7983-3 | 54±29 | 78±14 | 823±102 | 167±23 | 73±18 | 1.62±0.16 |
| T7983-4 | 40±7 | 79±14 | 627±208 | 133±15 | 62±11 | 2.04±0.57 |
| T7983-5 | 42±19 | 66±19 | 198±118 | 85±2 | 29±6 | 0.98±0.31 |
| T7983-6 | 38±5 | 79±19 | 276±169 | 88±23 | 32±14 | 1.13±0.33 |
| T7983-7 | 34±3 | 78±8 | 201±173 | 105±6 | 35±5 | 1.18±0.52 |
| T7983-8 | 44±11 | 88±17 | 802±101 | 158±5 | 75±2 | 1.21±0.20 |
| T7983-9 | 30±6 | 71±9 | 137±38 | 58±15 | 23±7 | 1.11±0.36 |
| T7983-10 | 30±3 | 82±9 | 249±91 | 83±25 | 30±8 | 1.46±0.73 |

Figure 49

**CitLeuATI-5261 (CS6253) analogs with Isoleucine, C*= citrulline**

| | | |
|---|---|---|
| T8212-1 | EVC*SKLEEWIAALC*ELAEELLARLKS | L10→I in CitLeuATI-5261 |
| T8212-2 | EVC*SKLEEWLAAIC*ELAEELLARLKS | L13→I in CitLeuATI-5261 |
| T8212-3 | EVC*SKLEEWLAALC*EIAEELLARLKS | L16→I in CitLeuATI-5261 |
| T8212-4 | EVC*SKLEEWIAALC*ELAEEILARLKS | L10, 20→I in CitLeuATI-5261 |
| T8212-5 | EVC*SKIEEWIAALC*ELAEEILARLKS | L6, 10, 20→I in CitLeuATI-5261 |
| T8212-6 | EVC*SKIEEWLAAIC*EIAEELLARLKS | L6, 13, 16→I in CitLeuATI-5261 |
| T8212-7 | EVC*SKIEEWIAAIC*EIAEELLARLKS | L6, 10, 13, 16→I in CitLeuATI-5261 |
| T8212-8 | EVC*SKIEEWIAAIC*EIAEEILARLKS | L6, 10, 13, 16, 20→I in CitLeuATI-5261 |
| T8212-9 | EVC*SKIEEWIAAIC*EIAEEIIARLKS | L6, 10, 13, 16, 20, 21→I in CitLeuATI-5261 |
| T8212-10 | EVC*SKIEEWIAAIC*EIAEEIIARIKS | L6, 10, 13, 16, 20, 21, 24→I in CitLeuATI-5261 (i.e. all isoleu) |

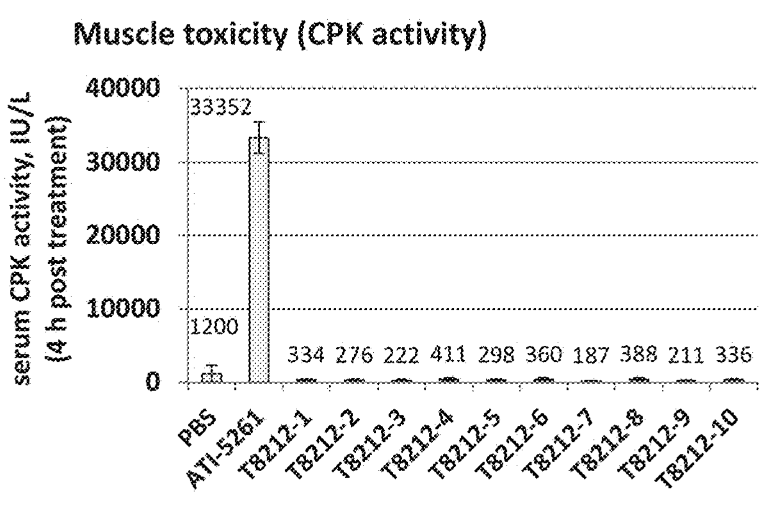

Serum clinical markers- 4 hour post treatment

| | ALT(IU/l) | AST(IU/l) | TG (mg/dl) | TC (mg/dl) | FC (mg/dl) | NEFA (mg/dl) |
|---|---|---|---|---|---|---|
| PBS | 56±8 | 185±93 | 25±16 | 51±7 | 17±2 | 0.80±0.05 |
| ATI-5261 | 247±26 | 3279±528 | 770±225 | 104±25 | 59±11 | 0.46±0.15 |
| T8212-1 | 40±5 | 123±10 | 355±287 | 72±18 | 39±21 | 1.60±0.89 |
| T8212-2 | 49±20 | 121±31 | 373±46 | 63±13 | 31±1 | 1.71±0.19 |
| T8212-3 | 40±9 | 98±15 | 335±30 | 61±2 | 40±7 | 1.72±0.31 |
| T8212-4 | 44±10 | 118±19 | 309±13 | 67±3 | 41±3 | 1.76±0.19 |
| T8212-5 | 58±2 | 112±14 | 252±106 | 43±4 | 27±9 | 1.09±0.05 |
| T8212-6 | 35±5 | 117±13 | 305±168 | 55±19 | 36±15 | 1.15±0.36 |
| T8212-7 | 45±32 | 87±14 | 185±182 | 68±15 | 36±16 | 1.04±0.32 |
| T8212-8 | 52±8 | 104±27 | 384±31 | 72±7 | 45±3 | 1.80±0.11 |
| T8212-9 | 51±33 | 95±27 | 376±289 | 77±32 | 44±21 | 1.57±0.36 |
| T8212-10 | 42±2 | 116±28 | 670±92 | 110±25 | 68±8 | 1.95±0.36 |

Figure 52
T6991-2 with Y26, C* = citrulline
Batch T7983-11    EVC*SKLEEWIAAIC*EIAEEILARLKY
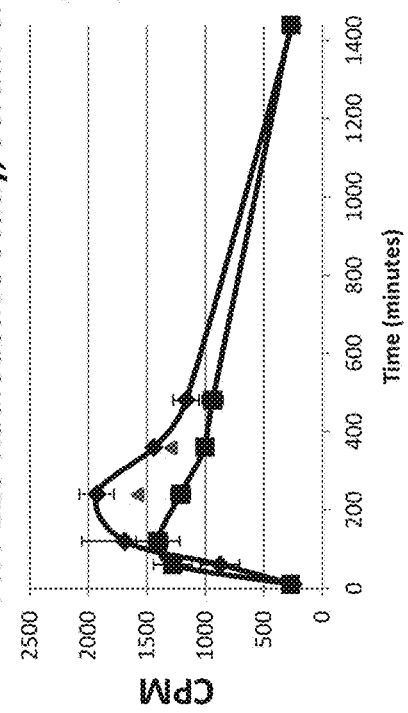
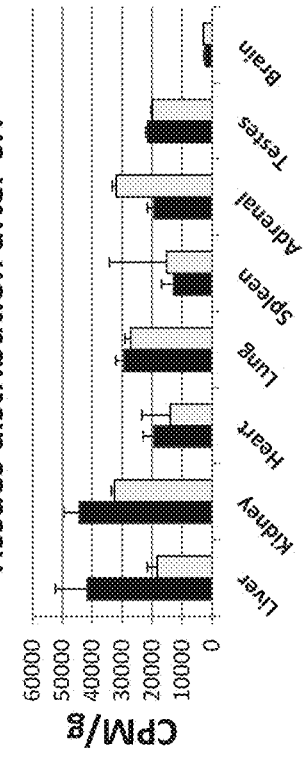
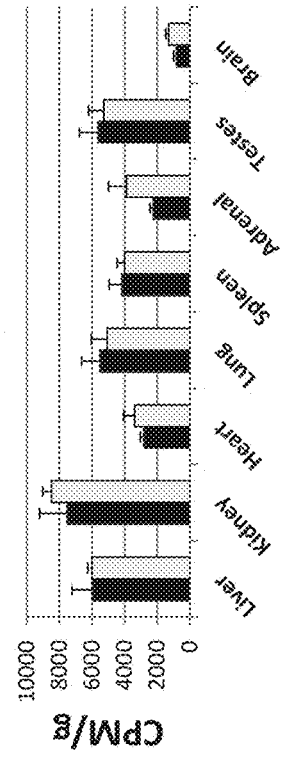
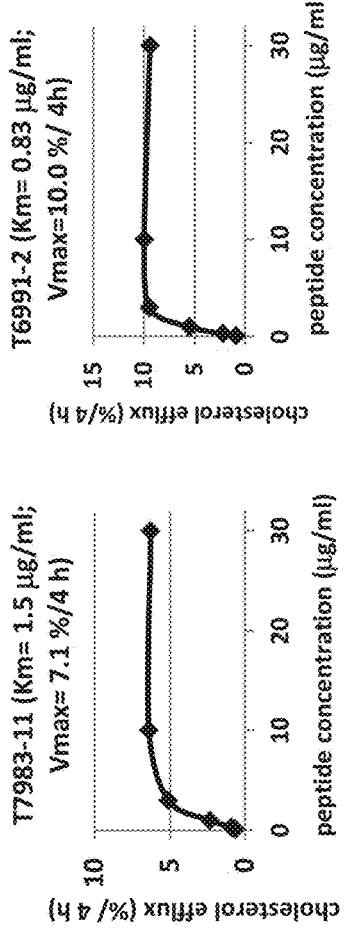
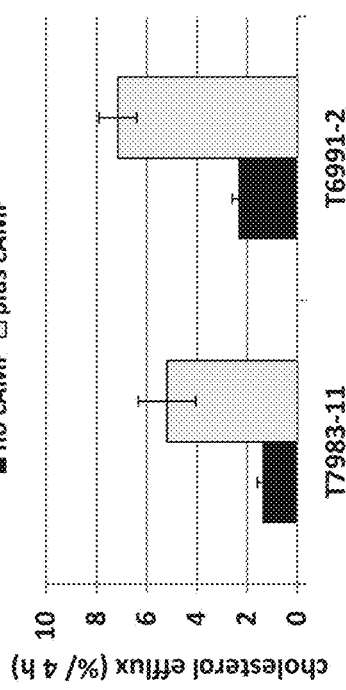

US 10,774,118 B2

PEPTIDES HAVING REDUCED TOXICITY THAT STIMULATE CHOLESTEROL EFFLUX

CROSS-REFERENCE TO RELATED APPLICATIONS

This application is a divisional of U.S. application Ser. No. 14/774,682, filed Sep. 10, 2015, which is a National Stage of International Application No. PCT/US2014/029232, filed Mar. 14, 2014, which claims priority benefit of U.S. provisional application No. 61/798,191, filed Mar. 15, 2013. Each of the aforementioned applications are herein incorporated by reference.

STATEMENT AS TO RIGHTS TO INVENTIONS MADE UNDER FEDERALLY SPONSORED RESEARCH AND DEVELOPMENT

This invention was made with government support under Contract No. DE-AC02-05CH11231 awarded by the U.S. Department of Energy and Grant No. HL085791 awarded by the National Institutes of Health. The Government has certain rights in this invention.

REFERENCE TO SEQUENCE LISTING

This application includes a Sequence Listing as a text file named "077429_1093795_SEQLIST.txt" created Jun. 25, 2018, and containing 51,590 bytes. The material contained in this text file is incorporated by reference in its entirety for all purposes.

BACKGROUND OF THE INVENTION

Elevated levels of plasma HDL cholesterol are associated with reduced risk of atherosclerosis (Gordon et al., "High Density Lipoprotein As A Protective Factor Against Coronary Heart Disease," *Am. J. Med.*, 62:707-14 (1977)). The beneficial effects of HDL are related, in part, to activity in mediating the anti-atherogenic reverse cholesterol transport (RCT) pathway. RCT involves the transport of cholesterol from peripheral macrophages to the liver for excretion of sterol in feces (Lewis et al., "New Insights Into The Regulation of HDL Metabolism and Reverse Cholesterol Transport," *Circ. Res.*, 96:1221-32 (2005)). The rate-limiting step of RCT involves stimulation of cholesterol efflux from macrophages, mediated by native apolipoproteins such as Apo A-I and Apo E. This process of cholesterol efflux generates nascent HDL and requires the ATP-binding cassette transporter A1 (ABCA1) or else atherosclerosis is developed (Calpe-Berdiel et al., "Direct Evidence In Vivo of Impaired Macrophage-Specific Reverse Cholesterol Transport in ATP-Binding Cassette Transporter A1-Deficient Mice," *Biochim. Biophys. Acta.*, 1738(1-3):6-9 (2005). ABCA1 is the defective molecule in Tangiers disease, which is characterized by severe deficiency in plasma HDL and premature atherosclerosis (Attie et al., "Pivotal Role of ABCA1 in Reverse Cholesterol Transport Influencing HDL Levels and Susceptibility to Atherosclerosis," *J Lipid Res.*, 42(11):1717-26 (2001)). Apolipoproteins A and E also stabilize cellular ABCA1 protein by preventing its degradation, which ensures high-levels of cellular cholesterol export and HDL assembly.

The clinical importance of HDL has sparked interest in the development of strategies to manipulate RCT for therapeutic purposes. Peptides have been identified that can stimulate cholesterol efflux in vivo (see, e.g., WO 2008/115303 and WO 2009/155366). These peptides are characterized by alpha helices having a polar and non-polar surface and an alignment of acidic amino acids residues. However, in some contexts, these peptides have exhibited toxicity when administered at very high pharmacological doses. Accordingly, there is a need to provide improved peptides that have reduced toxicity. The present invention fulfills this need.

SUMMARY OF THE INVENTION

The present invention relates to peptides that have cholesterol efflux activity and that have superior properties in terms of cytotoxicity profile.

In one aspect, the invention provides a family of peptides having cholesterol efflux activity that parallels that of full-length apolipoproteins (e.g., Apo AI and Apo E); and having high selectivity for ABCA1 that parallels that of full-length apolipoproteins. Moreover, the family of peptides has a desirable cytotoxicity profile in that they display little or no cytotoxicity when administered at high pharmacological doses. The polypeptides of the present invention also stimulate cholesterol efflux from macrophage foam cells in vivo, promote a sustained increase in fecal sterol secretion, and reduce the severity of established atherosclerosis in the presence of hypercholesterolemia and a high-fat dietary insult in an apolipoprotein E-deficient mouse model of disease.

The peptides of the present invention can be used therapeutically to promote ABCA1-stabilization as well as ABCA1-lipid efflux activity, and can be used alone or, alternatively, in combination with other known pharmacological agents, for the treatment of cardiovascular disease to reduce atherosclerosis. In addition, the polypeptides of the present invention can be used alone or, alternatively, in combination with other known pharmacological agents, for the treatment of acute coronary syndrome to reduce plaque lipid content and to stabilize vulnerable plaques. Further, the peptides of the present invention can be used alone or, alternatively, in combination with other known pharmacological agents, for the treatment of dyslipidemia, hypercholesterolemia and inflammation to raise plasma HDL concentrations and/or to promote reverse cholesterol transport. Further, the peptides of the present invention can be used therapeutically, alone or with other pharmacological agents, to lower glucose in patients having diseases of abnormal glucose metabolism. In some embodiments, the peptides of the present invention can be used therapeutically to treat or prevent one or more symptoms of Alzheimer's Disease or frontotemporal dementia. In various aspects, the invention includes, but is not limited to, the following embodiments.

The peptides of the invention comprise certain features that together define the pharmacokinetic and pharmacodynamic properties of the peptides. In some embodiments, the peptides comprise a core sequence of 24 amino acid residues that selectively bind to HDL in plasma and target the ABCA1 transporter in cells. Features of the peptides include an amphipathic α-helix structure, with alignment of acidic residues down the center of the polar surface and positively charged amino acids at the lipid-water interface. Further a peptide of the invention has one or more uncharged residues at the polar surface of the lipid water interface, e.g., at position 3, 14, and/or 23 of the 24 amino acid sequence, as numbered with reference to SEQ ID NO:1. In some embodiments the one or more uncharged residues is a polar uncharged residue. In some embodiments, the peptide comprises one or more uncharged hydrophobic amino acids at the polar surface, e.g., at one or two of positions 3, 14, and 23. In some embodiments, the peptide comprises one or more uncharged aliphatic amino acids at the polar surface, e.g., at one or two of positions 3, 14, and 23. In typical embodiments, a peptide of the invention has a net negative charge. In some embodiments, aliphatic amino acids are preferred at the non-polar surface. In some embodiments, alanine can be used to reduce hydrophobicity.

The peptides also lack substantial stereo-specific effect, e.g., peptides that comprise L and D amino acids and inverted forms work equally well.

In one aspect, the invention provides an isolated peptide having cholesterol efflux activity and little or no toxicity at high pharmacological doses, where the peptide comprises an amino acid sequence that is an amphipathic α-helix having a non-polar surface and a polar surface, where the polar surface comprises charged and uncharged amino acid residues at the lipid-water interface. In some embodiments, the peptide comprises the amino acid sequence EVcitSKLEE-WLAALcitELAEELLARL (SEQ ID NO:1), wherein "cit" represents citrulline. In some embodiments, the peptide comprises a variant of SEQ ID NO:1 that has at least 50% identity, or at least 60% identity, or at least 70%, at least 80%, at least 85%, at least 90% identity, or at least 91%, 92%, 93%, 94%, 95%, 96%, 97%, 98, or 99% identity to SEQ ID NO:1). In some embodiments, the peptide comprises the amino acid sequence EVcitSKLEEWIAAIcitEI-AEEILARL (SEQ ID NO:2), wherein "cit" represents citrulline. In some embodiments, the peptide comprises a variant of SEQ ID NO:2 that has at least 50% identity, or at least 60% identity, or at least 70%, at least 80%, at least 85%, at least 90% identity, or at least 91%, 92%, 93%, 94%, 95%, 96%, 97%, 98, or 99% identity to SEQ ID NO:2. The amino acid positions described here are determined with reference to SEQ ID NO:1 or SEQ ID NO:2. Peptide variants of SEQ ID NO:1 or SEQ ID NO:2 typically have an acidic amino acid residue at position 1, 7, 8, 15, 18, and 19 as numbered with reference to SEQ ID NO:1. In some embodiments, a variant has an uncharged residue at the polar surface, e.g., at at least one of positions 3, 14, or 23 as numbered with reference to SEQ ID NO:1. In some embodiments, the variant has citrulline at two of positions 3, 14, or 23 as numbered with reference to SEQ ID NO:1. In some embodiments, a variant has citrulline at positions 3 and 14, positions 3 and 23, or positions 14 and 23. In some embodiments, a variant has citrulline at positions 3 and 14 and an R or K at position 23; citrulline at positions 3 and 23 and an R or K at position 14; or citrulline at positions 14 and 23 and an R or K at position 3. In some embodiments, a variant has no more than two R residues. For example, in some embodiments, a variant may have an R at position 5 and an R at position 23. In some embodiments, the amino acid sequence comprises an uncharged residue at one or two of positions 3, 14, and 23 where the residue is a hydrophobic amino acid, such as Q, N, Y, W, A, I, L, V. In some embodiments, the uncharged residue at one or two of positions 3, 14, and 23 is an aliphatic amino acid, such as A, I, L, or V. In embodiments when there is a hydrophobic or aliphatic amino acid at one or two of positions 3, 14, and 23, the third positions is an R, K, or citrulline. In some embodiments, a variant comprises a hydrophobic amino acid at position 2, 6, 9, 10, 13, 16, 17, 20, 21, 22, and 24 as determined with reference to SEQ ID NO:1. In some embodiments, a variant comprises an aliphatic amino acid at at least one, or at least two, three, four, five, six, seven, eight, or nine of positions 2, 6, 10, 13, 16, 17, 20, 21, 22, and 24. In some embodiments, a variant comprises an aliphatic residue at each of positions 2, 6, 10, 13, 16, 20, 21, and 24. In some embodiments, the aliphatic amino acid is L, V, or I. In some embodiment, the aliphatic amino acid residue at position 2, 6, 10, 13, 16, 20, and 21 is L. In some embodiment, the aliphatic amino acid residue at position 2, 6, 10, 13, 16, 20, and 21 is I. In some embodiments, the aliphatic amino acid residue at position 2 is V. In some embodiments, the aliphatic amino acid residue at position 2 is V and the aliphatic amino acid residue at position 6, 10, 13, 16, 20, and 21 is L. In some embodiments, the aliphatic amino acid at each of positions 10, 13, 16, and 20 is the same amino acid. In some embodiments, the aliphatic amino acid is a branched chain amino acid. In some embodiments, the aliphatic amino acid at each of positions 10, 13, 16, and 20 is the same amino acid selected from the group consisting of L, I, or V. In some embodiments, the aliphatic amino acid at each of positions 10, 13, 16, and 20 is I. In some embodiments, the aliphatic amino acid at each of positions 10, 13, 16, and 20 is L. In some embodiments, the aliphatic amino acid at position 2 is V, the aliphatic amino acid at position 6, 21, and 24 is L, and the aliphatic amino acid residue at position 10, 13, 16, and 20 is I or L. In some embodiments, a variant comprises A at positions 11 and 12. In some embodiments, a peptide of the invention has glucose-lowering activity and/or treats or prevents one or more symptoms of Alzheimer's Disease or frontotemporal dementia. In some embodiments, a peptide of the invention can sensitize a subject to insulin. For example, in some embodiments, the peptide has the same aliphatic residue at $X_{10}$, $X_{13}$, $X_{16}$ and $X_{21}$ wherein the residue is a branched chain aliphatic amino acid residue. In some embodiments, $X_{10}$, $X_{13}$, $X_{16}$ and $X_{21}$ is L or $X_{10}$, $X_{13}$, $X_{16}$ and $X_{21}$ is I. In some embodiments, the polypeptide comprises SEQ ID NO:1 or SEQ ID NO:2.

In some embodiments, a peptide of the invention, e.g., SEQ ID NO:1 or a variant as described herein, further comprises amino acids at positions 25 and 26, as numbered with reference to SEQ ID NO:1. In some embodiments, the amino acid residue at position 25 is K or N and the amino acid residue at positions 26 is S or Y. In some embodiments, the amino acid at position 25 is K and the amino acid at position 26 is S. In some embodiments, the peptide comprises the amino acid sequence EVcitSKLEEWLAALcitE-LAEELLARLKS (SEQ ID NO:3). In some embodiments, the polypeptide comprises EVcitSKLEEWIAAIcitEIAEE-ILARLKS (SEQ ID NO:4).

In some embodiments, the invention provides an isolated polypeptide having cholesterol efflux activity and little or no cytotoxicity, where the polypeptide comprises an amino acid sequence that has the following features: an amphipathic α-helix structure, with alignment of acidic residues down the center of the polar surface and positively charged amino acids at the lipid-water interface. Further a peptide of the invention has one or more uncharged residues at the polar surface of the lipid water interface, e.g., at positions 3, 14, or 23. Thus, in some embodiments, the invention provides a peptide that comprises the following 24-amino acid sequence:

$$X_1X_2X_3X_4X_5X_6X_7X_8X_9X_{10}X_{11}X_{12}X_{13}X_{14}X_{15}X_{16}X_{17}$$
$$X_{18}X_{19}X_{20}X_{21}X_{22}X_{23}X_{24} \quad \text{(sequence 1)}$$

wherein $X_1$, $X_7$, $X_8$, $X_{15}$, $X_{18}$ and $X_{19}$ are independently selected from the group consisting of E and D; $X_2$, $X_6$, $X_9$, $X_{10}$, $X_{12}$, $X_{13}$, $X_{16}$, $X_{17}$, $X_{20}$, $X_{21}$ and $X_{24}$ are hydrophobic amino acid residues; $X_3$, $X_{14}$ and $X_{23}$ are uncharged amino acids; $X_4$, $X_{11}$, and $X_{22}$ are amino acids independently selected from the group consisting of S, T, G, A and Y; and $X_5$ is R or K. In embodiments in which $X_5$ is R, the peptide typically has no more than two R residues. In some embodiments, $X_2$, $X_6$, $X_{10}$, $X_{12}$, $X_{13}$, $X_{16}$, $X_{17}$, $X_{20}$, $X_{21}$ and $X_{24}$ are aliphatic amino acids. In some embodiments, two of positions $X_3$, $X_{14}$, and $X_{23}$ are citrulline and the third position is R or K. In some embodiments, the 24-amino acid sequence comprises no more than two aromatic amino acids. In some embodiments, a peptide of the invention has glucose-lowering activity and/or treats or prevents one or more symptoms of Alzheimer's Disease or frontotemporal dementia. In some embodiments, a peptide of the invention can sensitize a subject to insulin. For example, in some embodiments, the peptide has the same aliphatic residue at $X_{10}$, $X_{13}$, $X_{16}$ and $X_{21}$ wherein the residue is a branched chain aliphatic amino acid residue. In some embodiments, $X_{10}$, $X_{13}$, $X_{16}$ and $X_{21}$ is L or $X_{10}$, $X_{13}$, $X_{16}$ and $X_{21}$ is I.

The invention additionally provides an isolated peptide having cholesterol efflux activity that has little or no cytotoxicity that comprises the following 24-amino acid sequence:

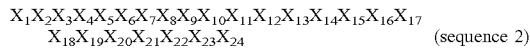  (sequence 2)

wherein $X_1$, $X_7$, $X_8$, $X_{15}$, $X_{18}$ and $X_{19}$ are acid amino acids; and $X_2$, $X_6$, $X_9$, $X_{10}$, $X_{11}$, $X_{12}$, $X_{13}$, $X_{16}$, $X_{17}$, $X_{20}$, $X_{21}$, $X_{22}$, and $X_{24}$ are hydrophobic amino acids, e.g., aliphatic amino acids. In some embodiments, $X_3$, $X_{14}$ and $X_{23}$ are uncharged amino acids. In some embodiments, two of positions $X_3$, $X_{14}$ and $X_{23}$ are citrulline and the third position is R or K. In some embodiments, $X_{11}$ and $X_{22}$ are A. In some embodiments, $X_4$ is a polar amino acid, preferably a polar uncharged amino acid. In some embodiments, $X_4$ is S, T, G, or Y. In some embodiments, $X_4$ is S. In some embodiments, $X_5$ is a positively charged amino acid. In some embodiments, $X_5$ is R or K. In some embodiments, $X_5$ is R. In some embodiments, $X_3$ and $X_{14}$ are citrulline. In some embodiments, $X_{10}$, $X_{13}$, $X_{16}$, and $X_{20}$ are I. In some embodiments, the 24-amino acid sequence comprises no more than two aromatic amino acids. In some embodiments, where $X_5$ is R, the peptide has no more than two R residues. In some embodiments, $X_1$, $X_7$, $X_8$, $X_{15}$, $X_{18}$ and $X_{19}$ are independently selected from D and E; $X_{10}$, $X_{13}$, $X_{16}$, and $X_{20}$ are I; $X_2$, $X_6$, $X_9$, $X_{11}$, $X_{12}$, $X_{17}$, $X_{21}$, $X_{22}$, and $X_{24}$ are hydrophobic amino acids; and two of positions $X_3$, $X_{14}$ and $X_{23}$ are citrulline and the third position is R or K. In some embodiments, $X_1$, $X_7$, $X_8$, $X_{15}$, $X_{18}$ and $X_{19}$ are independently selected from D and E; $X_{10}$, $X_{13}$, $X_{16}$, and $X_{20}$ are L; $X_2$, $X_6$, $X_{11}$, $X_{12}$, $X_{17}$, $X_{21}$, $X_{22}$, and $X_{24}$ are aliphatic amino acids; and two of positions $X_3$, $X_{14}$ and $X_{23}$ are citrulline and the third position is R or K. In some embodiments, $X_1$, $X_7$, $X_8$, $X_{15}$, $X_{18}$ and $X_{19}$ are independently selected from D and E; $X_{10}$, $X_{13}$, $X_{16}$, and $X_{20}$ are I; $X_2$, $X_6$, $X_9$, $X_{11}$, $X_{12}$, $X_{17}$, $X_{21}$, $X_{22}$, and $X_{24}$ are hydrophobic amino acids, e.g., aliphatic amino acids; positions $X_3$, and $X_{14}$ are citrulline, and position $X_{23}$ is R or K. In some embodiments, $X_1$, $X_7$, $X_8$, $X_{15}$, $X_{18}$ and $X_{19}$ are independently selected from D and E; $X_{10}$, $X_{13}$, $X_{16}$, and $X_{20}$ are L; $X_2$, $X_6$, $X_{11}$, $X_{12}$, $X_{17}$, $X_{21}$, $X_{22}$, and $X_{24}$ are aliphatic amino acids; positions $X_3$, and $X_{14}$ are citrulline, and position $X_{23}$ is R or K. In some embodiments, a peptide of the invention has glucose-lowering activity and/or treats or prevents one or more symptoms of Alzheimer's Disease or frontotemporal dementia. In some embodiments, a peptide of the invention can sensitize a subject to insulin.

In some embodiments, the invention provides an isolated peptide having cholesterol efflux activity that has little or no cytotoxicity and comprises the following 24-amino acid sequence:

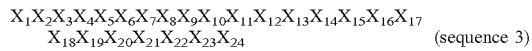  (sequence 3)

wherein $X_1$, $X_7$, $X_8$, $X_{15}$, $X_{18}$ and $X_{19}$ are amino acids independently selected from the group consisting of E and D; $X_2$, $X_6$, $X_{10}$, $X_{12}$, $X_{13}$, $X_{16}$, $X_{17}$, $X_{20}$, $X_{21}$ and $X_{24}$ are amino acids independently selected from the group consisting of A, V, L, or I; $X_9$ is selected from the group consisting of A, V, L, I and W; at least two of $X_3$, $X_{14}$ and $X_{23}$ are citrulline; $X_5$ is K or R, and $X_4$, $X_{11}$, and $X_{22}$ are amino acids independently selected from the group consisting of S, T, G, A and Y. In some embodiments, $X_3$ and $X_{14}$ are citrulline. In some embodiments, $X_3$ and $X_{14}$ are citrulline and $X_{23}$ is R or K. In some embodiments, $X_3$ and $X_{23}$ are citrulline and $X_{14}$ is R or K. In some embodiments, $X_{14}$ and $X_{23}$ are citrulline and $X_3$ is R or K. In some embodiments, e.g., in which $X_5$ is R, the peptide has no more than two R residues. In some embodiments, the 24-amino acid sequence comprises no more than two aromatic amino acids. In some embodiments, a peptide of the invention has glucose-lowering activity and/or treats or prevents one or more symptoms of Alzheimer's Disease or frontotemporal dementia.

In some embodiments, a peptide of the invention can sensitize a subject to insulin. For example, in some embodiments, $X_{10}$, $X_{13}$, $X_{16}$, and $X_{20}$ are the same aliphatic amino acid residue, e.g., I or L.

In some embodiments, the invention provides an isolated peptide having cholesterol efflux activity that has little or no cytotoxicity and comprises the following 24-amino acid sequence:

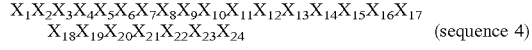  (sequence 4)

wherein $X_1$, $X_7$, $X_8$, $X_{15}$, $X_{18}$ and $X_{19}$ are D or E; $X_2$, $X_6$, $X_{10}$, $X_{12}$, $X_{13}$, $X_{16}$, $X_{17}$, $X_{20}$, $X_{21}$ and $X_{24}$ are amino acids independently selected from the group consisting of A, V, L, or I; at least two of $X_3$, $X_{14}$ and $X_{23}$ are citrulline; $X_9$ is W; $X_5$ is K, and $X_4$, $X_{11}$, and $X_{22}$ are independently selected from the group consisting of S and A. In some embodiments, $X_3$ and $X_{14}$ are citrulline. In some embodiments, $X_3$ and $X_{14}$ are citrulline and $X_{23}$ is R or K. In some embodiments, the 24-amino acid sequence comprises no more than two aromatic amino acids. In some embodiments, a peptide of the invention has glucose-lowering activity and/or treats or prevents one or more symptoms of Alzheimer's Disease or frontotemporal dementia.

In some embodiments, a peptide of the invention can sensitize a subject to insulin. For example, in some embodiments, $X_{10}$, $X_{13}$, $X_{16}$, and $X_{20}$ are the same aliphatic amino acid residue, e.g., I or L.

In some embodiments, the invention provides an isolated peptide having cholesterol efflux activity that has little or no cytotoxicity and comprises the following 24-amino acid sequence:

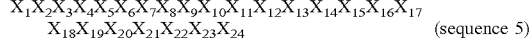  (sequence 5)

wherein $X_1$, $X_7$, $X_8$, $X_{15}$, $X_{18}$ and $X_{19}$ are E; $X_2$, $X_6$, $X_{10}$, $X_{12}$, $X_{13}$, $X_{16}$, $X_{17}$, $X_{20}$, $X_{21}$ and $X_{24}$ are amino acids independently selected from the group consisting of L and I; at least two of $X_3$, $X_{14}$ and $X_{23}$ are citrulline; $X_9$ is W; $X_5$ is K, $X_4$, is S; and $X_{11}$ and $X_{22}$ are A. In some embodiments, $X_3$ and $X_{14}$ are citrulline. In some embodiments, $X_3$ and $X_{14}$ are citrulline and $X_{23}$ is R or K. In some embodiments, a peptide of the invention has glucose-lowering activity and/or treats or prevents one or more symptoms of Alzheimer's Disease or frontotemporal dementia. In some embodiments, a peptide of the invention can sensitize a subject to insulin.

For example in some embodiments, $X_{10}$, $X_{13}$, $X_{16}$, and $X_{20}$ are the same aliphatic amino acid residue, e.g., I or L.

The invention further provides an isolated polypeptide having cholesterol efflux activity that has little or no cytotoxicity, where the peptide comprises an amino acid sequence that is an amphipathic α-helix having a non-polar surface and a polar surface, wherein the peptide has at least 60% identity, or at least 70%, at least 80%, or at least 90% identity to SEQ ID NO:1 or has at least 60% identity, or at least 70%, at least 80%, or at least 90% identity to SEQ ID NO:2, wherein the peptide comprises at least one chemical staple at position 3, 14, or 23. The positions described here are determined with reference to SEQ ID NO:1 or SEQ ID NO:2. Thus, for example, the peptide may comprise a residue at position 14 that forms a staple with a residue at position 21. Preferably, the peptide has acidic amino acid residues at positions 1, 7, 8, 15, 18, and 19. In some embodiments, a variant comprises a hydrophobic residue at positions 2, 6, 9, 10, 13, 16, 17, 20, 21, 22, and 24 as determined with reference to SEQ ID NO:1. In some embodiments, the variant comprises an aliphatic amino acid at at least one, or at least two, three, four, five, six, seven, eight, or nine of positions 2, 6, 10, 13, 16, 17, 20, 21, 22, and 24 as determined with reference to SEQ ID NO:1. In some embodiments a variant comprises an aliphatic residue at each of positions 2, 6, 10, 13, 16, 20, 21, and 24. In some embodiments, the aliphatic amino acid is L, V, or I. In some embodiments, the aliphatic amino acid residue at position 2, 6, 10, 13, 16, 20, and 21 is L. In some embodiments, the aliphatic amino acid residue at position 2, 6, 10, 13, 16, 20, and 21 is I. In some embodiments, the aliphatic residue at each of positions 10, 13, 16, and 20 is I. In some embodiments, the aliphatic residue at each of positions 10, 13, 16, and 20 is L. In some embodiments, the aliphatic amino acid residue at position 2 is V. In some embodiments, the aliphatic amino acid residue at position 2 is V and the aliphatic amino acid residue at position 10, 13, 16, and 20 is L. In some embodiments, the aliphatic amino acid at position 2 is V, the aliphatic amino acid at position 6, 21, and 24 is L, and the aliphatic amino acid residue at position 10, 13, 16, and 20 is I. In some embodiments, a variant comprises A at positions 11 and 12. In some embodiments, a peptide of the invention has glucose-lowering activity and/or treats or prevents one or more symptoms of Alzheimer's Disease or frontotemporal dementia. In some embodiments, a peptide of the invention can sensitize a subject to insulin. For example, in some embodiments, $X_{10}$, $X_{13}$, $X_{16}$, and $X_{20}$ are the same aliphatic amino acid residue, e.g., I or L.

As understood in the art, a variant peptide of any of the foregoing embodiments can comprise one or more non-naturally occurring amino acid residues. In some embodiments, at least one citrulline in any one of the foregoing embodiments is replaced with a citrulline amino acid analog. Thus, in some embodiments, one or more of positions $X_3$, $X_{14}$ and $X_{23}$ may be an analog of citrulline. In some embodiments, one or more hydrophobic amino acids is replaced with a non-naturally occurring analog amino acid that has long aliphatic carbon changes, e.g., long carbon ($C_{5-8}$) alkenyl or alkanyl side chains.

In one embodiment, the polypeptides of the present invention further comprise a protecting group. For instance, the polypeptides can be modified so that the R-groups on the constituent amino acids and/or the terminal amino acids are blocked, i.e., protected, by a protecting group. It has been found that blockage of the amino and/or carboxy termini, can greatly improve oral delivery and significantly increases serum half-life. Thus, in one embodiment, the polypeptides of the present invention further comprise a protecting group coupled to the amino or carboxy terminus. In one embodiment, the polypeptides further comprise a first protecting group coupled to the amino terminus and a second protecting group coupled to the carboxyl terminus.

Suitable protecting groups include, but are not limited to, acetyl (Ac), amide, 3 to 20 carbon alkyl groups, Fmoc, t-butoxycarbonyl (Tboc), 9-fluoreneacetyl group, 1-fluorenecarboxylic group, 9-fluorenecarboxylic group, 9-fluorenone-1-carboxylic group, benzyloxycarbonyl, xanthyl (Xan), trityl (Trt), 4-methyltrityl (Mtt), 4-methoxytrityl (Mmt), 4-methoxy-2,3,6-trimethyl-benzenesulphonyl (Mtr), mesitylene-2-sulphonyl (Mts), 4,4-dimethoxybenzhydryl (Mbh), tosyl (Tos), 2,2,5,7,8-pentamethyl chroman-6-sulphonyl (Pmc), 4-methylbenzyl (MeBzl), 4-methoxybenzyl (MeOBzl), benzyloxy (BzlO), benzyl (Bzl), benzoyl (Bz), 3-nitro-2-pyridinesulphenyl (Npys), 1-(4,4-dimethyl-2,6-dioxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), benzyloxymethyl (Bom), cyclohexyloxy (cHxO), t-butoxymethyl (Bum), t-butoxy (tBuO), t-butyl (tBu), and trifluoroacetyl (TFA).

In a preferred embodiment, the polypeptides comprise a first protecting group coupled to the amino terminus, the first protecting group including, but not limited to, acetyl, propionyl, and a 3 to 20 carbon alkyl. In a preferred embodiment, the first protecting group is an acetyl. In another preferred embodiment, the polypeptides comprise a second protecting group coupled to the carboxyl terminus, the second protecting being an amide.

The polypeptides of the present invention can comprise all "L" amino acids, all "D" amino acids or a mixture of "L" and "D" amino acids.

A polypeptide of the present invention has cholesterol efflux activity and/or has ABCA1 stabilizing activity. In yet another embodiment, a polypeptide of the present invention protects a phospholipids from oxidation by an oxidizing agent (i.e., the polypeptide has anti-oxidant activity). In still another embodiment, a polypeptide of the present invention has anti-inflammatory activity, including inhibition of adhesion molecules. In another embodiment, administration of a polypeptide of the invention lowers LDL and/or has favorable effects on glucose control, i.e., glucose-lowering effects. In some embodiments, a peptide of the invention treats or prevents symptoms of Alzheimer's disease or frontotemporal dementia. In some embodiments, a polypeptide of the present invention comprises each of these activities.

A further aspect of the invention provides pharmaceutical compositions comprising at least one peptide of the invention as described herein and a pharmaceutically acceptable carrier or excipient. In some embodiments, the pharmaceutical compositions comprise an additional therapeutic agent (e.g., a statin such as atorvastatin, lovastatin, pravastatin, simvastatin, fluvastatin, or rosuvastatin; a bile acid binder such as cholestyramine or colestipol; a Nieman-Pick C1-Like 1 sterol transporter channel inhibitor such as Ezetimibe; a platelet clumping inhibitor such as aspirin, ticlopidine, or clopidogrel, niacin/nicotinamide, a PPAR activator, Vitamin E, or combinations thereof, for treating a disease or disorder associated with cholesterol efflux (e.g., cardiovascular disease).

In another aspect, the invention provides peptidomimetics of the polypeptides disclosed herein, wherein the peptidomimetic is an analog peptide, e.g., a retro-inverso analog or retro-enantio analog; or surrogate peptide having a non-amide backbone. In yet another embodiment, the analog is a trans-olefin surrogate peptide or derivative. In some embodiments, a peptide of the invention can comprise other back-bone modifications. Such peptide analogs or surrogates can further comprise a protecting group as described herein and, preferably, a protecting group at both the amino and carboxyl termini.

In a further aspect, the present invention provides a composition comprising a polypeptide of the present invention as described herein, e.g., a polypeptide comprising SEQ ID NO:1 or SEQ ID NO:2, or variants thereof, or a peptidomimetic thereof complexed with a lipid. In one embodiment, the lipid is a phospholipid. In another embodiment, the phospholipids is 1-palmitoyl-2-oleoyl-sn-glycerol-3-phosphatidylcholine ("POPC"). In yet another embodiment, the composition further comprises a pharmaceutically acceptable carrier.

Yet another aspect of the invention provides methods of mediating cholesterol efflux in a mammalian subject (e.g., a primate such as a human or chimpanzee, or a rodent such as a rat or mouse) by administering at least one polypeptide or peptidomimetic described herein to the subject. Those of skill in the art will appreciate that a nucleic acid encoding such a polypeptide (or peptidomimetic) can be administered to the subject in lieu of administering the polypeptide (or peptidomimetic). The present invention provides such nucleic acids. Based on their cholesterol efflux activity, the polypeptides and peptidomimetics of the present invention can be advantageously used to treat, ameliorate or prevent a disease or condition associated with dyslipidemia, hypercholesterolemia, abnormal glucose metabolism, Alzheimer's Disease, frontotemporal dementia, and inflammation.

Still another aspect of the present invention provides methods for treating or preventing a symptom of atherosclerosis in a mammal by administering at least one polypeptide or peptidomimetic described herein to the subject. Again, those of skill in the art will appreciate that a nucleic acid encoding such a polypeptide (or peptidomimetic) can be administered to the subject in lieu of administering the polypeptide (or peptidomimetic). Such nucleic acids are provided by the present invention. In one embodiment of this method, the mammal is a mammal diagnosed as having one or more symptoms of atherosclerosis. In another embodiment, the mammal is diagnosed as at risk for atherosclerosis. Preferably, the mammal is a human, but can also be a non-human animal. In one embodiment, the polypeptide comprises an amino acid sequence of SEQ ID NO:1 or a variant thereof as described herein. In one embodiment, the polypeptide comprises SEQ ID NO:2, or a variant thereof as described herein.

In another related embodiment, the methods further comprise administering at least one additional therapeutic agent. Examples of such therapeutic agents include, but are not limited to, agents that treat abnormalities of glucose metabolism, e.g., anti-diabetic agents, agents that treat Alzheimer's disease and/or frontotemporal dementia, an antibody, an enzyme inhibitor, an antibacterial agent, an antiviral agent, a steroid, a non-steroidal anti-inflammatory agent, an antimetabolite, a cytokine, or a soluble cytokine receptor. The enzyme inhibitor may be a protease inhibitor or a cyclooxygenase inhibitor. The additional agent may be added as a part of a pharmaceutical composition, or may be administered concomitantly or within a time period when the physiological effect of the additional agent overlaps with the physiological effect of the polypeptide(s) or peptidomimetic(s) of the present invention. For example, more specifically, an additional agent may be administered concomitantly one week, several days, 24 hours, 8 hours, or immediately before the administration of the polypeptide(s) or peptidomimetic(s). Alternatively, an additional agent may, for example, be administered one week, several days, 24 hours, 8 hours, or immediately after the administration of the polypeptide(s) or peptidomimetic(s).

Yet another aspect of the present invention provides methods for stabilizing a vulnerable plaque, the method comprising administering to a mammal at least one polypeptide or peptidomimetic described herein. Again, those of skill in the art will appreciate that a nucleic acid encoding such a polypeptide can be administered to the subject in lieu of administering the polypeptide. Such nucleic acids are provided by the present invention. In one embodiment of this method, the mammal is a mammal diagnosed as having one or more vulnerable plaques. In another embodiment, the mammal is diagnosed as at risk for having a vulnerable plaque(s). Preferably, the mammal is a human, but can also be a non-human animal. In one embodiment, the polypeptide has an amino acid sequence of SEQ ID NO:1 or is a variant as described herein. In one embodiment, the polypeptide has an amino acid sequence of SEQ ID NO:2, or is a variant as described herein.

In another aspect, the present invention provides methods of lowering LDL, the method comprising administering to a mammal at least one polypeptide or peptidomimetic described herein. Again, those of skill in the art will appreciate that a nucleic acid encoding such a polypeptide can be administered to the subject in lieu of administering the polypeptide. Such nucleic acids are provided by the present invention. In one embodiment of this method, the mammal is a mammal diagnosed as having elevated LDL. In another embodiment, the mammal is diagnosed as at risk for having elevated LDL. Preferably, the mammal is a human, but can also be a non-human animal. In one embodiment, the polypeptide has an amino acid sequence of SEQ ID NO:1 or is a variant as described herein. In one embodiment, the polypeptide has an amino acid sequence of SEQ ID NO:2 or is variant as described herein.

In another aspect of the present invention provides methods of lowering glucose levels in a patient having abnormal glucose metabolism, e.g., in a patient having diabetes, e.g., Type II or Type I diabetes, or metabolic syndrome, or pre-diabetes, the method comprising administering to a mammal at least one polypeptide or peptidomimetic described herein. Again, those of skill in the art will appreciate that a nucleic acid encoding such a polypeptide can be administered to the subject in lieu of administering the polypeptide. Such nucleic acids are provided by the present invention. In one embodiment of this method, the mammal is a mammal diagnosed as having abnormal glucose metabolism. In another embodiment, the mammal is diagnosed as at risk for having abnormal glucose metabolism. Preferably, the mammal is a human, but can also be a non-human animal. In one embodiment, the polypeptide has an amino acid sequence of SEQ ID NO:1 or is a variant as described herein. In one embodiment, the polypeptide has an amino acid sequence of SEQ ID NO:2 or is a variant as described herein. In some embodiments, the polypeptide that is administered to lower glucose is a polypeptide as described herein, with the proviso that the polypeptide does not comprise the amino acid sequence of SEQ ID NO:2. In some embodiments, the polypeptide that is administered to lower glucose comprises SEQ ID NO:2.

In another aspect of the present invention provides methods of preventing or treating a symptom of frontotemporal dementia, Alzheimer's Disease or Mild Cognitive Impairment, the method comprising administering to a subject at least one polypeptide or peptidomimetic described herein. Again, those of skill in the art will appreciate that a nucleic acid encoding such a polypeptide can be administered to the subject in lieu of administering the polypeptide. Such nucleic acids are provided by the present invention. In one embodiment of this method, the subject is diagnosed as having Alzheimer's Disease. In another embodiment, the subject is diagnosed as having Mild Cognitive Impairment. In some embodiments, the subject has an ApoE4 allele. In one embodiment, the polypeptide has an amino acid sequence of SEQ ID NO:1 or is a variant as described herein. In one embodiment, the polypeptide has an amino acid sequence of SEQ ID NO:2 or is a variant as described herein.

The present invention also provides kits for treating or preventing a disease or condition associated with dyslipidemia, hypercholesterolemia, abnormal glucose metabolism, inflammation, and/or Alzheimer's Disease or frontotemporal dementia. In one embodiment, the present invention provides kits for treating or preventing a symptom of atherosclerosis, the kit comprising a container containing a polypeptide or peptidomimetic of the present invention. In one embodiment, the present invention provides kits for treating or preventing a disease associated with abnormal glucose metabolism, e.g., diabetes or metabolic syndrome, the kit comprising a container containing a polypeptide or peptidomimetic of the present invention. In one embodiment, the present invention provides kits for treating or preventing a symptom of Alzheimer's Disease, the kit comprising a container containing a polypeptide or peptidomimetic of the present invention. The kit can further comprise a pharmaceutically acceptable carrier. In addition, the kit can further comprise instructional materials teaching the use of the polypeptide or peptidomimetic for treating or preventing the disease or condition. The polypeptides and peptidomimetics provided in the kits of the present invention can comprise all L amino acids, all D amino acids or a mixture of L and D amino acids in either natural sequence or (retro)inverted sequence.

In connection with the above kits, instructional material can include a document or recorded media including a written or audible instruction for the use of a pharmaceutical composition. Instruction material includes, for example, a label on a bottle, a paper inserted in a box, printing on the box or carton, instructions provided by a website at an address given in any of these locations, etc.

In yet another aspect, the present invention provides use of at least one polypeptide or peptidomimetic of the present invention in the preparation of a medicament for mediating cholesterol efflux in a mammal, e.g., a human. In one embodiment, the polypeptide has an amino acid sequence of SEQ ID NO:1 or is a variant as described herein. In one embodiment, the polypeptide has an amino acid sequence of SEQ ID NO:2 or is a variant as described herein.

In a further aspect, the present invention provides use of at least one polypeptide or peptidomimetic of the present invention in the preparation of a medicament for treating a symptom of atherosclerosis in a mammal, e.g., a human. In one embodiments, the polypeptide has an amino acid of SEQ ID NO:1 or a variant as described herein. In one embodiment, the polypeptide has an amino acid sequence of SEQ ID NO:2 or is a variant as described herein.

In yet a further aspect, the present invention provides use of at least one polypeptide or peptidomimetic of the present invention in the preparation of a medicament for stabilizing a vulnerable plaque in a mammal, e.g., a human. In one embodiment, the polypeptide has an amino acid of SEQ ID NO:1 or a variant as described herein. In one embodiment, the polypeptide has an amino acid sequence of SEQ ID NO:2 or is a variant as described herein.

In yet a further aspect, the present invention provides use of at least one polypeptide or peptidomimetic of the present invention in the preparation of a medicament for treating dyslipidemia or hypercholesterolemia in a patient. In one embodiment, the polypeptide has an amino acid of SEQ ID NO:1 or is a variant as described herein. In one embodiment, the polypeptide has an amino acid sequence of SEQ ID NO:2 or is a variant as described herein.

In yet a further aspect, the present invention provides use of at least one polypeptide or peptidomimetic of the present invention in the preparation of a medicament for decreasing blood glucose levels in a mammal, e.g., a human. In one embodiment, the polypeptide has an amino acid of SEQ ID NO:1 or is a variant as described herein. In one embodiment, the polypeptide has an amino acid sequence of SEQ ID NO:2 or is a variant as described herein.

In yet a further aspect, the present invention provides use of at least one polypeptide or peptidomimetic of the present invention in the preparation of a medicament for preventing or treating a symptom of frontotemporal dementia, Alzheimer's Disease or Mild Cognitive Impairment in a human. In one embodiment, the polypeptide has an amino acid of SEQ ID NO:1 or is a variant as described herein. In one embodiment, the polypeptide has an amino acid sequence of SEQ ID NO:2 or is a variant as described herein.

Another aspect of the invention provides an isolated nucleic acid encoding a polypeptide of the present invention, an expression vector comprising the nucleic acid, and a host cell comprising the expression vector.

A polypeptide and peptidomimetic of the invention is also useful as a research tool and/or diagnostic tool. For example, such a peptide can be used to identify subjects having reverse cholesterol deficient plasma and those subjects that are responders to reverse cholesterol treatment. Also, a polypeptide of the invention can be used to evaluate the anti-atherosclerotic potential of other compounds (including, e.g., peptidomimetics).

In addition, a polypeptide or peptidomimetic of the invention can be used for investigating lipoprotein-receptor interactions in animals and animal models, particularly when a polypeptide or peptidomimetic of the present invention is labeled (e.g., radioactive label, fluorescent label, etc.).

A polypeptide or peptidomimetic of the invention can also be used to identify appropriate animal models for elucidation of lipid metabolic pathways. For example, a polypeptide or peptidomimetic can be used to identify animal models and gene and/or drug interactions that have an effect on reverse cholesterol transport.

Other features, objects and advantages of the invention and its preferred embodiments will become apparent from a reading of the detailed description, examples, claims and figures that follow.

BRIEF DESCRIPTION OF THE DRAWINGS

FIG. 10—Panels A-C: Hydrophobicity can be modulated to reduce the residual toxicity of ATI-5261 analogs. Peptides=SEQ ID NOS:15-18.

FIG. 11—Panels A-C: Further evidence that hydrophobicity can be modulated to reduce the residual toxicity of ATI-5261 analogs. Peptides=SEQ ID NOS:19-22.

FIG. 12—Panels A-C: Additional substitutions of less hydrophobic amino acids for tryptophan can be used to reduce toxicity of ATI-5261. Peptides=SEQ ID NOS:23 and 24.

FIG. 14—Panels A-C: The R14L substitution can be used in other ATI-5261 analogs to create safe and effective HDL mimetic peptides. Peptides=SEQ ID NOS:30-33.

FIG. 15—Citrulline substitutions for arginine can be used to create safe and effective HDL mimetic peptides. Peptides=SEQ ID NOS:34-40.

FIG. 17—Panels A and B: Citrulline analogs of ATI-5261 are compatible with other amino acid substitutions in generating safe and efficacious peptides. Peptides=SEQ ID NOS:41-43.

FIG. 20—The presence of negatively charged residues along the polar surface of amphipathic α-helix plays a major role tempering the toxic properties of HDL mimetic peptides. Peptides=SEQ ID NOS:53-62.

FIG. 22—Panels A-C: Small 24-mer forms of Leu-ATI5261 and its citrulline analog are safe and effective in mediating ABCA mediated cholesterol efflux. Peptides=SEQ ID NOS:63 and 64.

FIG. 23—Panels A-C: Hydrophobic leucine can be used to replace citrulline at the lipid-water interface of an amphipathic α-helix to create safe and effective HDL mimetic peptides. Peptides=SEQ ID NOS:65 and 66.

FIG. 24—The citrulline form of LeuATI-5261 supports other amino acid substitutions to create safe and effective peptides. Peptides=SEQ ID NOS:67, 68, 65, and 69-78.

FIG. 26—Isoleucine can be used to replace phenylalanine in ATI-5261 to create safe and effective cholesterol efflux peptides. Peptides=SEQ ID NOS:79-87.

FIG. 36—Panels A-C: Plasma half-life of CS6253 in rats. CS6253 was designed with a S26→Y substitution to facilitate labeling with $^{125}$I (sequence at the top of the figure). Peptide=SEQ ID NO:82.

FIG. 47—The leucine form of CitATI-5261 supports various amino acid substitutions to create safe and effective peptides. Peptides=SEQ ID NOS:92-101.

FIG. 49—Analogs of CS6253 with increasing numbers of isoleucine residues are safe and effective. Peptides=SEQ ID NOS:102-111.

FIG. 52—Panels A-D: Plasma clearance of CS6253 and T6991-2 in rats. Peptide=SEQ ID NOS:1112.

DETAILED DESCRIPTION OF THE INVENTION

Definitions

Figure 1:
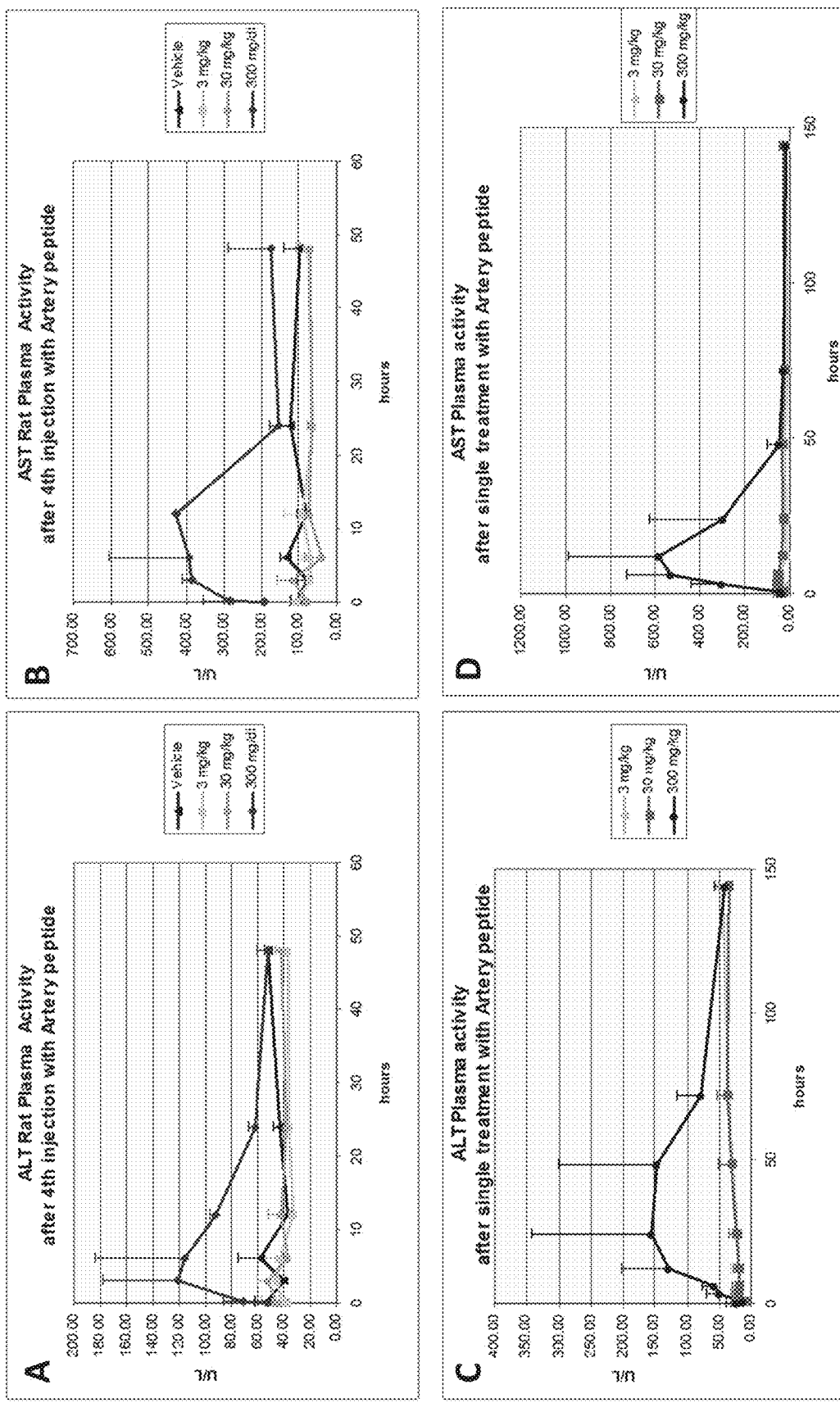
FIG. 1—Panels A-D: High dose administration of HDL mimetic peptide ATI-5261 induces a cytotoxic response in rats and rabbits.

The term "ABC" or "ATP Binding Cassette" refers to multidomain membrane proteins, responsible for the controlled efflux and influx of allocrites (e.g. cholesterol) across cellular membranes. ABC proteins comprise four domains, with two transmembrane domains (TMDs) responsible for allocrite binding and transport and two nucleotide-binding domains (NBDs) responsible for coupling the energy of ATP hydrolysis to conformational changes in the TMDs. The family members include, e.g., ABCA1 and ABCA7 (see, e.g., Dean et al., *J Lipid Res.*, 42:1007-1017 (2001)). ABCA1 is characterized in Denis et al., *J Biol Chem.*, 279(40):41529-36 (2004). ABCA1 plays a role in cholesterol efflux and is upregulated in cells that are exposed to cholesterol enriching conditions and is the defective molecule in Tangiers Disease (Brooks-Wilson et al., *Nat. Gen.*, 22:336-344 (1999); Bodzioch et al., *Nat. Gen.*, 22:347-351 (1999); Rust et al., *Nat. Gen.*, 22:352-355 (1999)). ABCA1 turns over rapidly and has a half life of about 1 hour in the absence of a suitable stabilizer, such as an apolipoprotein (see, e.g., Wang et al., *J. Clin. Invest.*, 111:99-107 (2003)) ABCA1 sequences are set forth in Genbank Accession Nos.: AJ012376; NM_173076; NM_015657; NM_005502; NP_005493; 095477. ABCA family members are reviewed in Broccardo et al., *Biochimica et Biophysica Acta*, 1461: 395-404 (1999).

The term "amphipathic alpha helix" or "amphipathic α helix" refers to a polypeptide sequence that can adopt a secondary structure that is helical with one surface, i.e., face, being polar and comprised primarily of hydrophilic amino acids (e.g., Asp, Glu, Lys, Arg, His, Gly, Ser, Thr, Cys, Tyr, Asn and Gln), and the other surface being a nonpolar face that comprises primarily hydrophobic amino acids (e.g., Leu, Ala, Val, Ile, Pro, Phe, Trp and Met) (see, e.g., Kaiser and Kezdy, *Ann. Rev. Biophys. Biophys. Chem.*, 16:561 (1987), and *Science*, 223:249 (1984)).

The polar face of an amphipathic α helix can, in some instances, display an "alignment of negatively charged amino acids" or "an alignment of acidic amino acids," i.e., a series of negatively charged or acidic amino acids (e.g., Asp and/or Glu) positioned approximately evenly (e.g., at about every one, two or three helical turns) within the polypeptide secondary structure. Amphipathic α helices play a role in both intra- and inter-molecular protein-protein interactions, and proteins and lipoproteins (e.g., including apolipoproteins) comprising amphipathic α helices have been postulated to play a role in lipid (e.g., HDL) transport and metabolism (see, e.g., Anantharamaiah et al., *Adv. Exp. Med. Biol.*, 285:131-40 (1991)). The structure and function of amphipathic α helices has been reviewed in, e.g., Segrest et al., *Proteins*, 8(2):103-17 (1990). In silico methods of identifying amphipathic α helices have been described by, e.g., Jones et al., *J. Lipid Res.*, 33(2):141-66 (1992). Multiple proteins comprising amphipathic α helices have been identified including, e.g., apolipoproteins and serum amyloid proteins.

The terms "cholesterol efflux" and "cholesterol efflux activity" refer to efflux of cholesterol from any cell type. For example, macrophage foam-cells in the artery wall release (i.e., export) cholesterol to appropriate acceptors, such as apolipoproteins and/or HDL. A compound that mediates cholesterol efflux enhances the release, i.e., movement, of cholesterol out of the cell and into the extracellular medium or compartment. Cholesterol efflux is often accompanied by or preceded by, i.e., follows, the efflux of phospholipids from cells. The coordinated release of both cholesterol and phospholipids produces HDL in the presence of a suitable lipid acceptor, e.g., apolipoprotein or peptide. Therefore, the processes of cholesterol- and phospholipid-efflux are linked and synonymous with one another. A compound that enhances the release of cholesterol from cells increases the amount of cholesterol and/or phospholipids appearing outside the cell by at least 25%, 50%, 75%, 100% or by at least 2-fold, 4-fold, 8-fold, 10-fold or more compared to the level of cholesterol efflux in the absence of the compound.

The term "ABCA stabilization activity" or "ABCA1 stabilization" refers to enhancing and/or extending the half life of an ABCA protein by preventing its degradation. A compound that has ABCA1 stabilization activity will significantly delay the proteins degradation. This will produce an increase in cellular ABCA1 protein levels of at least 25%, 50%, 75%, 100% or at least 2-fold, 4-fold, 8-fold, 10-fold or higher compared to ABCA1 protein detected in the absence of the compound.

The term "anti-inflammatory activity" refers to prevention or reduction of inflammation. Inflammation will be recognized as playing a role in atherosclerosis development and associated with dyslipidemia, hypercholesterolemia and/or lipoprotein lipid oxidation as well as other diseases. The inflammatory response can be local, such as in the artery wall or brain or other extra-vascular tissues, and/or systemic. A peptide that has anti-inflammatory activity will decrease an inflammatory response as measured by a decrease in inflammatory mediators (e.g., adhesion molecules, cytokines and/or oxidized lipids) and/or a decrease in macrophages and/or macrophage activation in plaques and tissues, compared to in the absence of the peptide.

The term "antioxidant activity" refers to prevention or reduction of oxidation caused by reactive oxygen species (ROS) including, e.g., hydrogen peroxide ($H_2O_2$); hypochlorite ion (—OCl); hydroxyl radical (—OH); and the superoxide anion ($O_2$—). Many naturally occurring substances possess antioxidant activity. For example, apolipoproteins can inhibit lipid peroxidation, thus protecting phospholipid surfaces from lipophilic, as well as, water soluble free radical initiators (see, e.g., *Biochemistry*, 41:2089-2096 (2002)). In the context of this invention, a peptide with an antioxidant activity has an antioxidant activity that is at least 25%, 50%, 75%, 100% or at least 2-fold, 4-fold, 8-fold, 10-fold or more higher than the antioxidant activity in the absence of the peptide.

"Plaque stabilization," as used herein, refers to the stabilization of vulnerable plaques from risk of rupture or erosion by removing cholesterol from lipid rich plaques, including but not limited to, removal of cholesterol from foam cell macrophages. Plaques contain thrombogenic substances, i.e., substances that when exposed to plasma are very powerful in aggregating platelets with the risk of local thrombosis and vessel occlusion, such as tissue factor. The rupture of the plaque and exposure of such material is prevented by the fibrous cap separating the plaque from the vessel. Lipid removal confers plaque stability.

"Reverse Cholesterol Transport (RCT)," as used herein, refers to the process of removing cholesterol from macrophage foam cells and the lipid rich plaque from the arterial wall, with subsequent transfer through plasma to the liver for uptake, processing and excretion as neutral sterols (cholesterol) or acidic sterols (hydroxylated cholesterol/bile) in feces. The efflux of cholesterol from macrophage foam cells is a requirement for RCT benefit in itself even though the cholesterol may be shifted to other less vulnerable adjacent cells. However, the further disposal of such cholesterol by transport in HDL-like particles to the liver for excretion is a favorable aspect of treatment. Such complete RCT provide a general rejuvenation of the arterial tree by actual net removal of the cholesterol content in the arteries. The RCT and plaque stabilizing effects are either conferred directly by the peptides, or the complexes that they naturally form with phospholipids in plasma and cells or, alternatively, apoA-I/HDL as the peptides bind to endogenous HDL particles, thereby changing their properties and making them more efficient to promote RCT.

A disease or disorder associated with "dyslipidemia" is any disease or disorder in which lipid metabolism is disregulated, due to alterations in tissue (i.e., blood) lipids and lipoprotein concentrations and/or aberrant mediation of cholesterol efflux or aberrant ABCA stabilization. Such diseases include, for example, heart disease, atherosclerotic lesions, stroke, Alzheimer's, and storage disorders.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. The amino acids may be neutral, positive or negative depending on the substituents in the side chain. "Neutral amino acid" means an amino acid containing uncharged side chain substituents. Examples of neutral amino acids include alanine, valine, leucine, isoleucine, proline, phenylalanine, tryptophan, methionine, glycine, serine, threonine and cysteine. "Positive amino acid" means an amino acid in which the side chain substituents are positively charged at physiological pH. Examples of positive amino acids include lysine, arginine and histidine. "Negative amino acid" means an amino acid in which the side chain substituents bear a net negative charge at physiological pH. Examples of negative amino acids include aspartic acid and glutamic acid. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified polypeptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Amino acid is also meant to include-amino acids having L or D stereochemistry at the α-carbon. A more detailed description of amino acid as well as conservative amino acid substitutions is provided below in the section entitled "Polypeptides."

A "non-natural amino acid" is included in the definition of an amino acid and refers to an amino acid that is not one of the 20 common naturally occurring amino acids or the rare naturally occurring amino acids e.g., selenocysteine or pyrrolysine. Other terms that may be used synonymously with the term "non-natural amino acid" is "non-naturally encoded amino acid," "unnatural amino acid," "non-naturally-occurring amino acid," and variously hyphenated and non-hyphenated versions thereof. The term "non-natural amino acid" includes, but is not limited to, amino acids which occur naturally by modification of a naturally encoded amino acid (including but not limited to, the 20 common amino acids or pyrrolysine and selenocysteine) but are not themselves incorporated into a growing polypeptide chain by the translation complex. Examples of naturally-occurring amino acids that are not naturally-encoded include, but are not limited to, N-acetylglucosaminyl-L-serine, N-acetylglucosaminyl-L-threonine, and O-phosphotyrosine. Additionally, the term "non-natural amino acid" includes, but is not limited to, amino acids which do not occur naturally and may be obtained synthetically or may be obtained by modification of non-natural amino acids.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl," "alkynyl," and the like. Furthermore, as used herein, the terms "alkyl," "alkenyl," "alkynyl," and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. Amino acid polymers may comprise entirely L-amino acids, entirely D-amino acids, or a mixture of L and D amino acids. The use of the term "peptide or peptidomimetic" in the current application merely emphasizes that peptides comprising naturally occurring amino acids as well as modified amino acids are contemplated.

"Stapling" or "hydrocarbon-stapling" as used herein introduces into a peptide at least two moieties capable of undergoing reaction to promote carbon-carbon bond formation that can be contacted with a reagent to generate at least one cross-linker between the at least two moieties. Stapling provides a constraint on a secondary structure, such as an alpha helix structure. The length and geometry of the cross-linker can be optimized to improve the yield of the desired secondary structure content. The constraint provided can, for example, prevent the secondary structure to unfold and/or can reinforce the shape of the secondary structure. A secondary structure that is prevented from unfolding is, for example, more stable.

A "stapled" peptide is a peptide comprising a selected number of standard or non-standard amino acids, further comprising at least two moieties capable of undergoing reaction to promote carbon-carbon bond formation, that has been contacted with a reagent to generate at least one cross-linker between the at least two moieties, which modulates, for example, peptide stability.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The terms "identical" or percent "identity," in the context of two or more polypeptide sequences (or two or more nucleic acids), refer to two or more sequences or subsequences that are the same or have a specified percentage of amino acid residues or nucleotides that are the same e.g., 60% identity, preferably 65%, 70%, 75%, 80%, 85%, 90%, 1%, 92%, 93%, 94%, 95%, 96%, 97%, 98%, 99% or 100% identity over a specified region (such as the 24 amino acids of SEQ ID NO:1 or the 24 amino acids of SEQ ID NO:2), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters are used.

The terms "numbered with reference to", or "corresponding to", or "determined with reference to" when used in the context of the numbering of a given amino acid, refers to the numbering of the residues of a specified reference sequence when the given amino acid sequence is compared to the reference sequence. Thus, a residue in a polypeptide "corresponds to" an amino acid at a position in SEQ ID NO:1 when the residue aligns with the amino acid in an alignment of SEQ ID NO:1 to the variant protein. The polypeptide that is aligned to the reference sequence need not be the same length as the reference sequence.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, polypeptide-nucleic acids (PNAs). Unless otherwise indicated, a particular nucleic acid sequence also encompasses "conservatively modified variants" thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., *J. Biol. Chem.*, 260:2605-2608 (1985); Rossolini et al., *Mol. Cell. Probes*, 8:91-98 (1994)). The term nucleic acid is used interchangeably with gene, cDNA, mRNA, oligonucleotide, and polynucleotide.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa and the like, e.g., cultured cells, explants, and cells in vivo.

A "label" or "detectable label" is a composition detectable by spectroscopic, photochemical, biochemical, immunochemical, or chemical means. For example, useful labels include radioisotopes (e.g., $^3$H, $^{35}$S, $^{32}$P, $^{51}$Cr, or $^{125}$I), fluorescent dyes, electron-dense reagents, enzymes (e.g., alkaline phosphatase, horseradish peroxidase, or others commonly used in an ELISA), biotin, digoxigenin, or haptens and proteins for which antisera or monoclonal antibodies are available (e.g., the polypeptide encoded by SEQ ID NOS: 1, 2, or 3 can be made detectable, e.g., by incorporating a radiolabel into the polypeptide, and used to detect antibodies specifically reactive with the polypeptide).

As used herein, "ameliorates" means alleviate, lessen, or decrease the extent of a symptom or decrease the number of occurrences of episodes of a disease manifestation.

The term "preventing" is art-recognized, and when used in relation to a condition, such as recurrence or onset of a disease such as hypercholesterolemia or atherosclerosis, is well understood in the art, and includes administration of a composition which reduces the frequency of, or delays the onset of, symptoms of a medical condition in a subject relative to a subject which does not receive the composition.

As used herein, "treating" means either slowing, stopping or reversing the progression of the disorder or disease. In a preferred embodiment, "treating" means reversing the progression to the point of eliminating the disorder or disease.

As used herein, "inhibits" means that the amount is reduced as compared with the amount that would occur in a control sample. In a preferred embodiment, inhibits means that the amount is reduced by at least 50% or more, or even more preferably by more than 75% or even 100%.

A "subject," "patient" or "mammal" to be treated by the methods disclosed herein can mean either a human or non-human animal.

Polypeptides

The present invention provides a family of non-naturally occurring polypeptides that use the potent Reverse Cholesterol Transport (RCT) pathway to mediate cholesterol efflux. The polypeptides of the present invention typically comprise a peptide having the amino acid sequence of SEQ ID NO:1 or non-naturally occurring peptide variants of SEQ ID NO:1; or comprise a peptide having the amino acid sequence of SEQ ID NO:2 or non-naturally occurring variants of SEQ ID NO:2. Amino acid positions of variants of SEQ ID NO:1 are determined with reference to SEQ ID NO:1. Similarly, amino acid positions of variants of SEQ ID NO:2 are determined with reference to SEQ ID NO:2. The peptides of the invention stimulate ABCA1-dependent cholesterol efflux with a molar potency similar to that of apolipoproteins (e.g., Apo A-I, Apo E, etc.). In addition to being potent and selective mediators of ABCA1-dependent cholesterol efflux, the polypeptides have little or no toxicity when administered at high doses. The polypeptides of the present invention also have ABCA stabilization activity, LDL-lowering activity, anti-oxidant activity as well as anti-inflammatory activity, can improve glucose metabolism, can treat symptoms of Alzheimer's Disease or have any combination of these activities and, preferably, all of these activities.

As used herein, the term "little or no toxicity" is used interchangeably with "little or no cytotoxicity" to refer to a level of cytotoxicity for a peptide of the invention administered at a high pharmacological that typically is essentially equivalent to that obtained using a control only, i.e., a vehicle such as PBS that does not contain the peptide. Toxicity can be measured in an in vitro or in vivo assay. For example, in a rat, mouse, or rabbit model in which a peptide is administered IP at a dose of 300 mg/kg a response 50% or more above PBS, and in some embodiments, 40%, 30%, or 20% above PBS is considered toxic.

As used herein, a "high pharmacological dose" refers to an amount that is above the therapeutic dose, e.g., at least two-fold to 10-fold higher. For example, using a rat, rabbit, or mouse model, a high pharmacological dose may range from 30 mg/kg to 300 mg/kg, or up to 500 mg/kg. In some embodiments, a high therapeutic dose in a rat, mouse or rabbit model to evaluate toxicity is 300 mg/kg.

Regarding amphipathic α-helix peptides, hydrophobic amino acids are concentrated on one side of the helix, usually with polar or hydrophilic amino acids on the other. This arrangement is common in alpha helices of apolipoproteins and globular proteins, where one face of the helix is oriented toward the hydrophobic core and one face is oriented toward the water-exposed surface. Different amino-acid sequences have different propensities for forming α-helical structure. Methionine, alanine, leucine, glutamate, and lysine all have especially high helix-forming propensities, whereas proline, glycine, tyrosine, and serine have relatively poor helix-forming propensities. Proline tends to break or kink helices because it cannot donate an amide hydrogen bond (having no amide hydrogen), and because its side chain interferes sterically. Its ring structure also restricts its backbone dihedral angle to the vicinity of −70°, which is less common in α-helices. One of skill understands that although proline may be present at certain positions in the sequences described herein, the presence of more than three prolines within the sequence would be expected to disrupt the helical structure. Accordingly, the polypeptides of the invention do not have more than three prolines, and commonly do not have more than two prolines present at positions in the alpha-helix forming sequence. Typically, when a proline is present in the sequence of a core helical structure of a peptide of the invention, e.g., a peptide variant of SEQ ID NO:1, it is present in only one position of the core helix sequence.

A polypeptide of the present invention having cholesterol efflux activity comprises an amino acid sequence that is an amphipathic α-helix having a non-polar surface and a polar surface where the polar surface comprises charged and uncharged amino acid residues at the lipid-water interface. In some embodiments, a peptide of the invention comprises an amino acid sequence of SEQ ID NO:1 or SEQ ID NO:2, or variants thereof, wherein the variants comprises an amino acid sequence having at least 50%, typically at least 55%, at least 60%, at least 65%, at least 70%, at least 80%, at least 85%, at least 90%, or at least 95%, or greater identity to SEQ ID NO:1 or SEQ ID NO:2. In typical embodiments, a variant has an uncharged residue at at least one of positions 3, 14, or 23 as numbered with reference to SEQ ID NO:1. In one embodiment, a peptide of the invention comprises the amino acid sequence of SEQ ID NO:1 or SEQ ID NO:2.

In some embodiments, the peptide has a citrulline, or analog of citrulline, that is present at the lipid-water interface, for example at 3, 14, or 23 as numbered with reference to SEQ ID NO:1. In some embodiments, a variant has a citrulline at position 3 and 14, position 3 and 23, or position 14 and 23.

Variants of SEQ ID NO:1 or SEQ ID NO:2 typically have only a limited number of R amino acid residues, typically no more than two R residues. For example, in some embodiments, a variant may have an R at position 5 and an R at position 23. In some embodiments, a variant may have a citrulline at position 3 and 14 and an R at position 23; or a citrulline at positions 3 and 23 and an R at position 14; or a citrulline at positions 14 and 23 and an R as position 3. In some embodiments, an R at an indicated position may be substituted with a K residue. Thus, in some embodiments, a variant may have a K at position 5 and an R at position 23, or an R at position 5 and a K at position 23, or a K at both positions 5 and 23. In some embodiments, a variant may have a citrulline at position 3 and 14 and a K at position 23; or a citrulline at positions 3 and 23 and a K at position 14; or a citrulline at positions 14 and 23 and a K at position 3.

In some embodiments, a variant comprises a hydrophobic amino acid, typically an aliphatic amino acid, at at least one, or at least two, three, four, five, six, seven, eight, nine, or ten of positions 2, 6, 9, 10, 13, 16, 17, 20, 21, 22, and 24 as determined with reference to SEQ ID NO:1. In some embodiments, a variant of SEQ ID NO:1 or SEQ ID NO:2 comprises no more than three or no more than two, or no more than one aromatic amino acids. In some embodiments a variant comprises an aliphatic residue at each of positions 2, 6, 10, 13, 16, 20, 21, and 24. In some embodiments, the aliphatic amino acid is L, V, A, or I. In some embodiments, a peptide of the invention comprises the same aliphatic amino acid at each of positions 10, 13, 16, and 20. In some embodiments, the same aliphatic amino acid at each of positions 10, 13, 16, and 20 is a branched chain aliphatic amino acid. In some embodiments, the same aliphatic amino acid at each of positions 10, 13, 16, and 20 is selected from the group consisting of L, I, or V. In some embodiments, the amino acid residue at position 10, 13, 16, and 20 is I. In some embodiments, the amino acid residue at position 10, 13, 16, and 20 is L. In some embodiments, the aliphatic amino acid residue at position 2 is V or L. In some embodiments, the aliphatic amino acid residue at position 2 is V and the aliphatic amino acid residue at position 10, 13, 16, and 20 is I or L. In some embodiments, the aliphatic amino acid at position 2 is V, the aliphatic amino acid at position 6, 21, and 24 is L, and the aliphatic amino acid residue at position 10, 13, 16, and 20 is I or L. In some embodiments, a variant comprises A at positions 11 and 12.

In some embodiments, a peptide of the invention further comprises amino acids at positions 25 and 26, as numbered with reference to SEQ ID NO:1. In typical embodiments, the amino acid residue at position 25 is K or N and the amino acid residue at position 26 is S, Y, or P. In some embodiments, the amino acid at position 25 is K and the amino acid at position 26 is S. In some embodiments, the peptide comprises the amino acid sequence of SEQ ID NO:3 or SEQ ID NO:4.

It will be readily understood by those of skill in the art that the foregoing polypeptides are not fully inclusive of the family of polypeptides of the present invention. In fact, using the teachings provided herein, other suitable polypeptides (e.g., additional conservative variants) can be routinely produced by, for example, conservative or semi-conservative substitutions (e.g., D replaced by E), extensions, deletions and the like. In addition, using the assays provided herein, other suitable polypeptides can be routinely screened for desired biological activities.

Non-identical amino acid residues can be naturally or non-naturally occurring. The term "percent identical" refers to sequence identity between two amino acid sequences (or between two nucleotide sequences, which are also provided by the present invention). Identity can each be determined by comparing a position in each sequence that may be aligned for purposes of comparison. When an equivalent position in the compared sequences is occupied by the same amino acid or base, then the molecules are identical at that position; when the equivalent site is occupied by the same or a similar amino acid residue (e.g., similar in steric and/or electronic nature), then the molecules can be referred to as homologous (similar) at that position. Expression as a percentage of homology, i.e., similarity, or identity refers to a function of the number of similar or identical amino acids at positions shared by the compared sequences. Various alignment algorithms and/or programs can be used, including, for example, FASTA, BLAST and ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid mismatch between the two sequences.

In another exemplary embodiment, which can overlap with the embodiments described above, variants of SEQ ID NO:1 or SEQ ID NO:2 are substituted with conservative (or semi-conservative) amino acid residues. The term "conservative amino acid substitutions" refers to the substitution (conceptually or otherwise) of an amino acid from one such group with a different amino acid from the same group. A functional way to define common properties between individual amino acids is to analyze the normalized frequencies of amino acid changes between corresponding proteins of homologous organisms (see, e.g., Schulz, G. E. and R. H. Schirmer, Principles of Protein Structure, Springer-Verlag). According to such analyses, groups of amino acids may be defined where amino acids within a group exchange preferentially with each other and, therefore, resemble each other most in their impact on the overall protein structure (see, e.g., Schulz, G. E. and R. H. Schirmer, Principles of Protein Structure, Springer-Verlag). One example of a set of amino acid groups defined in this manner include: (i) a charged group, consisting of Glu and Asp, Lys, Arg and His; (ii) a positively-charged group, consisting of Lys, Arg and His; (iii) a negatively-charged group, consisting of Glu and Asp; (iv) an aromatic group, consisting of Phe, Tyr and Trp; (v) a nitrogen ring group, consisting of His and Trp; (vi) a large aliphatic nonpolar group, consisting of Val, Leu and Ile; (vii) a slightly-polar group, consisting of Met and Cys; (viii) a small-residue group, consisting of Ser, Thr, Asp, Asn, Gly, Ala, Glu, Gln and Pro; (ix) an aliphatic group consisting of Val, Leu, Ile, Met and Cys; and (x) a small hydroxyl group consisting of Ser and Thr. In the context of this invention, reference to the charge of an amino acid refers to the charge at physiological pH.

In another exemplary embodiment, which again can overlap with the embodiments described above, "a conservative amino acid substitution" can refer to the substitution of an amino acid for another that is similar in molecular weight or similar in hydrophobicity. By "similar molecular weight" and "similar hydrophobicity" is meant a value that is within 25%, more preferably 20%, 15%, 10%, or less than 10% of the respective value. Data for amino acid molecular weights and hydrophobicities are set forth in Table 1. A hydrophobicity ranking is set forth in Table 2; a conservative substitution includes exchanging an amino acid that is designated "=" to another (e.g., Tyr=Trp) and exchanging one amino acid for another that is adjacent to it in the ranking order as delineated by the greater and lesser than symbols.

TABLE 1

Parameters for the Unmodified Physiological L-alpha-Amino Acids

| Amino Acid | 3-Letter Code | 1-Letter Code | Molecular Weight[†] | Hydrophobicity[‡] |
|---|---|---|---|---|
| Alanine | Ala | A | 89.09 | 0.616 |
| Cysteine | Cys | C | 121.16 | 0.680 |
| Aspartate | Asp | D | 133.10 | 0.028 |
| Glutamate | Glu | E | 147.13 | 0.043 |
| Phenylalanine | Phe | F | 165.19 | 1.00 |

TABLE 1-continued

Parameters for the Unmodified Physiological L-alpha-Amino Acids

| Amino Acid | 3-Letter Code | 1-Letter Code | Molecular Weight[†] | Hydrophobicity[‡] |
|---|---|---|---|---|
| Glycine | Gly | G | 75.07 | 0.501 |
| Histidine | His | H | 155.16 | 0.165 |
| Isoleucine | Ile | I | 131.18 | 0.943 |
| Lysine | Lys | K | 146.19 | 0.283 |
| Leucine | Leu | L | 131.18 | 0.943 |
| Methionine | Met | M | 149.21 | 0.738 |
| Asparagine | Asn | N | 132.12 | 0.236 |
| Proline | Pro | P | 115.13 | 0.711 |
| Glutamine | Gln | Q | 146.15 | 0.251 |
| Arginine | Arg | R | 174.20 | 0.000 |
| Serine | Ser | S | 105.09 | 0.359 |
| Threonine | The | T | 119.12 | 0.450 |
| Valine | Val | V | 117.15 | 0.825 |
| Tryptophan | Trp | W | 204.23 | 0.878 |
| Tyrosine | Tyr | Y | 181.19 | 0.880 |

[†]The molecular weights given are those of the neutral, free amino acids; residue weights can be obtained by subtraction of one equivalent of water (18 g/mol).
[‡]The hydrophobicities given are the "Scaled" values from computational log(P) determinations by the "Small Fragment Approach" (see, *"Development of Hydrophobicity Parameters to Analyze Proteins Which Bear Post-or Cotranslational Modifications"* Black, S. D. and Mould, D. R., *Anal. Biochem.*, 193: 72-82 (1991)). The equation used to scale raw log(P) values to the scaled values given is as follows: Scaled Parameters = (Raw Parameters + 2.061)/4.484.

TABLE 2

Trend of Hydrophobicity Parameters for the Physiological L-alpha-Amino Acids

Phe > Leu = Ile > Tyr = Trp > Val > Met > Pro > Cys > Ala > Gly > Thr > Ser > Lys > Gln > Asn > His > Glu > Asp > Arg

Another indication that two polypeptides are conservative variants of one another is that the two polypeptides carry out the same function and, in preferred embodiments, the same function at the same or very similar level of activity. Thus, in one embodiment, a conservative variant of a polypeptide of this invention will comprise an activity of at least 80%, 85%, 86%, 87%, 88%, 89%, 90%, 91%, 92%, 93%, 94%, 95%, 96%, 97%, 98%, 99%, or 100% of that found in a polypeptide of SEQ ID NO:1 or SEQ ID NO:2; and will also not exhibit toxicity when administered at high doses. Again, in some embodiments, the polypeptides of this invention will possess more than one activity. For example, a polypeptide of the invention can comprise cholesterol efflux mediating activity, ABCA stabilization activity, LDL-lowering activity, anti-inflammatory activity as well as antioxidant activity, any combination of these activities or, ideally, all of these activities. Conservative variants can have one or more of the same activities and, ideally, all of the same activities. The screening assays described herein can be readily used by those of skill in the art to determine whether two or more polypeptides possess similar activities. In addition, those of skill in the art will know of other screening assays that can be used to determine whether two or more polypeptides possess similar biological properties or activities.

One of skill understands that amino acid residues may be added to either the C-terminus and/or N-terminus of the polypeptides of the present invention without effecting the activity of such polypeptides. Thus, a polypeptide of the invention that comprises an α-helical sequence as described herein (e.g., SEQ ID NO:1 or SEQ ID NO:2), includes embodiments that are over 24 amino acids in length, e.g., peptide that are 25, 26, 28, 30, 32, 35, or 40 amino acids in length. One of skill also understands that polypeptides of the invention may also be linked, e.g., via a proline or other linker residues, to another amphipathic α helical peptide that can stimulate cholesterol efflux to form a bi-helix or multimer polypeptide, e.g., of 50, 60, 70, 80, 90, or 100 amino acids in length. Accordingly, a sequence of any of a peptide as described herein can have amino acid additions or can be joined. For example, one molecule of a polypeptide of the invention, e.g., SEQ ID NO:1 or SEQ ID NO:2, or variants thereof as described herein, may be joined to another molecule of the polypeptide through a proline residue to provide a polypeptide that is 49 residues in length. Such a polypeptide can have cholesterol efflux activity that exceeds that of a native full-length apolipoproteins (e.g., Apo AI and Apo E), or that of the cholesterol efflux-mediating domain of the apolipoprotein. Using the methodologies described herein, one of skill can readily add additional amino acids to either the C-terminus and/or N-terminus, and then screen the resulting polypeptides for the desired activity.

In some embodiments, a peptide of the invention may be joined to another peptide that has a short half-life to provide a bi-peptide that has a longer half-life than the latter peptide when administered to a subject at a comparable molar dose. In some embodiments, a peptide of the invention may be joined to another physiologically active peptide to provide a dual function hybrid peptide. In some embodiments, a peptide of the invention may be joined to another physiologically active peptide from a cellular protein, or the physiologically active peptide may target a cellular protein, such as a receptor. For example in some embodiments, SEQ ID NO:1 or SEQ ID NO:2, or variants thereof as described herein, may be joined to A and B-naturetic peptides (ANP, BNP and variants thereof), which have short half-lifes; bivalidrudin (and other thrombin and Xa inhibitors); or glucose regulating peptides (GLP-1, glucagon and variants of them).

In yet another embodiment, peptidomimetics of the polypeptides of the present invention are provided. A "peptidomimetic" includes any modified form of an amino acid chain, including, but not limited to, phosphorylation, capping, fatty acid modifications and including unnatural backbone and/or side chain structures. It will be readily apparent to those of skill in the art that a peptidomimetic comprises the structural continuum between an amino acid chain and a non-peptide small molecule. Peptidomimetics generally retain a recognizable polypeptide-like polymer unit structure. Thus, a peptidomimetic typically retains the function of binding to any target molecule that a natural polypeptide binds to. Examples of suitable peptidomimetics are disclosed in U.S. Patent Application Publication No. 2006/0069030, the teachings of which are incorporated by reference for all purposes. Other peptidomimetics and methods of making same will be known to those of skill in the art.

Peptidomimetics of the present invention fall into one of two categories: (i) surrogates; and (ii) analogs. Numerous surrogates have been developed for the amide bond of polypeptides. Frequently exploited surrogates for the amide bond include, but are not limited to, the following groups: (i) trans-olefins, (ii) fluoroalkene, (iii) methyleneamino, (iv) phosphonamides, and (v) sulfonamides. Examples of such surrogates are disclosed in U.S. Patent Application Publication No. 2006/0069030. Additionally, peptidomimetics based on more substantial modifications of the backbone of a polypeptide can be used. Peptidomimetics that fall in this category include (i) retro-inverso analogs, and (ii) N-alkyl glycine analogs (so-called peptoids). Again, examples of such analogs are disclosed in U.S. Patent Application Publication No. 2006/0069030.

In one embodiment of the present invention, the peptide or peptidomimetic is a retro-inverso analog. Retro-inverso analogs can be made according to the methods known in the art, in a manner similar to synthesizing L-amino acid based polypeptides. More specifically, examples of methods suitable for preparing such retro-inverso analogs are described in U.S. Pat. No. 4,522,752, which issued to Sisto et al. The final product, or intermediates thereof, can be purified by HPLC or any other suitable chromatographic method known to those of skill in the art.

In another embodiment, the peptide or peptidomimetic is a retro-enantio analog. Retro-enantio analogs can be synthesized from commercially available D-amino acids (or analogs thereof) using standard solid- or solution-phase polypeptide-synthesis techniques.

In still another embodiment, the peptidomimetic is a trans-olefin surrogate peptide or derivative. Such trans-olefin peptides can be readily synthesized according to the method of Shue et al., *Tetrahedron Lett.*, 28:3225 (1987). In addition, other methods known in the art can also be used. It will be appreciated that variations in the procedure of Sjue et al., or other procedures available, may be necessary depending on the nature of the reagents used in synthesizing the trans-olefin derivative.

It is also possible to couple the pseudodipeptides synthesized by the above method to other pseudodipeptides, to make pseudodipeptides with several olefinic functionalities in place of amide functionalities. For example, pseudodipeptides corresponding to certain di-peptide sequences can be made and then coupled together by standard techniques to yield an analog of the polypeptide that has alternating olefinic bonds between residues.

Still another class of peptidomimetic derivatives includes phosphonate derivatives. The synthesis of such phosphonate derivatives can be adapted from known synthesis schemes (see, for example, Loots et al. in "Peptides: Chemistry and Biology," (Escom Science Publishers, Leiden, p. 118, 1988); Petrillo et al. in "Peptides: Structure and Function (Proceedings of the 9th American Peptide Symposium)," (Pierce Chemical Co. Rockland, 1985).

In other embodiments, a polypeptide of the invention can be modified. One example of a modification is the introduction of carbohydrate or lipid moieties. Such modifications can change the solubility of the polypeptides in various mediums so that they can advantageously be prepared as a suitable pharmaceutical composition. Modifying lipid groups include, but are not limited to, farnesyl groups and myristoyl groups. Modifying carbohydrate groups include, but are not limited to, single sugars or oligosaccharides of any naturally occurring and/or synthetic sugar and sugar alcohols including, for example, glucose, galactose, rhamnose, mannose, arabinose, and other sugars, and their respective alcohols.

In certain embodiments, a polypeptide of the invention may further comprise modifications analogous to post-translational modifications. Such modifications include, but are not limited to, acetylation, carboxylation, glycosylation, phosphorylation, lipidation, and acylation. As a result, the modified peptidomimetics may contain non-amino acid elements, such as polyethylene glycols, lipids, poly- or monosaccharide, and phosphates. Effects of such non-amino acid elements on the functionality of a peptidomimetic can be tested using the assay methods disclosed herein.

In particular embodiments, the peptidomimetics include at least one backbone linkage that is not an amide linkage in the amino to carboxy direction, such as a retro-inverso polypeptide relative to a naturally-occurring polypeptide, or at least one backbone linkage that is not an amide linkage.

As previously described, reference to an "amino acid" in the present context refers to both naturally occurring and unnaturally occurring amino acids. Accordingly, a peptide of present invention may comprise one or more amino acid analogs. Examples of amino acid analogs, include, but are not limited to, the following:

an alkyl, aryl, acyl, azido, cyano, halo, hydrazine, hydrazide, hydroxyl, alkenyl, alkynyl, ether, thiol, sulfonyl, sulfo, seleno, ester, thioacid, borate, boronate, phospho, phosphono, heterocyclic, enone, imine, aldehyde, alkoxyamine, hydroxylamine, keto, or amino substituted amino acid, or any combination thereof; a glycosylated or carbohydrate modified amino acid; a keto containing amino acid; a sugar substituted amino acid, e.g., a sugar substituted serine or the like; a carbon-linked sugar-containing amino acid; a sugar-substituted cysteine; a redox-active amino acid; an α-hydroxy containing acid; an amino thio acid containing amino acid; an α,α disubstituted amino acid; a β-amino acid; sulfotyrosine, 4-borono-phenylalanine, an aminooxy amino acid, an aminooxy lysine, an aminooxy ornithine, an aminooxy tyrosine, or a cyclic amino acid other than proline. Other unnatural amino acids include, but are not limited to, unnatural amino acids comprising any one or more of the following functional groups: an aldehyde moiety, a keto moiety, a beta-diketo moiety, an alkoxyamine moiety, an acyl hydrazide moiety, a dehydroalanine moiety, a thioester moiety, an ester moiety, a boronate moiety, an azide moiety, an acetylenic moiety, an olefinic moiety, a vicinal thiol amine moiety, and the like. Unnatural amino acids include, N-substituted glycines, N-methyl amino acids, phenylalanine analogs, and derivatives of lysine (Lys), ornithine (Orn) and α, γ-diaminobutyric acid (Dbu) in either the L- or D-configuration that function in a manner similar to the naturally-occurring amino acids.

Additional examples of unnatural amino acids include, but are not limited to, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodemosine, allo-isoleucine, N-methylalanine, N-methylglycine, N-methylisoleucine, N-methylpentylglycine, N-methylvaline, naphthalanine, norvaline, ornithine, pentylglycine, pipecolic acid, thioproline, aminophenylalanine, hydroxytyrosine, and aminotyrosine. In some other embodiments, an unnatural amino acid may be 1-aminocyclopentane-1-carboxylic acid (Acp), 1-aminocyclobutane-1-carboxylic acid (Acb), 1-aminocyclopropane-1-carboxylic acid (Acpc), homocitrulline (HoCit), α-aminohexanedioic acid (Aad), 3-(4-pyridyl)alanine (4-Pal), 3-(3-pyridyl)alanine (3-Pal), propargylglycine (Pra), α-aminoisobutyric acid (Aib), α-aminobutyric acid (Abu), norvaline (Nva), α,β-diaminopropionic acid (Dpr), α,γ-diaminobutyric acid (Dbu), α-tert-butylglycine (Bug), 3,5-dinitrotyrosine Tyr(3, 5-di $NO_2$), norleucine (Nle), 3-(2-naphthyl)alanine (Nal-2), 3-(1-naphthyl)alanine (Nal-1), cyclohexylalanine (Cha), di-n-propylglycine (Dpg), cyclopropylalanine (Cpa), homoleucine (Hle), homoserine (HoSer), homoarginine (Har), homocysteine (Hcy), methionine sulfoxide (Met(O)), methionine methylsulfonium (Met (S-Me)), α-cyclohexylglycine (Chg), 3-benzo-thienylalanine (Bta), taurine (Tau), hydroxyproline (Hyp), O-benzyl-hydroxyproline (Hyp(Bzl)), homoproline (HoPro), β-homoproline (βHoPro), thiazolidine-4-carboxylic acid (Thz), nipecotic acid (Nip), isonipecotic acid (IsoNip), 3-carboxymethyl-1-phenyl-1,3,8-triazaspiro[4,5]decan-4-one (Cptd), tetrahydro-isoquinoline-3-carboxylic acid (3-Tic), 5H-thiazolo [3,2-a]pyridine-3-carboxylic acid (Btd), 3-aminobenzoic acid (3-Abz), 3-(2-thienyl)alanine (2-Thi), 3-(3-thienyl)alanine (3-Thi), α-aminooctanedioic acid (Asu), diethylglycine (Deg), 4-amino-4-carboxy-1,1-dioxo-tetrahydrothiopyran (Acdt), 1-amino-1-(4-hydroxycyclohexyl) carboxylic acid (Ahch), 1-amino-1-(4-ketocyclohexyl)carboxylic acid (Akch), 4-amino-4-carboxytetrahydropyran (Actp), 3-nitrotyrosine (Tyr(3-$NO_2$)), 1-amino-1-cyclohexane carboxylic acid (Ach), 1-amino-1-(3-piperidinyl)carboxylic acid (3-Apc), 1-amino-1-(4-piperidinyl)carboxylic acid (4-Apc), 2-amino-3-(4-piperidinyl) propionic acid (4-App), 2-aminoindane-2-carboxylic acid (Aic), 2-amino-2-naphthylacetic acid (Ana), (2S, 5R)-5-phenylpyrrolidine-2-carboxylic acid (Ppca), 4-thiazoylalanine (Tha), 2-aminooctanoic acid (Aoa), 2-aminoheptanoic acid (Aha), ornithine (Orn), azetidine-2-carboxylic acid (Aca), α-amino-3-chloro-4,5-dihydro-5-isoxazoleacetic acid (Acdi), thiazolidine-2-carboxylic acid (Thz (2-COOH)), allylglycine (Agl), 4-cyano-2-aminobutyric acid (Cab), 2-pyridylalanine (2-Pal), 2-quinoylalanine (2-Qal), cyclobutylalanine (Cba), a phenylalanine analog, a lysine derivative, a ornithine (Orn) derivative, an α, γ-diaminobutyric acid Dbu derivative, stereoisomers thereof, and combinations thereof (see, Liu and Lam, *Anal. Biochem.*, 295:9-16 (2001)). As such, the unnatural α-amino acids are present either as unnatural L-α-amino acids, unnatural D-α-amino acids, or combinations thereof. Additional suitable amino acid analogs include, without limitation, β-amino acids and γ-amino acids. Suitable R groups for β- or γ-amino acids include, but are not limited to, side-chains present in naturally-occurring amino acids and unnatural amino acids. N-methyl amino acids include N-methyl-Ala, N-methyl-Cys, N-methyl-Asp, N-methyl-Glu, N-methyl-Phe, N-methyl-Gly, N-methyl-His, N-methyl-Ile, N-methyl-Arg, N-methyl-Lys, N-methyl-Leu, N-methyl-Met, N-methyl-Asn, N-methyl-Gln, N-methyl-Ser, N-methyl-Thr, N-methyl-Val, N-methyl-Trp, N-methyl-Tyr, N-methyl-Acp, N-methyl-Acb, N-methyl-Acpc, N-methyl-Cit, N-methyl-HoCit, N-methyl-Aad, N-methyl-4-Pal, N-methyl-3-Pal, N-methyl-Pra, N-methyl-Aib, N-methyl-Abu, N-methyl-Nva, N-methyl-Dpr, N-methyl-Dbu, N-methyl-Nle, N-methyl-Nal-2, N-methyl-Nal-1, N-methyl-Cha, N-methyl-Cpa, N-methyl-Hle, N-methyl-HoSer, N-methyl-Har, N-methyl-Hcy, N-methyl-Chg, N-methyl-Bta, N-methyl-2-Thi, N-methyl-3-Thi, N-methyl-Asu, N-methyl-Acdt, N-methyl-Ahch, N-methyl-Akch, N-methyl-Actp, N-methyl-Tyr(3-$NO_2$), N-methyl-Ach, N-methyl-3-Apc, N-methyl-4-Apc, N-methyl-4-App, N-methyl-Tha, N-methyl-Aoa, N-methyl-Aha, N-methyl-Orn, N-methyl-Aca, N-methyl-Agl, N-methyl-Cab, N-methyl-2-Pal, N-methyl-Cba, N-methyl-HoPhe, N-methyl-Phg, N-methyl-Phe(4-$NH_2$), N-methyl-4-Phe(4-Me), N-methyl-Phe(4-F), N-methyl-Phe(4-C1), N-methyl-Phe(2-Br), N-methyl-Phe(3-Br), N-methyl-Phe(4-Br), N-methyl-Phe(3-$CF_3$), N-methyl-Phe(4-$CF_3$), N-methyl-Phe(4-$NO_2$), N-methyl-Phe(4-CN), N-methyl-Bpa, N-methyl-Phg(4-C1), N-methyl-Phg(4-Br), N-methyl-Tyr (Me), N-methyl-Lys38, N-methyl-Lys27, N-methyl-Lys73, N-methyl-Lys55, N-methyl-Lys28, N-methyl-Lys72, N-methyl-Lys12, N-methyl-Lys123, N-methyl-Lys63, N-methyl-Lys124, N-methyl-Lys82, N-methyl-Lys31, N-methyl-Lys15, N-methyl-Lys125, N-methyl-Lys43, N-methyl-Lys24, N-methyl-Lys5, N-methyl-Lys4, N-methyl-Lys50, N-methyl-Lys81, N-methyl-Orn38, N-methyl-Orn27, N-methyl-Orn73, N-methyl-Orn55, N-methyl-Orn28, N-methyl-Orn72, N-methyl-Orn12, N-methyl-Orn123, N-methyl-Orn63, N-methyl-Orn124, N-methyl-Orn82, N-methyl-Orn31, N-methyl-Orn15, N-methyl-Orn125, N-methyl-Orn43, N-methyl-Orn24, N-methyl-Orn5, N-methyl-Orn4, N-methyl-Orn50, N-methyl-Orn81, N-methyl-Dbu38, N-methyl-Dbu27, N-methyl-Dbu73, N-methyl-Dbu55, N-methyl-Dbu28, N-methyl-Dbu72, N-methyl-Dbu12, N-methyl-Dbu123, N-methyl-Dbu63, N-methyl-Dbu124, N-methyl-Dbu82, N-methyl-Dbu31, N-methyl-Dbu15, N-methyl-Dbu125, N-methyl-Dbu43, N-methyl-Dbu24, N-methyl-Dbu5, N-methyl-Dbu4, N-methyl-Dbu50, N-methyl-Dbu81, stereoisomers thereof, and combinations thereof.

Analogs of lysine (Lys), ornithine (Orn) and α, γ-diaminobutyric acid (Dbu) include, without limitation, Lys38, Lys27, Lys73, Lys55, Lys28, Lys72, Lys12, Lys123, Lys63, Lys124, Lys82, Lys31, Lys15, Lys125, Lys43, Lys24, Lys5, Lys4, Lys50, Lys81, Orn38, Orn27, Orn73, Orn55, Orn28, Orn72, Orn12, Orn123, Orn63, Orn124, Orn82, Orn31, Orn15, Orn125, Orn43, Orn24, Orn5, Orn4, Orn50, Orn81, Dbu38, Dbu27, Dbu73, Dbu55, Dbu28, Dbu72, Dbu12, Dbu123, Dbu63, Dbu124, Dbu82, Dbu31, Dbu15, Dbu125, Dbu43, Dbu24, Dbu5, Dbu4, Dbu50, Dbu81, stereoisomers thereof, and combinations thereof. Derivatives of Orn and Dbu are similar to the lysine derivatives with corresponding carboxylic acid attached to the side chain of Orn and Dbu, respectively. Hydrophobic amino acid analogs of leucine, valine, isoleucine, glycine, alanine, methionine include norvaline (Nva), 1-aminocyclopropane-1-carboxylic acid (Acpc), 1-aminocyclobutane-1-carboxylic acid (Acb), α-cyclohexylglycine (Chg), α-aminoisobutyric acid (Aib), α-aminobutyric acid (Abu), 3-(2-thienyl)alanine (2-Thi), 3-(3-thienyl)alanine (3-Thi), 3-(3-pyridyl)alanine (3-Pal), 3-(2-naphthyl)alanine (Nal-2), 2-amino-2-naphthylacetic acid (Ana), 3,5-dinitrotyrosine (Tyr(3,5-di $NO_2$)), diethylglycine (Deg), 4-amino-4-carboxy-1,1-dioxo-tetrahydrothiopyran (Acdt), 1-amino-1-(4-hydroxycyclohexyl) carboxylic acid (Ahch), 1-amino-1-(4-ketocyclohexyl)carboxylic acid (Akch), 4-amino-4-carboxytetrahydropyran (Actp), 3-nitrotyrosine (Tyr(3-$NO_2$)), 1-amino-1-cyclohexane carboxylic acid (Ach), 2-aminoindane-2-carboxylic acid (Aic), (2S, 5R)-5-phenylpyrrolidine-2-carboxylic acid (Ppca), 4-thiazoylalanine (Tha), 2-aminooctanoic acid (Aoa), 2-aminoheptanoic acid (Aha), and a stereoisomer thereof. Preferably, the proline analog is hydroxyproline.

Analogs of negatively charged amino acids include α-aminohexanedioic acid, α-aminooctanedioic acid, homoaspartic acid, γ-carboxy-glutamic acid, 4-carboxyphenylalanine, and a stereoisomer thereof. In other embodiments, the negatively charged amino acid is selected from Aad, Bec and Bmc.

Protecting Groups

The polypeptides as well as the peptidomimetics of the present invention, including, for example, the retro-inverso peptidomimetics, can be modified so that the R-groups on the constituent amino acids and/or the terminal amino acids are blocked, i.e., protected, by a protecting group. It has been found that blockage, particularly of the amino and/or carboxy termini, greatly improves oral delivery and significantly increases serum half-life. As used herein, "protecting group" refers to a temporary substituent that protects a potentially reactive functional group from undesired chemical transformations. Examples of such protecting groups generally include esters of carboxylic acids, silyl ethers of alcohols, and acetals and ketals of aldehydes and ketones, respectively. The field of protecting group chemistry has been reviewed (Greene, T. W.; Wuts, P. G. M. Protective Groups in Organic Synthesis, $2^{nd}$ ed.; Wiley: New York, 1991).

A wide number of protecting groups are suitable for this purpose. Such groups include, but are not limited to, acetyl, $CH_3$—$(CH_2)_n$—CO—, amide, Fmoc, t-butoxycarbonyl (t-BOC), 9-fluoreneacetyl group, 1-fluorenecarboxylic group, 9-fluorenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimethyl-2,6-dioxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), Benzyloxymethyl (Bom), cyclohexyloxy (cHxO), t-butoxymethyl (Bum), t-butoxy (tBuO), t-Butyl (tBu), and Trifluoroacetyl (TFA). The variable "n" is an integer from 0 to 12, typically 0 to 6 such as 0 to 4. Other suitable protecting groups are disclosed in U.S. Pat. No. 6,933,279, the teachings of which are incorporated by reference.

In one embodiment, preferred protecting groups include, but are not limited to, acetyl, amide, and alkyl groups with acetyl and alkyl groups being particularly preferred for N-terminal protection and amide groups being particularly preferred for carboxyl terminal protection. In one preferred embodiment, an acetyl group is used to protect the amino terminus and an amide group is used to protect the carboxyl terminus. In this embodiment, acetylation can be accomplished during the synthesis when the polypeptide is on the resin using acetic anhydride. Amide protection can be achieved by the selection of a proper resin for the synthesis. For instance, a rink amide resin can be used. After the completion of the synthesis, the semipermanent protecting groups on acidic bifunctional amino acids, such as Asp and Glu, and basic amino acids, such as Lys, as well as the hydroxyl of Tyr, are all simultaneously removed. The polypeptides released from such a resin using acidic treatment comes out with the N-terminal protected as acetyl and the C-terminal protected as $NH_2$, with the simultaneous removal of all of the other protecting groups.

In a particularly preferred embodiment, the polypeptides of the present invention comprise one or more D-amino acids as described herein. In certain embodiments, every amino acid (e.g., every enantiomeric amino acid) is a D-amino acid. It has been found that polypeptides comprising all D-amino acids stimulate cholesterol efflux with high-capacity and high-affinity like the L-amino acid polypeptides. D-amino acids are readily incorporated at one or more positions in the polypeptide simply by using a D-form derivatized amino acid residue in the chemical synthesis. D-form residues for solid phase polypeptide synthesis are commercially available from a number of suppliers (see, e.g., Advanced Chem Tech, Louisville, Ky.; Nova Biochem, San Diego, Calif.; Sigma, St Louis, Mo.; Bachem California Inc., Torrance, Calif., etc.). The D-form amino acids can be incorporated at any position in the polypeptide as desired. Thus, for example, in one embodiment, the polypeptide can comprise a single D-amino acid, while in other embodiments, the polypeptide comprises at least two, generally at least three, more generally at least four, most generally at least five, preferably at least six, more preferably at least seven and most preferably at least eight D amino acids. In one embodiment, essentially every other (enantiomeric) amino acid is a D-form amino acid. In certain embodiments, at least 80%, preferably at least 90%, more preferably at least 95% of the enantiomeric amino acids are D-form amino acids. In one particularly preferred embodiment, essentially every enantiomeric amino acid is a D-form amino acid.

While in preferred embodiments, the polypeptides of this invention utilize naturally-occurring amino acids or D forms of naturally occurring amino acids, substitutions with non-naturally occurring amino acids (e.g., methionine sulfoxide, methionine methylsulfonium, norleucine, epsilon-aminocaproic acid, 4-aminobutanoic acid, tetrahydroisoquinoline-3-carboxylic acid, 8-aminocaprylic acid, 4-aminobutyric acid, Lys(N(epsilon)-trifluoroacetyl), α-aminoisobutyric acid, and the like) can be used in the polypeptides of the present invention. As with the other amino acid substitutions, non-naturally occurring amino acids are typically substituted so that, upon substitution, they retain the spatial and ionic or non-ionic character of the residue that they substitute.

In some embodiments, a citrulline is replaced with a citrulline analog amino acid. Such analogs and their preparation are known to the person skilled in the art. For example, Sonke, et al., in Stereoselective Biocatalysis (2000), pp. 23-58, and Greene: Protective Groups in Organic Synthesis (Wiley, New York 1999). Example of citrulline amino acid analogs can be found in U.S. Pat. No. 7,888,133).

In some embodiments, non-naturally occurring amino acids are employed at positions in the peptide where non-naturally occurring amino acids have long, e.g., $C_{5-8}$, carbon alkenyl or alkanyl side chains.

In some embodiments, a variant of SEQ ID NO:1 or SEQ ID NO:2 may comprise a chemical staple. For example, α-methylated amino acids containing olefinic side chains of varying length are introduced at the (i) and (i+7) positions of the peptide sequence and then cyclized by olefin metathesis. As used herein, (i) refers to a reference amino acid residue and the term (i+x) refers to an amino acid x residues from the (i) amino acid. By making the peptides more resistant to degradation and enabling their cellular uptake, the hydrocarbon staple overcomes some of the classic shortcomings of peptide therapeutics. Stapled peptides retain their natural shape, are resistant to degradation, and can enter and exert their intended function in cells. Stapled peptides are known in the art. (See, for example, Verdine and Helinski Methods Enzymol. 2012; 503:3-3; Schafineister et al. J Am Chem Soc 122:5891-92 (2000)). See, also U.S. Patent Publication No. US2005/0250680, which is herein incorporated by reference in its entirety. In the present invention, it is understood that when a chemical staple is said to be present at a particular residue, e.g., at a position 3, 14, or 23 of SEQ ID NO:1 or SEQ ID NO:2, or variants thereof, there is a corresponding residue in the peptide e.g. at a position 4 or 7 residues from the recited position that is also a stapling residue such that a staple linkage is formed.

In a further embodiment, the invention provides a method of reducing the toxicity of a peptide having cholesterol efflux activity, the polypeptide comprising an amino acid sequence that forms an amphipathic α-helix that has non-polar and polar surfaces; wherein the polar surface has positively charged amino acids at the lipid-water interface such that the polar surface comprises positively charged and uncharged amino acids. Replacement of cationic residues with uncharged amino acids creates a polypeptides that a) is non-toxic at high pharmacological doses and b) stimulates cellular cholesterol efflux efficiently. In typical embodiments, the method comprises utilizing citrulline and/or its analogs in place of cationic residues at the lipid-water interface. In some embodiments, a peptide such as ATI-5261 can be modified to replace cationic residues at the lipid water interface with uncharged amino acids at at least one, typically two, of positions 3, 14, and 23. WO 2008/115303, which is incorporated by reference, additionally describes variants of ATI-5261 that can be modified in accordance with the invention, i.e, to replace cationic residues at the lipid water interface with uncharged amino acids, e.g., at at least one, typically two of positions 3, 14, and 23.

Preparation of Peptides

Polypeptides of the invention can be prepared using known techniques. For example, peptides can be chemically synthesized using methods well known in the art including, e.g., solid phase synthesis (see, e.g., Merrifield, *J. Am. Chem. Soc.*, 85:2149-2154 (1963) and Abelson et al., Methods in Enzymology, Volume 289: Solid-Phase Peptide Synthesis (1st ed. 1997)). Polypeptide synthesis can be performed to generate a full-length peptide. Alternatively, various fragments of the polypeptide can be chemically synthesized separately and then combined using chemical methods to produce the full length polypeptide.

The polypeptides described herein can also be expressed recombinantly, especially when the polypeptide does not comprise a "D" amino acid residues. This embodiment relies on routine techniques in the field of recombinant genetics. Generally, the nomenclature and the laboratory procedures in recombinant DNA technology described herein are those well known and commonly employed in the art. Standard techniques are used for cloning, nucleic acid isolation, amplification and purification. Many manuals that provide direction for performing recombinant DNA manipulations are available, e.g., Sambrook & Russell, Molecular Cloning, A Laboratory Manual (3rd Ed, 2001); and Current Protocols in Molecular Biology (Ausubel, et al., John Wiley and Sons, New York, 2009, supplements through 2013). One of skill can generate a nucleic acid encoding a polypeptide of the invention and obtain high level expression using known techniques.

To obtain high level expression of a nucleic acid sequence, such as the nucleic acid sequences encoding a polypeptide of this invention, one typically subclones a nucleic acid sequence that encodes a polypeptide sequence of the invention into an expression vector that is subsequently transfected into a suitable host cell for expression. Expression vector components, including promoters, sequences encoding selectable markers and the like are well known in the art. The particular expression vector used to transport the genetic information into the cell is not particularly critical. Any of the conventional vectors used for expression in eukaryotic or prokaryotic cells may be used.

Methods of Identifying Polypeptides with Desired Activity

The polypeptides or peptidomimetics of the present invention can be readily evaluated for their ability to mediate cholesterol efflux and/or stabilize ABCA (e.g., ABCA1) using methods well known to those of skill in the art. Peptides may be additionally evaluated for toxicity.

A number of different screening protocols can be utilized to identify polypeptides or peptidomimetics of the present invention that mediate cholesterol efflux and/or stabilize ABCA (e.g., ABCA1). In one embodiment, the screening methods involve screening a plurality of test polypeptides to identify those polypeptides that mediates cholesterol efflux and/or stabilizes ABCA (e.g., ABCA1) in, e.g., mammalian cells, including human cells.

In addition to screening for their ability to mediate cholesterol efflux and/or stabilize ABCA, candidate test polypeptides can also be screened for other activities including, e.g., anti-oxidant activities and anti-inflammatory activities. A number of different screening protocols can be utilized to identify polypeptides or peptidomimetics of the present invention that have anti-oxidant activity and/or anti-inflammatory activity.

It will be readily apparent to those of skill in the art that numerous other screening assays, in addition to those disclosed herein, can be used to screen the polypeptides or peptidomimetics of the present invention for the desired biological activities.

Activity Assays—Cholesterol Efflux Activity

Suitable cholesterol efflux assays are described in, e.g., Bielicki, J. K and Oda, M. N., *Biochemistry*, 41:2089-2096 (2002); Jia et al., *Biochem. Biophys. Res. Common.*, 297: 206-213 (2002). In some embodiments, a polypeptide known to mediate cholesterol efflux (e.g., helix 9/10 of Apo A-I) is used to screen for additional mediators of cholesterol efflux in a cell based assay. For example, cell lines in which cholesterol efflux can be enhanced using a cAMP analog that up-regulates ABCA1 protein expression (e.g., J774 macrophages) can conveniently be used to assess the ability of a polypeptide of the present invention to mediate cholesterol efflux. The cells are incubated with labeled cholesterol (e.g., [$^3$H]cholesterol) under conditions appropriate for cholesterol uptake by the cells. Thus, cAMP or cAMP analogs (e.g., CPT-cAMP) are incubated with the cells for a suitable time before the initiation of cellular cholesterol efflux, i.e., prior to contacting the cells with a test polypeptide. Measurement of labeled cholesterol appearing in the medium is used to determine the cholesterol efflux mediating activity of the test polypeptide.

Activity Assays—ABCA Stabilization Activity

Multiple assays known in the art can be used to measure the ABCA stabilization activity of a polypeptide of the invention. For example, binding assays can be used to test the ability of the test polypeptide to bind to ABCA (e.g., ABCA1). It has been found that polypeptides having ABCA stabilization activity are also likely mediators of cholesterol efflux. As such, in a preferred embodiment, the polypeptides or peptidomimetics of the present invention have the ability to mediate cholesterol efflux and to stabilize ABCA. In one screening embodiment, the binding assays can be competitive assays. Other assays include, for example, direct measurement of ABCA (e.g., ABCA protein or nucleic acids) following contact with the test polypeptide.

Binding Assays

Binding assays usually involve contacting ABCA with one or more test polypeptides, and allowing sufficient time for ABCA and the test polypeptides to form a binding complex. Any binding complexes formed can be detected using any of a number of established analytical techniques. Protein binding assays include, but are not limited to, immunohistochemical binding assays, flow cytometry or other assays. In some embodiments, competition assays are used to determine whether a test polypeptide has ABCA stabilization activity. Competition assays are well known in the art. Typically, a competitor compound, i.e., a compound known to bind ABCA, is labeled so that differences in binding to ABCA (e.g., in the presence of increasing amount of a test polypeptide of the invention that may bind to ABCA) can be measured. The particular label or detectable group used in the assay is not a critical aspect of the invention, as long as it does not significantly interfere with the binding of the test compound to ABCA. As described herein, the detectable group (or, alternatively, detectable moiety or label) can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include, but are not limited to, magnetic beads (e.g., DYNABEADS™), fluorescent dyes (e.g., fluorescein isothiocyanate, Texas red, rhodamine, and the like), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

In some embodiments, ABCA expressing and non-expressing cells are used to measure the ABCA (e.g., ABCA1) stabilization activity of a test polypeptide by measuring the relative ABCA binding affinities of the test polypeptide and a competitor compound (e.g., full-length Apo A-I A or Apo A-I 9/10 polypeptide) for ABCA. In some embodiments, the binding affinity of full-length Apo A-I A to ABCA is compared to the binding affinity of a labeled polypeptide of the invention as described in, e.g., Remaley et al., *J. Lipid Res.*, 44:828-836 (2003). Cells expressing ABCA are incubated in the presence and absence of the competitor compound, and then exposed to a range of concentrations of individual labeled test polypeptides (e.g., a radiolabeled polypeptide of the invention). Typically, the concentrations of test polypeptides will range from about 0.1 µg/ml to about 200 µg/ml, about 0.5 µg/ml to about 100 µg/ml, about 1 µg/ml to about 40 µg/ml, or about 5 µg/ml to about 20 µg/ml.

Direct Measurement of ABCA

In some embodiments, the stabilization of ABCA is measured by direct measurement of ABCA (e.g., ABCA protein, or nucleic acid) using a cell based assay. Cell based assays can be performed in any cells in which ABCA is expressed (e.g., J774 macrophages), including cells which have been transfected with ABCA (e.g. HeLa cells). Any cell type can be used. For example, J774 macrophages can be used to assess relative ABCA1 protein levels in the presence and absence of polypeptides of the invention. The cells are first contacted with a compound that will induce ABCA (e.g., cAMP or a cAMP analogue such as, 8-bromo-cAMP) to upregulate ABCA (e.g., ABCA1) expression, then exposed to synthetic ABCA1 protein levels in the presence and absence of polypeptides of the invention in the absence of the cAMP stimulus to evaluate whether ABCA1 protein was stabilized or degraded. Relative levels of ABCA1 protein can be assessed using any means known in the art including, e.g., immunoblot analysis of cell membranes (Oram et al., *J. Biol. Chem.*, 278:52379-52385 (2003)) or hybridization of nucleic acid probes to ABCA mRNA.

Toxicity Assays

Peptides or peptidomimetics of the invention can be evaluated for toxicity using known assays. Examples of such assays are illustrated in the Examples section. Toxicity is typically assayed in a rat, rabbit, mouse, monkey or dog model. In an illustrative assay such as that described in Example 1, a peptide is administered intravenously using a rabbit or rat model at doses of 3, 30, and 300 mg/kg and vehicle alone is also administered at 48 hour intervals for a total of four injections. Safety chemistry panels including plasma alanine aminotransferase (ALT), aspartate amino transferase (AST), and creatine kinase (CK) can then be determined in the blood. The presence of elevated levels of these enzymes in the blood compared to control normal values is indicative of toxicity. A peptide of the invention is typically considered to be non-toxic or to have little toxicity, when the results using the highest dose, 300 mg/kg in this illustrative assay, are equivalent (fall within the standard deviation) of the values measured for the control animals that received vehicle alone, or are no more than 2 or 3 times background obtained with vehicle alone. In some embodiments, a toxicity assay is performed where the toxicity of a peptide of the invention is compared to that to ATI-5261. A peptide of the invention that has no or little toxicity typically exhibits less than 50%, preferably less than 20%, or more preferably less than 10% of the toxicity observed with ATI-5261 when administered to a mouse, rat or rabbit at a dose of 300 mg/kg, e.g., 4 hours after injection. Other animal models, e.g., monkeys, may also be used to evaluate toxicity Antioxidant Activity Peptides or peptidomimetics of the invention can be evaluated for antioxidant activity using methods known in the art. For example, U.S. Patent Publication No. 2003/0087819 describes multiple assays that can be used to determine the antioxidant activity of a polypeptide, including, e.g., micelle substrate assays. A micelle substrate comprising a phospholipids (e.g., 1-palmitoyl-2-linoleoylphosphatidylcholine) is used to measure rates of lipid peroxidation catalyzed by specific enzymes (e.g., soybean lipoxygenase and/or xanthine/xanthine oxidase). The enzymes initiate lipid peroxidation following the addition of recombinant polypeptides of the invention to the phospholipid micelles. Increases in conjugated dienes (a product of lipid peroxidation) are monitored by ultraviolet absorption spectroscopy (234 nm) at 25° C. The mass of phospholipid hydroperoxides is calculated using the molar absorptivity coefficient ($\varepsilon$=29,500 Lcm$^{-1}$ mol$^{-1}$) of conjugated dienes. Initial rates of lipoxygenase mediated lipid peroxidation are calculated from the slopes of the linear portion of the oxidation curves and results can be expressed as nmoles of phospholipid peroxide formed/min. Based on the maximum levels of lipid peroxide accumulation obtained in the absence of polypeptide (i.e., the plateau associated with the oxidation curves), it is possible to derive quantitative information regarding the potency of the polypeptides of the invention (e.g., a concentration of polypeptides resulting in 50% protection against lipid peroxidation). Other methods relates to screening for polypeptides capacity to prevent oxidation of ApoB lipoproteins as LDL, VLDL and Lp(A).

Other assays for screening for anti-oxidant activity are disclosed in PCT Publication No. WO 02/15923, the teachings of which are incorporated herein by reference.

Anti-Inflammatory Activity

Polypeptides or peptidomimetics of the invention can be evaluated for anti-inflammatory activity using any means known in the art. For example, assays to assess the activity of enzymes (e.g., lecithin:cholesterol acetyltransferase (LCAT) or paraoxonase (PON)) sensitive to inflammatory events can be used to assess the anti-inflammatory activity of the polypeptides of the inventions. Suitable assays are described in, e.g., Chen et al., *J. Lipid Res.*, 23:680-691 (1982), which describes quantification of LCAT activity using an exogenous proteoliposome substrate, and Forte et al., *J. Lipid Res.*, 43:477-485 (2002), which describes quantification of PON activity. Other screens can include monitoring the polypeptides capacity to inhibit the mRNA expression and/or protein production of target cells following various stimulations (for example, adhesion molecules, TNF-α, LPS or combinations thereof).

Further Testing

Polypeptides that are initially identified as mediating cholesterol efflux or interacting with ABCA can be further tested to validate their ability to mediate cholesterol efflux and/or stabilize ABCA. The basic format of such methods involves administering a lead compound identified during an initial screen to an animal that serves as a model. The animal models utilized in validation studies generally are mammals of any kind. Specific examples of suitable animals include, but are not limited to, primates (e.g., chimpanzees, monkeys, and the like) and rodents (e.g., mice, rats, guinea pigs, rabbits, and the like). In a preferred embodiment, Apo E−/− mice, Apo A-II −/− mice, or Apo C-III −/− mice are used. Additional animal models are described in, e.g., Marschang et al., *Sem. Cell Dev. Biol.,* 14:25-35 (2003).

Peptide may additionally be screened for the ability to lower glucose using methods illustrated in the EXAMPLES section, e.g., Example 31. For example, the ability to lower glucose can be evaluated using animal models, such as mice or rats. Mice, e.g., C57Bl/6 mice, fed a normal lab chow diet are injected IP with a peptide that is undergoing evaluation, e.g., at a does of 300 mg/kg, and the glucose levels in the blood are measured at a time period, e.g. 6 hours, following injection and compared to the levels of blood glucose in a control animal that received PBS. Alternatively, peptides may be screened for the ability to lower glucose as illustrated in Example 36. For example, 300 mg/kg peptide injected IP into to fasted animals and 3 h thereafter a glucose tolerance test is performed by injecting 2 g/kg glucose during which the glucose concentration is followed for 120 minutes. Peptides that have glucose lowering activity show statistically significant lowered glucose relative to controls. Typically, peptides lower glucose by at least 5%, often at least 10% or greater, relative to controls. Peptides may also be evaluated for glucose-lowering activity in animal models of obesity, e.g., DIO mice. Further, peptides may be evaluated for the ability to improve sensitivity to insulin, e.g., as described in Example 31 of the EXAMPLES section.

Additionally, peptides may be screened for the ability to treat a symptom of Alzheimer's Disease using know methods, such as those illustrated in the EXAMPLES section, including general or selective effects on apoE4 and apoE3 allele-associated Alzheimer's disease. An example of such an assay is provided in Example 40. In this example, the levels of P-tau and/or amyloidβ42 in the brain of human apoE3 or apoE4 replacement mice that express human apoE3 or apoE4. Peptides that have the ability to treat a symptom of Alzheimer's Disease show statistically significant lowered P-tau and/or amyloidβ42 levels relative to controls.

Peptides may be screened for activity using any format. For example, high throughput screening (HTS) methods may be used to identify polypeptides or peptidomimetics of the present invention that mediate cholesterol efflux and/or stabilize ABCA. HTS methods involve providing a combinatorial polypeptide library containing a large number of potential therapeutic compounds (i.e., polypeptides or peptidomimetics that mediate cholesterol efflux or stabilize ABCA). Such libraries are then screened in one or more assays, as described herein, to identify those library members (i.e., particular polypeptides or peptidomimetics) that display a desired characteristic activity. The compounds thus identified can serve as conventional "lead compounds" or can themselves be used as potential or actual therapeutics.

Pharmacokinetics and Cell Targeting

The peptides bind to HDL and assume the long HDL half-life, estimated to be 8 hours in rats (see rat PK example in the EXAMPLES section, FIGS. 36 and 52A) and 3-5 days in humans, thereby allowing administration with long intervals. The peptides when bound to other peptides, small molecules or moieties (the cargo molecules) can in an analogous manner increase the half-life of these molecules. The HDL binding properties in plasma and the ABCA1 cell binding of the peptide creates unique PK, tissue and cell distribution properties of the peptide and its cargo that can be used for diagnostic and therapeutic purposes, including but not limited to heart failure, vascular disease, diabetes mellitus, cancer and neurological diseases.

Methods of Use

The non-naturally occurring polypeptides of the present invention use the potent Reverse Cholesterol Transport (RCT) pathway to mediate cholesterol efflux. In addition to being potent and selective mediators of ABCA1-dependent cholesterol efflux, the polypeptides of the present invention also have ABCA stabilization activity, anti-diabetic activity, anti-oxidant activity as well as anti-inflammatory activity, any combination of these activities and, preferably, all of these activities.

In view of their biological activities and, in particular, their ability to mediate cholesterol efflux, the polypeptides of the present invention (or peptidomimetics thereof) can be used to treat elevated cholesterol levels in a mammal, or to treat prophylactically a mammal at risk of developing elevated cholesterol levels. In addition, the polypeptides or peptidomimetics can also be used for improving the lipid parameters in a mammal. An improvement in "lipid parameters" includes, for example, one or more of a decrease in the propensity of lipoproteins to adhere to a blood vessel, a decrease in the amount of atherosclerotic plaque (even though plasma LDL and/or HDL concentrations may not significantly changed), a reduction in the oxidative potential of an HDL or LDL particle, a regression in atherosclerosis (e.g., as measured by carotid angiography or ultrasound) and a reduction in cardiac events. Thus, the polypeptides or peptidomimetics of the present invention can be used to treat or prevent (i.e., prophylactically treat) diseases and conditions associated with dyslipidemia, hypercholesterolemia and inflammation, diabetes, or diseases and conditions that are treatable by altering lipid parameters, such as those diseases and conditions disclosed herein. In some embodiments, the peptides can be used to treat a patient that has a complication of a disease as described herein. Thus, in some embodiments, the patient has macro or microvascular disease, chronic kidney disease, or congestive heart failure.

In addition to the diseases and conditions specifically disclosed herein, those of skill in the art will know of other diseases and conditions associated with dyslipidemia, hypercholesterolemia and inflammation that can be treated or prevented using the polypeptides or peptidomimetics of the present invention.

Treating or Preventing a Symptom(s) of Atherosclerosis

In one embodiment, the present invention provides methods for treating, ameliorating and/or preventing one or more symptoms of atherosclerosis. The methods preferably involve administering to an organism, preferably a mammal and, more preferably, a human, one or more of the polypeptides of this invention (or peptidomimetics of such polypeptides). The polypeptide(s) can be administered, as described herein, according to any of a number of standard methods including, but not limited to, injection, suppository, nasal spray, time-release implant, transdermal patch, orally and the like. In one particularly preferred embodiment, the polypeptide(s) is administered orally (e.g., as a syrup, capsule, tablet, etc.).

The methods of the present invention are not limited to treating humans or non-human animals having one or more symptom(s) of atherosclerosis (e.g., hypertension, narrowing of vessels, plaque formation and rupture, heart attack, angina, or stroke, high levels of plasma cholesterol, high levels of low density lipoprotein, high levels of very low density lipoprotein, or inflammatory proteins, etc.), but are also very useful in a prophylactic context. Thus, the polypeptides of this invention (or peptidomimetics thereof) can be administered to an organism, such as a human or non-human animal, to prevent the onset, i.e., development, of one or more symptoms of atherosclerosis. Suitable candidate subjects for prophylactic treatment include, for example, those subjects having one or more risk factors for atherosclerosis (e.g., family history, genetic markers that correlate with atherosclerosis, hypertension, obesity, high alcohol consumption, smoking, high blood cholesterol, high blood triglycerides, elevated blood LDL, VLDL, IDL, or low HDL, diabetes, or a family history of diabetes, high blood lipids, heart attack, angina or stroke, etc.).

Treatment can complement or obviate the need for invasive procedures and vascular surgery making anti-atherosclerosis treatment systemic and sustainable. Thus, the peptide can be given before intervention to optimize circulation before surgery, during surgery for regional administration in the vasculature or its vicinity, or post-surgery to lessen inflammation and atherosclerosis caused by mechanical trauma by surgical intervention.

Treating or Preventing a Symptom(s) of Atherosclerosis Associated with an Acute Inflammatory Response The atherosclerosis-inhibiting polypeptides of this invention are also useful in a number of other contexts. In particular, it has been found that cardiovascular complications (e.g., atherosclerosis, stroke, etc.) frequently accompany or follow the onset of an acute phase inflammatory response. Such an acute phase inflammatory response is often associated with a recurrent inflammatory disease (e.g., leprosy, tuberculosis, systemic lupus erythematosus, rheumatoid arthritis, etc.), a viral infection (e.g., influenza, HIV, etc.), a bacterial infection, a fungal infection, an organ transplant, a wound or other trauma, an implanted prosthesis, a biofilm, and the like.

In view of their antioxidant activity, the polypeptides described herein can be used to reduce or prevent the formation of oxidized phospholipids during or following an acute phase inflammatory response, thereby mitigating or eliminating cardiovascular complications associated with such a condition. The inflammatory response can also be of more chronic nature as in alcoholic and non-alcoholic liver disease, chronic kidney disease and congestive heart failure.

Treating or Preventing a Disorder Involving Abnormal Glucose Metabolism

In a further aspect, the invention provides a method of altering mammal that has abnormal glucose metabolism. In some embodiment, the mammal has Type II diabetes. In some embodiments, the mammal has Type I diabetes. In some embodiment, the mammal has pre-diabetes or metabolic syndrome. In some embodiments, the mammal is a human. I some embodiments, the mammal is a human that has a fasting blood glucose level of over 100 mg/dL. In some embodiments the mammal has complications of diabetes as macro or microvascular disease, kidney disease or congestive heart failure.

In some embodiments, the mammal is administered a peptide that comprises the following sequence: $X_1X_2X_3X_4X_5X_6X_7X_8X_9X_{10}X_{11}X_{12}X_{13}X_{14}X_{15}X_{16}X_{17}X_{18}X_{19}X_{20}X_{21}X_{22}X_{23}X_{24}$, wherein $X_1$, $X_7$, $X_8$, $X_{15}$, $X_{18}$ and $X_{19}$ are acidic amino acids; $X_4$ is a polar amino acid; $X_5$ is a positively charged amino acid; $X_2$, $X_6$, $X_9$, $X_{11}$, $X_{12}$, $X_{17}$, $X_{21}$, $X_{22}$, and $X_{24}$ are hydrophobic amino acids; $X_{10}$, $X_{13}$, $X_{16}$, and $X_{20}$ are the same aliphatic amino acid residue, e.g., the same branched chain aliphatic amino acid residue; and $X_3$, $X_{14}$ and $X_{23}$ are uncharged amino acids. In some embodiments, at least two of positions $X_3$, $X_{14}$ and $X_{23}$ are citrulline and the third position is R or K. In some embodiments, $X_4$ is a polar uncharged amino acid; and two or more of $X_2$, $X_6$, $X_{11}$, $X_{12}$, $X_{17}$, $X_{21}$, $X_{22}$, and $X_{24}$ are aliphatic amino acids. In some embodiments, $X_2$, $X_6$, $X_{11}$, $X_{12}$, $X_{17}$, $X_{21}$, $X_{22}$, and $X_{24}$ are all aliphatic amino acids. In some embodiments, $X_9$ is W. In some embodiments, $X_{10}$, $X_{13}$, $X_{16}$, and $X_{20}$ are I. In some embodiments, $X_{10}$, $X_{13}$, $X_{16}$, and $X_{20}$ are L. In some embodiments, $X_1$, $X_7$, $X_8$, $X_{15}$, $X_{18}$ and $X_{19}$ are independently selected from D and E; $X_{10}$, $X_{13}$, $X_{16}$, and $X_{20}$ are I or $X_{10}$, $X_{13}$, $X_{16}$, and $X_{20}$ are L; $X_{11}$ and $X_{22}$ are aliphatic amino acids, $X_4$ is S, T, G, or Y; $X_9$ is W, $X_5$ is R or K; and $X_3$, $X_{14}$ and $X_{23}$ are selected from the following: $X_3$ and $X_{14}$ are citrulline and $X_{23}$ is R or K; citrulline at positions 3 and 23 and an R or K at position 14; and citrulline at positions 14 and 23 and an R or K at position 3.

Treating or Preventing Alzheimer's Disease or Mild Cognitive Impairment

In a further aspect, the invention provides a method of treating a human patient that has Alzheimer's Disease or Mild Cognitive Impairment, frontotemporal dementia; or vascular dementia.

As used herein, "Alzheimer's disease" refers to senile dementia as diagnosed using commonly accepted criteria in the art, such as the criteria set forth by The National Institute of Neurological and Communicative Disorders and Stroke and the Alzheimer's disease and Related Disorders Association and/or the criteria as listed in the Diagnostic and Statistical Manual of Mental Disorders (DSM-IV-TR) published by the American Psychiatric Association. The Diagnostic and Statistical Manual of Mental Disorders (Fourth Edition, revised in 2000), also known as the DSM-IV-TR, outlines a detailed set of criteria for the diagnosis of Alzheimer's disease.

In some embodiments, a patient may have mild to moderate dementia, or early-stage Alzheimer's disease, which can be identified using neurological testing and other clinical endpoints. For example, a subject with mild to moderate dementia, e.g., Alzheimer's disease, can be identified using the Mini-Mental State Examination (MMSE), Typically, a score of 16 to 26 (both inclusive) is indicative of mild to moderate Alzheimer's disease. Patients with advanced Alzheimer's disease can also be identified based on clinical parameters. Subjects with this form of Alzheimer's disease may no longer respond to therapy with acetylcholinesterase inhibitors, and may have a markedly reduced acetylcholine level.

In some embodiments, a patient treated with a peptide of the invention may have Mild Cognitive Impairment. Such patients are at risk for development of Alzheimer's disease. Mild Cognitive Impairment can be diagnosed and evaluated using any of the many objective tests or criteria well-known and accepted in the fields of psychology or psychiatry.

"Frontotemporal dementia" is a neurodegenerative disease characterized by progressive neuronal loss predominantly involving the frontal and/or temporal lobes. The disorder was first identified in 1994 by Kirk Wilhelmsen and colleagues, who distinguished it from Alzheimer's disease and Lewy body dementia based on the fact that it did not manifest with amyloid plaques, neurofibrillary tangles, or Lewy bodies. The term "frontotemporal lobar degeneration" or "FTLD" is used to describe the specific pathological diseases that result in frontotemporal dementia syndromes. These tare united by their impact on frontal and temporal brain structures. Subtyping is based on the specific proteins found within neuronal inclusions. Most degeneration subtypes are either FTLD-tau, which includes Pick's disease, CBD and PSP, all of which show tau-containing inclusions or FTLD-TDP, which includes several subtypes in which TDP-43 containing inclusions are seen.

In some embodiments, the patient having Alzheimer's disease, frontotemporal dementia, or vascular dementia; or who is at risk for having Alzheimer's disease, e.g., a patient having Mild Cognitive Impairment, is administered a peptide that comprises the following sequence: $X_1X_2X_3X_4X_5X_6X_7X_8X_9X_{10}X_{11}X_{12}X_{13}X_{14}X_{15}X_{16}X_{17}X_{18}X_{19}X_{20}X_{21}X_{22}X_{23}X_{24}$, wherein $X_1$, $X_7$, $X_8$, $X_{15}$, $X_{18}$ and $X_{19}$ are acidic amino acids; $X_4$ is a polar amino acid; $X_5$ is a positively charged amino acid; $X_2$, $X_6$, $X_9$, $X_{11}$, $X_{12}$, $X_{17}$, $X_{21}$, $X_{22}$, and $X_{24}$ are hydrophobic amino acids; $X_{10}$, $X_{13}$, $X_{16}$, and $X_{20}$ are the same aliphatic amino acid residue, e.g., the same branched chain aliphatic amino acid residue; and $X_3$, $X_{14}$ and $X_{23}$ are uncharged amino acids. In some embodiments, at least two of positions $X_3$, $X_{14}$ and $X_{23}$ are citrulline and the third position is R or K. In some embodiments, $X_4$ is a polar uncharged amino acid; and two or more of $X_2$, $X_6$, $X_{11}$, $X_{12}$, $X_{17}$, $X_{21}$, $X_{22}$, and $X_{24}$ are aliphatic amino acids. In some embodiments, $X_2$, $X_6$, $X_{11}$, $X_{12}$, $X_{17}$, $X_{21}$, $X_{22}$, and $X_{24}$ are all aliphatic amino acids. In some embodiments, $X_9$ is W. In some embodiments, $X_{10}$, $X_{13}$, $X_{16}$, and $X_{20}$ are I. In some embodiments, $X_{10}$, $X_{13}$, $X_{16}$, and $X_{20}$ are L. In some embodiments, $X_1$, $X_7$, $X_8$, $X_{15}$, $X_{18}$ and $X_{19}$ are independently selected from D and 3; $X_{10}$, $X_{13}$, $X_{16}$, and $X_{20}$ are I or $X_{10}$, $X_{13}$, $X_{16}$, and $X_{20}$ are L; $X_{11}$ and $X_{22}$ are aliphatic amino acids, $X_4$ is S, T, G, or Y; $X_9$ is W, $X_5$ is R or K; and $X_3$, $X_{14}$ and $X_{23}$ are selected from the following: $X_3$ and $X_{14}$ are citrulline and $X_{23}$ is R or K; citrulline at positions 3 and 23 and an R or K at position 14; and citrulline at positions 14 and 23 and an R or K at position 3.

Additional Therapeutic Uses

In some embodiments, a peptide of the invention may be used to deliver a therapeutic agent. Thus, for example, in some embodiments, a peptide may be linked to an agent such as a toxin or radiolabel to treat cancer. Any type of cancer can be treated.

In other embodiments, the polypeptides of the present invention are used to reduce or prevent the formation of oxidized phospholipids. In such methods, the polypeptides of the present invention can be administered to a human or non-human animal to reduce or prevent the formation of oxidized phospholipids, thereby inhibiting or preventing a symptom of a disease such as polymyalgia rheumatica, polyarteritis nodosa, scleroderma, idiopathic pulmonary fibrosis, chronic obstructive pulmonary disease, AIDS, coronary calcification, calcific aortic stenosis, osteoporosis and the like.

Typically, all of the above methods involve the administration of a single polypeptide of this invention or, alternatively, the administration of two or more different polypeptides of this invention. Such polypeptides can be administered alone or in combination with other therapeutic agents, such as those disclosed herein. The polypeptides can be provided as monomers or in dimeric, oligomeric or polymeric forms. In certain embodiments, the multimeric forms may comprise associated monomers (e.g., ionically or hydrophobically linked); whereas, in other embodiments, other multimeric forms comprise covalently linked monomers (directly linked or through a linker).

In addition, although all of the foregoing methods are described herein with respect to humans, it will be readily apparent to those of skill that such methods are also useful for other animals, i.e., for veterinary use. Thus, preferred organisms include, but are not limited to, humans, non-human primates, canines, equines, felines, porcines, ungulates, largomorphs, and the like.

Stabilization of Vulnerable Plaques

In some embodiments, polypeptides of the present invention can stabilize vulnerable plaques prone to rupture potentially causing thrombotic arterial occlusion, e.g., by reducing plaque lipid content through reverse cholesterol transport. Thus, in another embodiment, the present invention provides methods for stabilizing a vulnerable plaque in a blood vessel of a mammal by administering to the mammal (and, more preferably, a human), one or more of the polypeptides of this invention (or peptidomimetics of such polypeptides). A "vulnerable" plaque is generally defined as a lipid-rich plaque with a thinned fibrous cap lacking proper collagen and smooth muscle cell support. A mammal, preferably a human, can be diagnosed as having one or more vulnerable plaques using known methods, including temperature detection strategies, labeling strategies, imaging strategies (e.g., devices utilizing magnetic resonance, ultrasound, infra-red, fluorescence, visible light, radio waves, x-ray, etc.), general strategies for discriminating the vulnerable plaque from surround healthy vascular tissue and the like (see, e.g., U.S. Pat. Nos. 6,245,026, 6,475,159, 6,475,210 and 7,118,567). In another embodiment, the mammal, preferably a human, is at risk of having one or more vulnerable plaques. In this embodiment, a clinical symptom has developed and/or a clinical event has occurred that leads one of skill in the art to believe that the mammal is at risk of having one or more vulnerable plaques.

Combination Therapy

In some embodiments, the polypeptides or peptidomimetics of the present invention are administered in combination with one or more additional therapeutic agents for treating or preventing diseases and disorders associated with dyslipidemia, hypercholesterolemia and inflammation, such as cardiovascular disease, including atherosclerosis. For instance, in one embodiment, a polypeptide of the present invention is administered in conjunction with any of the standard treatments for atherosclerosis including, for example, statins (e.g., atorvastatin, lovastatin, pravastatin, simvastatin, fluvastatin, or rosuvastatin); a Nieman-Pick C1-Like 1 sterol transporter channel inhibitor (e.g., Ezetimibe); bile acid binders (e.g., cholestyramine or colestipol); platelet clumping inhibitors (e.g., aspirin, ticlopidine, or clopidogrel); niacin/nicotinamide; PPAR activators; Vitamin E; surgical intervention (e.g., angioplasty, stents, stents, or endarterectomy); and lifestyle changes (e.g., low-fat diets, weight loss, and exercise).

More particularly, the polypeptides or peptidomimetics of the present invention can be used in combination, either as separate units or fixed combinations, with one or more of the following: an antibody which binds to an unwanted inflammatory molecule or cytokine such as interleukin-6, interleukin-8, granulocyte macrophage colony stimulating factor, and tumor necrosis factor-$\alpha$; an enzyme inhibitor such as a protease inhibitor aprotinin or a cyclooxygenase inhibitor; an antibiotic such as amoxicillin, rifampicin, erythromycin; an antiviral agent such as acyclovir; a steroidal anti-inflammatory such as a glucocorticoid; a non-steroidal anti-inflammatory such as aspirin, ibuprofen or acetaminophen; or a non-inflammatory cytokine such as interleukin-4 or interleukin-10. Other cytokines and growth factors such as interferon-β, tumor necrosis factors, antiangiogenic factors, erythropoietins, thrombopoietins, interleukins, maturation factors, chemotactic protein, and their variants and derivatives that retain similar physiological activities may also be used as an additional therapeutic agents.

The polypeptides or peptidomimetics of the present invention can be used in combination with drugs commonly used to treat lipid disorders in, for example, diabetic patients. Such drugs include, but are not limited to, HMG-CoA reductase inhibitors, nicotinic acid, ezetimide, bile acid sequestrants, fibric acid derivatives, MTP inhibitor, ACAT inhibitor and CETP inhibitors. Examples of HMG-CoA reductase inhibitors include lovastatin, pravastatin, simvastatin, rosuvastatin, fluvastatin and atorvastatin. Examples of bile acid sequestrants include cholestyramine, colestipol and colesevelam. Examples of fibric acid derivatives include gemfibrozil and fenofibrate, The polypeptides or peptidomimetics of the invention can also be used in combination with anti-hypertensive drugs, such as, for example, diuretics, β-blockers, cathepsin S inhibitors, methyldopa, α2-adrenergic agonists, guanadrel, reserpine, β-adrenergic receptor antagonists, a 1-adrenergic receptor antagonists, hydralazine, minoxidil, calcium channel antagonists, ACE inhibitors and angiotensin II-receptor antagonists. Examples of β-blockers include acebutolol, bisoprolol, esmolol, propranolol, atenolol, labetalol, carvedilol and metoprolol. Examples of ACE inhibitors include captopril, enalapril, lisinopril, benazepril, fosinopril, ramipril, quinapril, perindopril, trandolapril and moexipril.

The polypeptides or peptidomimetics of the invention can also be used in combination with cardiovascular drugs such as calcium channel antagonists, β-adrenergic receptor antagonists and agonists, aldosterone antagonists, ACE inhibitors, angiotensin II receptor antagonists, nitrovasodilators, and cardiac glycosides. The polypeptides or peptidomimetics of the invention can also be used in combination with anti-inflammatory drugs such as H1-receptor antagonists, H2-receptor mediated agonists and antagonists, COX-2 inhibitors, NSAID, salicylates, acetaminophen, propionic acid derivatives, enolic cids, diaryl substituted fuanones, cyclooxygenase inhibitors, and bradykinin agonists and antagonists.

Other therapeutic agents suitable for use in combination with the polypeptides or peptidomimetics of the present invention are disclosed in U.S. Patent Application Publication No. 2005/0142180, which was published Jun. 30, 2005, the teachings of which are incorporated herein by reference.

The polypeptide (or peptidomimetics thereof) and the additional therapeutic agent can be administered simultaneously or sequentially. For example, the polypeptide may be administered first, followed by the additional therapeutic agent. Alternatively, the additional therapeutic agent may be administered first, followed by the polypeptide of the invention. In some cases, the polypeptide of the invention and the additional therapeutic agent are administered in the same formulation. In other cases, the polypeptide and the additional therapeutic agent are administered in different formulations. When the polypeptide and the additional therapeutic agent are administered in different formulations, their administration may be simultaneous or sequential.

Pharmaceutical Formulations

In order to carry out the methods of the invention, one or more polypeptides of this invention or peptidomimetics thereof are administered to an individual diagnosed as having or at risk of having a disease or disorder associated with dyslipidemia, hypercholesterolemia and inflammation (e.g., to an individual diagnosed as having one or more symptoms of atherosclerosis, or as being at risk for atherosclerosis); or a disease associated with abnormal glucose metabolism; or Alzheimer's Disease. The polypeptides or peptidomimetics thereof can be administered in their "native" form or, if desired, in the form of, for example, salts, esters, amides, prodrugs, derivatives, and the like, provided that the salt, ester, amide, prodrug or derivative is suitable pharmacologically, i.e., effective in the methods of the present invention.

In one embodiment of the methods described herein, the route of administration can be oral, intraperitoneal, transdermal, subcutaneous, by intravenous or intramuscular injection, by inhalation, topical, intralesional, infusion; liposome-mediated delivery; topical, intrathecal, gingival pocket, rectal, intrabronchial, nasal, transmucosal, intestinal, ocular or otic delivery, or any other methods known in the art as one skilled in the art may easily perceive. Other embodiments of the compositions of the invention incorporate particulate forms protective coatings, protease inhibitors or permeation enhancers for various routes of administration, including parenteral, pulmonary, nasal and oral. The pharmaceutical compositions can be administered in a variety of unit dosage forms depending upon the method/mode of administration. Suitable unit dosage forms include, but are not limited to, powders, tablets, pills, capsules, lozenges, suppositories, patches, nasal sprays, injectables, implantable sustained-release formulations, etc.

As such, in another aspect, the present invention provides pharmaceutical compositions comprising a pharmaceutically effective amount of a polypeptide or peptidomimetic of the present invention and an acceptable carrier and/or excipients. A pharmaceutically acceptable carrier includes any solvents, dispersion media, or coatings that are physiologically compatible and that preferably does not interfere with or otherwise inhibit the activity of the polypeptide or peptidomimetic. Preferably, the carrier is suitable for intravenous, intramuscular, oral, intraperitoneal, transdermal, topical, or subcutaneous administration. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the active agents, or excipients or other stabilizers and/or buffers.

Other physiologically acceptable compounds include, but are not limited to, wetting agents, emulsifying agents, dispersing agents or preservatives which are particularly useful for preventing the growth or action of microorganisms. Various preservatives are well known and include, for example, phenol and ascorbic acid. One skilled in the art will appreciate that the choice of pharmaceutically acceptable carrier(s), including a physiologically acceptable compound depends, for example, on the route of administration of the polypeptide(s) or peptidomimetic(s) and on the particular physio-chemical characteristics of the polypeptide(s) or peptidomimetic(s).

In a preferred embodiment, the pharmaceutically acceptable carrier is physiological saline. Other pharmaceutically acceptable carriers and their formulations are well-known and generally described in, for example, Remington's Pharmaceutical Science (18*th* Ed., ed. Gennaro, Mack Publishing Co., Easton, Pa., 1990). Various pharmaceutically acceptable excipients are well-known in the art and can be found in, for example, Handbook of Pharmaceutical Excipients (4*th* ed., Ed. Rowe et al., Pharmaceutical Press, Washington, D.C.). Again, the pharmaceutical composition can be formulated as a solution, microemulsion, liposome, capsule, tablet, or other suitable form. The active component may be coated in a material to protect it from inactivation by the environment prior to reaching the target site of action.

In certain embodiments, the polypeptides or peptidomimetics of this invention can be administered orally (e.g., via a tablet) or as an injectable in accordance with standard methods well known to those of skill in the art. In other preferred embodiments, the polypeptides or peptidomimetics can also be delivered through the skin using conventional transdermal drug delivery systems, i.e., transdermal "patches," wherein the polypeptide(s) or peptidomimetic(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

Other formulations for topical drug delivery include, but are not limited to, ointments and creams. Ointments are semisolid preparations that are typically based on petrolatum or other petroleum derivatives. Creams containing the selected active agent are typically viscous liquid or semi-solid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

In some embodiments, implanted devices (e.g., arterial and intravenous stents, including eluting stents, and catheters) are used to deliver the formulations comprising the polypeptides and peptidomimetics of the invention. For example, aqueous solutions comprising the polypeptides and peptidomimetics of the invention are administered directly through the stents and catheters. In some embodiments, the stents and catheters may be coated with formulations comprising the polypeptides and peptidomimetics described herein. In some embodiments, the polypeptides and peptidomimetics will be in time-release formulations an eluted from the stents. Suitable stents are described in, e.g., U.S. Pat. Nos. 6,827,735; 6,827,735; 6,827,732; 6,824,561; 6,821,549; 6,821,296; 6,821,291; 6,818,247; 6,818,016; 6,818,014; 6,818,013; 6,814,749; 6,811,566; 6,805,709; 6,805,707; 6,805,705; 6,805,704; 6,802,859; 6,802,857; 6,802,856; and 49 6,802,849. Suitable catheters are described in, e.g., U.S. Pat. Nos. 6,829,497; 6,827,798; 6,827,730; 6,827,703; 6,824,554; 6,824,553; 6,824,551; 6,824,532; and 6,819,951.

Polypeptides of this comprising L-form or D-form amino acids can be administered without protection against proteolysis by stomach acid, etc. Nevertheless, in certain embodiments, polypeptide delivery can be enhanced by the use of protective excipients, as known in the art (see, e.g., U.S. Pat. No. 5,391,377).

Elevated serum half-life can be maintained by the use of sustained-release polypeptide "packaging" systems. Such sustained release systems are well known to those of skill in the art. In one preferred embodiment, the ProLease biodegradable microsphere delivery system for proteins and polypeptides is used (Tracy, *Biotechnol. Prog.*, 14:108 (1998); Johnson et al., *Nature Med.*, 2:795 (1996); Herbert et al., *Pharmaceut. Res.*, 15:357 (1998)), which involves the use of a dry powder composed of biodegradable polymeric microspheres containing the polypeptide in a polymer matrix that can be compounded as a dry formulation with or without other agents.

In another embodiment, one or more components of the solution can be provided as a "concentrate," e.g., in a storage container (e.g., in a premeasured volume) ready for dilution, or in a soluble capsule ready for addition to a volume of water.

In certain embodiments of the present invention, the pharmaceutical compositions are sustained release formulations. Polypeptides or peptidomimetics of the present invention may be admixed with biologically compatible polymers or matrices which control the release rate of the copolymers into the immediate environment. Controlled or sustained release compositions include formulation in lipophilic depots (e.g., fatty acids, waxes, oils). Also contemplated by the invention are particulate compositions coated with polymers (e.g., poloxamers or poloxamines). Other embodiments of the compositions of the invention incorporate particulate forms, protective coatings, protease inhibitors or permeation enhancers for various routes of administration, including parenteral, pulmonary, nasal and oral. Acceptable carriers include carboxymethyl cellulose (CMC) and modified CMC.

The pharmaceutical composition of the present invention is preferably sterile and non-pyrogenic at the time of delivery, and is preferably stable under the conditions of manufacture and storage. These pharmaceutical compositions can be sterilized by conventional, well known sterilization techniques.

In therapeutic applications, the compositions of this invention are administered to an individual diagnosed as having or at risk of having a disease or disorder associated with dyslipidemia, hypercholesterolemia and inflammation (and, in preferred embodiments, to an individual diagnosed as having one or more symptoms of atherosclerosis or as being at risk for atherosclerosis) or a disease associated with abnormal glucose metabolism, or Alzheimer's Disease, in an amount sufficient to cure or at least partially prevent or arrest the disease, condition and/or its complications. An amount adequate to accomplish this is defined as a "therapeutically effective dose." Amounts effective for this use will depend upon the severity of the disease and the general state of the patient's health. Single or multiple administrations of the compositions can be administered depending on the dosage and frequency as required and tolerated by the patient. In any event, the composition should provide a sufficient quantity of the active agents, i.e., polypeptides or peptidomimetics, of the formulations of this invention to effectively treat (ameliorate one or more symptoms) the individual or patient.

The concentration of polypeptide or peptidomimetic can vary widely, and will be selected primarily based on fluid volumes, viscosities, body weight, circulating plasma levels of the polypeptide, polypeptide toxicities, progression of the disease (e.g., atherosclerosis), the production of antibodies that specifically bind to the polypeptide, and the like in accordance with the particular mode of administration selected and the patient's needs. Typically, the dose equivalent of a polypeptide or peptidomimetic is from about 0.1 to about 50 mg per kg, preferably from about 1 to about 25 or 30 mg per kg, or from about 1 to about 20 mg per kg body weight. It will be appreciated that such dosages may be varied to optimize a therapeutic regimen in a particular subject or group of subjects.

For administration, polypeptides of the present invention can be administered at a rate determined by the LD50 of the polypeptide, and the side-effects of the polypeptide at various concentrations, as applied to the mass and overall health of the patient. Administration can be accomplished via single or divided doses, e.g., doses administered on a regular basis (e.g., daily) for a period of time (e.g., 2, 3, 4, 5, 6, days or 1-3 weeks or more).

As explained herein, the polypeptides or peptidomimetics of the present invention can be modified in a number of different ways. For instance, the polypeptides can be modified so that the R-groups on the constituent amino acids and/or the terminal amino acids are blocked, i.e., protected, by a protecting group. It has been found that blockage, particularly of the amino and/or carboxy termini, can greatly improve oral delivery and significantly increases serum half-life. In addition, to enhance delivery and/or biological activities in vivo, salts, esters, amides, prodrugs and other derivatives of the polypeptides or peptidomimetics of the present invention can be prepared using standard procedures known to those skilled in the art of synthetic organic chemistry and described, for example, by March (1992) Advanced Organic Chemistry; Reactions, Mechanisms and Structure, 4th Ed. N.Y. Wiley-Interscience.

For example, acid addition salts are prepared from the free base using conventional methodology, which typically involves reaction with a suitable acid. Generally, the base form of the drug is dissolved in a polar organic solvent such as methanol or ethanol and the acid is added thereto. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the polypeptides described herein are halide salts, such as may be prepared using hydrochloric or hydrobromic acids. Conversely, preparation of basic salts of the polypeptides or peptidomimetics of the present invention are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., sodium salts and copper salts.

Preparation of esters typically involves functionalization of hydroxyl and/or carboxyl groups that may be present within the polypeptides or peptidomimetics of the present invention. The esters are typically acyl-substituted derivatives of free alcohol groups, i.e., moieties that are derived from carboxylic acids of the formula RCOOH, wherein R is alkyl and, preferably, lower alkyl. Esters can be reconverted to the free acids, if desired, by using conventional hydrogenolysis or hydrolysis procedures.

Amides and prodrugs can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety that results in a compound that is therapeutically inactive until modified by an individual's metabolic system.

The foregoing formulations and administration methods are clearly intended to be illustrative and not limiting in any way. It will be appreciated that, using the teaching provided herein, other suitable formulations and modes of administration can be readily devised.

Lipid-Based Formulations

In another aspect, the polypeptides and peptidomimetics of the present invention are preferably administered in conjunction with one or more lipids. The lipids can be formulated as an excipient to protect and/or enhance transport/uptake of the polypeptides or peptidomimetics or they can be administered separately.

The lipids can be formulated into liposomes, nanocapsules, microparticles, microspheres, lipids particles, lipid vesicles and the like. Such lipid formulations can be used to encapsulated the polypeptides and peptidomimetics of the present invention and/or they can be simply complexed/admixed with such polypeptides and peptidomimetics. Those of skill in the art will know how to use such lipid formulations to either encapsulate or complex the polypeptides or peptidomimetics of the present invention. For instance, the formation and use of liposomes is generally known to those of skill in the art. Recently, liposomes were developed with improved serum stability and circulation half-times (see, U.S. Pat. No. 5,741,516). Further, various methods of liposome and liposome-like preparations as potential drug carriers have been reviewed (see, U.S. Pat. Nos. 5,567,434; 5,552,157; 5,565,213; 5,738,868 and 5,795,587).

In one embodiment, the polypeptides or peptidomimetics of the present invention are complexed with a lipid, such as a phospholipid (e.g., 1-palmitoyl-2-oleoyl-sn-glycerol-phosphatidylcholine ("POPC") in a manner similar to that disclosed in U.S. Patent Application Publication No. 2005/0142180, which was published Jun. 30, 2005, the teachings of which are incorporated herein by reference. As such, the present invention provides polypeptide-lipid complexes (or, alternatively, peptidomimetic-lipid complexes) having an increased ability to efflux cholesterol from cells. Typically, the lipid is mixed with the polypeptide prior to administration. The polypeptides of the present invention and lipids can be mixed in an aqueous solution in appropriate ratios and can be complexed by methods known in the art, including, but not limited to, freeze-drying, detergent solubilization followed by dialysis, microfluidization, sonication, and homogenization. Complex efficiency can be optimized, for example, by varying pressure, ultrasonic frequency or detergent concentration. An example of a detergent commonly used to prepare polypeptide-lipid complexes is sodium cholate.

In certain embodiments, the polypeptide-lipid (e.g., phospholipids) complex can be in solution with an appropriate pharmaceutical diluent or carrier. In other embodiments, freeze-dried or lyophilized preparations of the polypeptide-lipid complexes can be hydrated or reconstituted with an appropriate pharmaceutical diluent prior to administration. In another embodiment, the polypeptide-lipid complexes can be frozen preparations that are thawed until a homogenous solution is achieved prior to administration to a subject in need thereof.

The lipid can be any suitable lipid known to those of skill in the art. In one embodiment, non-phosphorus containing lipids can be used, including stearylamine, dodecylamine, acetyl palmitate, (1,3)-D-mannosyl-(1,3)digly-ceride, aminophenylglycoside, 3-cholesteryl-6'-(glycosylthio)hexyl ether glycolipids, N-(2,3-di(9-(Z)-octadecenyloxy))-prop-1-yl-N,N,N-trimethylammonium chloride and fatty acid amides.

In another embodiment, a phospholipids or a mixture of phospholipids is used.

Suitable phospholipids include, but are not limited to, can be a small alkyl chain phospholipid, phosphatidylcholine, egg phosphatidylcholine, soybean phosphatidylcholine, dipalmitoylphosphatidylcholine, soy phosphatidylglycerol, egg phosphatidylglycerol, distearoylphosphatidylgly-cerol, dimyristoylphosphatidylcholine, distearoylphosphatidyl-choline, dilaurylphosphatidylcholine, 1-myristoyl-2-palmitoylphosphatidylcholine, 1-palmitoyl-2-myristoylphosphati-dylcholine, 1-palmitoyl-2-stearoylphospha-tidylcholine, 1-stearoyl-2-palmitoylphosphatidylcholine, dioleoylphos-phatidylcholine, 1-palmitoyl-2-oleoylphosphatidylcholine, 1-oleoyl-2-palmitylphosphatidylcholine, dioleoylphosphati-dylethanolamine, dilauroylphosphatidylglycerol, phosphati-dylserine, phosphatidylethanolamine, phosphatidylinositol, phosphatidylglycerol, diphosphatidylglycerol, dimyristoyl-phosphatidylglycerol, dipalmitoylphosphatidylglycerol, dis-tearoylphosphatidylglycerol, dioleoylphosphatidylglycerol, phosphatidic acid, dimyristoylphosphatidic acid, dipalmi-toylphosphatidic acid, dimyristoylphosphatidyletha-nolamine, dipalmitoylphosphatidylethanolamine, dimyris-toylphosphatidylserine, dipalmitoylphosphatidylserine, brain phosphatidylserine, sphingomyelin, sphingolipids, brain sphingomyelin, dipalmitoylsphingomyelin, distearoyl-sphingomyelin, galactocerebroside, gangliosides, cerebro-sides, phosphatidylglycerol, phosphatidic acid, lysolecithin, lysophosphatidylethanolamine, cephalin, cardiolipin, dice-tylphosphate, distearoyl-phosphatidylethanolamine and cholesterol and its derivatives. Similarly, the phospholipid can be a derivative or analogue of any of the foregoing phospholipids or, again, a mixture of two or more of any of the foregoing phospholipids. Such phospholipids can be obtained from commercial sources, natural sources or by synthetic or semi-synthetic means known to those of skill in the art.

In preferred embodiments, the polypeptide-lipid complex is a polypeptide-phospholipid-complex. In a more preferred embodiment, the lipid is 1-palmitoyl-2-oleoyl phosphatidyl-choline ("POPC") or ("1-palmitoyl-2-oleoyl-sn-glycero-3-phosphocholine").

It will be readily apparent to those of skill in the art that the complex comprising a polypeptide of the present invention and a lipid, preferably a phospholipids, can comprise any amount of lipid and any amount of the polypeptide, provided the complex is effective to mediate cholesterol efflux and, in turn, to treat diseases or symptoms associate therewith. As previously mentioned, it has surprisingly been found that when the polypeptides of the present invention are complexed with, for example, POPC at ratios ranging from about 1:0.5 to about 1:5 (polypeptide:POPC), distinct lipid-polypeptide particles are formed having sizes of between about 5 and about 20 nm, which result in a significantly enhanced capacity, i.e., ability, to efflux cholesterol from cells. However, the polypeptide-lipid complexes of the present invention can comprise complexes with other ratios of phospholipid to polypeptide, such as about 100:1, about 10:1, about 5:1, about 3:1, about 2:1, about 1:1, about 1:2, about 1:3, about 1:5, about 1:10 and about 1:100 (wt of polypeptide/wt of lipid).

The polypeptide-lipid complexes of the present invention can be made by any method known to one of skill in the art. In some cases, it is desirable to mix the lipid and the polypeptide prior to administration. Lipids can be in solution or in the form of liposomes or emulsions formed using standard techniques, such as homogenization, sonication or extrusion. Sonication is generally performed with a tip sonifier, such as a Branson tip sonifier, in an ice bath. Typically, the suspension is subjected to several sonication cycles. Extrusion can be carried out by biomembrane extruders, such as the Lipex Biomembrane Extruder™ (Lipex Biomembrane Extruder, Inc. Vancouver, Canada). Defined pore size in the extrusion filters can generate unilamellar liposomal vesicles of specific sizes. The liposomes can also be formed by extrusion through an asymmetric ceramic filter, such as a Ceraflow Microfilter™, which is commercially available from the Norton Company, Worcester, Mass., or through a polycarbonate filter or other types of polymerized materials (i.e., plastics) known to those of skill in the art.

As previously mentioned, the polypeptide-lipid complexes of the present invention can be prepared in a variety of forms including, but not limited to, vesicles, liposomes or proteoliposomes. A variety of methods well known to those skilled in the art can be used to prepare the polypeptide-lipid complexes. A number of available techniques for preparing liposomes or proteoliposomes can be used. For example, a polypeptide of the present invention (e.g., a polypeptide of SEQ ID NO:1 or SEQ ID NO:2, or a variant thereof) can be co-sonicated (using a bath or probe sonicator) with the appropriate lipid to form the polypeptide-lipid complexes. In certain embodiments, the polypeptide can be combined with preformed lipid vesicles resulting in the spontaneous formation of a polypeptide-lipid complex. In another embodiment, the polypeptide-lipid complex can also be made by a detergent dialysis method. In this method, a mixture of the polypeptide, lipid and a detergent, such as sodium cholate, can be dialyzed to remove the detergent and reconstituted to make the polypeptide-lipid complexes (see, e.g., Jonas et al., *Methods Enzymol.*, 128:553-82 (1986)).

In other embodiments, the polypeptide-lipid complexes can be made by co-lyophilization as described in U.S. Pat. Nos. 6,287,590 and 6,455,088, the teachings of both of which are hereby incorporated by reference in their entirety. Other methods are disclosed in, for example, U.S. Pat. Nos. 6,004,925, 6,037,323 and 6,046,166, the teachings of all of which are incorporated herein by reference in their entireties. Other methods of preparing polypeptide-lipid complexes will be apparent to those of skill in the art.

In one preferred embodiment, the polypeptide-lipid complexes can be made by homogenization.

Nucleic Acids

In another embodiment, the present invention provides isolated nucleic acids encoding the polypeptides disclosed herein, expression vectors comprising the nucleic acids, and host cells comprising the expression vectors. More particularly, the present invention provides isolated nucleic acids encoding the polypeptides of the present invention having cholesterol efflux activities similar to full-length apolipoproteins, on a per molecule basis, and having high selectivity for ABAC1 in a manner similar to full-length apolipoproteins, the polypeptides including, but not limited to, polypeptides having an amino acid sequence of SEQ ID NO:1 or SEQ ID NO:2, or a variant as described herein.

In certain embodiments, nucleic acids encoding the polypeptides of the invention are used for transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acids, under the control of a promoter, then express a polypeptide of the present invention, thereby mitigating the effects of a disease associated with dyslipidemia, hypercholesterolemia, inflammation, abnormal glucose metabolism, or Alzheimer's Disease.

Use as Research Tools and in Methods of Diagnosis

The polypeptides and peptidomimetics of the invention are also useful as research tools. For example, the polypeptides or peptidomimetics of the invention can be used for investigating lipoprotein-receptor interactions in animals and animal models. In addition, the polypeptides of the invention can also be used to identify appropriate animal models for elucidation of lipid metabolic pathways. For example, the polypeptides can be used to identify animal models where lipid peroxidation contributes to the progression of atherosclerosis. Moreover, the polypeptides of the invention can be used to evaluate the anti-atherosclerotic potential of other compounds (including, e.g., polypeptide variants and other peptidomimetics).

In some cases, the polypeptides or peptidomimetics of the invention are used to target therapeutic agents to cells and tissues expressing ABCA.

In other embodiments, the polypeptides or peptidomimetics of the invention can be used in methods of diagnosing diseases and disorders associated with aberrant cholesterol efflux or with ABCA. For example, the peptides can be used in assays to diagnose reverse cholesterol transport deficiency and to identify individuals predicted to be responders to peptide treatment. Such diagnostic assays include in vitro assays. For example, cholesterol efflux can be evaluated in an assay in which a polypeptide of the invention is mixed with plasma from a subject and exposed to cells to indicate whether a subject would respond to treatment (e.g., a large increase in efflux in the presence of the peptide compared with plasma-mediated efflux in the absence of the peptide suggests that the subject would be responsive). Similarly, a polypeptide of the invention can be mixed with plasma from a subject to detect changes in HDL subclass distribution and/or to detect changes in anti-oxidative properties of the plasma in the presence of the peptide.

In some embodiments, the polypeptides or peptidomimetics are used for in vivo imaging methods. The polypeptides or peptidomimetics are conjugated to a detectable moiety and administered to a subject (e.g., a mammal such as a human). Detection of the detectable moiety allows imaging of a cell, tissue, or organ of interest, including, e.g., an atherosclerotic lesion or an amyloid plaque.)

Imaging methods are well known in the art. Examples of imaging modalities include, but are not limited to, magnetic resonance, nuclear magnetic resonance, radioscintigraphy, positron emission tomography, computed tomography, near-infrared fluorescence, X-ray, ultra sound, ultraviolet light, or visible light (see, e.g., Dahnhert, Radiology Review Manual (4th ed. 1999); Brant et al., Fundamentals of Diagnostic Radiobiology (2nd ed. 1999); Weissleder et al., Primer of Diagnostic Imaging (2nd ed. 1997); Buddinger et al., Medical Magnetic Resonance A Primer, Society of Magnetic Resonance, Inc. (1988); and Weissleder et al., *Nature Biotech.*, 17:375-378 (1999)).

The phrase "detectable moiety," as used herein, refers to a moiety or label that can be imaged and/or detected in vivo, ex vivo, or in vitro by a procedure or modality described herein or known to one of skill in the art. The detectable moiety can be directly or indirectly linked to a polypeptide or peptidomimetic of the invention. Linking of a detectable moiety to a polypeptide or peptidomimetic of the invention may be achieved by covalent or non-covalent means using well known methods, usually involving interaction with one or more functional groups located on the detectable moiety, the linker and/or the polypeptide. The particular linker is not a critical aspect of the invention. Any linker known in the art may be used as long it binds the polypeptide or peptidomimetic and the detectable moiety together for an adequate period, i.e., a period sufficient for the polypeptide the desired target and be detected.

The detectable moieties used in the methods of the present invention can be any moiety capable of detection either directly or indirectly in an imaging procedure described herein or known to one of skill in the art. These may be include moieties which emit or may be caused to emit detectable radiation (e.g., by radioactive decay, fluorescence excitation, spin resonance excitation, etc.), moieties which affect local electromagnetic fields (e.g., paramagnetic, superparamagnetic, ferrimagnetic or ferromagnetic species), moieties which absorb or scatter radiation energy (e.g., chromophores, particles (including gas or liquid containing vesicles), heavy elements and compounds thereof, etc.), and moieties which generate a detectable substance (e.g., gas microbubble generators). See, for example, U.S. Pat. Nos. 5,228,446; 4,647,447; 4,863,715; 4,770,183, and 5,387,080; PCT Publication No. WO 97/25073, WO 96/09840, WO 85/02772, WO 92/17212, WO 97/29783, WO 91/15243, WO 93/05818, WO 96/23524, WO 95/26205 and WO 96/17628; EP-A-554213; and GB 9624918.0; WO 91/14460, WO 89/00557, WO 92/17215, WO 96/40287 and WO 96/22914; and U.S. Pat. Nos. 4,647,447, 5,367,080 and 5,364,613; Matsuoka, Topics in Applied Chemistry: Infrared absorbing dyes (1990); Waring et al., Topics in Applied Chemistry: The Chemistry and Application of Dyes (1990); "Handbook of Fluorescent Probes and Research Chemicals" Haugland, Molecular Probes Inc, 1996, DE-A-4445065, DE-A-4326466, JP-A-3/228046, Narayanan et al., *J. Org. Chem.*, 60:2391-2395 (1995), Lipowska et al., *Heterocyclic Comm.*, 1:427-430 (1995), Fabian et al., *Chem. Rev.*, 92:1197 (1992); PCT Publication No. WO96/23525: Strekowska et al., J. Org. Chem., 57:4578-4580 (1992); and PCT Publication No. WO 96/17628; visible dyes as described in, Waring and Hallas, The Chemistry and Application of Dyes, Topics in Applied Chemistry (1990); Haugland, Handbook of Fluorescent Probes and Research Chemicals (6th ed. 1996).

In certain circumstances, it may be desirable that the linker biodegrade after administration. By selecting an appropriately biodegradable linker, it is possible to modify the biodistribution and bioelimination patterns for the polypeptide and/or detectable moiety.

Kits

In another aspect, the present invention provides kits for the treatment, i.e., amelioration, or prevention of a disease or disorder, i.e., condition, associated with dyslipidemia, hypercholesterolemia and inflammation; or a disease or condition associated with abnormal glucose metabolism; or Alzheimer's Disease. In a preferred embodiment, the present invention provides kits for the treatment, i.e., amelioration, of one or more symptoms of a disease or for the prophylactic treatment of a subject (e.g., human or animal) at risk for the disease. The kits preferably comprise a container containing one or more of the polypeptides (or peptidomimetics) of this invention. The polypeptide or peptidomimetic can be provided in a unit dosage formulation (e.g., tablet, caplet, patch, suppository, etc.) and/or can be optionally combined with one or more pharmaceutically acceptable excipients.

The kit can, optionally, further comprise one or more other agents used in the treatment of a disease or condition associated with dyslipidemia, hypercholesterolemia and inflammation (such as heart disease and/or atherosclerosis); or a disease or condition associated with abnormal glucose metabolism; or Alzheimer's Disease. Such agents include, but are not limited to, those set forth above in connection with the sections above and the section on "Combination Therapy." For instance, in certain embodiments, the kit can include beta blockers, vasodilators, aspirin, statins, ace inhibitors or ace receptor inhibitors (ARBs) and the like.

In addition, the kits can optionally include labeling and/or instructional materials providing directions (i.e., protocols) for the practice of the methods or use of the "therapeutics" or "prophylactics" of this invention. Preferred instructional materials describe the use of one or more polypeptides or peptidomimetics of this invention, for example, to mitigate one or more symptoms of atherosclerosis and/or to prevent the onset or increase of one or more of such symptoms in an individual at risk for atherosclerosis or to mitigate one or more symptoms of a disease associated with abnormal glucose metabolism; or to mitigate one or more symptoms of Alzheimer's Disease or Mild Cognitive Impairment. The instructional materials can also, optionally, teach preferred dosages/therapeutic regiment, counter indications and the like.

While the instructional materials typically comprise written or printed materials, they are not limited to such. Any medium capable of storing such instructions and communicating them to an end user is contemplated by this invention. Such media include, but are not limited to, electronic storage media (e.g., magnetic discs, tapes, cartridges, chips, etc.), optical media (e.g., CD ROM), and the like. Such media may include addresses to internet sites that provide such instructional materials.

The invention will be described in greater detail by way of specific examples. The following examples are offered for illustrative purposes, and are not intended to limit the invention in any manner. Those of skill in the art will readily recognize a variety of non-critical parameters that can be changed or modified to yield essentially the same results.

EXAMPLES

Example 1

This example shows toxicity of a peptide ATI-5261 when the peptide was administered at high doses.

Cytotoxicity of an HDL mimetic peptide ATI-5261 at high doses was evaluated in rats and rabbits (FIG. 1). Male chow-fed Wistar rats (Panels A and B) were intravenously (IV) administered peptide ATI-5261 (lipid-free) at doses of 3, 30 and 300 mg/kg or vehicle alone at 48 h intervals for a total of 4 injections. Blood was collected for assessment of plasma alanine aminotransferase (ALT, panel A) and aspartate aminotransferase (AST, panel B) activities at the indicated times. Male New Zealand White rabbits (Panels C and D) fed standard chow were administered a single IV bolus injection of 3, 30 or 300 mg/kg ATI-5261, and blood subsequently collected for assessment of ALT (panel C) and AST (panel D). Values are means±SD, n=5 animals per group, with duplicate determinations made for rats at 0.2-24 h. The results showed that high-dose administration induced a cytotoxic response in rats and rabbits.

Figure 2:
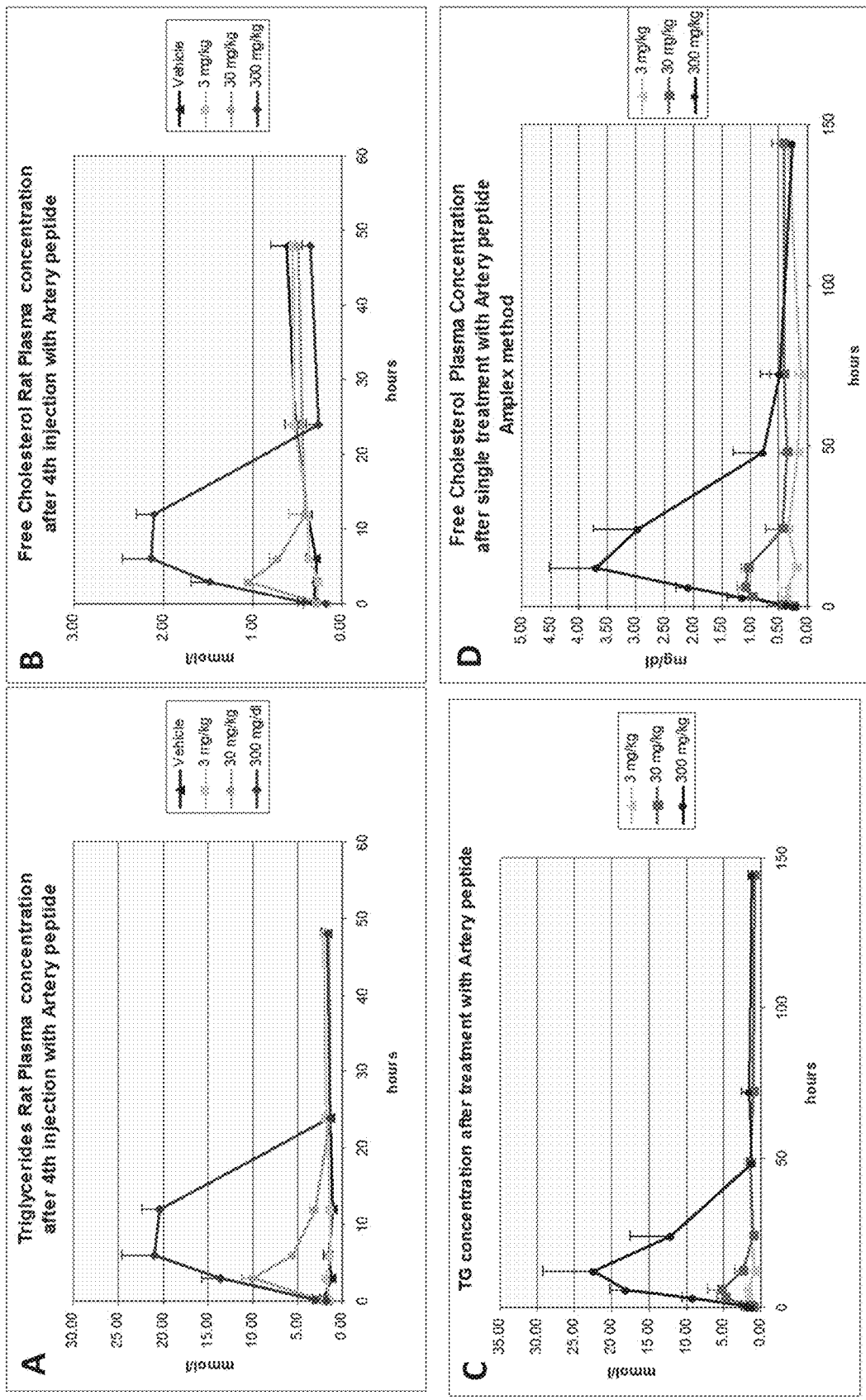
FIG. 2—Panels A-D: High dose administration of HDL mimetic ATI-5261 increases plasma triglycerides and cholesterol in rats and rabbits.

High-dose administration also increased plasma triglycerides and cholesterol (FIG. 2). For the experiments in FIG. 2, male chow-fed Wistar rats (Panels A and B) were administered ATI-5261 at doses of 3, 30, and 300 mg/kg as described in FIG. 1. Plasma triglyceride (TG, Panel A) and unesterified cholesterol (Panel B) concentrations were determined enzymatically at the times indicated. Male New Zealand White rabbits (Panels C and D) were administered a single bolus injection of ATI-5261 of 3, 30 or 300 mg/kg, and plasma TG (Panel C) and unesterified cholesterol (Panel C) determined. Values are means±SD, n=5 animals per group, with duplicate determinations made for rats at 0.2-24 h.

Figure 3:
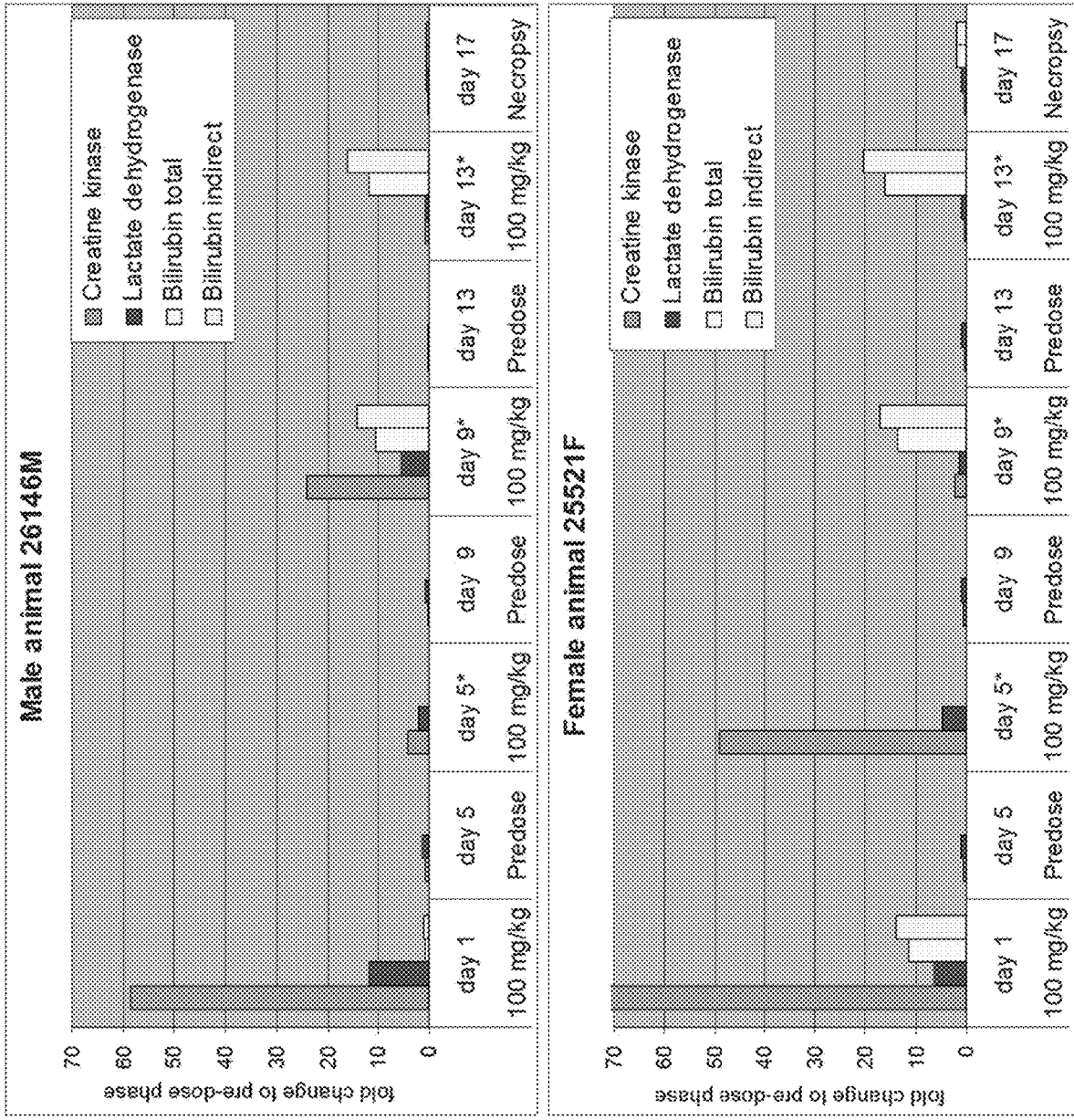
FIG. 3—Intravenous infusion of high dose ATI-5261 induces a cytotoxic response in monkeys.

Intravenous infusion of high dose ATI-5261 additionally induced a cytotoxic response in monkeys (FIG. 3). Male (upper panel) and female (lower panel) cynomolgus monkeys were administered ATI-5261 at a fixed dose of 100 mg/kg by IV infusion (60 min) every 96 hours for a total of 4 injections. Blood was collected 24 h post infusion and levels of plasma ALT, AST, creatine kinase (CPK), and total and indirect bilirubin determined. Values are expressed as a fold-increase vs. pre-dose levels. A marked increase in plasma creatine kinase was seen after the first infusion (male and female monkeys), with relatively modest increases returning to base-line with subsequent infusions.

Figure 4:
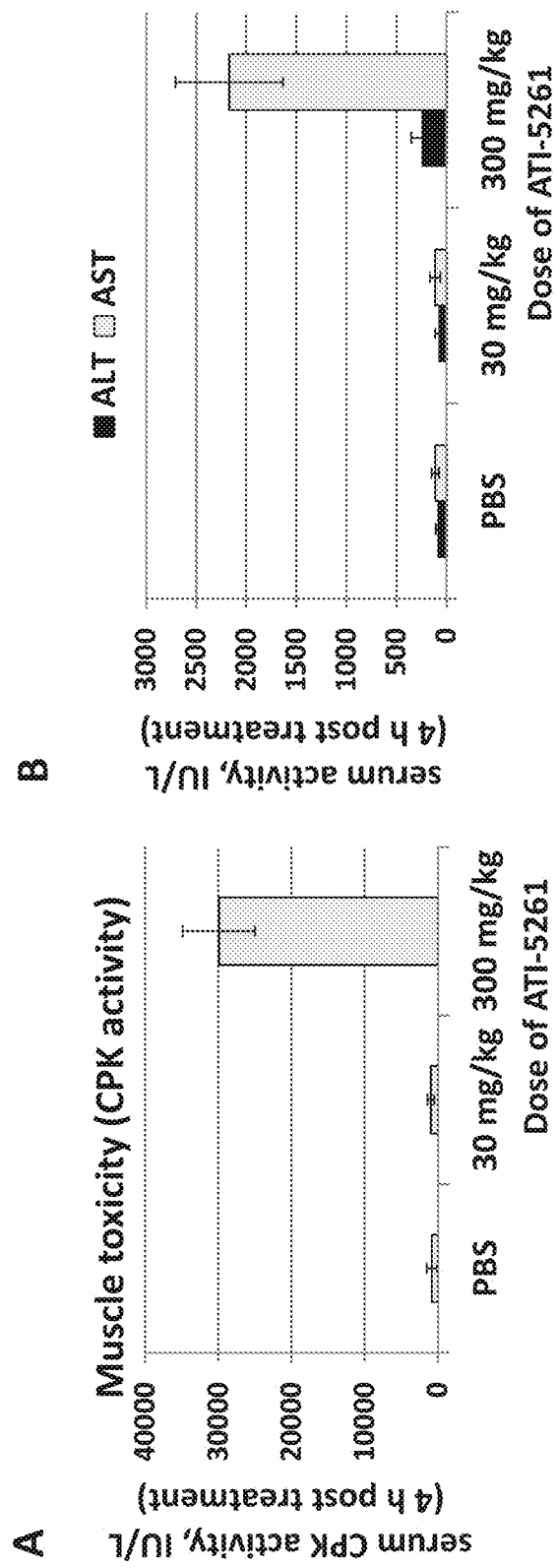
FIG. 4—Panels A and B: The cytotoxic response of ATI-5261 found in rat, rabbit and cynomolgus monkey is recapitulated in mice.

The high-dose cytotoxic response of ATI-5261 observed in rat, rabbit and cynomolgus monkey is additionally recapitulated in mice (FIG. 4). Male chow-fed C57bl/6 mice were injected intraperitonelly (IP) with 30 or 300 mg/kg of lipid-fee ATI-5261. Blood was collected via the retro-orbital plexus 4 h after peptide injection and plasma subsequently obtained for measurement of CPK (Panel A) and ALT and AST activities (Panel B, ALT left bars, AST, right bars).

Values are means±SD, n=4 mice per group. High levels of cytotoxic markers were seen following administration of 300 mg/kg ATI-5261.

Example 2

Figure 5:
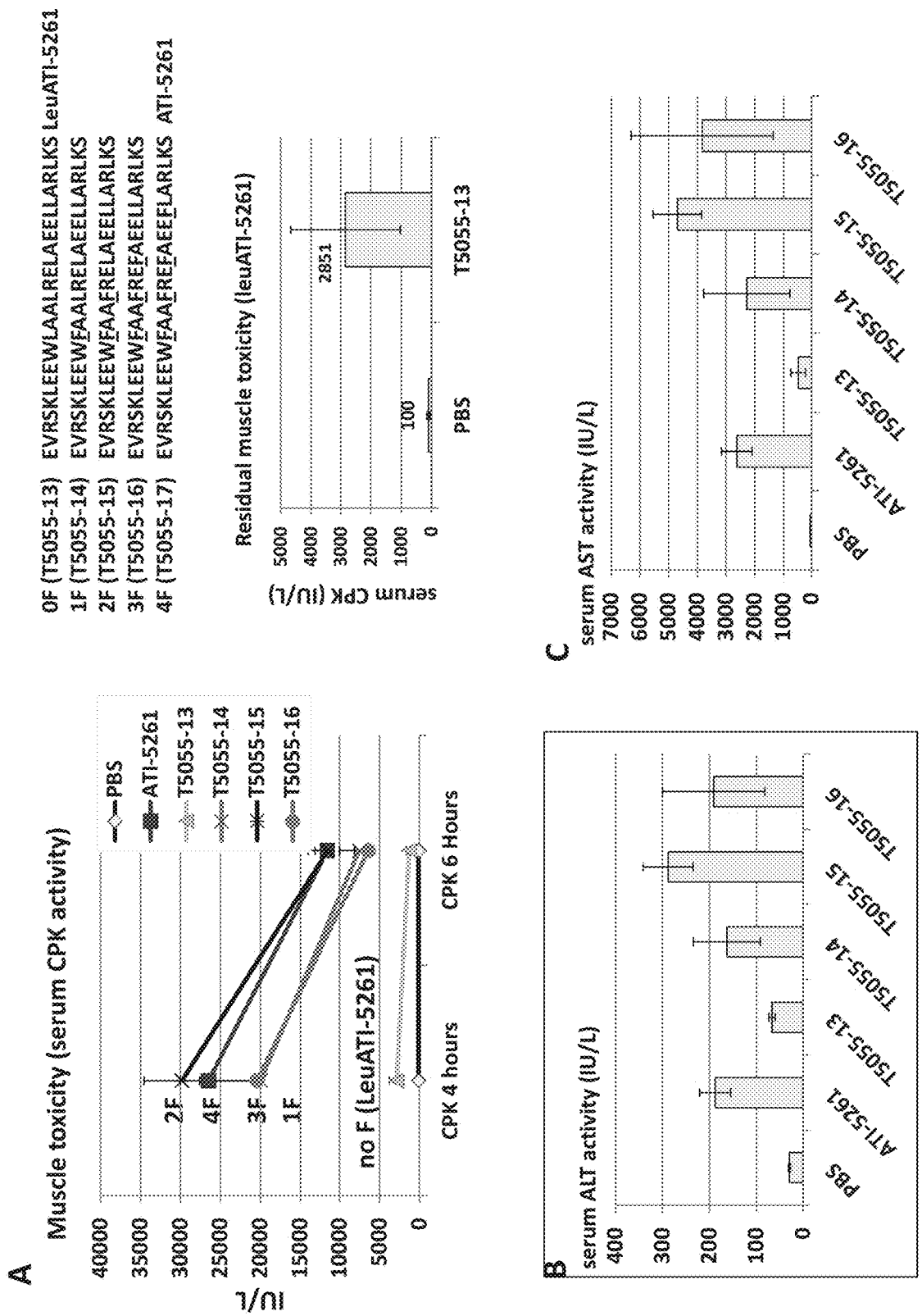
FIG. 5—Panels A-C: Aromatic phenylalanine residues associated with the non-polar surface of ATI-5261 contributed to a majority of the peptide toxicity. Peptides=SEQ ID NOS:5-9.

This example illustrates that aromatic phenylalanine residues associated with the non-polar surface of ATI-5261 contributed to the majority of the peptide toxicity (FIG. 5). Analogs of ATI-5261 with aliphatic leucine (L) were created to evaluate toxicity (FIG. 5). Variants of ATI-5261 with aliphatic leucine (L) systematically used (sequence list Panel A) to replace phenylalanine (F) were injected IP into male chow-fed C57Bl/6 mice. Blood was collected via retro-orbital plexus 4 h after injection for isolation of plasma. Levels of plasma CPK (Panel A), ALT (panel B) and AST (Panel C) were determined as described in FIG. 1. Values are means±SD, n=4 mice per group. Inset in panel A shows residual toxicity associated with the all aliphatic analog lacking phenylalanine residues (T5055-13, i.e. zero or no F) vs. vehicle alone (PBS control).

Figure 6:
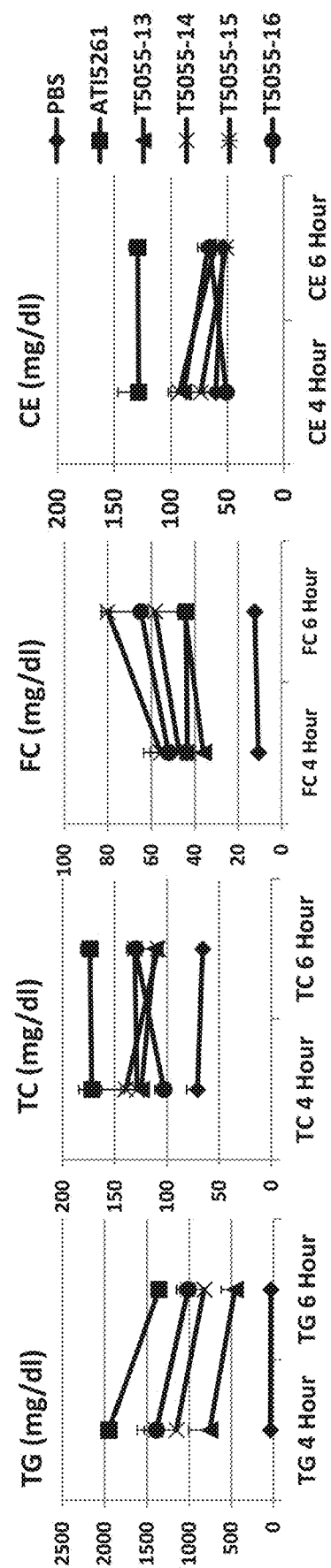
FIG. 6—Concentrations of plasma lipids in C57Bl/6 mice following administration of the aliphatic analogs of ATI-5261.

The concentrations of plasma lipids in C57Bl/6 mice following administration of the aliphatic analogs of ATI-5261 was also determined. FIG. 6 shows the concentration of lipids in blood plasma collected from mice in FIG. 5, following administration of peptide at 300 mg/kg. All values (mg/dl) are means±SD, n=4, determined at 4 and 6 h post treatment with peptide. ATI-5261 produced a marked increase in plasma TG, total and unesterified (free) cholesterol (FC), which was greatly attenuated using an aliphatic analog lacking aromatic phenylalanine residues (i.e., T5055-13).

Figure 7:
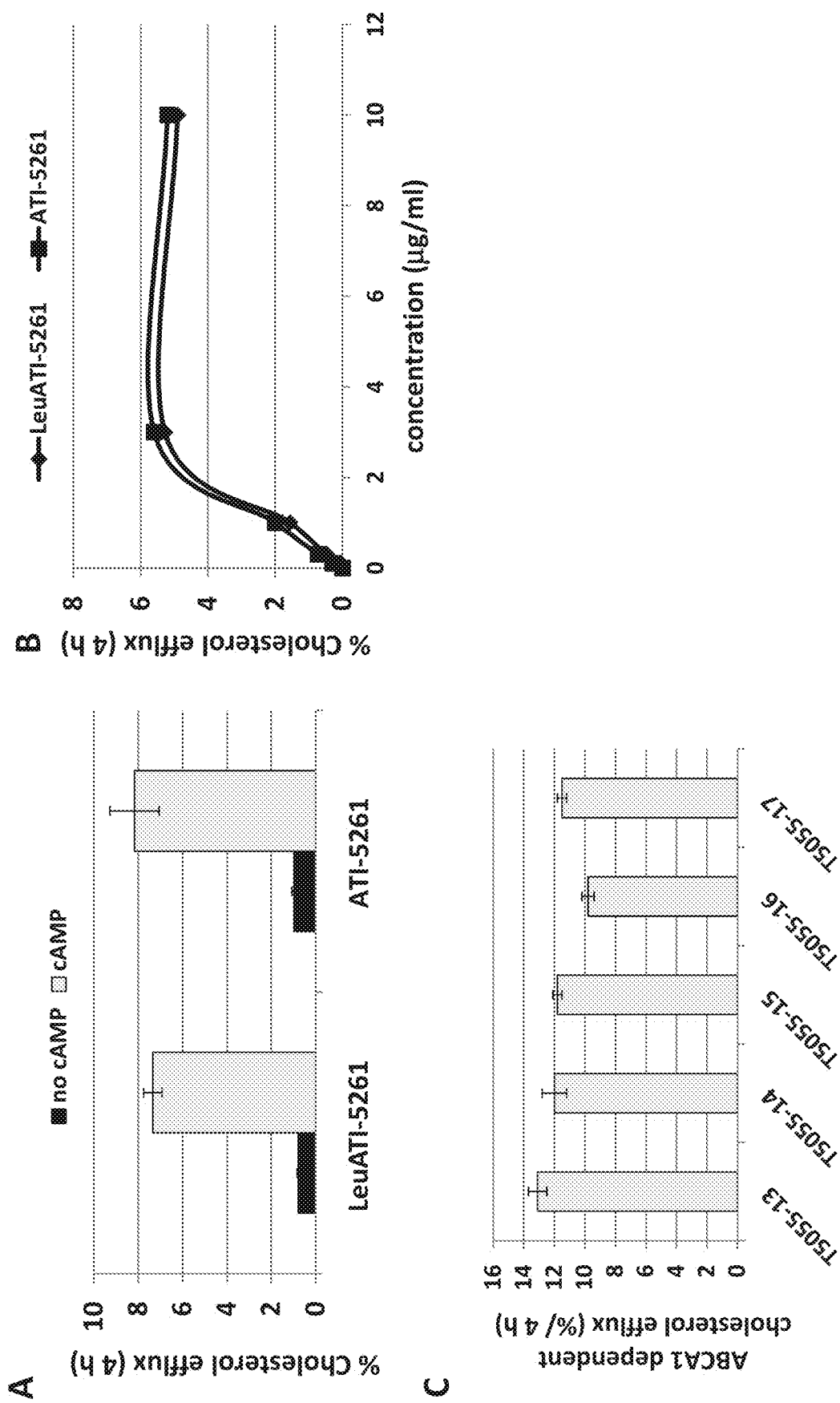
FIG. 7—Panels A-C: Demonstration that aliphatic analogs of ATI-5261 lacking phenylalanine residues retain potent ABCA1 selective cholesterol efflux activity. In panel A and all similar two-bar graphs in the Figures that show cholesterol efflux activity with and without cAMP, the left bar represents cholesterol efflux without cAMP and the right bar represents cholesterol efflux after cAMP (i.e. ABCA-dependent efflux).

Aliphatic analogs of ATI-5261 lacking phenylalanine residues retained potent ABCA1 selective cholesterol efflux activity (FIG. 7). J774 macrophages were labeled (48 h) with [$^3$H]cholesterol and treated (18 h) with a cAMP analog to induce ABCA1 protein expression; cells incubated in the absence of cAMP (left bars) served as controls. Panel A—The all aliphatic analog of ATI-5261 (LeuATI-5261, i.e. T5055-13) stimulated cholesterol efflux in an ABCA1-dependent manner. Peptides were used at a concentration of 30 µg/ml, which was maximal for promoting cholesterol efflux activity. Panel B—Dependence of cholesterol efflux on the concentration of peptides. Similar saturation in cholesterol efflux was obtained at roughly 3 µg/ml peptide, indicating the LeuATI-5261 analog retained ability to stimulate cholesterol efflux with high efficiency, similar to the parent ATI-5261 peptide. Panel C shows a summary of ABCA1-dependent cholesterol efflux activity of peptides with various leucine substitutions. Results are expressed as the difference in cholesterol efflux (%/4 h) observed using cAMP treated vs. non-treated J774 cells. Values are means±SD, n=3. The results show that aliphatic analogs of ATI-5261 lacking phenylalanine residues retained potent ABCA1-selective cholesterol efflux activity.

Example 3

Figure 8:
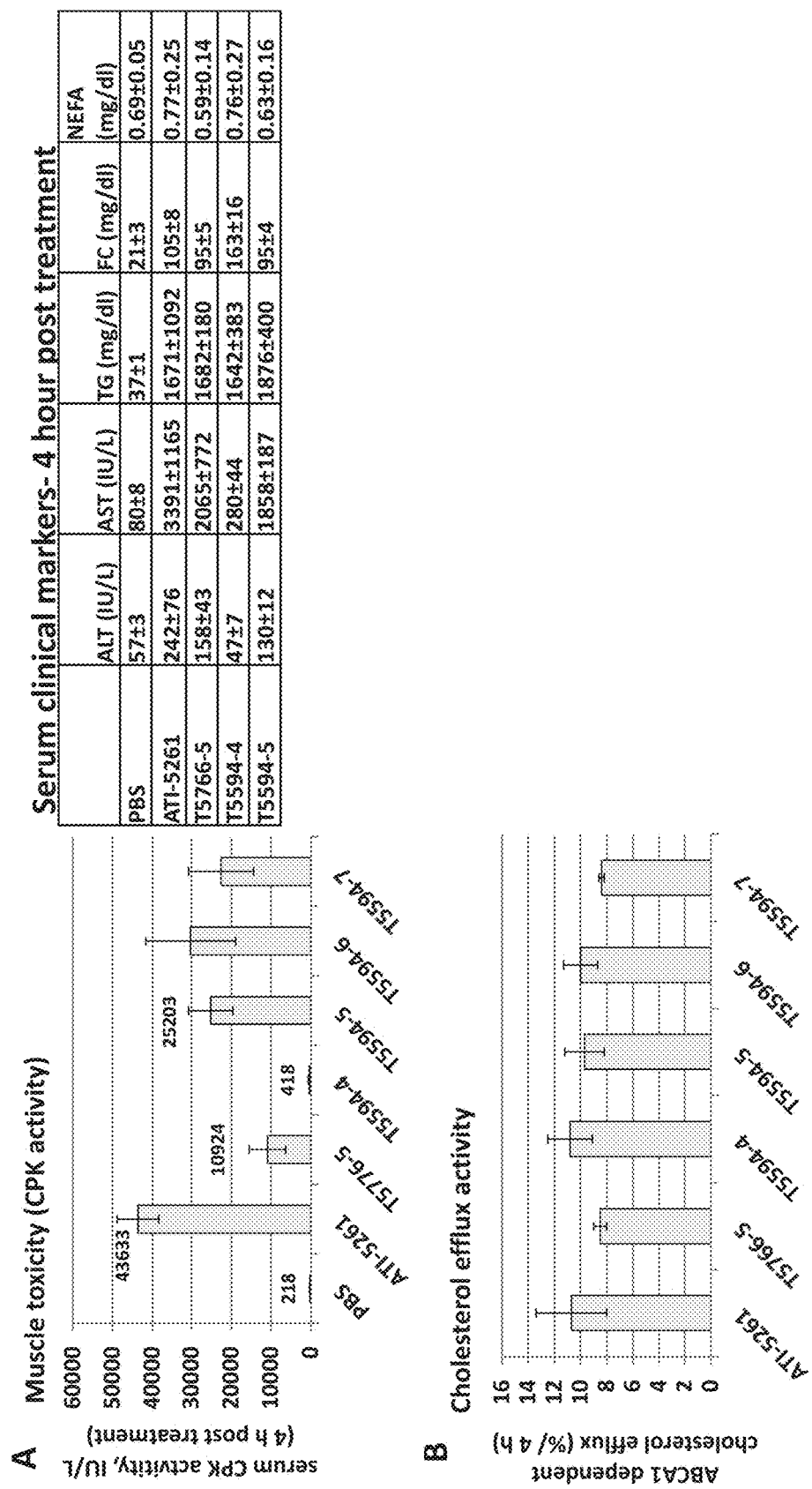
FIG. 8—Panels A and B: Toxic properties of lysine residues in ATI-5261. Peptides=SEQ ID NOS:10-12.

To test whether the cytotoxic response of ATI-5261 was preferentially linked to arginine or lysine residues, peptide analogs of ATI-5261 with lysine eliminations or R>K substitutions were created and evaluated in mice (FIG. 8). Panel A-Safety and TG elevating effects were evaluated by injecting (IP) peptides (300 mg/kg) into male, chow-fed C57Bl/6 mice, as described in FIG. 5. Values are means SD, n=4. Removal of lysine25 (K25) from C-terminal end of ATI-5261, by either ablation (T5766-5) or amino acid substitution (K25→N, T5594-4) greatly reduced muscle toxicity as judged by decreased CPK activity in plasma (left panel), suggesting lysine residues promote toxicity. Peptides with all lysine residues (i.e. R>K substitutions, T5594-5) also displayed cytotoxic and TG elevating activity, consistent with a role of either lysine or arginine in mediating negative effects of the peptides. Panel B—ABCA1-dependent cholesterol efflux activity of peptides determined using J774 macrophages labeled with [$^3$H]cholesterol. Results are expressed as the ABCA1 component of efflux, as described in FIG. 7. All peptides were functional and stimulated high-levels of cholesterol efflux at a saturating concentration of 3 µg/ml, similar to that seen using the parent ATI-5261 peptide.

Figure 9:
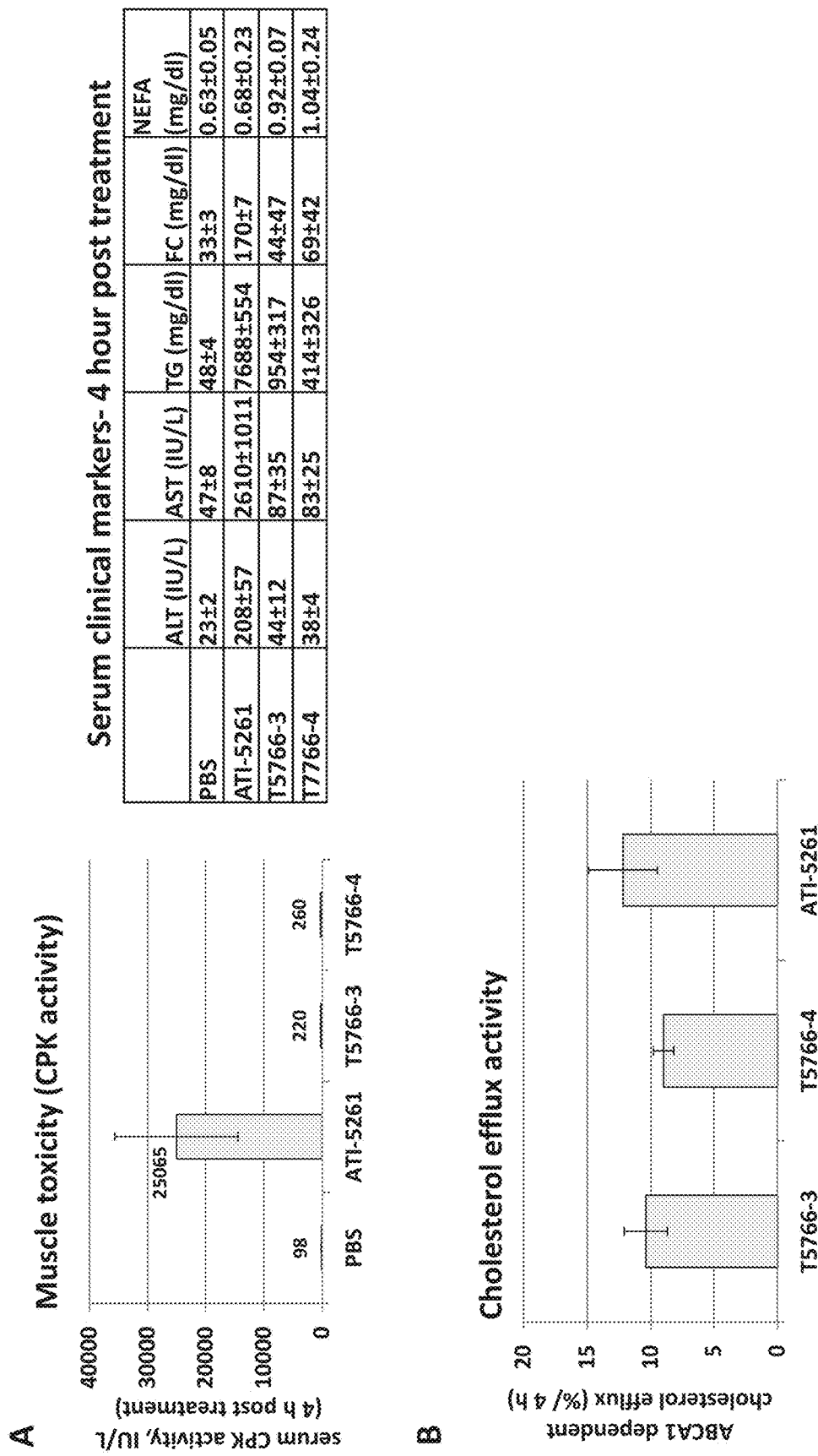
FIG. 9—Panels A and B: Toxic properties of arginine residues in ATI-5261. Peptides=SEQ ID NOS:13 and 14.

To further evaluate the role of specific charged residues in the toxic response of ATI-5261, arginine residues were replaced with uncharged glutamine (Q) or asparagine (N) (FIG. 9). Panel A—Safety and TG elevating effects were evaluated by injecting (IP) peptides (300 mg/kg) into male, chow-fed C57Bl/6 mice, as described in FIG. 5. Values are means SD, n=4. Use of either glutamine or asparagine at positions 3 and 14, i.e. R3,14>Q (T5766-3) or R3,14>N (T5766-4) respectively, greatly reduced the increase in CPK and TG elevating effects of ATI-5261, indicating that the positively charged arginine was, in part, contributing to toxic responses of the peptide. Panel B—ABCA1-dependent cholesterol efflux activity of peptides determined using J774 macrophages labeled with [$^3$H]cholesterol. Results are expressed as the ABCA1 component of efflux, as described in FIG. 7. All peptides were functional and stimulated high-levels of cholesterol efflux at a saturating concentration of 3 µg/ml, similar to that seen using the parent ATI-5261 peptide.

Example 4

This example demonstrates that hydrophobicity can be modulated to reduce the residual toxicity of ATI-5261 analogs. To identify factors in addition to charged residues that eliminate the toxicity of ATI-5261, hydrophobicity was systematically reduced using alanine substitutions (FIG. 10). Panel A—Safety and TG elevating effects were evaluated by injecting (IP) peptides (300 mg/kg) into male, chow-fed C57Bl/6 mice, as described in FIG. 5. Values are means SD, n=4. Use of single leucine to alanine substitution (L24A or L21A, i.e. T4883-6 or T4883-7) in the LeuATI-5261 peptide was sufficient to eliminate the residual muscle toxicity (i.e. CPK activity) and further reduced cytotoxic response and TG elevating effects. Panel B—ABCA1-dependent cholesterol efflux activity of peptides determined using J774 macrophages labeled with [$^3$H]cholesterol. Results are expressed as the ABCA1 component of efflux, as described in FIG. 7. Peptides with single L24A or L21A substitutions were functional and stimulated high-levels of cholesterol efflux at a saturating concentration of 3 µg/ml, similar to that seen using the parent ATI-5261 peptide. Panel C-Detailed study verifying the potent functionality of peptides. [$^3$H] cholesterol labeled, J774 cells treated with cAMP were incubated with increasing concentration of peptides and cholesterol efflux into the medium assessed after 4 h. Peptides with single alanine substitutions supported highly potent efflux activity, as judged by low Km (3 µg/ml or less) and saturation in cholesterol efflux, indicating amino acids substitutions reducing overall hydrophobicity can be used to create safe and effective peptides.

Further evidence that hydrophobicity can be modulated to reduce the residual toxicity of ATI-5261 analogs is provided in the results provided in FIG. 11. To identify additional amino acid substitutions that can be used to reduce the residual toxicity of ATI-5261 analogs, alanine was systematically used to replace valine (V) or leucine (L) within different regions of the peptide. Panel A—Safety and TG elevating effects were evaluated by injecting (IP) peptides (300 mg/kg) into male, chow-fed C57Bl/6 mice, as described in FIG. 5. Values are means SD, n=4. Use of a single leucine to alanine substitution (L24A) in combination with tryptophan (W) substitution (T5505-9) markedly reduced the increase in plasma CPK and AST as well as TG elevating activity. This combination appeared to be most favorable as substitution involving V2 and L10 retained some cytotoxic and TG elevating effects, albeit at greatly reduced levels compared to ATI-5261. Panel B—ABCA1-dependent cholesterol efflux activity of peptides determined using J774 macrophages labeled with [3H]cholesterol. Results are expressed as the ABCA1 component of efflux, as described in FIG. 7. All peptides were functional and stimulated high levels of cholesterol efflux at a saturating concentration of 10 µg/ml. Panel C—Detailed study verifying the potent functionality of peptide T5505-9 (L24A; W9L substitutions), determined as described for FIG. 11. Peptide T5505-9 stimulated cellular cholesterol efflux with high efficiency, as judged by low Km (0.58 µg/ml) and saturation in cholesterol efflux at ~3 µg/ml concentrations.

Additional substitutions of less hydrophobic amino acids for tryptophan can be used to reduce toxicity of ATI-5261 (FIG. 12). Peptides with either alanine (A) or valine (V) substitutions for tryptophan (W) were evaluated for toxic responses, TG elevating effects and functionality in mediating cellular cholesterol efflux. Panel A—Safety and TG elevating effects were evaluated by injecting (IP) peptides (300 mg/kg) into male, chow-fed C57Bl/6 mice, as described in FIG. 5. Values are means SD, n=4. Peptides with W→A or V substitutions produced low levels of plasma CPK, AST and TG elevating effects compared to ATI-5261. Panel B—ABCA1-dependent cholesterol efflux activity of peptides determined using J774 macrophages labeled with [³H]cholesterol. Cholesterol efflux from cells treated with and without cAMP is shown. All peptides were functional and stimulated cholesterol efflux in an ABCA1 dependent manner. Panel C—Peptide analogs with W9A or L24A; W9V substitutions stimulated cellular cholesterol efflux with high efficiency, as judged by low Km and saturation in cholesterol efflux at ~3 µg/ml concentrations.

Example 5

Figure 13:
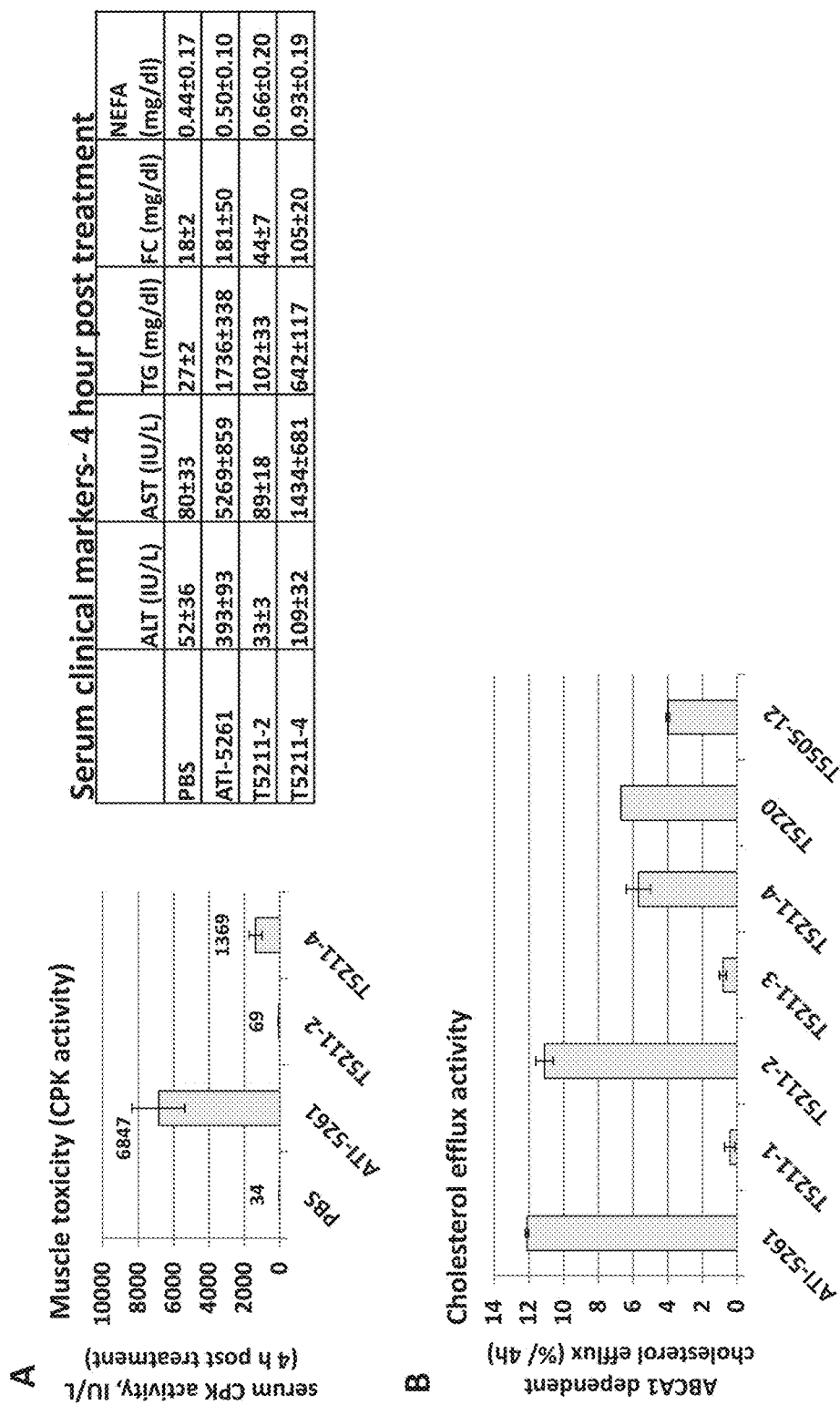
FIG. 13—Panels A and B: Hydrophobic amino acids can be used at position R14 to create safe and effective peptides. Peptides=SEQ ID NOS:25-29.

This example demonstrates that hydrophobic amino acids can be used at position R14 to create safe and effective peptides. Use of multiple alanine substitutions down the length of LeuATI-5261 produced low toxicity and greatly ablated TG elevating effects of ATI-5261 analogs (FIG. 11, peptide T5505-12). However, excessive use of alanine substitutions produces a loss of functionality in mediating cellular cholesterol efflux. To rescue the cholesterol efflux activity of peptides with multiple alanine substitutions, we deleted R14 or replaced R14 with hydrophobic leucine within T5505-12 or ATI-5261 (FIG. 13). These deletions/ substitutions expand the hydrophobic surface while removing a harmful positively charged residue from the lipid-water interface of the peptide. Panel A—Safety and TG elevating effects were evaluated by injecting (IP) peptides (300 mg/kg) into male, chow-fed C57Bl/6 mice, as described in FIG. 5. Values are means SD, n=4. A peptide (T5211-2) with an R14L substitution displayed little or no toxic responses and low TG in plasma, despite the use of alanine at various positions (V2, L6 and L24>A). Panel B—ABCA1-dependent cholesterol efflux activity of peptides determined using J774 macrophages labeled with [³H] cholesterol. Results are expressed as the ABCA1 component of efflux, as described in FIG. 7. The peptide analog of T5055-12 with R14L substitution (i.e. T5211-2) displayed high-levels of cholesterol efflux activity at a saturating concentration (10 µg/ml) similar to ATI-5261 and markedly improved vs. the parent T5055-12 peptide. Thus, the use of hydrophobic leucine residues at the lipid-water interface of an amphipathic α-helix peptide can be used to restore cholesterol efflux activity of peptides rendered less toxic through use of alanine substitutions.

Example 6

This example demonstrates that an R14L substitution can be used in other ATI-5261 analogs to create safe and effective HDL mimetic peptides. Peptide analogs of T5211-2 containing the R14L substitution were created by substituting valine (V) for various alanine residues (FIG. 14). Panel A—Safety and TG elevating effects were evaluated by injecting (IP) peptides (300 mg/kg) into male, chow-fed C57Bl/6 mice, as described in FIG. 5. Values are means SD, n=4. Peptide analogs of T5211-2 containing single or multiple A→V substitutions and lacking C-terminal residues KS exhibited relatively low cytotoxic responses compared to ATI-5261 positive control. Panel B—ABCA1-dependent cholesterol efflux activity of peptides determined using J774 macrophages labeled with [3H]cholesterol. Peptide analogs of T5211-2 were functional, mediating high-levels of cholesterol efflux in an ABCA1-dependent manner at concentrations (10 µg/ml) similar to ATI-5261. Panel C-Concentration dependence studies demonstrated that the R14L peptides with and without valine substitutions stimulated cholesterol efflux in a highly efficient manner, displaying a low Km and saturation of cholesterol efflux at 3 µg/ml. The panel on the left shows the efflux activity of the R14L peptide (batch # T6023-3, i.e., T5211-2 original), illustrating that the R14L substitution imparted potent functionality in comparison to weak activity of the parent T5055-12 peptide (see FIG. 11, panel C).

Example 7

This example demonstrates that citrulline substitutions for arginine can be used to create safe and effective HDL mimetic peptides (FIG. 15). Citrulline is a natural amino acid analog of arginine that lacks a positive charge, but retains hydrogen bonding to preserve salt-bridge configurations. To test whether lack of positive charge, per se, eliminates toxicity and TG elevating effects of ATI-5261, a series of peptide analogs were created with R→Citrulline substitutions at positions 3, 14 and 23 (see sequence list in FIG. 15). The figure and table show safety and TG elevating effects of peptides injected IP (300 mg/kg) into male, chow-fed C57Bl/6 mice, as described in FIG. 5. Values are means SD, n=4. For the peptides tested, use of citrulline at position 3 and 14 greatly reduced the muscle toxicity of ATI-5261, while overall general toxicity (AST) and plasma TG remained increased.

Figure 16:
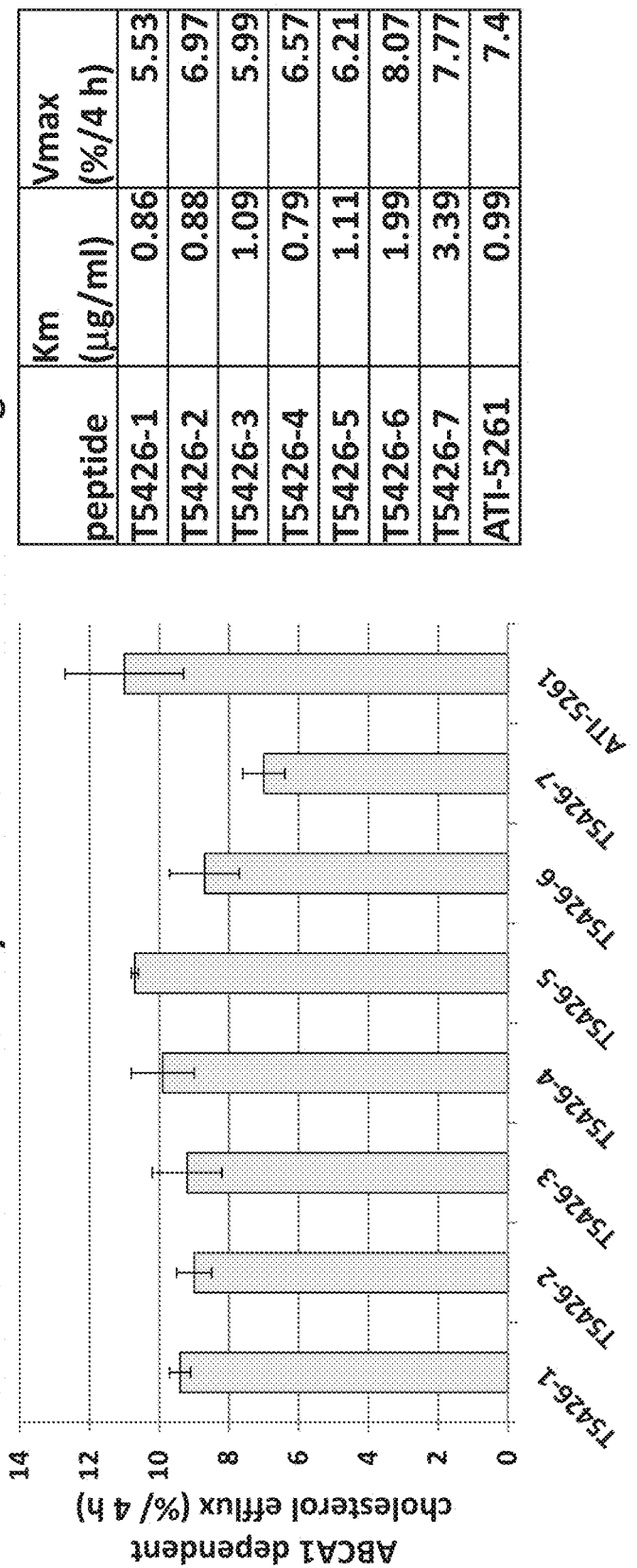
FIG. 16—Citrulline analogs of ATI-5261 retained functionality and stimulated cholesterol efflux with high potency.

Citrulline analogs of ATI-5261 retained functionality and stimulated cholesterol efflux with high potency. FIG. 16 shows activity of peptides to stimulate cholesterol efflux determined using J774 macrophages labeled with [3H]cholesterol. Results are expressed as the ABCA1 component of efflux, as described in FIG. 7. High levels of ABCA1-dependent cholesterol efflux were obtained with saturating concentrations (3 µg/ml) of all peptides, similar to ATI-5261. Km and Vmax values characterizing the peptides potency for mediating cholesterol efflux are shown in the table. All peptides tested, with the exception of triple R3,14, 23→Citrulline substitution (T5426-7), proved highly efficient in mediating cholesterol efflux, as judged by low Km (i.e. high affinity for ABCA1) similar to the parent ATI-5261 peptide.

Example 8

This example demonstrates that citrulline analogs of ATI-5261 support other amino acid substitutions. Various hydrophobic amino acid (W→L, V or A) substitutions were created in the double citrulline form of ATI-5261 (i.e. R3, 14→Citrulline, T5426-4), to test whether the peptide could support other amino acid changes to further eliminate toxic responses and TG elevating effects. Results of these experiments are shown in FIG. 17. Panel A—Safety and TG elevating effects were evaluated by injecting (IP) peptides (300 mg/kg) into male, chow-fed C57Bl/6 mice, as described in FIG. 5. Values are means SD, n=4. Citrulline forms of ATI-5261 with W9→L, V or A substitution(s) displayed little or no toxic- and TG elevating-responses in plasma. Panel B—ABCA1-dependent cholesterol efflux activity of peptides determined using J774 macrophages. Results are expressed as the ABCA1 component of efflux, as described in FIG. 7. Peptide analogs with citrulline substitutions were functional and displayed high-levels of cholesterol efflux activity at a saturating concentration (3 µg/ml) similar to ATI-5261.

Example 9

Figure 18:
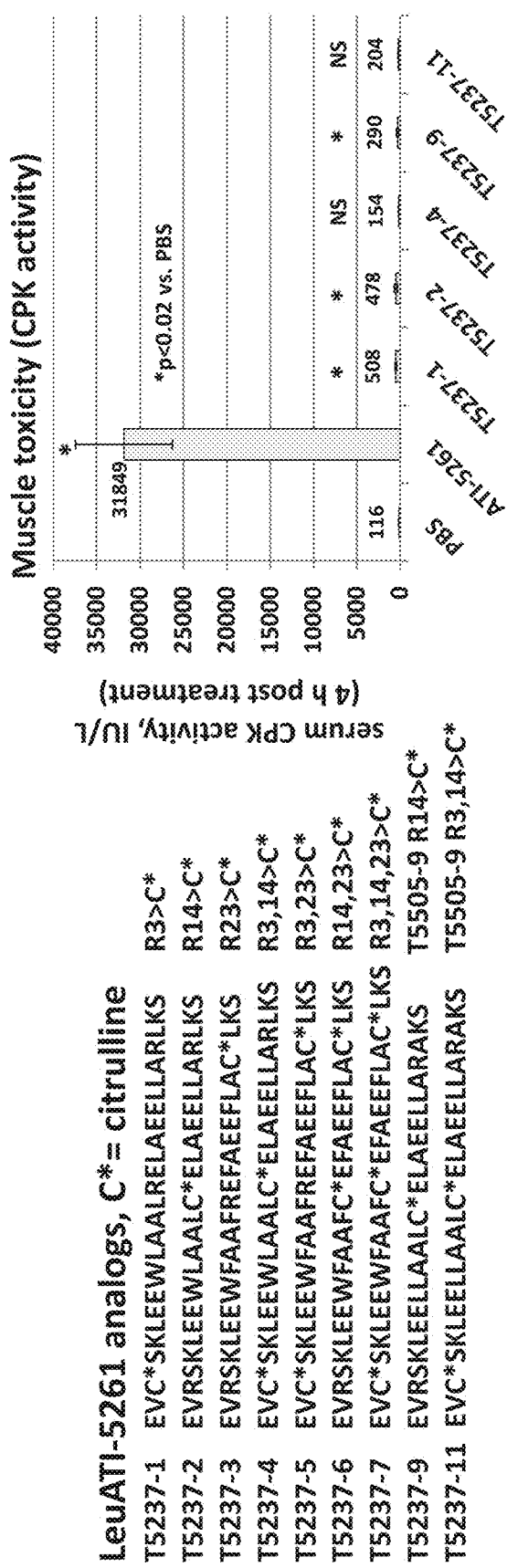
FIG. 18—The LeuATI-5261 peptide can support citrulline substitutions to create safe and effective HDL mimetic peptides. Peptides=SEQ ID NOS:44-52.

This example demonstrates that LeuATI-5261 peptide can support citrulline substitutions to create safe and effective HDL mimetic peptides. To test whether elimination of both positively charged arginine and aromatic phenylalanine (F) residues created safe peptides that retained potent cholesterol efflux activity, a series of citrulline substitutions were created in the LeuATI-5261 analogs (see sequence list in FIG. 18). Results evaluating the peptides are provided in FIG. 18. The graph and table show safety and TG elevating effects of peptides injected IP (300 mg/kg) into male, chow-fed C57Bl/6 mice, as described in FIG. 5. Values are means SD, n=4. For the peptides tested, use of citrulline at position 3 and 14 greatly reduced muscle toxicity (CPK activity) and overall cytotoxic responses (ALT and AST) and TG elevating effects of ATI-5261. Most notable, peptides with two citrulline substitutions, at positions 3 and 14 (i.e. R3,14→Citrulline) displayed no detectable muscle or hepatic toxicity compared to PBS controls. This is in contrast to the modest increase in AST and TG observed with the citrulline forms of ATI-5261 possessing F residues (FIG. 15, i.e. T5426 peptides), indicating that the citrulline analogs of LeuATI-5261 were exceptionally safe when administered at high doses.

Figure 19:
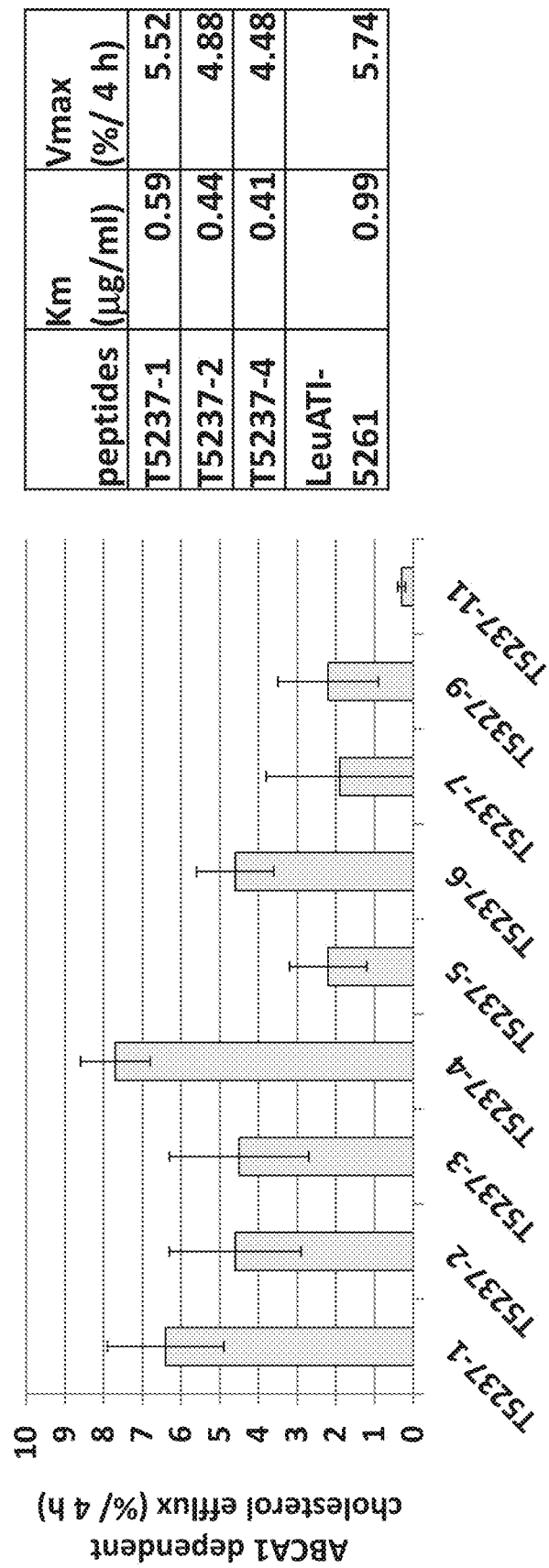
FIG. 19—Citrulline analogs of ATI-5261 retain functionality and stimulate cholesterol efflux with high potency.

Citrulline analogs of ATI-5261 retained functionality and stimulated cholesterol efflux with high potency (FIG. 19). The bar graph shows activity of peptides to stimulate cholesterol efflux from J774 macrophages labeled with [3H]cholesterol. Results are expressed as the ABCA1 component of efflux, as described in FIG. 7. High levels of cholesterol efflux were obtained with saturating concentrations (3 µg/ml) of peptides possessing either one (R3→citrulline) or two (R3,14→Citrulline) substitutions, similar to ATI-5261. This was verified through detailed dose-response studies shown in the table, where the peptides tested possessed a low Km value for stimulating cholesterol efflux with high efficiency.

Example 10

This example shows that the presence of negatively charged residues along the polar surface of the amphipathic α-helix plays a major role tempering the toxic properties of HDL mimetic peptides (FIG. 20). Uncharged glutamine (Q) was used to replace negatively charged glutamate (E) at various positions throughout ATI-5261, LeuATI-5261 and its citrulline analogs, as shown in the sequence list in FIG. 20. The net-charge of the peptides ranged from +1 (T5554-1) to −1 (T5554-5 and T5554-6) for the sequences shown. The graph and table show safety and TG elevating effects of peptides injected IP (300 mg/kg) into male, chow-fed C57Bl/6 mice, as described in FIG. 5. Values are means SD, n=4. Removal of acidic residues from ATI-5261 (E7, 18→Q, i.e. T5554-1) produced a large increase in the toxic response compared to that seen with the parent ATI-5261 peptide. This was somewhat dampened in the presence of the favorable citrulline substitutions (i.e. T5554-5 and T5554-4); however, both retained strong toxic (CPK, ALT, and AST) and TG elevating responses. These results indicate that the safety profile of HDL mimetic peptide ATI-5261 was partially dependent on the presence and position of negatively charged amino acids.

Figure 21:
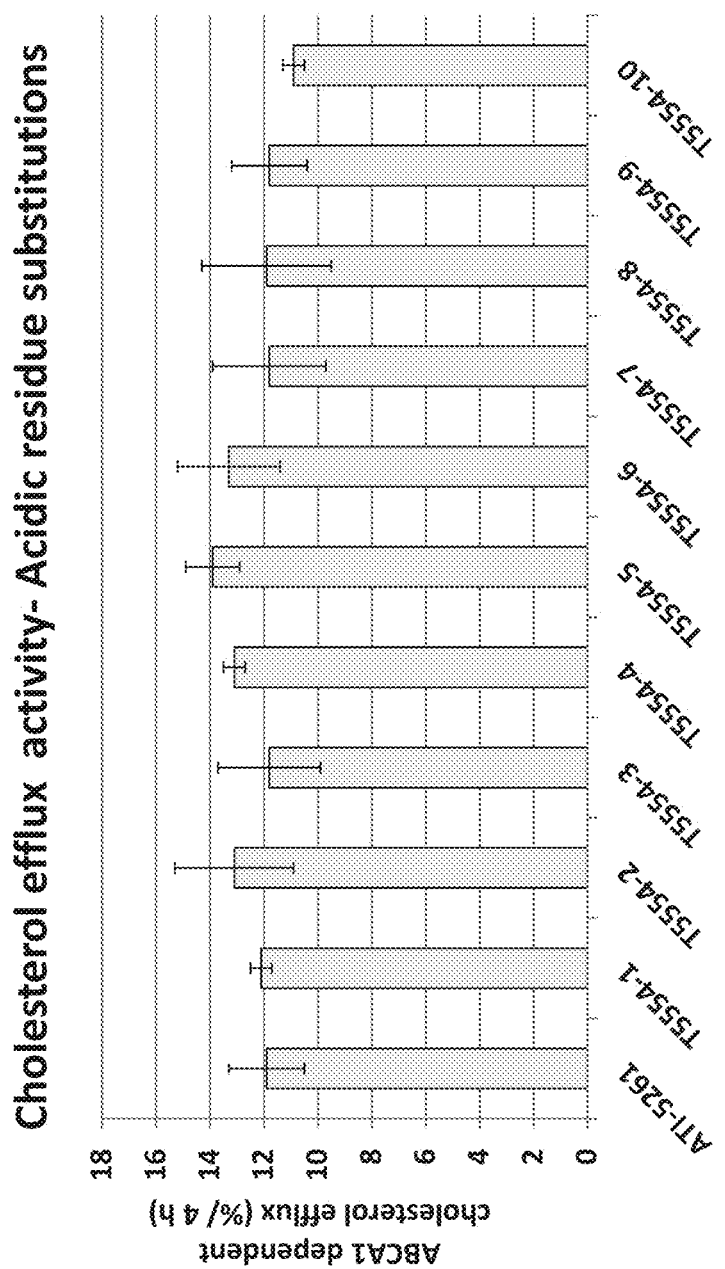
FIG. 21—Peptides with acidic residue substitutions retain functionality in mediating cellular cholesterol efflux.

Peptides with acidic residue substitutions retained functionality in mediating cellular cholesterol efflux. The bar graph depicted in FIG. 21 shows activity of peptides to stimulate cholesterol efflux from J774 macrophages labeled with [3H]cholesterol. Results are expressed as the ABCA1 component of efflux, as described in FIG. 7. High levels of cholesterol efflux were obtained with saturating concentrations (3 µg/ml) of all peptides, indicating the peptides possessed sufficient acidic residues, structure and charge-character for mediating ABCA1 dependent cholesterol efflux.

Example 11

This example demonstrates that small 24-mer forms of Leu-ATI5261 and its citrulline analog are safe and effective (FIG. 22). Removal of C-terminal residues appeared to reduce the toxic responses of ATI-5261 without altering peptide activity (FIG. 8, T5766-5). To test if this effect was recapitulated with other more safe forms of ATI-5261, amino acids 25 and 26 (KS respectively) were deleted from LeuATI-5261 and its citrulline analog (FIG. 22). Panel A—Safety and TG elevating effects were evaluated by injecting (IP) peptides (300 mg/kg) into male, chow-fed C57Bl/6 mice, as described in FIG. 5. Values are means SD, n=4. Peptides lacking the C-terminal residues KS exhibited relatively low cytotoxic responses but retained TG elevating effects, as seen using 24-mers based on ATI-5261 (FIG. 8). Panel B—Cholesterol efflux activity of peptides determined using J774 macrophages labeled with [3H]cholesterol. The peptides were functional, mediating high-levels of cholesterol efflux in an ABCA1-dependent manner at concentrations (10 µg/ml) similar to a parent 26-mer peptide based on citrulline form of LeuATI-5261 (CS6253, i.e. equivalent to batch T5237-4). Panel C— Dose response demonstrating that the 24-mer peptides stimulated cholesterol efflux in a highly efficient manner, displaying a low Km and saturation of cholesterol efflux at 3 µg/ml.

Example 12

This example demonstrates that hydrophobic leucine can be used to replace citrulline at the lipid-water interface of an amphipathic α-helix to create safe and effective HDL mimetic peptides (FIG. 23). To verify that a double citrulline form of LeuATI-5261 (T5237-4) can be used as a platform to create safe and effective HDL mimetic peptides, hydrophobic leucine was used at position 3 or in place of valine at position 2. Panel A-Safety and TG elevating effects were evaluated by injecting (IP) peptides (300 mg/kg) into male, chow-fed C57Bl/6 mice, as described in FIG. 5. Values are means SD, n=4. Peptides with leucine substitutions displayed little or no cytotoxic properties, similar to analogs with R14L substitutions (FIG. 13). This indicates that positions R3 and 14 are highly robust and can be targeted by a wide array of amino acid substitutions to create safe and effective HDL mimetic peptides. Panel B— Cholesterol efflux activity of peptides determined using J774 macrophages labeled with [3H]cholesterol. The peptides were functional, mediating high-levels of cholesterol efflux in an ABCA1-dependent manner at concentrations (10 µg/ml) similar to a parent citrulline form of LeuATI-5261 (CS6253, i.e. equivalent batch of T5237-4). Panel C— Dose response demonstrating that peptides with leucine substitutions stimulated cholesterol efflux in a highly efficient manner, displaying a low Km and saturation of cholesterol efflux at 3 µg/ml.

Example 13

This example demonstrates that a citrulline form of LeuATI-5261 supports other amino acid substitutions to create safe and effective peptides (FIG. 24). Various analogs of leuATI-5261 were created with either leucine or citrulline at positions 3 and 14 or leucine at position 2. Panel A—Safety and TG elevating effects were evaluated by injecting (IP) representative peptides (300 mg/kg) into male, chow-fed C57Bl/6 mice, as described in FIG. 5. Values are means SD, n=4. A peptide possessing leucine at position 14 (Citrulline14→L) displayed little or no cytotoxic properties, similar to analogs with R14L substitutions (FIG. 13).

Example 14

Figure 25:
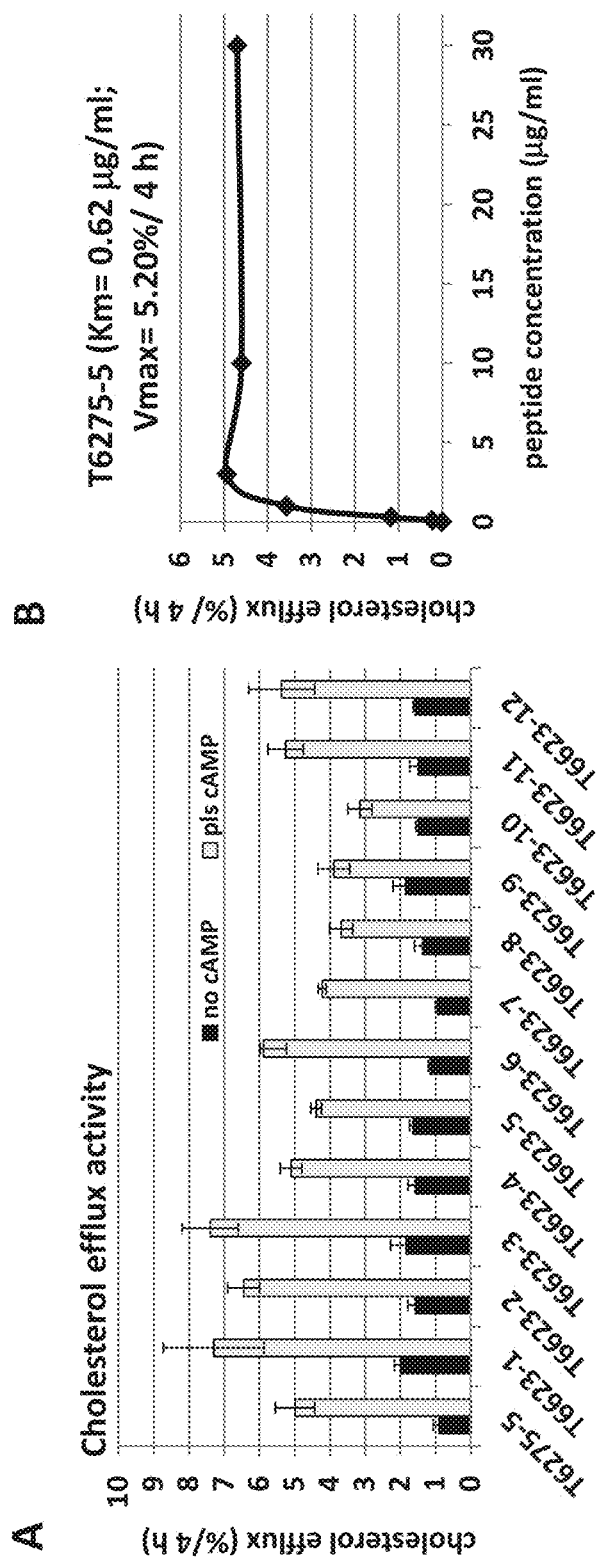
FIG. 25—Panels A and B: Citrulline forms of LeuATI-5261 with various leucine substitutions retain cholesterol efflux activity.

This example demonstrates that citrulline forms of LeuATI-5261 with various leucine substitutions retained cholesterol efflux activity. Cholesterol efflux activity of peptides (FIG. 25) was determined using J774 macrophages labeled with [$^3$H]cholesterol and treated with (right bars) and without (left bars) cAMP to modulate ABCA1 expression. Panel A-Peptide analogs with citrulline and/or leucine substitutions were functional, mediating high-levels of cholesterol efflux in an ABCA dependent manner at concentrations of 10 µg/ml. Panel B— Dose-response demonstrating the T6275-5 peptide (single citrulline14→L substitution) stimulated cholesterol efflux in a highly efficient manner, displaying a low Km and saturation of cholesterol efflux at 3 µg/ml.

Example 15

Figure 26:
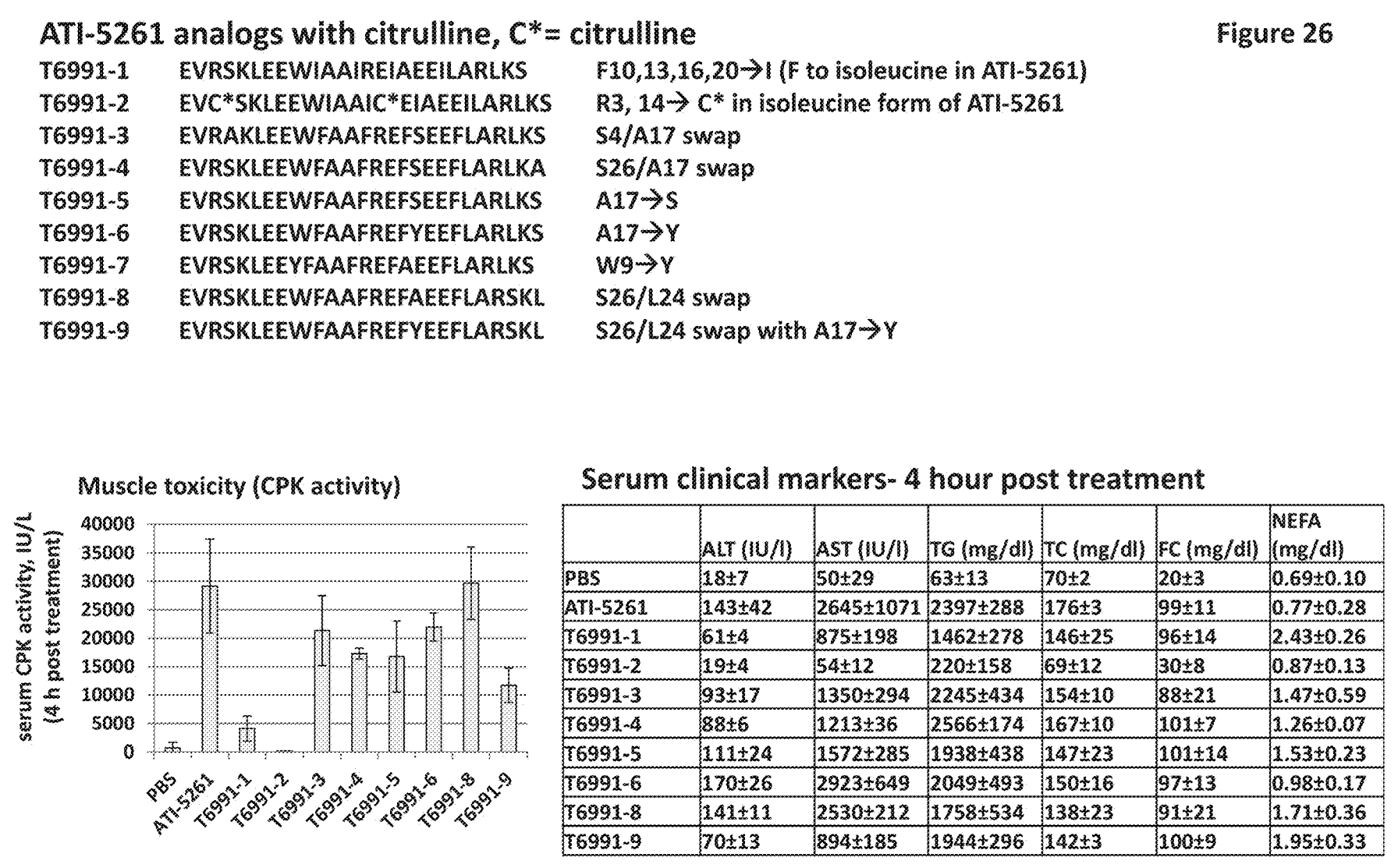

This example demonstrates that isoleucine can be used to replace phenylalanine in ATI-5261 to create safe and effective cholesterol efflux peptides (FIG. 26). Peptide analogs of ATI-5261 were created to identify amino acid substitutions that can be used on the non-polar surface to create safe peptides. Safety and TG elevating effects were evaluated by injecting (IP) peptides (300 mg/kg) into male, chow-fed C57Bl/6 mice, as described in FIG. 5. The bar graph (lower left) shows that analogs of ATI-5261 (T6991-1) and Cit.ATI-5261 (T6991-2) possessing isoleucine substitutions (F10, 13, 16, 20→I) displayed little or no cytotoxic properties related to CPK elevations. Serum ALT and AST values were also markedly reduced with isoleucine peptides vs. ATI-5261 control (Table). In contrast, analogs of ATI-5261 with serine or tyrosine replacements on the non-polar surface induced relatively high CPK, ALT and AST responses, indicating that the position of polar residues on the lipid-binding surface of the peptide did not lower cytotoxic responses. These results provide evidence that toxic properties of ATI-5261 were related to aromatic and positively charged residues, which could be eliminated by strategic use of citrulline and aliphatic amino acid residues. Values are means SD, n=4.

Example 16

Figure 27:
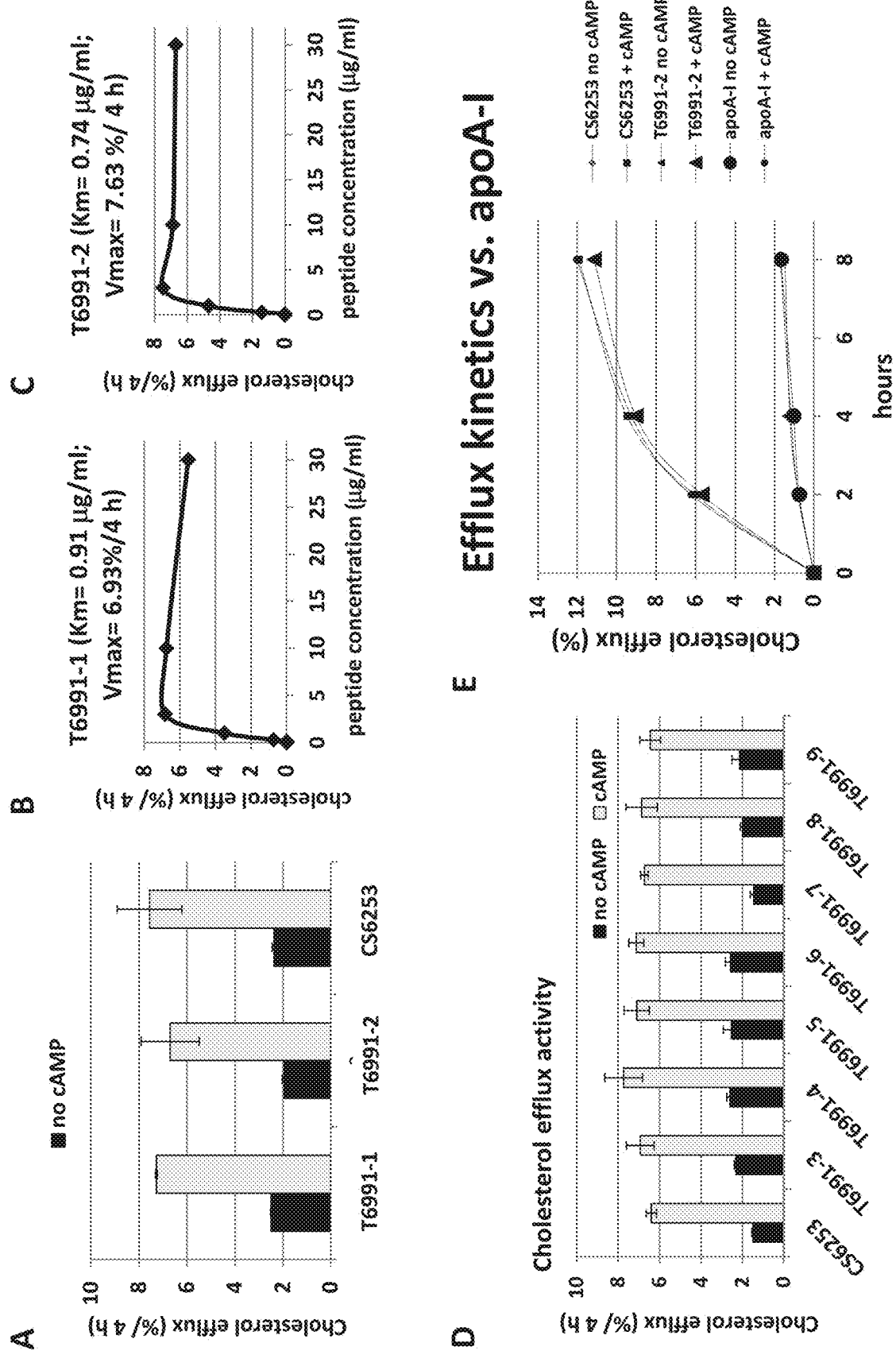
FIG. 27—Panels A-E: Isoleucine forms of ATI-5261 retain cholesterol efflux activity.

This example demonstrates that isoleucine forms of ATI-5261 retain cholesterol efflux activity (FIG. 27). Cholesterol efflux activity of peptides was determined using J774 macrophages labeled with [3H]cholesterol and treated with (right bars) and without (left bars) cAMP to modulate ABCA1 expression. Panel A—Isoleucine forms of ATI-5261 (T6991-1) and Cit.ATI-5261 (T6991-2) were functional, mediating high-levels of cholesterol efflux in an ABCA-dependent manner at concentrations of 10 µg/ml. Panel B— Demonstration that the isoleucine form of ATI-5261 stimulated ABCA1 cholesterol efflux in a highly efficient manner. Panel C— Demonstration that the isoleucine form of Cit.ATI-5261 (T6991-2) stimulated ABCA1 cholesterol efflux in a highly efficient manner. Panel D—Peptides (10 µg/ml) with serine or tyrosine on the non-polar surface retained ability to mediate high levels of cholesterol efflux in an ABCA1-dependent manner, i.e. using J774 cells treated with and without cAMP. Panel E—Data showing that peptides T6991-2 and CS6253 stimulated cholesterol efflux with the same rate kinetics as full-length apoA-I from J774 macrophages. Peptides and apoAI were used in lipid-free form at 10 µg/ml concentrations. Values are means SD, n=4.

Example 17

Figure 28:
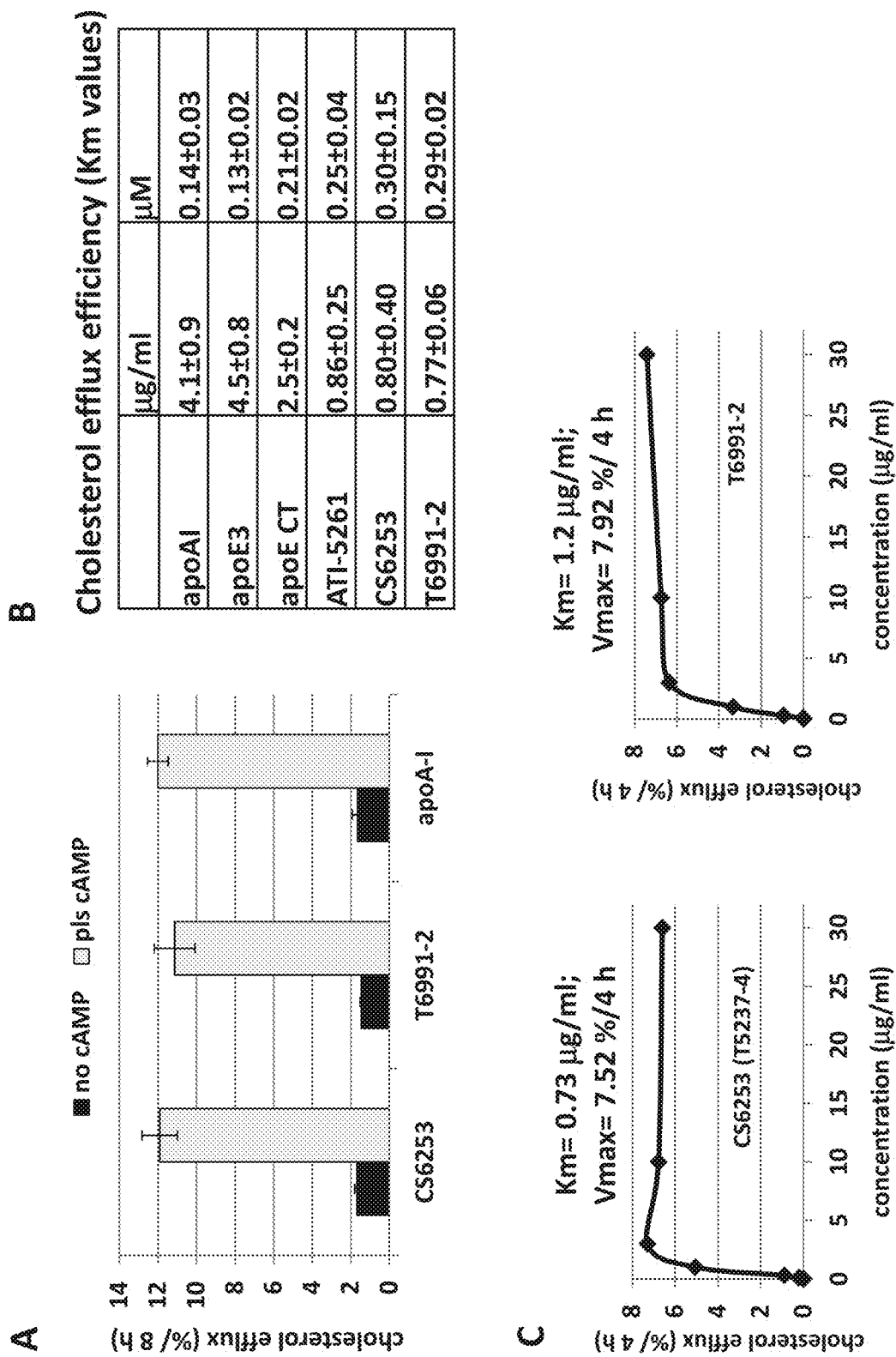
FIG. 28—Panels A-C: Peptides CS6253 and T6991-2 stimulate cellular cholesterol efflux via ABCA1 with high potency.

This example demonstrates that peptides CS6253 and T6991-2 stimulated cellular cholesterol efflux via ABCA1 with high potency. (FIG. 28). Cholesterol efflux activity of peptides was determined using J774 macrophages labeled with [3H]cholesterol and treated with (right bars) and without (left bars) cAMP to modulate ABCA1 expression. Panel A-Leucine (CS6253) and isoleucine (T6991-2) forms of Cit.ATI-5261 were functional, mediating high-levels of cholesterol efflux in an ABCA1-dependent manner at concentrations of 10 µg/ml. Panel B— Summary of the cholesterol efflux potency (Km values) for peptides, apoA-I, apoE and apoE C-terminal (CT) domain calculated using the Michaelis Menten equation (Graph-Pad Prism5 software) and efflux data obtained from cAMP treated J774 cells. Km values are expressed on a mass (µg/ml) or molar basis (µM). The latter indicates that CS6253 and T6991-2 stimulated cholesterol efflux with near apolipoprotein molar potency, particularly when compared to the native efflux domain (CT) of apoE.

Panel C—Dose-response demonstrating that T6991-2 and CS6253 stimulated cholesterol efflux in a highly efficient manner, displaying a low Km and saturation of cholesterol efflux at 3 µg/ml.

Example 18

Figure 29:
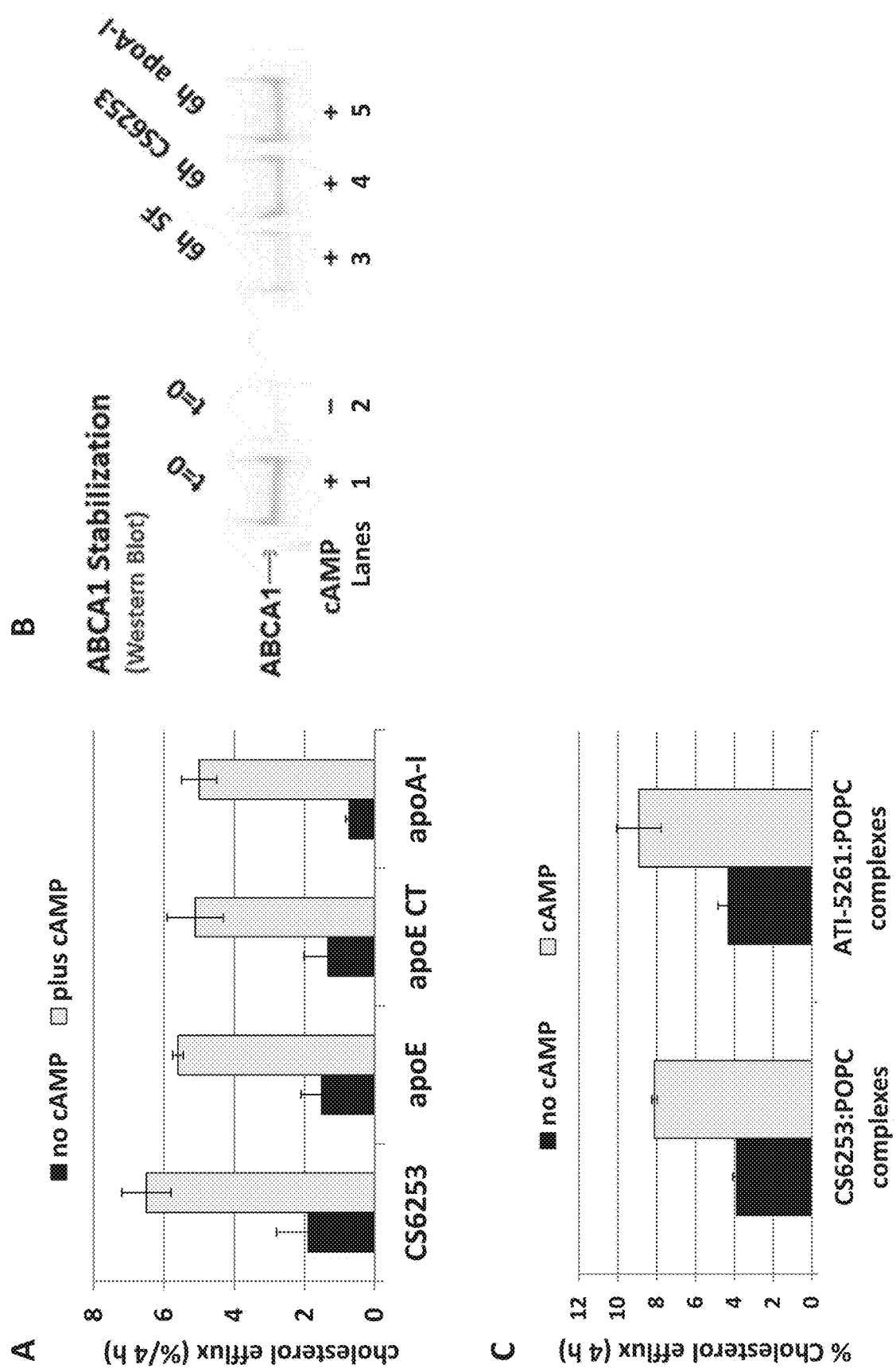
FIG. 29—Panels A-C: The leucine form of Cit.ATI-5261 stabilizes macrophage ABCA1 and stimulates cholesterol efflux in an ABCA1 dependent manner.

This example demonstrates that the leucine form of Cit.ATI-5261 stabilizes macrophage ABCA1 and stimulates cholesterol efflux in an ABCA1-dependent manner. (FIG. 29). J774 macrophages were used for experiments. Panel A—Cells were labeled (48 h) with 3H cholesterol and treated with (right bars) and without (left bars) a cAMP analog to modulate ABCA1 expression. Apolipoprotein(apo)s A-I, E, the C-terminal (CT) domain of apoE, and peptide CS6253 were added (10 µg/ml) to cells in lipid-free form to initiate cellular cholesterol efflux. After 4 h, medium was assayed for effluxed [3H]cholesterol. Values and means±SD, n=3. High levels of cholesterol efflux were seen for all apolipoproteins and peptides using cells up-regulated for the ABCA1 response using cAMP vs. the low response in the absence of cAMP. Therefore, peptide CS6253 stimulated ABCA1 dependent cholesterol efflux similar to native apolipoproteins. Panel B— Western-blot of whole-cell lysates showing ABCA1 protein expression following treatment of J774 cells with cAMP (lane 1, t=0). ABCA1 was maintained at high-levels in the continued presence of either peptide CS6253 (lane 4) or apoA-I (lane 5) during a subsequent 6 h chase; whereas ABCA1 protein was degraded with serum free medium alone (lane3). These data indicate that the leucine form of Cit.ATI-5261 stabilized ABCA1 protein in cellular membranes. Panel C— ABCA1-dependent cholesterol efflux activity of CS6253:phospholipid complexes. Small 7-8 nm complexes of CS6253 peptide and POPC were prepared by cholate dialysis and incubated with [3H]cholesterol labeled J774 cells treated with and with cAMP. Values are means±SD, n=3. The cholesterol efflux activity of the POPC-complexed, new, safe peptide CS6253 was identical to the corresponding parent ATI-5261 peptide, thus providing additional supporting data for retained functionality.

Example 19

Figure 30:
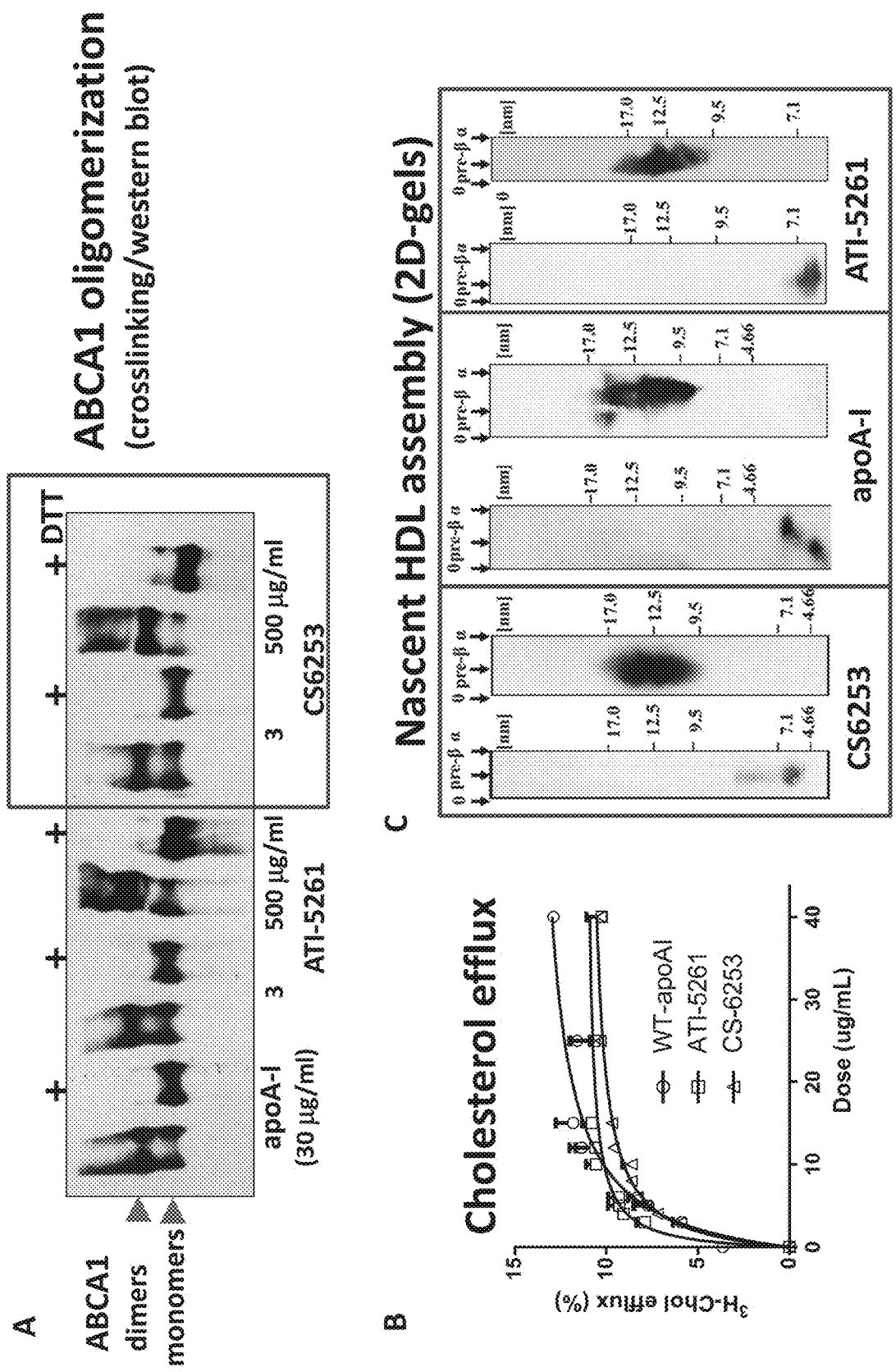
FIG. 30—Panels A-C: Peptide CS6253 interacts with native ABCA1 oligomeric forms to mediate cellular lipid efflux and nascent HDL assembly.

This example demonstrates that peptide CS6253 interacts with native ABCA1 oligomeric forms to mediate cellular lipid efflux and nascent HDL assembly (FIG. 30). BHK cells stably transfected with ABCA1 or mock transfected control cells were labeled with [3H]cholesterol, as described in FIG. 5. Panel A—Demonstration that CS6253 interacted with native forms of ABCA1 in cellular membranes similar to ATI-5261 and apoA-I, as determined via crosslinking assay and western blot analysis using antibodies to either peptide or apoA-I. Panel B—CS6253 stimulated cholesterol efflux via ABCA1 with high potency, similar to apoA-I and ATI-5261. Panel C— Peptides mediated the assembly of nascent HDL particles of similar size compared to apoA-I, as determined by native PAGE. The data indicate single α-helix peptides of the present invention, as exemplified by CS6253, were sufficient to mediate ABCA1 lipid efflux with high potency, including cholesterol and phospholipid efflux, and support the assembly/structure of nascent HDL particles.

Example 20

Figure 31:
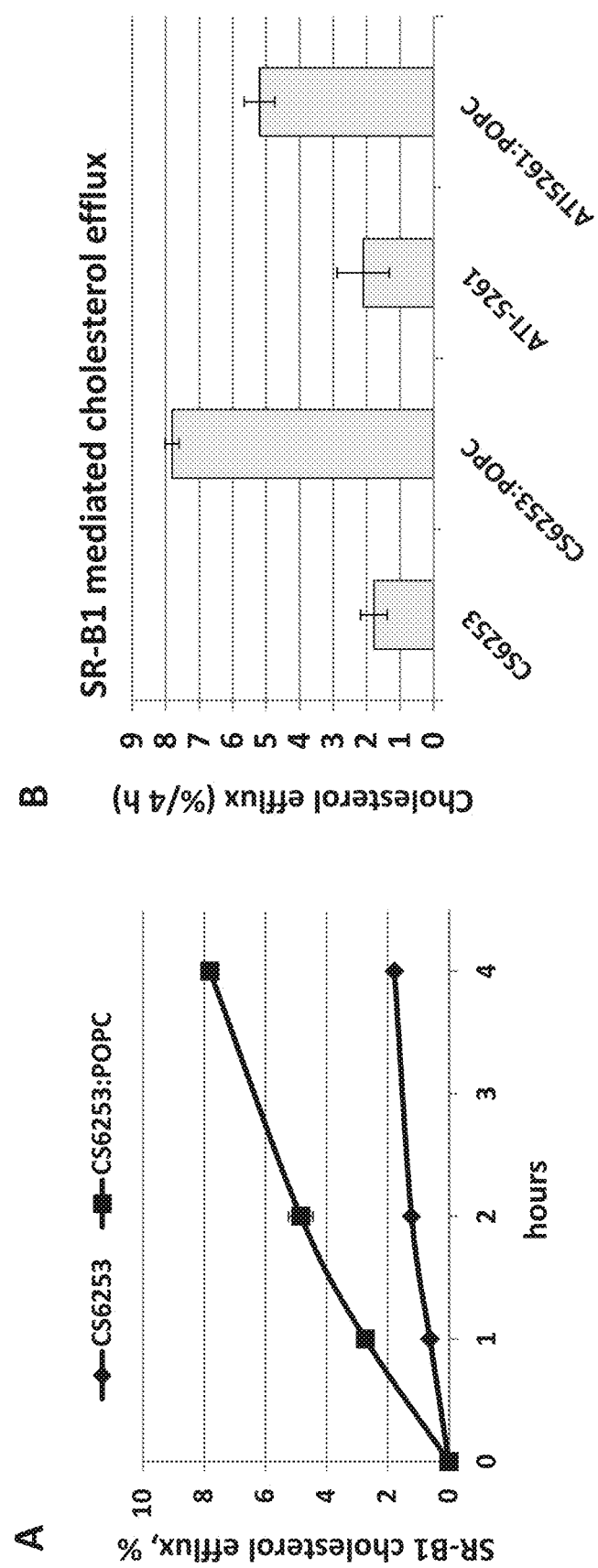
FIG. 31—Panels A and B: CS6253 formulated with phospholipid stimulates cholesterol efflux via SRB1.

This example demonstrates that peptide CS6253 formulated with phospholipid stimulated cholesterol efflux via SRB1 (FIG. 31). To further evaluate potential anti-atherogenic mechanisms of CS6253, Fu5AH cells, that express primarily SR-B1 for mediating cellular lipid efflux, were labeled with [3H]cholesterol and used in efflux experiments. The leucine form of Cit.ATI-5261 (CS6253) lipidated with POPC was used as a cholesterol acceptor in the medium at 50 µg peptide/ml concentration. Panel A—Time-course for SR-B1 mediated cholesterol efflux. Complexes of CS6253: POPC stimulated high-levels of cholesterol efflux versus the poor activity of the lipid-free peptide, consistent with involvement of SR-B1 which requires lipidated acceptor particles as substrate. Panel B—Comparison between CS6253 and ATI-5261 in mediating cellular cholesterol efflux via SR-B1. [3H]cholesterol labeled Fu5AH cells were incubated with either lipid free peptides or peptides formulated with POPC. Relatively high-levels of cholesterol efflux (4 h) to CS6253:POPC complexes were achieved, exceeding that obtained with ATI-5261:POPC complexes. The data indicate that peptide formulations with phospholipid produced HDL-like particles that are highly effective in mediating cholesterol efflux via SR-B1.

Example 21

Figure 32:
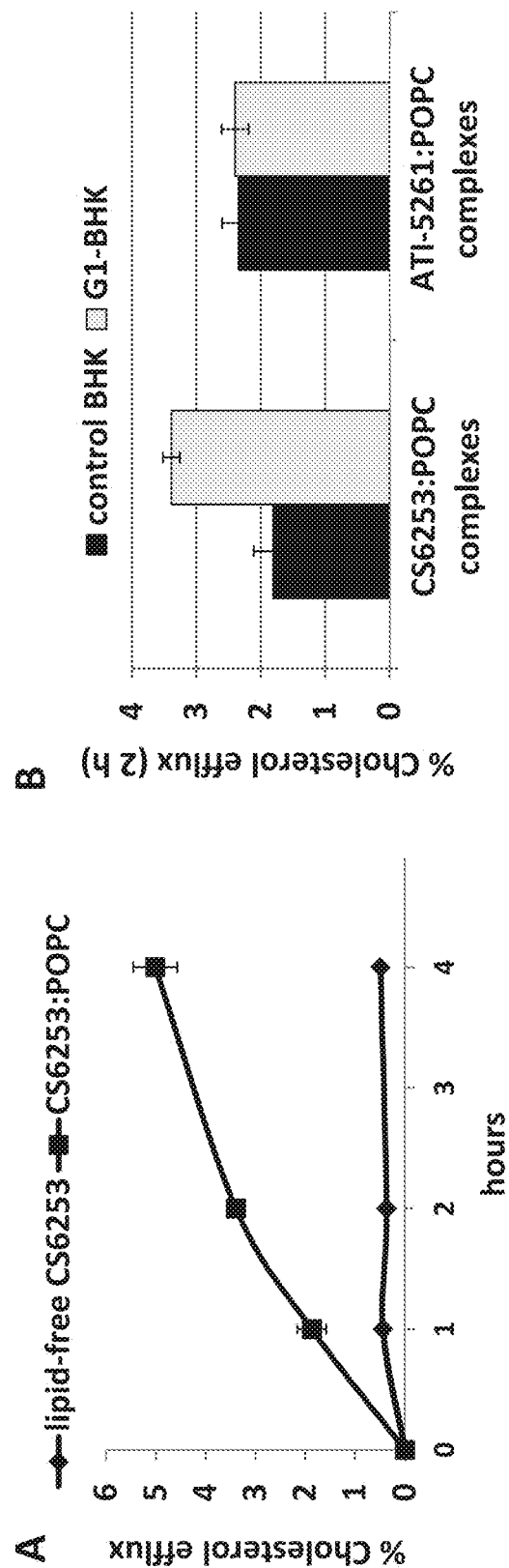
FIG. 32—Panels A and B: CS6253 formulated with phospholipid stimulates cholesterol efflux via ABCG1.

This example demonstrates that peptide CS6253 formulated with phospholipid stimulates cholesterol efflux via ABCG1 (FIG. 32). To further evaluate potential anti-atherogenic mechanisms of CS6253, BHK cells stably transfected with ABCG1 and mock-transfected control cells were labeled with [3H]cholesterol and used in efflux experiments. The leucine form of Cit.ATI-5261 (CS6253) and ATI-5261 lipidated with POPC were used as cholesterol efflux acceptors at 50 µg peptide/ml serum-free medium. Panel A—Time-course for ABCG1 mediated cholesterol efflux from cells to lipid-free CS6253 peptide or CS6253:POPC complexes. Complexes of CS6253:POPC stimulated high-levels of cholesterol efflux versus the poor activity of the lipid-free peptide, consistent with involvement of ABCG1 which requires lipidated particles as substrate. Panel B—Comparison between CS6253 and ATI-5261 in mediating cellular cholesterol efflux via ABCG1. [3H]cholesterol labeled BHK cells (ABCG1 vs. mock transfected; left bars, control BHK, right bars, G1-BHK) were incubated with either lipid-free peptide or peptides formulated with POPC. Surprisingly, relatively high-levels of cholesterol efflux (4 h) were observed using CS6253:POPC complexes; whereas, ATI-5261 (free peptide or POPC complexes) was poorly active. Therefore, CS6253 proved to be a superior peptide based on several criteria, including safety and activity for mediating cholesterol efflux via various cell-surface receptors.

Example 22

Figure 33:
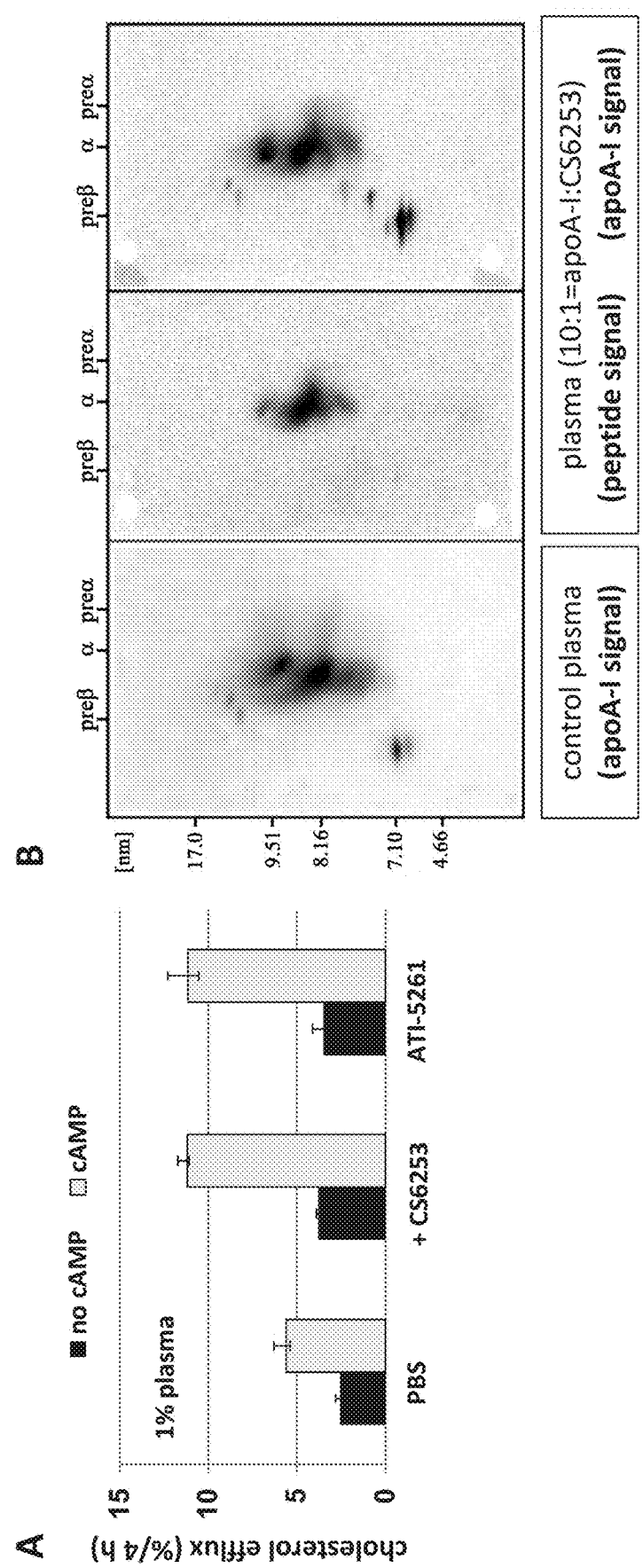
FIG. 33—Panels A and B: CS6253 induces formation of preβ-HDL and enhances the cholesterol efflux activity of human plasma.

This examples shows that CS6253 induces formation of preβ-HDL and enhances the cholesterol efflux activity of human plasma. (FIG. 33). To test whether CS6253 exerts anti-atherogenic effects in a biological milieu, human plasma was exposed (5 min) to lipid-free peptide. Interactions of CS6253 with HDL in plasma and activity of plasma to stimulate cholesterol efflux was assessed; the latter using J774 macrophages labeled with [3H]cholesterol. Panel A—Cholesterol efflux activity of plasma treated with lipid-free peptides. Human plasma was incubated with 300 µg/ml peptides for 5 minutes (4° C.), diluted to 1% in serum-free RPMI-1640 culture medium and immediately added to [3H]cholesterol-labeled J774 cells. Plasma treated with peptide (CS6253 or ATI-5261) possessed greater capacity to stimulate cholesterol efflux from cells via ABCA1 (i.e., from cAMP treated cells, right bars) versus control plasma treated with vehicle alone (left bars). Panel B— Induction of preβ HDL upon treatment of human plasma with CS6253. Plasma was exposed to a small amount of peptide relative to endogenous apoA-I (1:10 mole ratio, respectively) and formation of preβ HDL assessed by 2D non-denaturing gradient gel electrophoresis (NDGGE) and western blot analysis. The left panel shows the amount of preβ HDL (5-6% of total HDL) in plasma with no peptide treatment, as judged using antibody against apoA-I. The right panel shows an increase in preβ HDL with peptide treatment and a corresponding decrease in the α-migrating HDL species (apoA-I antibody). The middle panel illustrates that CS6253 associated with α-HDL in plasma, as judged using an antibody against CS6253. The results indicate that CS6253 displaced apoA-I from the surface of α-HDL to induce preβ HDL formation and cholesterol efflux activity (panel A). The results are consistent with the production of authentic preβ HDL particles composed entirely of endogenous apoA-I.

Example 23

Figure 34:
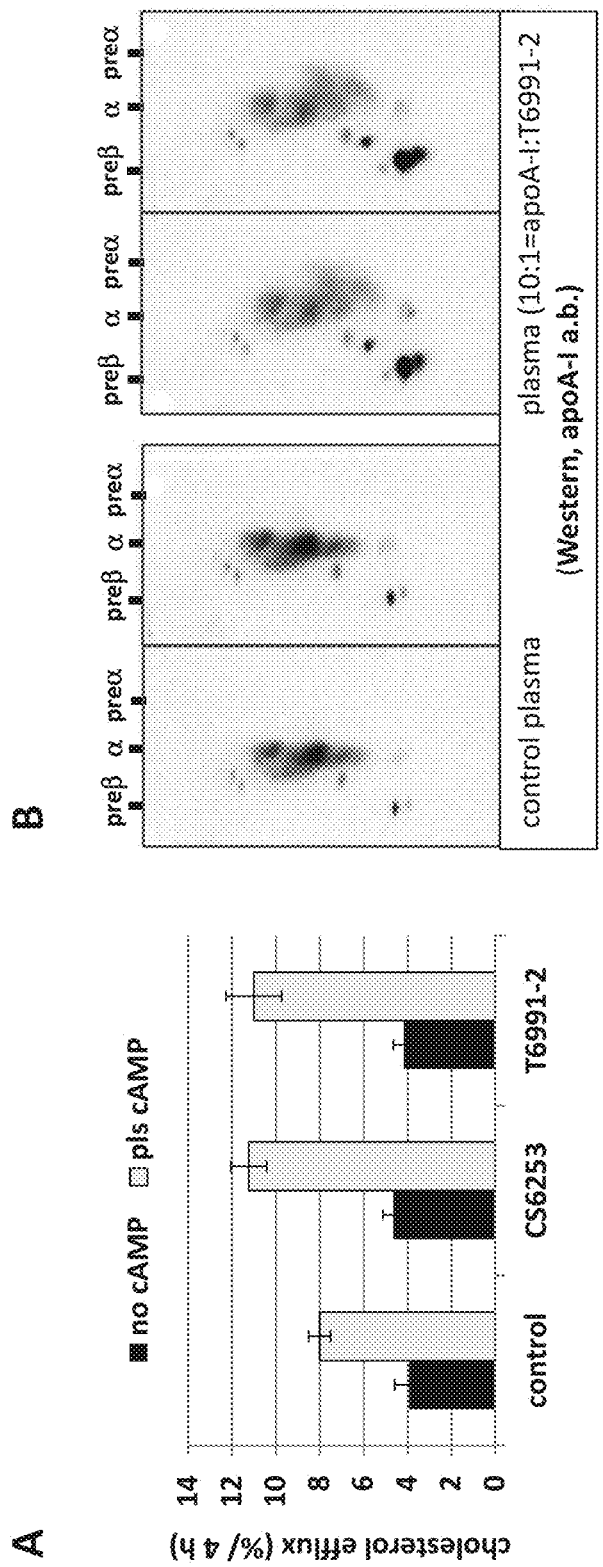
FIG. 34—Panels A and B: T6991-2 induces formation of preβ-HDL and enhances the cholesterol efflux activity of human plasma.

This example demonstrates that peptide T6991-2 induces formation of preβ-HDL and enhances the cholesterol efflux activity of human plasma (FIG. 34). To test whether T6991-2 exerts anti-atherogenic effects in a biological milieu, human plasma was exposed (5 min) to lipid-free peptide. Interactions of T6991-2 with HDL in plasma and activity of plasma to stimulate cholesterol efflux was assessed using J774 macrophages labeled with [3H]cholesterol. Panel A—Cholesterol efflux activity of plasma treated with lipid-free peptides. Human plasma was incubated with 300 μg/ml peptides for 5 minutes (4° C.), diluted to 1% in serum-free RPMI-1640 culture medium and immediately added to [3H]cholesterol-labeled J774 cells. Plasma treated with peptide (T6991-2 or CS6253) possessed greater capacity to stimulate cholesterol efflux from cells via ABCA1 (i.e. from cAMP treated cells, right bars) versus control plasma treated with vehicle alone (left bars). Panel B— Induction of preβ HDL upon treatment of human plasma with T6991-2. Plasma was exposed to a small amount of peptide relative to endogenous apoA-I (1:10 mole ratio, respectively) and formation of preβ HDL assessed by 2D non-denaturing gradient gel electrophoresis (NDGGE) and western blot analysis. The two left panels (i.e., duplicate runs) show the amount of preβ HDL (~6% of total HDL) in plasma with no peptide treatment, as judged using antibody against apoA-I. The right panels show an increase in preβ HDL with peptide treatment and a corresponding decrease in the α-migrating HDL species (apoA-I antibody). The results indicate that T6991-2 induced preβ HDL particles in plasma that are functional in mediating cholesterol efflux via ABCA1, similar to peptide CS6253.

Example 24

Figure 35:
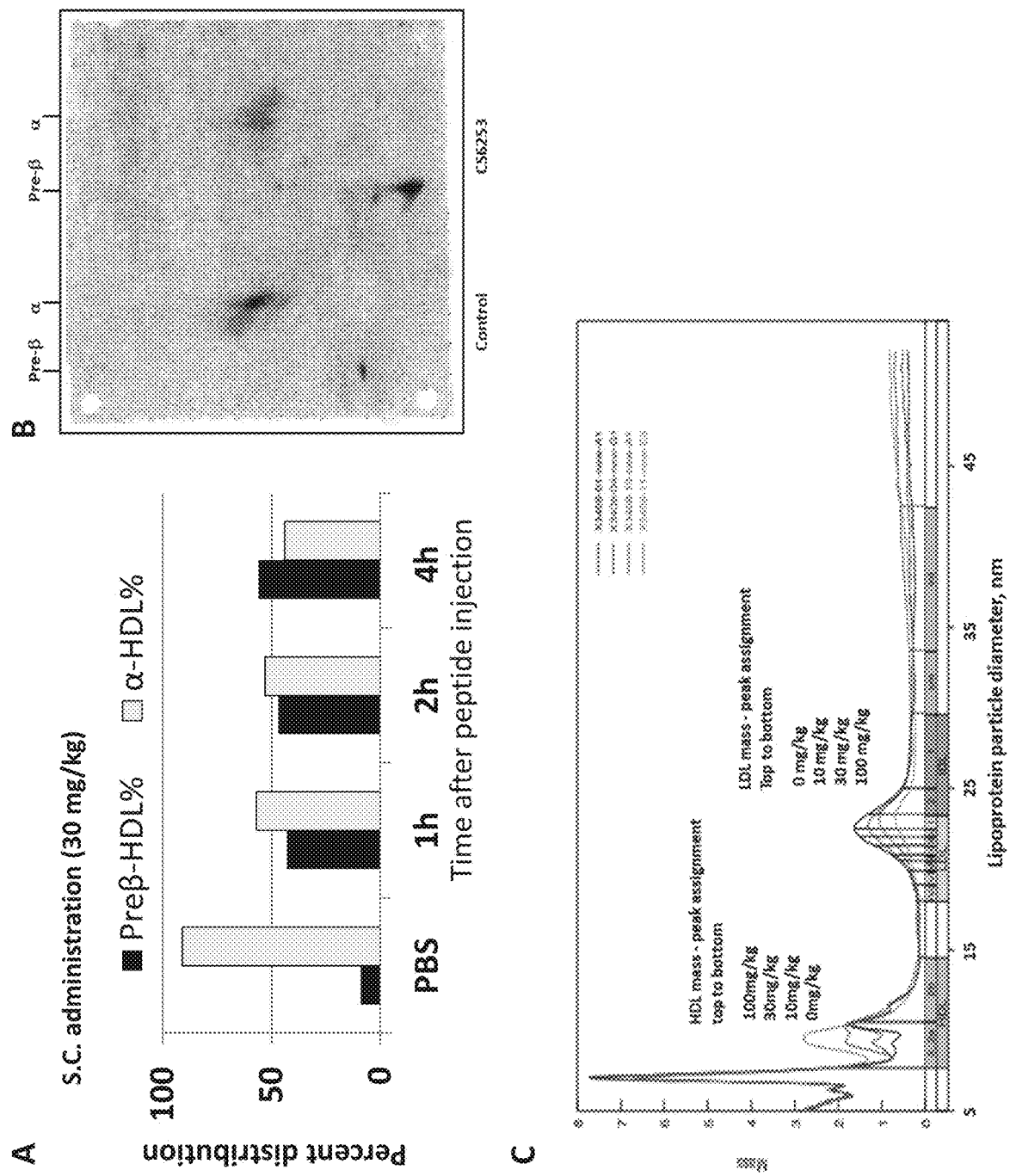
FIG. 35—Panels A-C: CS6253 induces preβ HDL formation in vivo in hamsters.

This example demonstrates that CS6253 induces preβ HDL formation in vivo in hamsters (FIG. 35). Gold Syrian hamsters, which are known to have more human like HDL metabolism than mice, were fed high-fat western diet for 4 weeks were injected subcutaneously (SC) with 30 mg/kg of lipid-free CS6253 peptide. At 1, 2, and 4 h post-injection, plasma was collected for analysis of preβ HDL levels by native 2D PAGE and Western-blotting using an antibody against apoA-I. Panel A—Bar graph showing distribution of HDL species, as preβ1 HDL (left bars) and the major α-HDL migrating species (right bars) for vehicle control injections (4 h time-point) and for peptide (1, 2 and 4 h). A large increase (~8-fold) in preβ1 HDL was observed with peptide treatment vs. control, indicating that CS6253 is able to interact with and favorable modulate HDL in vivo. Panel B—Representative Western blot (apoA-I antibody) of 2D-PAge1 (native), showing distribution of HDL subspecies for PBS control and CS6253 injections (4 h data). Panel C— Dose-response for small HDL increase and LDL lowering with peptide treatment in gold Syrian hamsters. Hamsters were injected SC with 10, 30 and 100 mg/kg peptide and PBS (n=3 per group) and plasma collected 4 h later. Following removal of albumin by centrifugation, plasma was injected and lipoproteins separated with gas-phase differential electrophoretic macromolecular mobility-based method (ion mobility, or IM) (Caulfield et al. *Clin Chem* 2008 54:8 1307-16). The dose-response for preβ HDL increase was associated with a dose-response for LDL particles, particularly LDL particles of small size.

Example 25

This example shows the half-life of CS6253 in rats (FIG. 36). CS6253 was designed with a S26→Y substitution to facilitate labeling with $^{125}$I (sequence at the top of the figure). Radiolabeled peptide was then injected into male, chow-fed Wistar rats via various administration routes and its uptake in plasma quantified. Panel A—Clearance kinetics from plasma following injection of $^{125}$I-CS6253. The table (right) shows the half-life of CS6253 calculated from clearance curves as well as its bioavailability as a % of injected dose. Panel B— Cholesterol efflux activity of Y26 form of CS6253 determined using J774 macrophages labeled with [3H]cholesterol. The peptide was functional, mediating high-levels of cholesterol efflux in an ABCA1 dependent manner at concentrations (10 μg/ml) similar to the parent CS6253 peptide. Panel C— Dose response demonstrating that peptides stimulated cholesterol efflux with high efficiency, displaying a low Km and saturation of cholesterol efflux at 3 μg/ml.

Example 26

Figure 37:
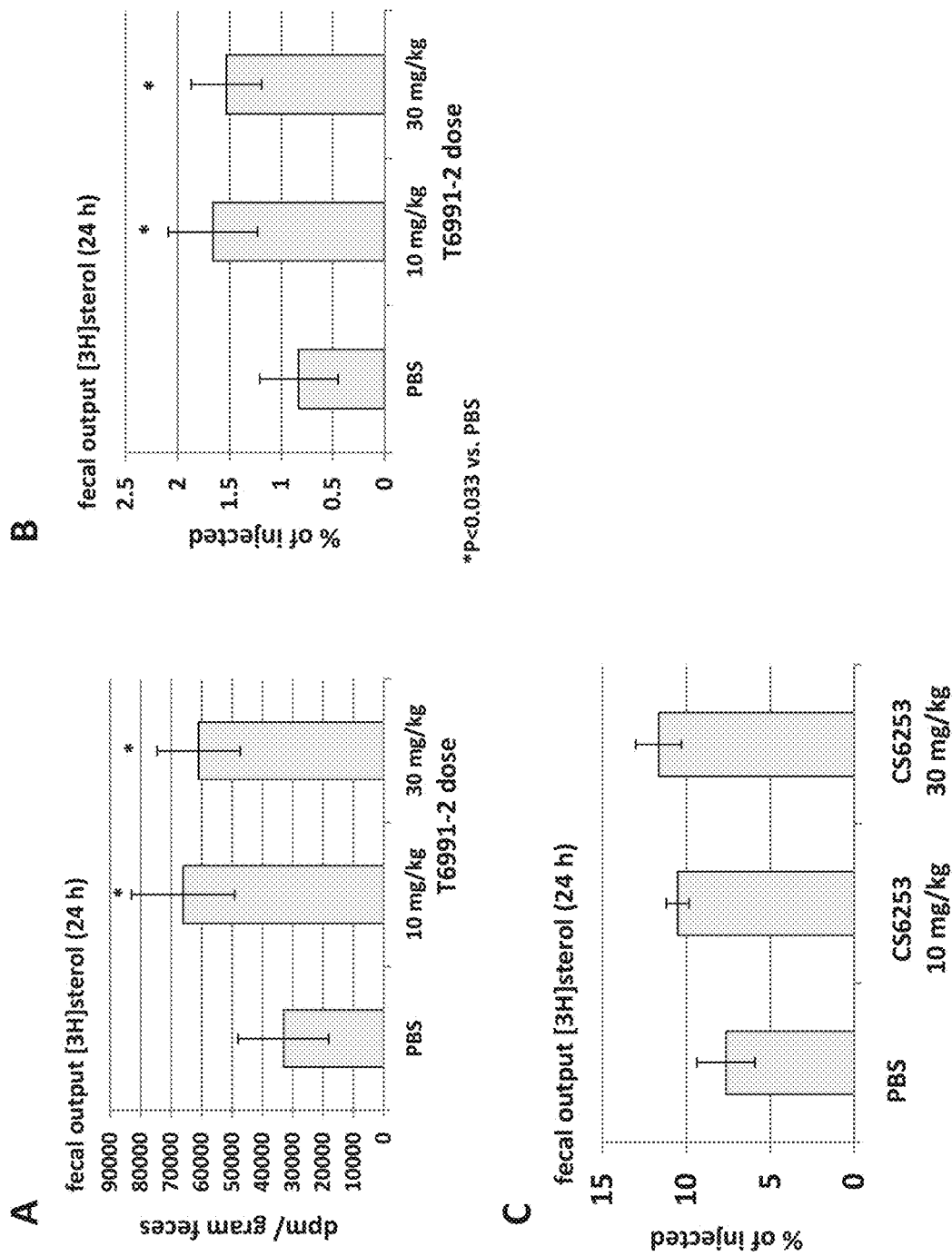
FIG. 37—Panels A-C: CS6253 stimulates macrophage reverse cholesterol transport (RCT) to feces in vivo.

This examples shows that T6991-2 and CS6253 stimulated macrophage reverse cholesterol transport (RCT) to feces in vivo (FIG. 37). J774 macrophage foam-cells loaded with acetylated LDL (100 μg/ml) and labeled with [3H] cholesterol were injected IP into male, atherosclerotic apoE deficient (apoE−/−) mice 4 months of age together with vehicle alone (PBS) or the indicated lipid-free peptides at doses of 10 or 30 mg/kg. Feces were collected at 24 h for assessment of [3H]sterol. Panels A and B— Output of [3H]sterol in response to T6991-2 injection compared to the PBS vehicle treatment group. Results were expressed as dpm per gram feces (panel A) or as % of injected [3H] cholesterol (B). Panel C-Output of [3H]sterol in response to CS6253. Peptides on average increased macrophage-specific reverse cholesterol transport. Values are means±SD, n=4 mice per group.

Example 27

Figure 38:
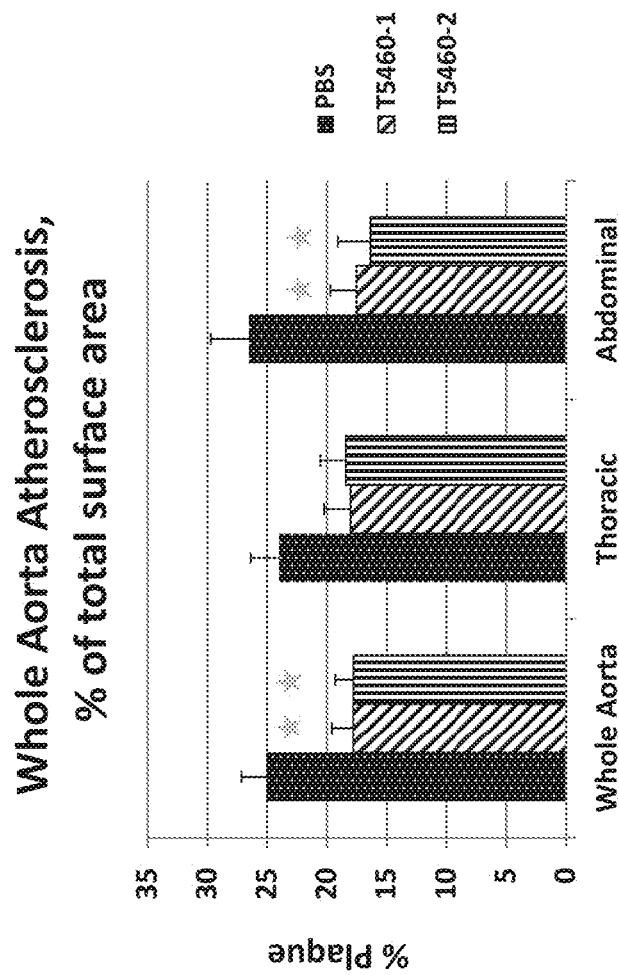
FIG. 38—CS6253 reduces substantial atherosclerosis in apoE−/− mice.

This example shows that CS6253 reduced substantial atherosclerosis in apoE−/− mice. (FIG. 38). Male apoE−/− mice at 8 weeks of age were fed a high-fat western diet for 14 weeks. Mice were subsequently randomized to either a control group to receive IP injection of vehicle alone (left bars) or lipid-free peptide (30 mg/kg) at 48 hour intervals for 6 weeks. Two citrulline forms of the leucine containing ATI-5261 peptide were evaluated: T5460-1 (middle bars), which was equivalent to T5237-1 possessing a single R3→Citrulline substitution and T5460-2 (right bars) equivalent to CS6253 (i.e. T5237-4) possessing R3,14→Citrulline, see FIG. 18. The extent of whole aorta covered with fatty lesions is shown, determined by Oil-Red O staining. Values are means±SD, n=10 mice per group.

Example 28

Figure 39:
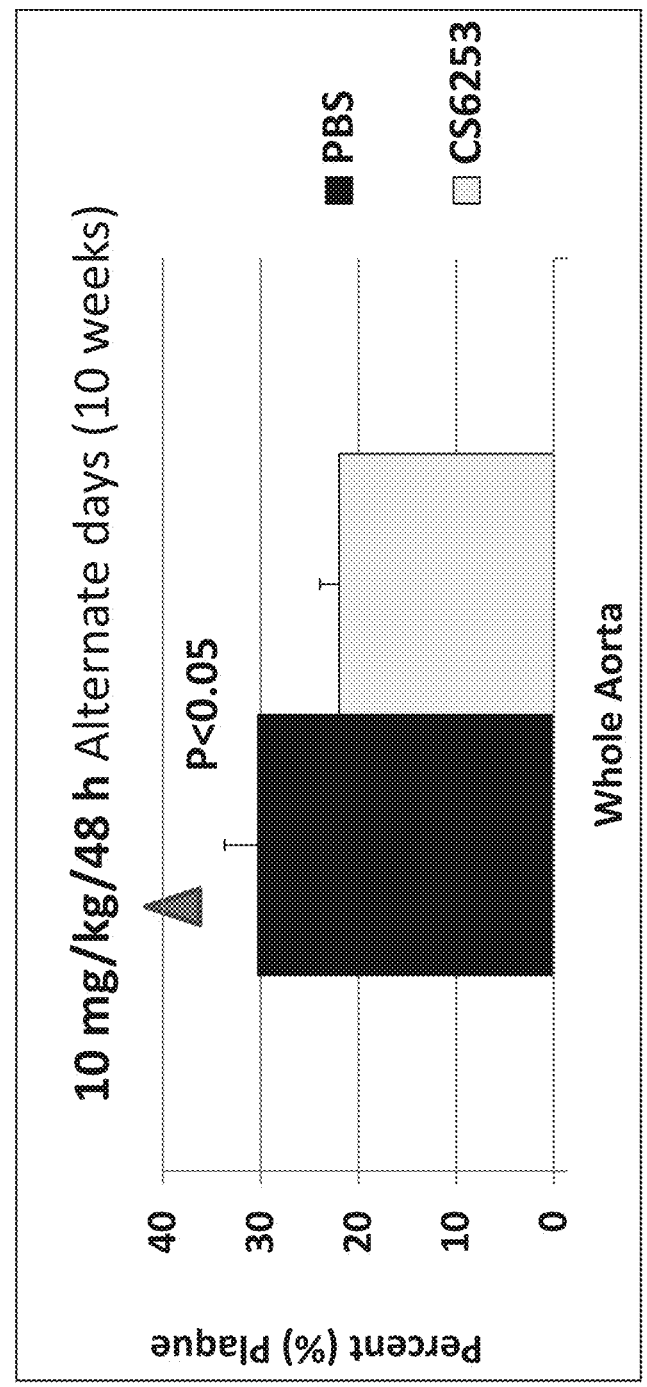
FIG. 39—Low-dose administration of CS6253 reduces substantial atherosclerosis in apoE−/− mice.

This example shows that low-dose administration of CS6253 reduced substantial atherosclerosis in apoE−/− mice (FIG. 39). Male apoE−/− mice at 8 weeks of age were fed a high-fat western diet for 14 weeks. Mice were subsequently randomized to either a control group to receive IP injection of vehicle alone (left bar) or lipid-free CS6253 (10 mg/kg, right bar) at 48 hour intervals for 10 weeks. The extent of whole aorta covered with fatty lesions is shown, determined by Oil-Red O staining. Values are means±SD, n=10 mice per group.

Example 29

Figure 40:
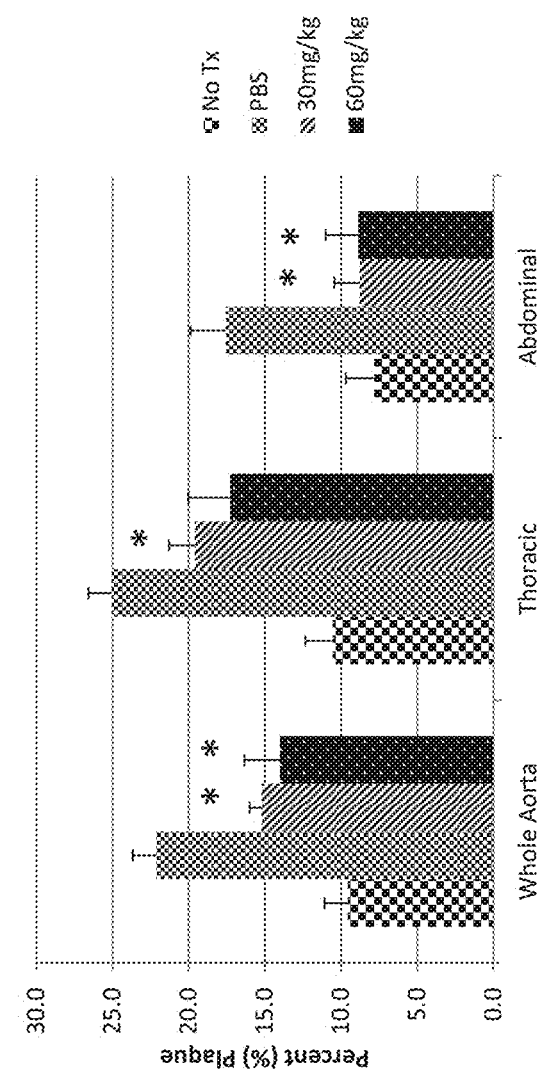
FIG. 40—CS6253 administered subcutaneously (SC) also reduces substantial atherosclerosis in apoE−/− mice.

This example shows that CS6253 administered subcutaneously (SC) also reduced substantial atherosclerosis in apoE−/− mice. (FIG. 40). Male apoE−/− mice at 8 weeks of age were fed a high-fat western diet for 14 weeks. One group was terminated before treatment start as baseline control. Mice were subsequently randomized to one of 3 arms to receive subcutaneous (SC) injections on alternate days for 6 weeks; vehicle alone, CS6253 30 mg/kg or CS6253 60 mg/kg. During the first 4 treatment weeks the mice remained on high-fat western diet while during the last two weeks they were switched to chow diet. The extent of whole aorta covered with fatty lesions is shown, determined by Oil-Red O staining. Values are means±SD, n=10 mice per group.

Example 30

This example shows that stapled peptides can be designed to mediate ABCA1 dependent cholesterol efflux.

Figure 41:
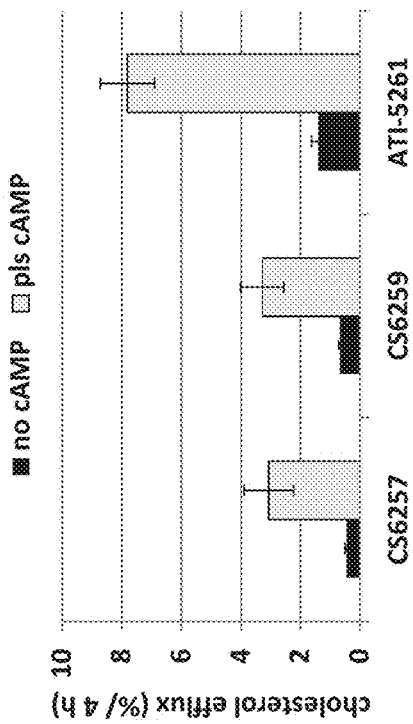
FIG. 41—Stapled peptides can be designed to mediate ABCA1 dependent cholesterol efflux. Peptides=SEQ ID NOS:89 and 90.

ATI-5261 with uncharged alanine (A) at positions 3 and 23, i.e. peptide CS6257, and the leucine form of ATI-5261 with glutamine (Q) at positions 3 and 23, peptide CS6259, were designed. Both possessed a chemical staple as shown in the sequences (FIG. 41). Ability of peptides to stimulate cholesterol efflux from [3H]cholesterol-labeled J774 macrophages treated with (right bars) and without (left bars) cAMP was evaluated. The peptides were used in lipid-free form at a concentration of 10 µg/ml. Values are means±SD, n=3 wells. Cholesterol efflux to both peptides (i.e. CS6257 and CS6259) was highly dependent on ABCA1 comparable to ATI-5261, which stimulated an overall greater efflux response.

Figure 42:
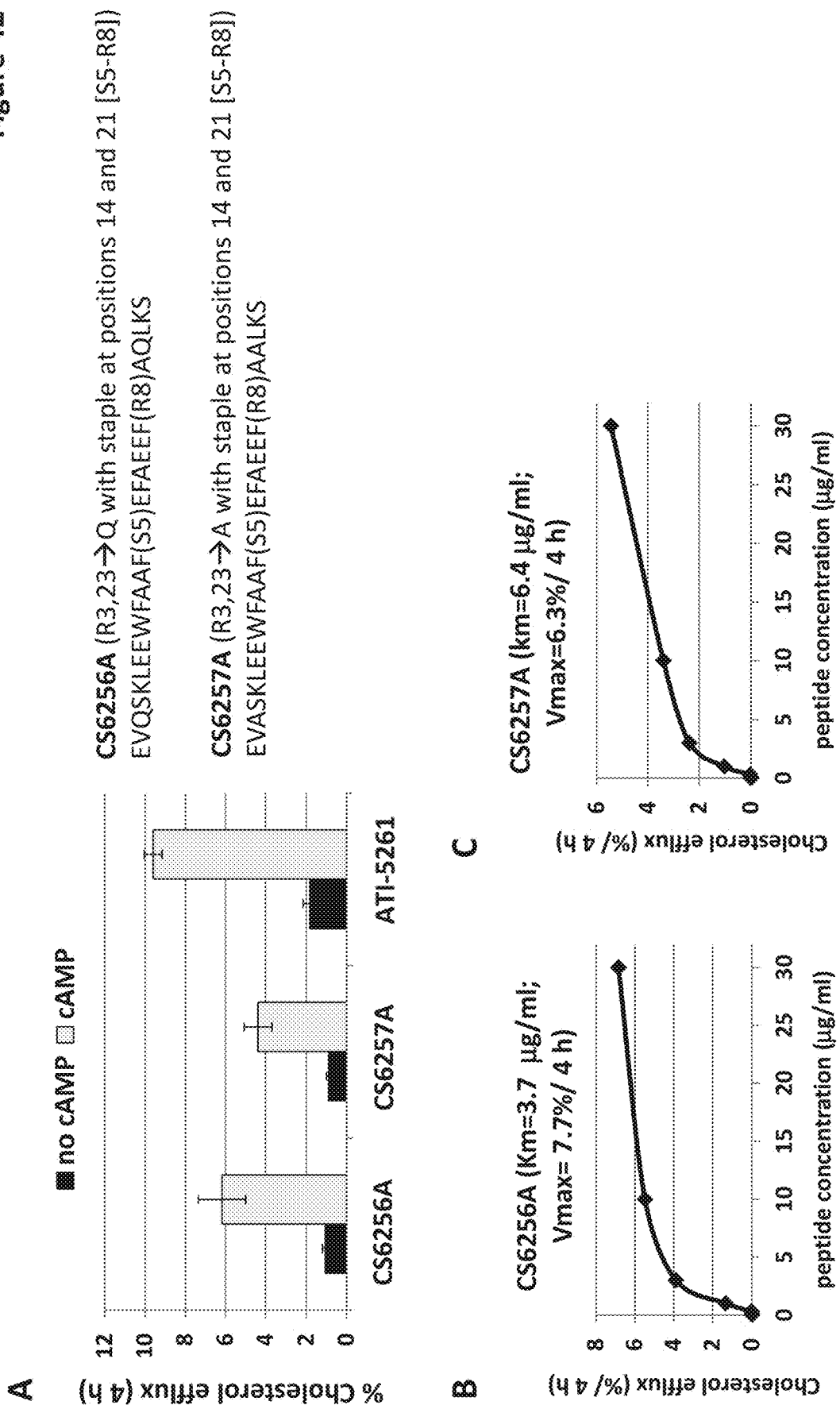
FIG. 42—Panels A-C: Stapled peptides based on the ATI-5261 design mediate ABCA1 dependent cholesterol efflux in a concentration dependent manner. Peptides=SEQ ID NOS:91 and 89.

Stapled peptides based on the ATI-5261 design mediated ABCA1 dependent cholesterol efflux in a concentration dependent manner (FIG. 42). ATI-5261 peptides were constructed with uncharged alanine (A) at positions 3 and 23, peptide CS6257A, above, and glutamine (Q) at positions 3 and 23, peptide CS6256A. Both also possessed a chemical staple as shown in the sequences. Panel A shows the ability of peptides to stimulate cholesterol efflux was determined using J774 macrophages labeled with [3H]cholesterol and treated with (right bars) and without (left bars) cAMP to modulate ABCA1 expression. The peptides were used in lipid-free form at a concentration of 10 µg/ml. Values are means±SD, n=3 wells. Cholesterol efflux to both peptides (i.e. CS6257A and CS6256A) was highly dependent on ABCA1 comparable to ATI-5261, which stimulated a greater efflux response. Panel B is a graph showing that the peptides were functional, stimulating cholesterol efflux in a concentration-dependent manner.

Example 31

This example illustrates blood glucose-lowering properties of an illustrative peptide of the invention.

Figure 43:
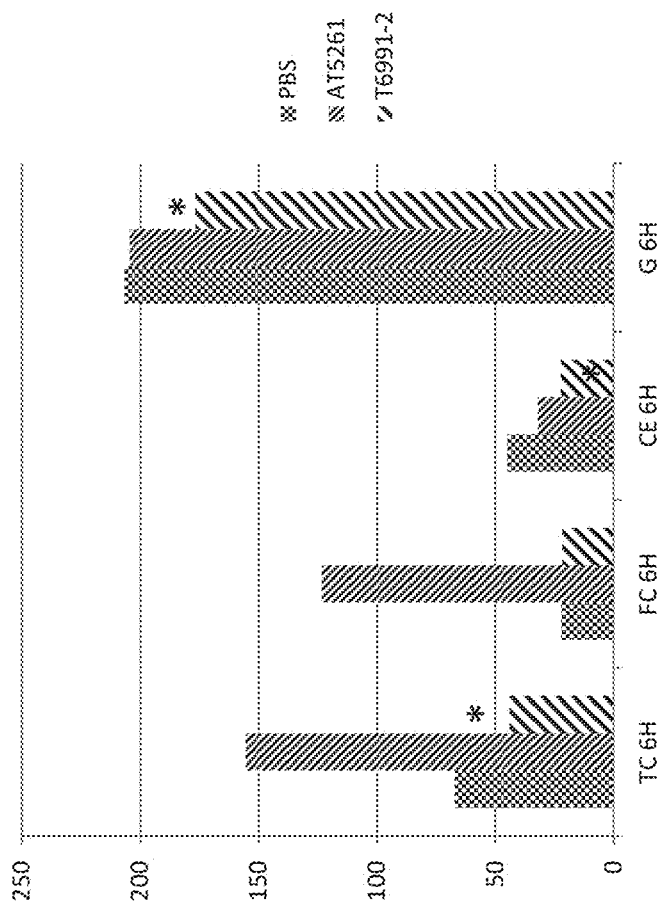
FIG. 43—Blood glucose lower properties of T6991-2 in mice. Peptide T6991-2.

The blood glucose lowering-properties of T6991-2 were evaluated in mice. Peptide T6991-2 has the sequence EVC*SKLEEWIAAIC*EIAEEILARLKS (SEQ ID NO:80), with R3, 14→Citrulline (C*) in an isoleucine form of ATI-5261. Cholesterol and glucose are shown 6 h following IP injection of 300 mg/kg peptide administered to C57Bl/6 mice fed chow diet (n=3) (FIG. 43). T6991-2 showed significantly lower total cholesterol (TC) cholesterol ester (CE) and glucose (G) values compared to animals receiving PBS injection, n=3 per group. The graph also shows the triglyceride (TG) elevation effects characteristic of the ATI-5261 toxic responses seen at high doses (300 mg/kg), which was used as positive control.

Figure 44:
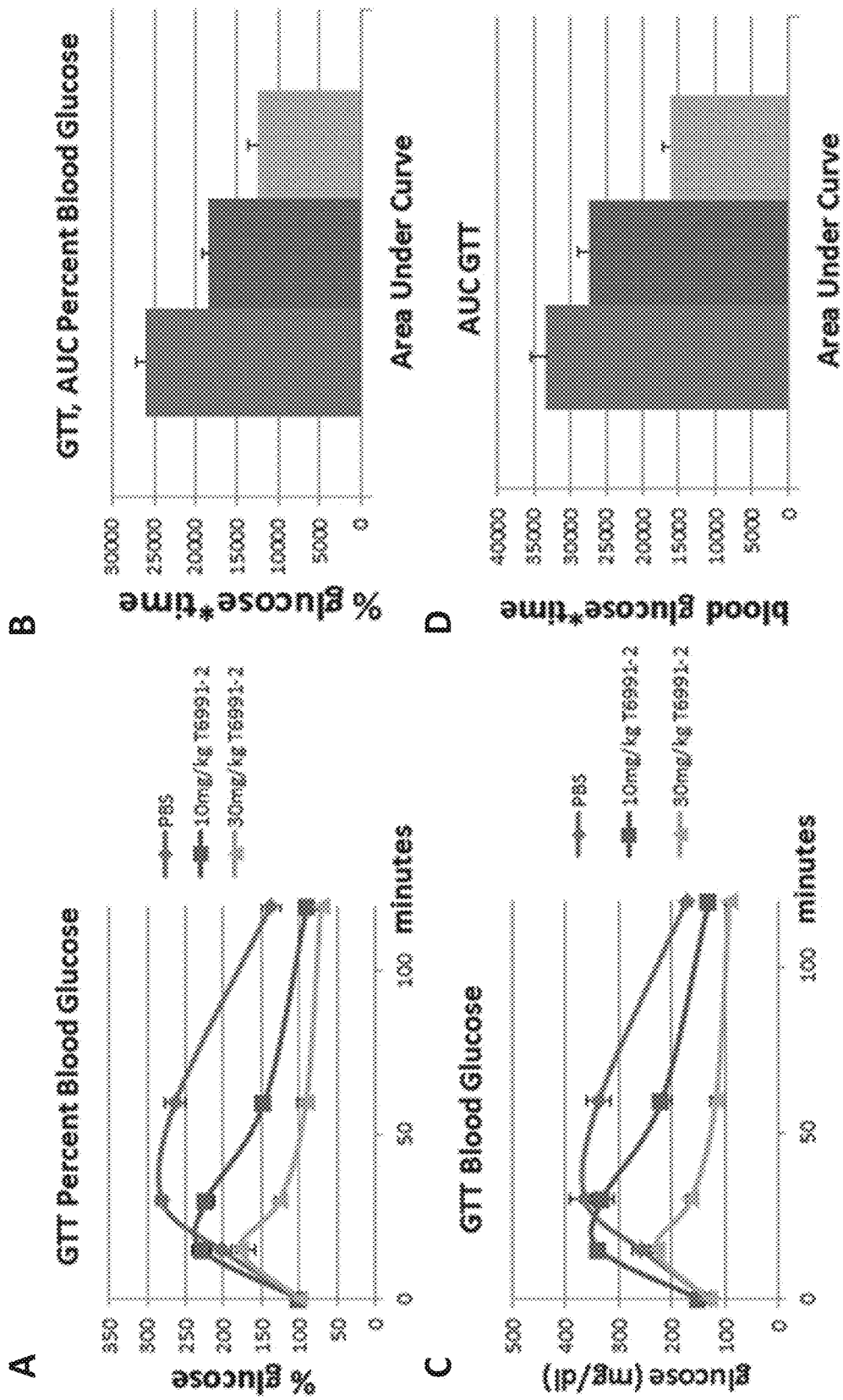
FIG. 44—Panels A-D: T6991-2 lowers blood glucose concentrations upon glucose challenge in DIO mice.

T6991-2 also lowered blood glucose concentrations upon glucose challenge in DIO mice (FIG. 44). Male C57Bl/6 mice were fed a 60% high-fat diet for 6 weeks (DIO model); then injected intraperitonelly (IP) with either vehicle alone, 10 or 30 mg/kg of lipid-fee T6991-2 on alternate days for 6 weeks. Following treatment, a glucose tolerance test was performed via IP injection of 1 g/kg glucose. Blood was collected via the tail vein at the indicated times and blood glucose measured using a glucometer. Panels A and B—Blood glucose concentrations expressed as percent of control values at t=0, with corresponding area under the curve plot, respectively. Panels C and D—Blood glucose concentrations expressed as absolute values over time following glucose challenge, with corresponding area under the curve, respectively. Values are means±SD, n=4 mice per group. (Panels B and D: left bar, PBS; middle bar, 10 mg/kg T6991-2; right bar, T6991-2, 30 mg/kg) The data indicated that low-dose T6991-2 attenuated the blood glucose response upon glucose challenge and that the effect was dose-dependent.

Figure 45:
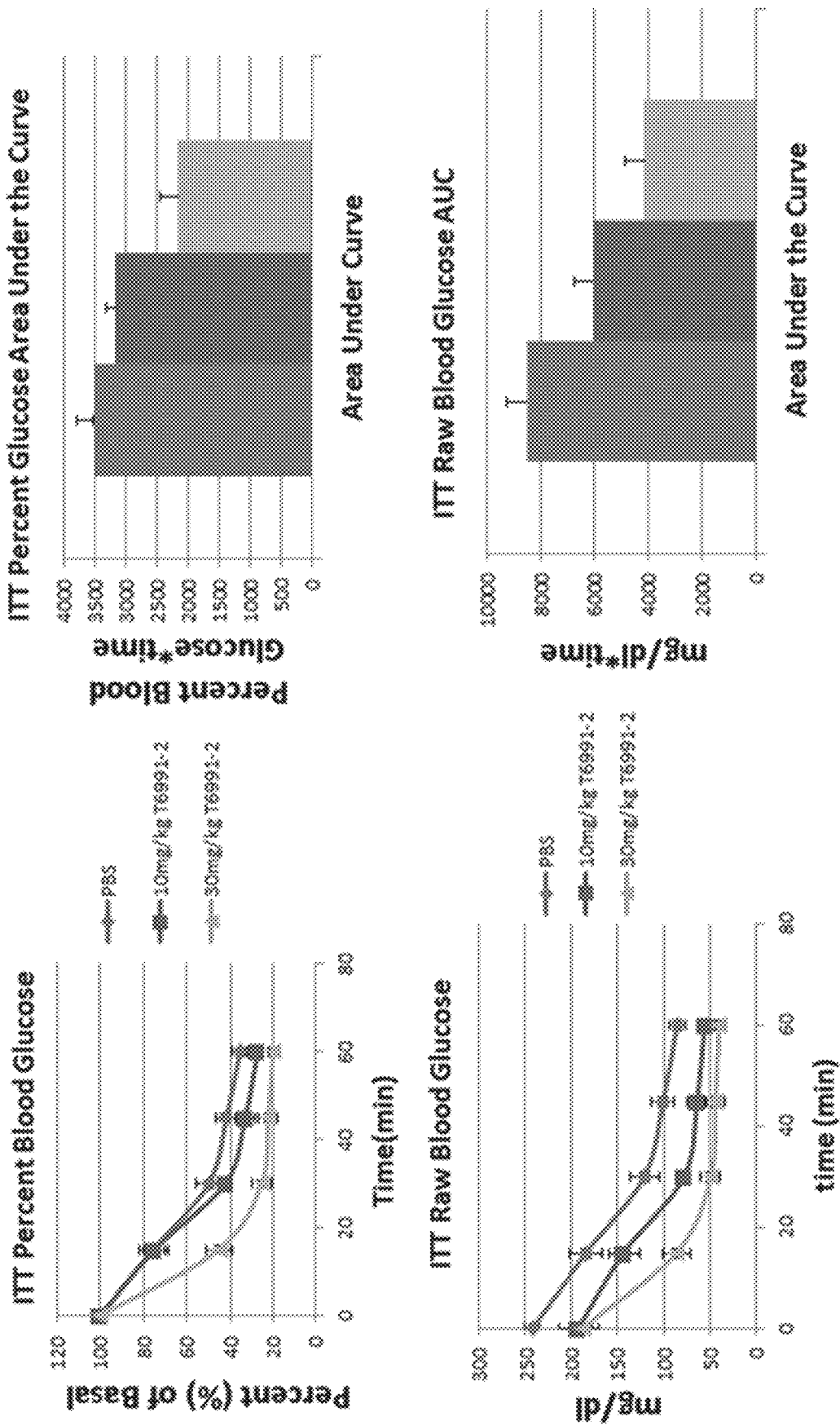
FIG. 45—T6991-2 improves sensitivity to insulin in DIO mice.

T6991-2 also improved sensitivity to insulin in DIO mice (FIG. 45). Male C57Bl/6 mice were fed a 60% high-fat diet for 6 weeks (DIO model); then injected intraperitonelly (IP) with either vehicle alone, 10 or 30 mg/kg of lipid-free T6991-2 on alternate days for 6 weeks as described in FIG. 44. Following treatment, an insulin tolerance test (ITT) was performed via IP injection of 0.75 Units/kg. Blood was collected via the tail vein at the indicated times and blood glucose measured using a glucometer. Panels A and B—Blood glucose concentrations expressed as percent of control values at t=0, with corresponding area under the curve plot, respectively. Panels C and D—Blood glucose concentrations expressed as absolute values over time following glucose challenge, with corresponding area under the curve, respectively. Values are means±SD, n=4 mice per group. (Right side of Figure-Panels B and D: left bar, PBS; middle bar, 10 mg/kg T6991-2; right bar, T6991-2, 30 mg/kg) The data indicated that low-dose T6991-2 improved sensitivity to insulin and that the effect was dose-dependent.

Figure 46:
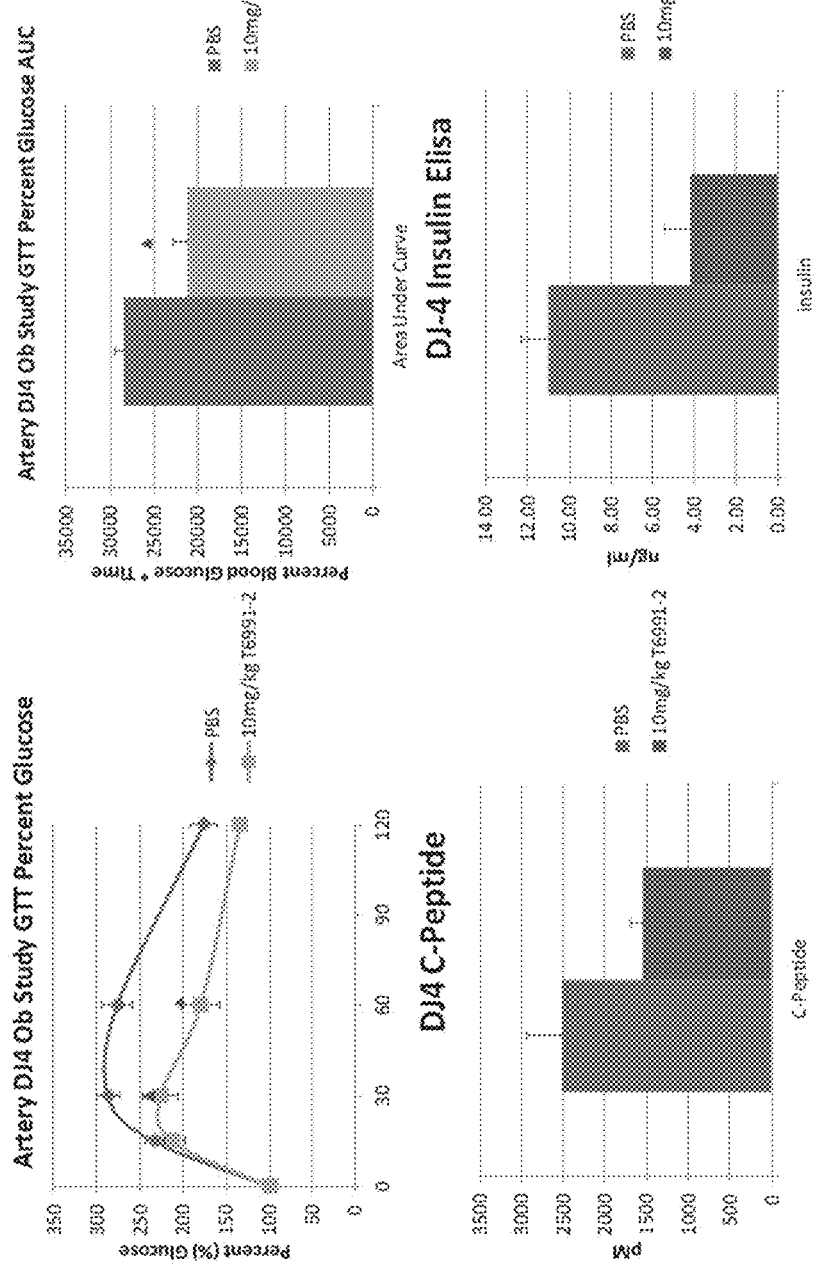
FIG. 46—T6991-2 lowers blood glucose concentrations upon glucose challenge in ob/ob genetic mouse model of obesity.

In addition, T6991-2 lowered blood glucose concentrations upon glucose challenge in ob/ob genetic mouse model of obesity (FIG. 46). Male ob/ob mice were fed chow diet for 6 weeks (DIO model); then injected intraperitonelly (IP) with either vehicle alone (left bars of bar graphs) or 10 mg/kg of lipid-fee T6991-2 (right bars of bar graphs) on alternate days for 6 weeks. Following treatment, a glucose tolerance test was performed via IP injection of 1 g/kg glucose. Blood was collected via the tail vein at the indicated times and blood glucose measured using a glucometer. Panels A and B—Blood glucose concentrations expressed as percent of control values at t=0, with corresponding area under the curve plot, respectively. Panels C and D—C-peptide and insulin concentrations following 6 h fasting and 2 post peptide injections are lower in treated mice suggesting that the improved glucose challenge response shown in panels A and B are not insulin mediated. Values are means±SD, n=4 mice per group. The data indicated that low-dose T6991-2 attenuated the blood glucose response upon glucose challenge in ob/ob mice.

Example 32

This example illustrates that the leucine form of CitATI-5261 supports various amino acid substitutions to create safe and effective peptides (FIG. 47). Analogs of ATI-5261 were created with isoleucine (I) at positions 10, 13, 16, 20 and/or citrulline at positions 3 and 14, as well as shorter 24-mers lacking C-terminal KS residues (sequences—top of FIG. 47, i.e. T7983 series of peptides). Panel A—Safety and TG elevating effects were evaluated by injecting (IP) peptides (300 mg/kg) into male, chow-fed C57Bl/6 mice, as described in FIG. 5. Values are means SD, n=4. All peptides having citrulline, leucine and isoleucine in various combinations at the specified positions were safe and displayed little or no TG elevating effects.

Example 33

Figure 48:
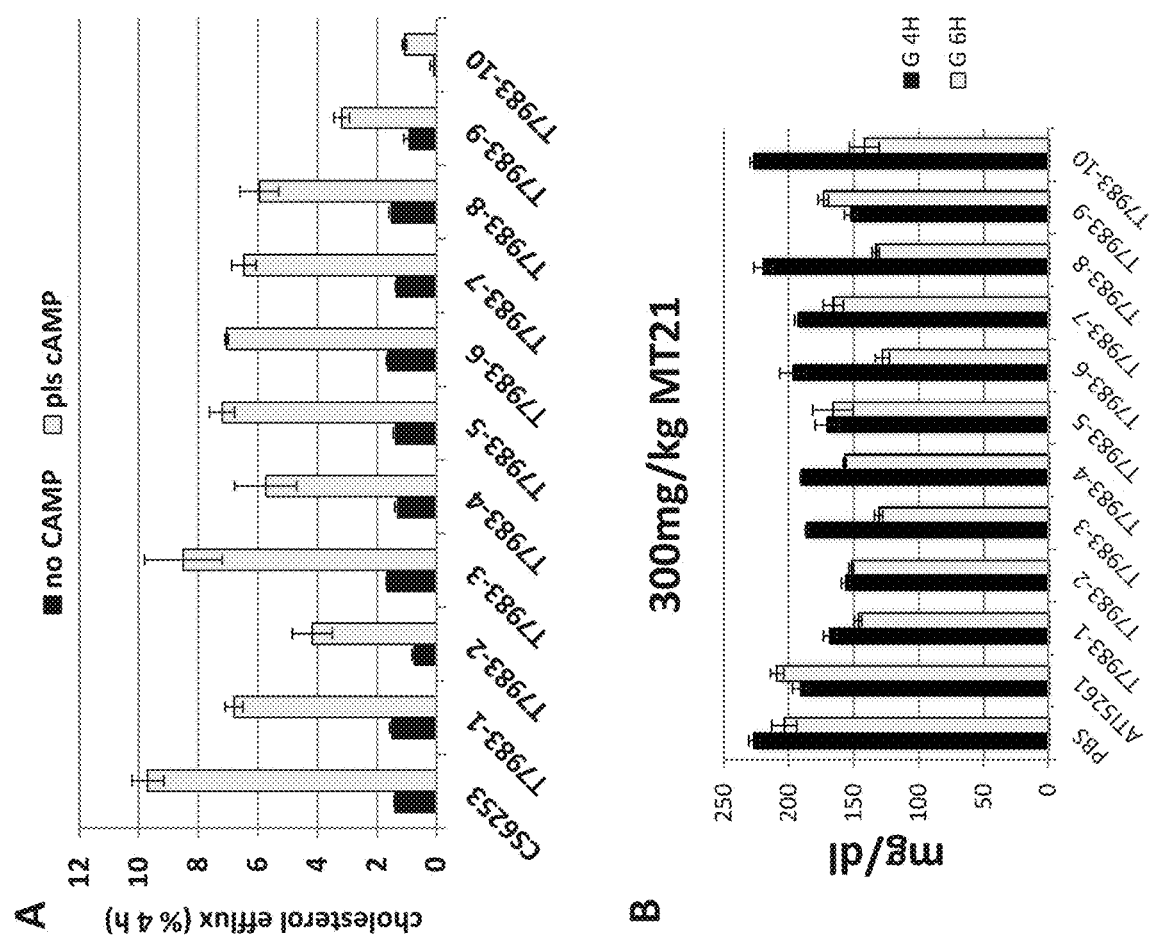
FIG. 48—Panels A and B: Aliphatic forms of CitATI-5261 with either leucine or isoleucine substitutions retain cholesterol efflux activity and reduce blood glucose in mice.

This example illustrates that aliphatic forms of CitATI-5261 with either leucine or isoleucine substitutions retain cholesterol efflux activity and reduce blood glucose in mice (FIG. 48). The peptides tested were from FIG. 47, i.e. T7983 series. Panel A-Cholesterol efflux activity of peptides was determined using J774 macrophages labeled with [3H]cholesterol and treated with (right bars) and without (left bars) cAMP to modulate ABCA1 expression. Peptide analogs with leucine, isoleucine and/or citrulline substitutions were functional, mediating high-levels of cholesterol efflux in an ABCA-dependent manner at concentrations of 10 µg/ml. Panel B— Glucose concentrations in blood of C57Bl/6 mice (chow fed) used in FIG. 47, following a single IP injection of 300 mg/kg of T7983 peptides. Nearly all the peptides tested reduced blood glucose levels following single injection.

Example 34

This example illustrates that analogs of CS6253 with increasing numbers of isoleucine residues are safe and effective (FIG. 49). Increasing numbers of isoleucine residues were systematically introduced into CS6253 via L→I substitutions at different locations down the hydrophobic length of the peptides (sequences—top of FIG. 49, i.e. T8212 series of peptides). Panel A—Safety and TG elevating effects were evaluated by injecting (IP) peptides (300 mg/kg) into male, chow-fed C57Bl/6 mice, as described in FIG. 5. Values are means SD, n=4. All peptides having the various combinations of leucine and isoleucine at the specified positions were safe and displayed little or no TG elevating effects.

Example 35

Figure 50:
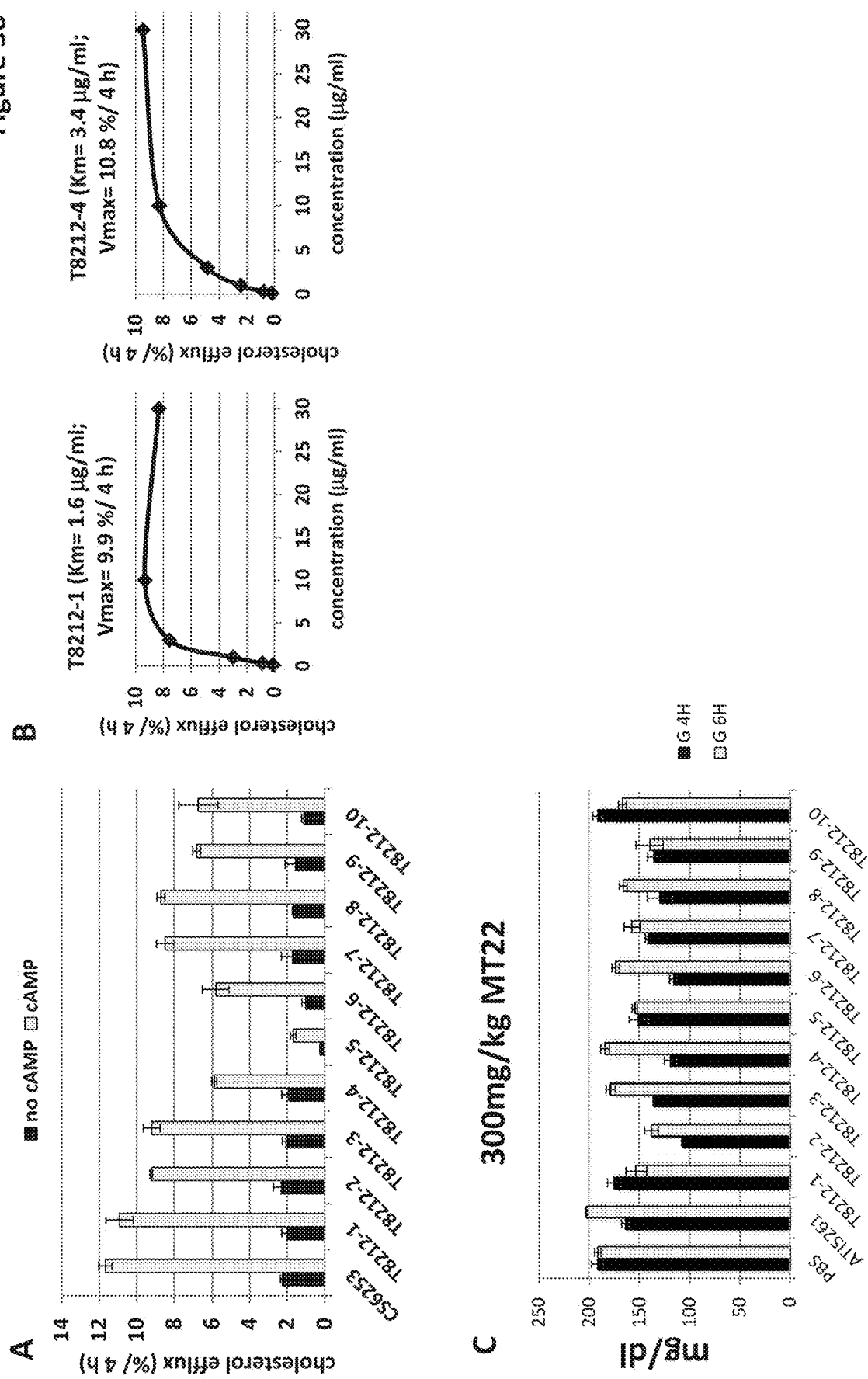
FIG. 50—Panels A-C: Aliphatic forms of CS6253 with increasing isoleucine substitutions retain cholesterol efflux activity and reduce blood glucose in mice.

This example illustrates that aliphatic forms of CS6253 with increasing isoleucine substitutions retain cholesterol efflux activity and reduce blood glucose in mice (FIG. 50). The peptides tested were from FIG. 49, i.e. T8212 series. Panel A—Cholesterol efflux activity of peptides was determined using J774 macrophages labeled with [3H]cholesterol and treated with (right bars) and without (left bars) cAMP to modulate ABCA1 expression. Peptide analogs with increasing isoleucine substitutions were functional, mediating high-levels of cholesterol efflux in an ABCA-dependent manner at concentrations of 10 µg/ml. Panel B— Representative CS6253 peptides with either one or two L→I substitutions stimulate ABCA1 cholesterol efflux in a concentration dependent manner and with high potency. Results were obtained using cAMP treated J774 macrophages. Panel C— Glucose concentrations in blood of C57Bl/6 mice (chow fed) used in FIG. 49, following a single (IP) injection of 300 mg/kg of T8212 peptides (left bars, 4H; right bars, 6H). Nearly all the peptides tested reduced blood glucose levels compared to PBS following a single injection.

Example 36

Figure 51:
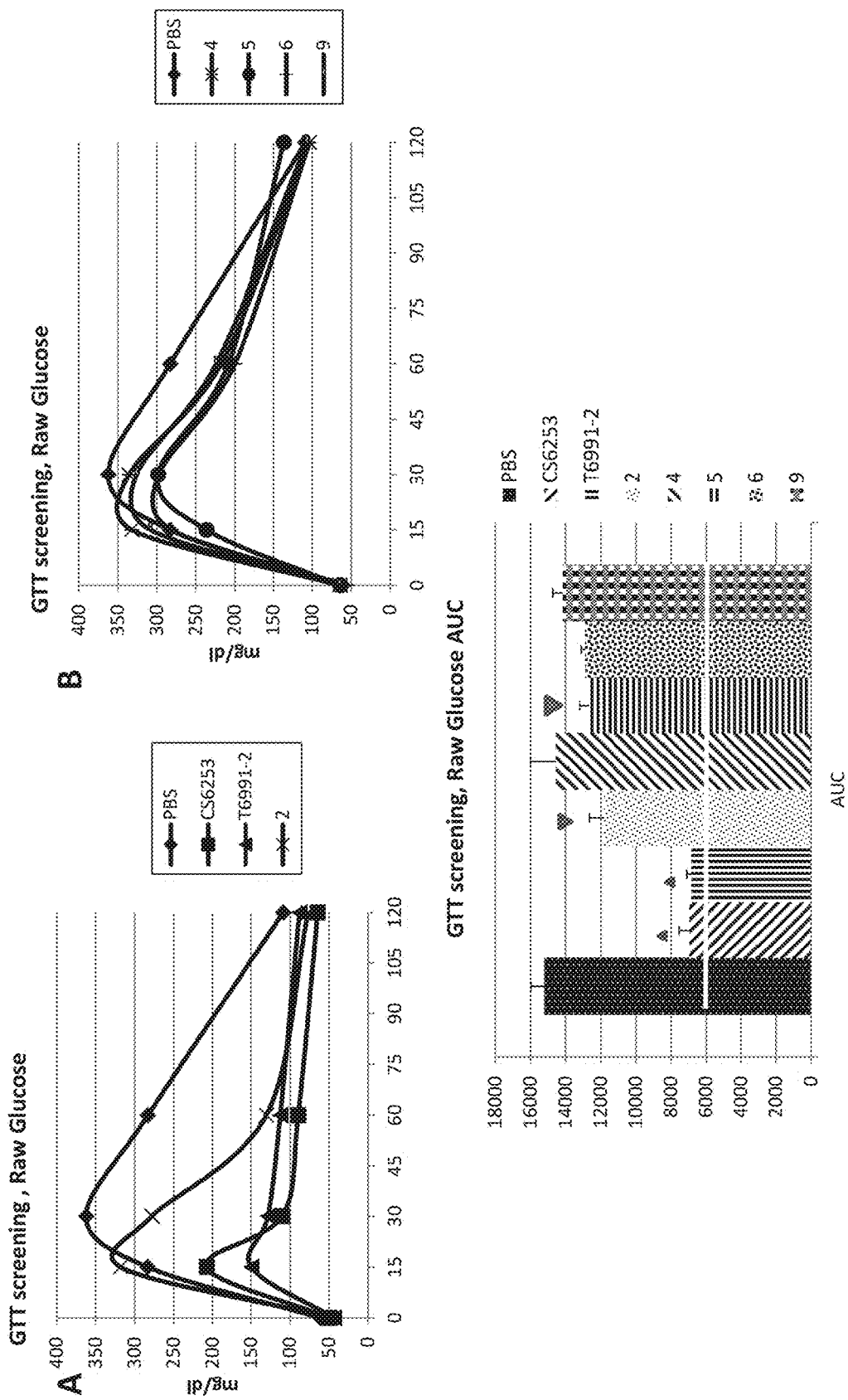
FIG. 51—Panels A and B: CS6253 and T6991-2 lower blood glucose concentrations upon glucose challenge in C57Bl/6 mice.

This example illustrates that CS6253 and T6991-2 lower blood glucose concentrations upon glucose challenge in C57Bl/6 mice (FIG. 51). Fasted male C57Bl/6 mice on chow diet received a single intraperitoneal (IP) injection of either vehicle alone or 300 mg/kg of lipid-free peptide, as described for safety studies in FIG. 5. Following treatment, a glucose tolerance test was performed via IP injection of 2 g/kg glucose. Blood was collected from the tail vein at the indicated times and blood glucose measured using a glucometer. Panels A and B—Blood glucose concentrations expressed as mass values over time following glucose challenge, with corresponding area under the curve, respectively. (Bar graph, panel B, bars from left to right are PBS, CS6253, T699102, 2, 4, 5, 6, and 9, respectively) Values are means±SD, n=4 mice per group. The two citrulline forms of ATI-5261 with either all leucine (CS6253) or all isoleucine (T6991-2) at positions 10, 13, 16 and 20, lowered blood glucose concentrations upon glucose challenge. In contrast, peptides 2, 4, 5, 6 and 9 (corresponding to sequences T8212-2, T8212-4, T8212-5, T8212-6, and T8212-9 in FIG. 49) with various combinations of leucine and isoleucine residues were poorly active in lowering blood glucose responses. Collectively, these data indicate that homogenous use of either leucine or isoleucine at important positions down the length of HDL mimetic peptides is a factor in creating highly efficacious anti-diabetic compounds.

Example 37

This example illustrates the plasma clearance of CS6253 and T6991-2 in rats (FIG. 52). Both peptides were designed with a S26→Y substitution to facilitate labeling with $^{125}$I, as described in FIG. 36. Radiolabeled peptides were injected IP into male, chow-fed Wistar rats and its appearance and subsequent clearance from plasma quantified. Panel A—Plasma kinetics following injection of $^{125}$I-CS6253 or $^{125}$I-T6991-2 peptide indicating a plasma half-life of approximately 7.5 h for both peptides. Panel B— Tissue distribution of $^{125}$I-peptides at 6 and 24 h post injection (CS6253=left bars and T6991-2=right bars). Note that small amounts of both peptides appeared in the brain, which increased over time. Panel C-Cholesterol efflux activity of T6991-2 and its Y26 analog (T7983-11) determined using J774 macrophages labeled with [3H]cholesterol (ABCA dependent efflux shown on right bars). The peptides were functional, mediating high-levels of cholesterol efflux in an ABCA1-dependent manner at concentrations (10 μg/ml). Panel D—Dose response demonstrating that T6991-2 and its Y26 analog (T7983-11) stimulated cholesterol efflux with high efficiency, displaying a low Km and saturation of cholesterol efflux at 3 μg/ml.

Example 38

Figure 53:
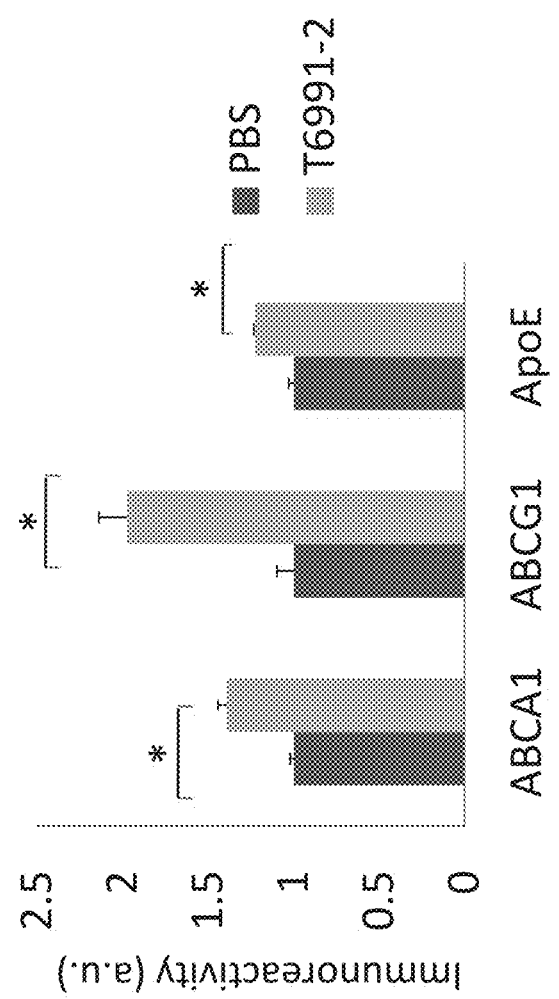
FIG. 53—Systemic administration of peptide T6991-2 increases brain ABC transporters in mice.

This example illustrates that peptides of the invention increase brain ABC transporters in mice. Illustrative data showing that systemic administration of peptide T6991-2 increased brain ABC transporters in mice are provided in FIG. 53. T6991-2: EVC*SKLEEWIAAIC*EIAEEILARLKS SEQ ID NO:80, an isoleucine form of ATI-5261, was administered IP at 30 mg/kg/48 h once daily for 5 weeks to ApoE3 mice. At termination hippocampus was assessed for ABCA1, ABCG1 and apoE by ELISA. T6991-2 (right bars) significantly increased their concentrations (p<0.05) compared to PBS (left bars).

Example 39

Figure 54:
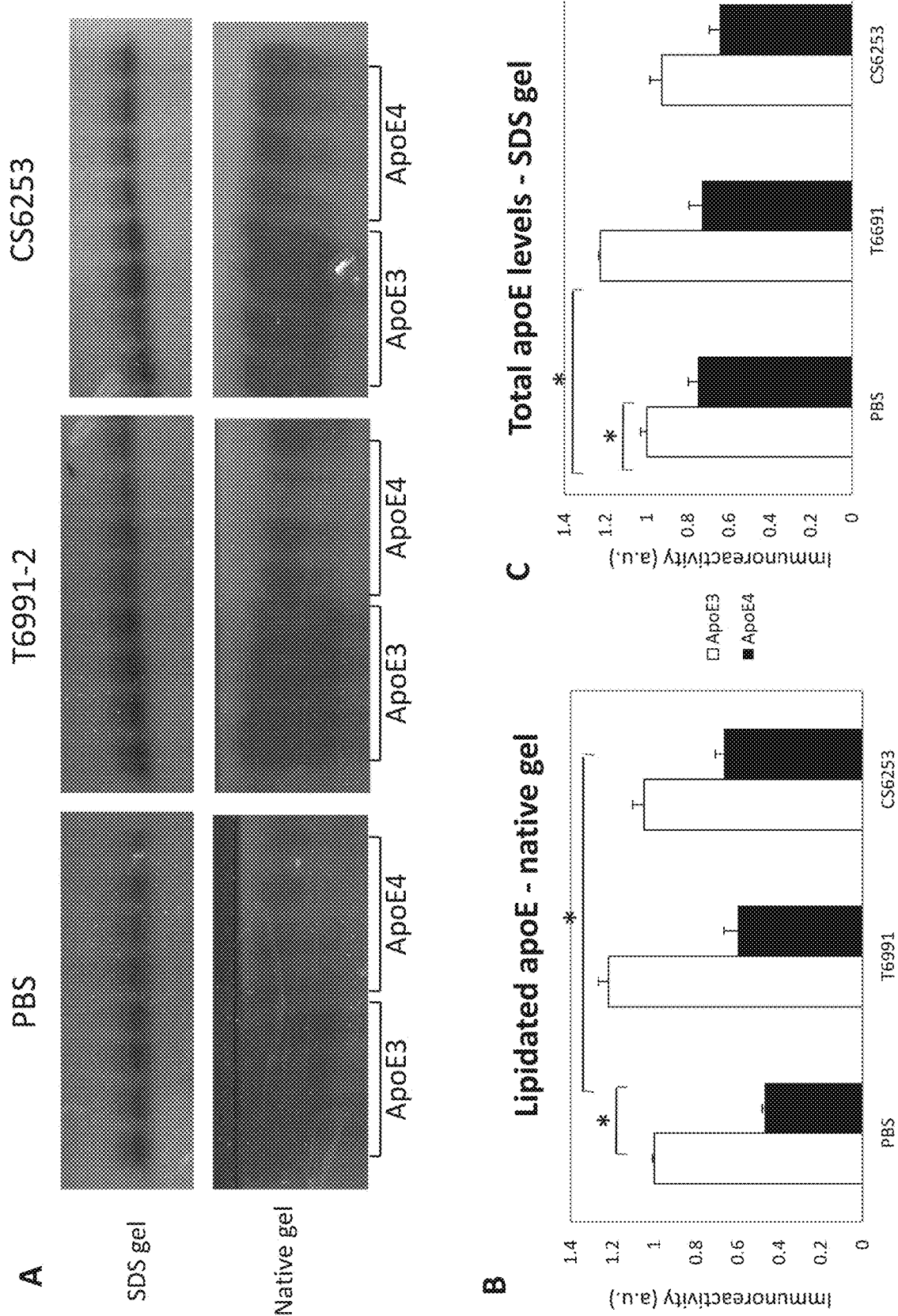
FIG. 54—Panels A-C: Systemic administration of either CS6253 or T6991-2 increases apoE levels and lipidation in brain of mice.

This example illustratives that peptides of the invention increase brain apoE levels and lipidation using human apoE3 and E4 replacement mouse models. Illustrative data showing that systemic administration of either CS6253 or T6991-2 increased brain apoE levels and lipidation are provided in FIG. 54. T5237-4 (i.e. CS6253): EVC*SKLEEWLAALC*ELAEELLARLKS (SEQ ID NO:47) (C*=citrulline), a leucine form of ATI-5261, and T6991-2: EVC*SKLEEWIAAIC*EIAEEILARLKS (SEQ ID NO:80), (C*=citrulline), an isoleucine form of ATI-5261, were administered to human apoE3 (huApoE3) and E4 (huApoE4) replacement mice, 30 mg/kg/48 h IP for 5 weeks and compared to PBS (n=mice per group), i.e. "the AD study". At termination, hippocampus was assessed for apoE protein levels (SDS gel) and lipidation (native gel). Panel A—Representative blots showing relative levels of apoE protein in their respective mouse model, i.e., human E3 vs. E4 protein and by peptide treatment. Panels B and C—Levels of lipidated (native) and total apoE protein (SDS-PAGE) in the E3 (open bars) vs. E4 (solid bars) mice, respectively. Lipidated apoE was markedly higher in huApoE3 mice than the corresponding levels of huApoE4. The peptides, in particular CS6253, increased the amount of lipidated apoE4 relative to corresponding samples of T6991-2 treated mice. T6991-2 increased apoE levels in huApoE3 mice.

Example 40

Figure 55:
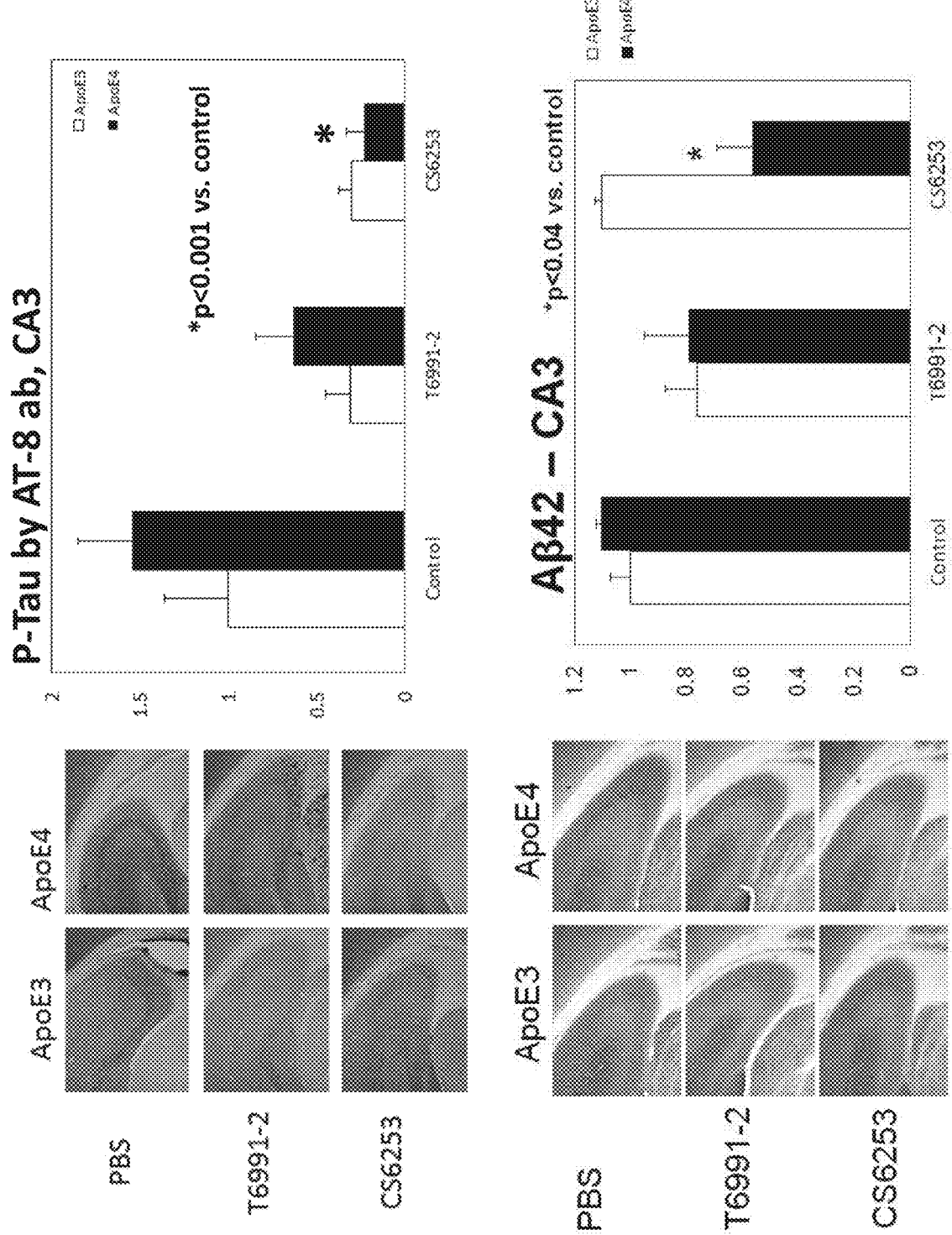
FIG. 55—Systemic administration of CS6253 and T6991-2 decrease P-tau and amyloidβ42 in brain of mice.

This example provides data (FIG. 55) illustrating that systemic administration of peptides of the invention decreased P-tau and amyloidβ42 in the brain of mice. At termination of the AD study described in Example 39 and FIG. 54, the CA3 region of hippocampus was assessed for P-Tau (AT-8 a.b.) and amyloidβ42. In huApoE4 mice, CS6253 significantly decreased P-Tau (p<0.001) and amyloidβ42 (p=0.04) compared to PBS. Peptide T6991-2 also decreased P-Tau and Amyloidβ42 in both huApoE3 and huApoE4 mice.

Example 41

Figure 56:
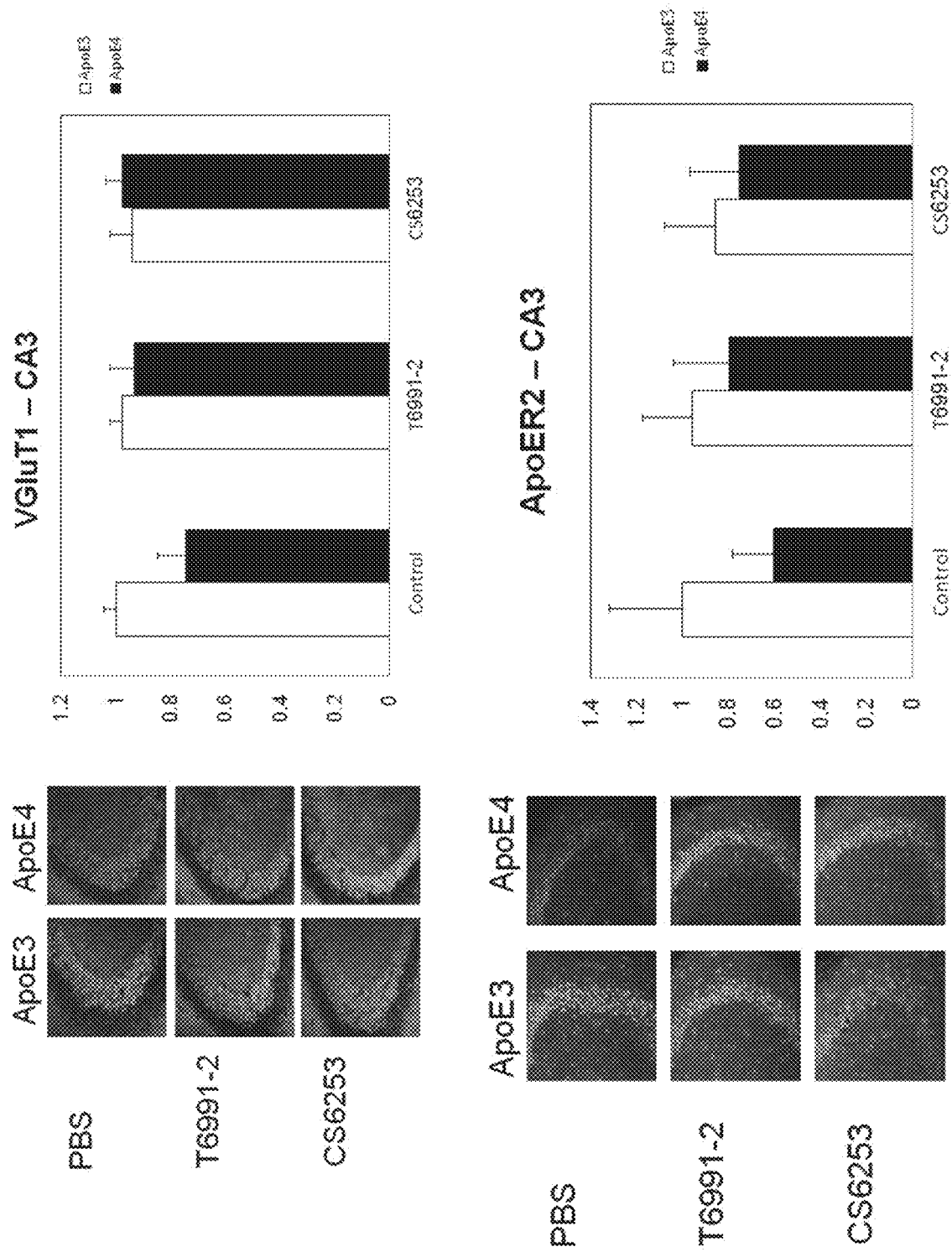
FIG. 56—Systemic administration of CS6253 and T6991-2 reverses E4 phenotype with regards to suppressed VGlut1 and apoEReceptor2 and increases neuronal plasticity.

This example provides data illustrating that systemic administration of peptides of the invention reversed E4 phenotype. Illustrative data showing that systemic administration of CS6253 and T6991-2 reversed the pathological apoE4 phenotype with regards to suppressed VGlut1 and apoEReceptor2 are provided in FIG. 56. At termination of the AD study described in Example 39 FIG. 54, the CA3 region of hippocampus was assessed for VGlut1 (glutaminergic neuron) and apoEReceptor2. Both peptides reversed the deficiency in the levels of VGluT1 and apoER2 of huAapoE4 mice compared to PBS.

The exemplary data provided above demonstrates that the polypeptides of the invention exhibited little to no cytotoxicity and demonstrated their in vivo efficacy, had glucose lowering effects, and reversed phenotypic indicators of Alzheimer's Disease in mice. Anti-diabetic, anti-atherosclerotic and effects in brain were found at pharmacological doses, e.g., ≤30 mg/kg.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, publications, and accession numbers are incorporated herein by reference for all purposes.

What is claimed is:

1. A method for mediating cholesterol efflux in a mammal, said method comprising administering to said mammal a polypeptide having cholesterol efflux activity, wherein the polypeptide comprises an amino acid sequence that is an amphipathic α-helix that has a non-polar surface and a polar surface, wherein the polar surface comprises charged and uncharged amino acid residues at the lipid-water interface, wherein the amino acid sequence:
has at least 60% identity to SEQ ID NO:1; and
comprises a citrulline, or an uncharged analog of citrulline that has a modified R group or modified backbone, but retains the chemical structure of citrulline and maintains a salt-bridge configuration in the α-helix, at one of the three positions 3, 14, and 23 as determined with reference to SEQ ID NO:1; an uncharged amino acid at the second of the three positions 3, 14, and 23; and an uncharged amino acid or R or K at the third of the three positions 3, 14, and 23;
comprises an aliphatic amino acid at positions 2, 6, 10, 11, 12, 13, 16, 17, 20, 21, 22, and 24 as determined with reference to SEQ ID NO:1; and a W or aliphatic residue at position 9;
comprises a positively charged amino acid at position $X_5$;
comprises a polar uncharged amino acid at position $X_4$; and
comprises an acidic amino acid residue at positions 1, 7, 8, 15, 18, and 19 as determined with reference to SEQ ID NO:1.

2. The method of claim 1, wherein the amino acid sequence comprises a citrulline at two of the three positions 3, 14, and 23; and an R or K at the third position.

3. The method of claim 1, wherein the amino acid sequence comprises an uncharged amino acid at the second and third of the three positions 3, 14, and 23.

4. The method of claim 1, wherein the α-helix amino acid sequence is 24 amino acids in length and further comprises a position 25 and 26, wherein position 25 is K or N and position 26 is S or Y.

5. The method of claim 1, wherein the amino acid sequence has Q, N, L, V, I, or A at at least one of the three position 3, 14, or 23.

6. The method of claim 5, wherein the amino acid sequence has Q or N at least one of the three positions 3, 14, or 23.

7. The method of claim 1, wherein the amino acid sequence comprises an amino acid residue at two of the three positions 3, 14, and 23 that are independently selected from Q, N, L, V, I, or A.

8. The method of claim 1, wherein the amino acid sequence comprises R or K at one of the three positions 3, 14, and 23.

9. The method of claim 1, wherein the amino acid sequence comprises a citrulline at positions 3 and 14 and an R or K at position 23.

10. The method of claim 1, wherein the aliphatic amino acids at positions 2, 6, 10, 11, 12, 13, 16, 17, 20, 21, and 24 are independently selected from the group consisting of L, V, A, and I.

11. The method of claim 10, wherein the amino acid sequence comprises an aliphatic amino acid independently selected from the group consisting of L, I, and V at positions 10, 13, 16, and 20.

12. The method of claim 1, wherein the amino acid sequence comprises SEQ ID NO:1 or SEQ ID NO:2.

13. The method of claim 1, wherein the polypeptide further comprises a protecting group.

14. The method of claim 1, wherein said mammal is a human.

15. The method of claim 14, wherein the human has an ApoE4 allele.

16. The method of claim 1, wherein the mammal has a symptom of atherosclerosis.

17. The method of claim 1, wherein the mammal has diabetes, metabolic syndrome or pre-diabetes.

18. The method of claim 1, wherein the mammal has macro or microvascular disease, chronic kidney disease, or congestive heart failure.

19. The method of claim 1, wherein the mammal is a human patient diagnosed with or at risk for Alzheimer's Disease, Mild Cognitive Impairment, or frontotemporal dementia.

20. The method of claim 1, wherein the method further comprises imaging peptide binding to cells or tissue.

21. The method of claim 1, wherein the method further comprises evaluating a sample from the mammal in vitro for cholesterol efflux.

22. The method of claim 10, wherein positions 10, 13, 16, and 20 are L.

23. The method of claim 1, wherein positions 10, 13, 16, and 20 are I.

24. The method of claim 1, wherein the amino acid sequence has at least 70% identity to SEQ ID NO:1.

25. The method of claim 1, wherein the amino acid sequence comprises: a citrulline at two of the three positions 3, 14, and 23 as determined with reference to SEQ ID NO: 1; and an uncharged amino acid, or R or K at the third of the three positions 3, 14, and 23; an aliphatic amino acid at positions 2, 6, 10, 11, 12, 13, 16, 17, 20, 21, 22, and 24 as determined with reference to SEQ ID NO:1; and a W or aliphatic residue at position 9; wherein the aliphatic amino acid at each position is independently selected from L, V, A, and I; an acidic amino acid residue at positions 1, 7, 8, 15, 18, and 19, wherein the acidic amino acid residue is independently selected from D and E; R or K at position X5; and S at position X4.

26. A method for mediating cholesterol efflux in a mammal, said method comprising administering to said mammal a polypeptide having cholesterol efflux activity, wherein the polypeptide comprises an amphipathic α-helix that has a non-polar surface and a polar surface, wherein the polar surface comprises charged and uncharged amino acid residues at the lipid-water interface and, wherein the α-helix amino acid sequence:

has at least 60% identity to SEQ ID NO:1;

has an acidic amino acid residue at positions 1, 7, 8, 15, 18, and 19 as determined with reference to SEQ ID NO:1;

has an aliphatic amino acid independently selected from V, L, and I, or an uncharged amino acid analog thereof that has a modified R group or modified backbone, but retains the chemical structure, at positions 10, 13, 16, and 20, as determined with reference to SEQ ID NO:1; wherein the uncharged amino acid analog has an aliphatic side chain and has a hydrophobicity of V or greater than V;

has an aliphatic amino acid residue at positions 2, 6, 11, 12, 17, 21, and 24 as determined with reference to SEQ ID NO:1; and a W or aliphatic residue at position 9;

has a positively charged residue at position 5; and has an uncharged polar amino acid residue at at least two of positions 3, 14, and 23 as determined with reference to SEQ ID NO:1.

* * * * *

UNITED STATES PATENT AND TRADEMARK OFFICE
CERTIFICATE OF CORRECTION

PATENT NO. : 10,774,118 B2
APPLICATION NO. : 16/020395
DATED : September 15, 2020
INVENTOR(S) : Bielicki et al.

Page 1 of 1

It is certified that error appears in the above-identified patent and that said Letters Patent is hereby corrected as shown below:

In the Claims

In Column 128, Line 28, Claim 6, after "at" insert --at--.

Signed and Sealed this
Twenty-second Day of December, 2020

Andrei Iancu
*Director of the United States Patent and Trademark Office*

SEQUENCE LISTING

```
<160> NUMBER OF SEQ ID NOS: 112

<210> SEQ ID NO 1
<211> LENGTH: 24
<212> TYPE: PRT
<213> ORGANISM: Artificial Sequence
<220> FEATURE:
<223> OTHER INFORMATION: synthetic amphipathic alpha-helix cholesterol
      efflux peptide
<220> FEATURE:
<221> NAME/KEY: MOD_RES
<222> LOCATION: (3)...(14)
<223> OTHER INFORMATION: Xaa = citrulline (cit, Cit)
```

```
<400> SEQUENCE: 1

Glu Val Xaa Ser Lys Leu Glu Glu Trp Leu Ala Ala Leu Xaa Glu Leu
1               5                   10                  15

Ala Glu Glu Leu Leu Ala Arg Leu
            20

<210> SEQ ID NO 2
<211> LENGTH: 24
<212> TYPE: PRT
<213> ORGANISM: Artificial Sequence
<220> FEATURE:
<223> OTHER INFORMATION: synthetic amphipathic alpha-helix cholesterol
      efflux peptide
<220> FEATURE:
<221> NAME/KEY: MOD_RES
<222> LOCATION: (3)...(14)
<223> OTHER INFORMATION: Xaa = citrulline (cit, Cit)

<400> SEQUENCE: 2

Glu Val Xaa Ser Lys Leu Glu Glu Trp Ile Ala Ala Ile Xaa Glu Ile
1               5                   10                  15

Ala Glu Glu Ile Leu Ala Arg Leu
            20

<210> SEQ ID NO 3
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide
<220> FEATURE:
<221> NAME/KEY: MOD_RES
<222> LOCATION: (3)...(14)
<223> OTHER INFORMATION: Xaa = citrulline (cit, Cit)

<400> SEQUENCE: 3

Glu Val Xaa Ser Lys Leu Glu Glu Trp Leu Ala Ala Leu Xaa Glu Leu
1               5                   10                  15

Ala Glu Glu Leu Leu Ala Arg Leu Lys Ser
            20                  25

<210> SEQ ID NO 4
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide
<220> FEATURE:
<221> NAME/KEY: MOD_RES
<222> LOCATION: (3)...(14)
<223> OTHER INFORMATION: Xaa = citrulline (cit, Cit)

<400> SEQUENCE: 4

Glu Val Xaa Ser Lys Leu Glu Glu Trp Ile Ala Ala Ile Xaa Glu Ile
1               5                   10                  15

Ala Glu Glu Ile Leu Ala Arg Leu Lys Ser
            20                  25

<210> SEQ ID NO 5
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T55055-13 (LeuATI-5261)
```

```
<400> SEQUENCE: 5

Glu Val Arg Ser Lys Leu Glu Glu Trp Leu Ala Ala Leu Arg Glu Leu
1               5                   10                  15

Ala Glu Glu Leu Leu Ala Arg Leu Lys Ser
            20                  25

<210> SEQ ID NO 6
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5055-14

<400> SEQUENCE: 6

Glu Val Arg Ser Lys Leu Glu Glu Trp Phe Ala Ala Leu Arg Glu Leu
1               5                   10                  15

Ala Glu Glu Leu Leu Ala Arg Leu Lys Ser
            20                  25

<210> SEQ ID NO 7
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5055-15

<400> SEQUENCE: 7

Glu Val Arg Ser Lys Leu Glu Glu Trp Phe Ala Ala Phe Arg Glu Leu
1               5                   10                  15

Ala Glu Glu Leu Leu Ala Arg Leu Lys Ser
            20                  25

<210> SEQ ID NO 8
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5055-16

<400> SEQUENCE: 8

Glu Val Arg Ser Lys Leu Glu Glu Trp Phe Ala Ala Phe Arg Glu Phe
1               5                   10                  15

Ala Glu Glu Leu Leu Ala Arg Leu Lys Ser
            20                  25

<210> SEQ ID NO 9
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5055-17 (ATI-5261)

<400> SEQUENCE: 9

Glu Val Arg Ser Lys Leu Glu Glu Trp Phe Ala Ala Phe Arg Glu Phe
1               5                   10                  15

Ala Glu Glu Phe Leu Ala Arg Leu Lys Ser
            20                  25

<210> SEQ ID NO 10
```

```
<211> LENGTH: 24
<212> TYPE: PRT
<213> ORGANISM: Artificial Sequence
<220> FEATURE:
<223> OTHER INFORMATION: synthetic amphipathic alpha-helix cholesterol
      efflux peptide T5766-5, ATI-5261 analog

<400> SEQUENCE: 10

Glu Val Arg Ser Lys Leu Glu Glu Trp Phe Ala Ala Phe Arg Glu Phe
1               5                   10                  15

Ala Glu Glu Phe Leu Ala Arg Leu
            20

<210> SEQ ID NO 11
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5594-4, ATI-5261 analog

<400> SEQUENCE: 11

Glu Val Arg Ser Lys Leu Glu Glu Trp Phe Ala Ala Phe Arg Glu Phe
1               5                   10                  15

Ala Glu Glu Phe Leu Ala Arg Leu Asn Ser
            20                  25

<210> SEQ ID NO 12
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5594-5, ATI-5261 analog

<400> SEQUENCE: 12

Glu Val Lys Ser Lys Leu Glu Glu Trp Phe Ala Ala Phe Lys Glu Phe
1               5                   10                  15

Ala Glu Glu Phe Leu Ala Lys Leu Lys Ser
            20                  25

<210> SEQ ID NO 13
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5766-3, LeuATI-5261 analog

<400> SEQUENCE: 13

Glu Val Gln Ser Lys Leu Glu Glu Trp Leu Ala Ala Leu Gln Glu Leu
1               5                   10                  15

Ala Glu Glu Leu Leu Ala Arg Leu Lys Ser
            20                  25

<210> SEQ ID NO 14
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5766-4, LeuATI-5261 analog

<400> SEQUENCE: 14

Glu Val Asn Ser Lys Leu Glu Glu Trp Leu Ala Ala Leu Asn Glu Leu
1               5                   10                  15
```

Ala Glu Glu Leu Leu Ala Arg Leu Lys Ser
            20                  25

<210> SEQ ID NO 15
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T4873-7 (LeuATI-5261)

<400> SEQUENCE: 15

Glu Val Arg Ser Lys Leu Glu Glu Trp Leu Ala Ala Leu Arg Glu Leu
1               5                   10                  15

Ala Glu Glu Leu Leu Ala Arg Leu Lys Ser
            20                  25

<210> SEQ ID NO 16
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T4883-6, LeuATI-5261 analog

<400> SEQUENCE: 16

Glu Val Arg Ser Lys Leu Glu Glu Trp Leu Ala Ala Leu Arg Glu Leu
1               5                   10                  15

Ala Glu Glu Leu Leu Ala Arg Ala Lys Ser
            20                  25

<210> SEQ ID NO 17
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T4883-7, LeuATI-5261 analog

<400> SEQUENCE: 17

Glu Val Arg Ser Lys Leu Glu Glu Trp Leu Ala Ala Leu Arg Glu Leu
1               5                   10                  15

Ala Glu Glu Leu Ala Ala Arg Leu Lys Ser
            20                  25

<210> SEQ ID NO 18
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T4883-12, LeuATI-5261 analog

<400> SEQUENCE: 18

Glu Val Arg Ser Lys Leu Glu Glu Trp Leu Ala Ala Leu Arg Glu Ala
1               5                   10                  15

Ala Glu Glu Leu Ala Ala Arg Ala Lys Ser
            20                  25

<210> SEQ ID NO 19
<211> LENGTH: 26
<212> TYPE: PRT
<213> ORGANISM: Artificial Sequence
<220> FEATURE:
<223> OTHER INFORMATION: synthetic amphipathic alpha-helix cholesterol efflux peptide T5505-1, LeuATI-5261 analog

<400> SEQUENCE: 19

Glu Ala Arg Ser Lys Leu Glu Glu Trp Leu Ala Ala Leu Arg Glu Leu
1               5                   10                  15

Ala Glu Glu Leu Leu Ala Arg Leu Lys Ser
            20                  25

<210> SEQ ID NO 20
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5505-3, LeuATI-5261 analog

<400> SEQUENCE: 20

Glu Val Arg Ser Lys Leu Glu Glu Trp Ala Ala Ala Leu Arg Glu Leu
1               5                   10                  15

Ala Glu Glu Leu Leu Ala Arg Leu Lys Ser
            20                  25

<210> SEQ ID NO 21
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5505-9, LeuATI-5261 analog

<400> SEQUENCE: 21

Glu Val Arg Ser Lys Leu Glu Glu Leu Leu Ala Ala Leu Arg Glu Leu
1               5                   10                  15

Ala Glu Glu Leu Leu Ala Arg Ala Lys Ser
            20                  25

<210> SEQ ID NO 22
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5505-12, LeuATI-5261 analog

<400> SEQUENCE: 22

Glu Ala Arg Ser Lys Ala Glu Glu Trp Leu Ala Ala Leu Arg Glu Leu
1               5                   10                  15

Ala Glu Glu Leu Leu Ala Arg Ala Lys Ser
            20                  25

<210> SEQ ID NO 23
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5325-4, LeuATI-5261 analog

<400> SEQUENCE: 23

Glu Val Arg Ser Lys Leu Glu Glu Ala Leu Ala Ala Leu Arg Glu Leu
1               5                   10                  15

Ala Glu Glu Leu Leu Ala Arg Leu Lys Ser
            20                  25

```
<210> SEQ ID NO 24
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5325-8, LeuATI-5261 analog

<400> SEQUENCE: 24

Glu Val Arg Ser Lys Leu Glu Glu Val Leu Ala Ala Leu Arg Glu Leu
1               5                   10                  15

Ala Glu Glu Leu Leu Ala Arg Ala Lys Ser
            20                  25

<210> SEQ ID NO 25
<211> LENGTH: 25
<212> TYPE: PRT
<213> ORGANISM: Artificial Sequence
<220> FEATURE:
<223> OTHER INFORMATION: synthetic amphipathic alpha-helix cholesterol
      efflux peptide T5211-1, LeuATI-5261 analog

<400> SEQUENCE: 25

Glu Ala Arg Ser Lys Ala Glu Glu Trp Leu Ala Ala Leu Glu Leu Ala
1               5                   10                  15

Glu Glu Leu Leu Ala Arg Ala Lys Ser
            20                  25

<210> SEQ ID NO 26
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5211-2, LeuATI-5261 analog

<400> SEQUENCE: 26

Glu Ala Arg Ser Lys Ala Glu Glu Trp Leu Ala Ala Leu Leu Glu Leu
1               5                   10                  15

Ala Glu Glu Leu Leu Ala Arg Ala Lys Ser
            20                  25

<210> SEQ ID NO 27
<211> LENGTH: 25
<212> TYPE: PRT
<213> ORGANISM: Artificial Sequence
<220> FEATURE:
<223> OTHER INFORMATION: synthetic amphipathic alpha-helix cholesterol
      efflux peptide T5211-3, LeuATI-5261 analog

<400> SEQUENCE: 27

Glu Val Arg Ser Lys Leu Glu Glu Trp Phe Ala Ala Phe Glu Phe Ala
1               5                   10                  15

Glu Glu Phe Leu Ala Arg Leu Lys Ser
            20                  25

<210> SEQ ID NO 28
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5211-4, LeuATI-5261 analog

<400> SEQUENCE: 28

Glu Val Arg Ser Lys Leu Glu Glu Trp Phe Ala Ala Phe Leu Glu Phe
```

```
1               5                   10                  15

Ala Glu Glu Phe Leu Ala Arg Leu Lys Ser
            20                  25

<210> SEQ ID NO 29
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5220, LeuATI-5261 analog

<400> SEQUENCE: 29

Glu Ala Arg Ser Lys Ala Glu Glu Trp Leu Ala Ala Leu Ala Glu Leu
1               5                   10                  15

Ala Glu Glu Leu Leu Ala Arg Ala Lys Ser
            20                  25

<210> SEQ ID NO 30
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T6023-3, LeuATI-5261 analog, HDL mimetic peptide

<400> SEQUENCE: 30

Glu Ala Arg Ser Lys Ala Glu Glu Trp Leu Ala Ala Leu Leu Glu Leu
1               5                   10                  15

Ala Glu Glu Leu Leu Ala Arg Ala Lys Ser
            20                  25

<210> SEQ ID NO 31
<211> LENGTH: 24
<212> TYPE: PRT
<213> ORGANISM: Artificial Sequence
<220> FEATURE:
<223> OTHER INFORMATION: synthetic amphipathic alpha-helix cholesterol
      efflux peptide T6023-4, LeuATI-5261 analog, HDL mimetic peptide

<400> SEQUENCE: 31

Glu Ala Arg Ser Lys Ala Glu Glu Trp Leu Ala Ala Leu Leu Glu Leu
1               5                   10                  15

Ala Glu Glu Leu Leu Ala Arg Ala
            20

<210> SEQ ID NO 32
<211> LENGTH: 24
<212> TYPE: PRT
<213> ORGANISM: Artificial Sequence
<220> FEATURE:
<223> OTHER INFORMATION: synthetic amphipathic alpha-helix cholesterol
      efflux peptide T6023-6, LeuATI-5261 analog, HDL mimetic peptide

<400> SEQUENCE: 32

Glu Val Arg Ser Lys Ala Glu Glu Trp Leu Ala Ala Leu Leu Glu Leu
1               5                   10                  15

Ala Glu Glu Leu Leu Ala Arg Ala
            20

<210> SEQ ID NO 33
<211> LENGTH: 24
<212> TYPE: PRT
<213> ORGANISM: Artificial Sequence
<220> FEATURE:
```

-continued

<223> OTHER INFORMATION: synthetic amphipathic alpha-helix cholesterol
      efflux peptide T6023-8, LeuATI-5261 analog, HDL mimetic peptide

<400> SEQUENCE: 33

Glu Val Arg Ser Lys Val Glu Glu Trp Leu Ala Ala Leu Leu Glu Leu
1               5                   10                  15

Ala Glu Glu Leu Leu Ala Arg Ala
            20

<210> SEQ ID NO 34
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5426-1, ATI-5261 analog, HDL mimetic peptide
<220> FEATURE:
<221> NAME/KEY: MOD_RES
<222> LOCATION: (3)...(3)
<223> OTHER INFORMATION: Xaa = citrulline (cit, Cit)

<400> SEQUENCE: 34

Glu Val Xaa Ser Lys Leu Glu Glu Trp Phe Ala Ala Phe Arg Glu Phe
1               5                   10                  15

Ala Glu Glu Phe Leu Ala Arg Leu Lys Ser
            20                  25

<210> SEQ ID NO 35
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5426-2, ATI-5261 analog, HDL mimetic peptide
<220> FEATURE:
<221> NAME/KEY: MOD_RES
<222> LOCATION: (14)...(14)
<223> OTHER INFORMATION: Xaa = citrulline (cit, Cit)

<400> SEQUENCE: 35

Glu Val Arg Ser Lys Leu Glu Glu Trp Phe Ala Ala Phe Xaa Glu Phe
1               5                   10                  15

Ala Glu Glu Phe Leu Ala Arg Leu Lys Ser
            20                  25

<210> SEQ ID NO 36
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5426-3, ATI-5261 analog, HDL mimetic peptide
<220> FEATURE:
<221> NAME/KEY: MOD_RES
<222> LOCATION: (23)...(23)
<223> OTHER INFORMATION: Xaa = citrulline (cit, Cit)

<400> SEQUENCE: 36

Glu Val Arg Ser Lys Leu Glu Glu Trp Phe Ala Ala Phe Arg Glu Phe
1               5                   10                  15

Ala Glu Glu Phe Leu Ala Xaa Leu Lys Ser
            20                  25

<210> SEQ ID NO 37
<211> LENGTH: 26
<212> TYPE: PRT
<213> ORGANISM: Artificial Sequence

```
<220> FEATURE:
<223> OTHER INFORMATION: synthetic amphipathic alpha-helix cholesterol
      efflux peptide T5426-4, ATI-5261 analog, HDL mimetic peptide
<220> FEATURE:
<221> NAME/KEY: MOD_RES
<222> LOCATION: (3)...(14)
<223> OTHER INFORMATION: Xaa = citrulline (cit, Cit)

<400> SEQUENCE: 37

Glu Val Xaa Ser Lys Leu Glu Glu Trp Phe Ala Ala Phe Xaa Glu Phe
1               5                   10                  15

Ala Glu Glu Phe Leu Ala Arg Leu Lys Ser
            20                  25

<210> SEQ ID NO 38
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5426-5, ATI-5261 analog, HDL mimetic peptide
<220> FEATURE:
<221> NAME/KEY: MOD_RES
<222> LOCATION: (14)...(23)
<223> OTHER INFORMATION: Xaa = citrulline (cit, Cit)

<400> SEQUENCE: 38

Glu Val Arg Ser Lys Leu Glu Glu Trp Phe Ala Ala Phe Xaa Glu Phe
1               5                   10                  15

Ala Glu Glu Phe Leu Ala Xaa Leu Lys Ser
            20                  25

<210> SEQ ID NO 39
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5426-6, ATI-5261 analog, HDL mimetic peptide
<220> FEATURE:
<221> NAME/KEY: MOD_RES
<222> LOCATION: (3)...(23)
<223> OTHER INFORMATION: Xaa = citrulline (cit, Cit)

<400> SEQUENCE: 39

Glu Val Xaa Ser Lys Leu Glu Glu Trp Phe Ala Ala Phe Arg Glu Phe
1               5                   10                  15

Ala Glu Glu Phe Leu Ala Xaa Leu Lys Ser
            20                  25

<210> SEQ ID NO 40
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5426-7, ATI-5261 analog, HDL mimetic peptide
<220> FEATURE:
<221> NAME/KEY: MOD_RES
<222> LOCATION: (3)...(23)
<223> OTHER INFORMATION: Xaa = cirulline (cit, Cit)

<400> SEQUENCE: 40

Glu Val Xaa Ser Lys Leu Glu Glu Trp Phe Ala Ala Phe Xaa Glu Phe
1               5                   10                  15

Ala Glu Glu Phe Leu Ala Xaa Leu Lys Ser
            20                  25
```

<210> SEQ ID NO 41
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5594-1, ATI-5261 analog
<220> FEATURE:
<221> NAME/KEY: MOD_RES
<222> LOCATION: (3)...(14)
<223> OTHER INFORMATION: Xaa = citrulline (cit, Cit)

<400> SEQUENCE: 41

Glu Val Xaa Ser Lys Leu Glu Glu Leu Phe Ala Ala Phe Xaa Glu Phe
1               5                   10                  15

Ala Glu Glu Phe Leu Ala Arg Leu Lys Ser
            20                  25

<210> SEQ ID NO 42
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5594-2, ATI-5261 analog
<220> FEATURE:
<221> NAME/KEY: MOD_RES
<222> LOCATION: (3)...(14)
<223> OTHER INFORMATION: Xaa = citrulline (cit, Cit)

<400> SEQUENCE: 42

Glu Val Xaa Ser Lys Leu Glu Glu Ala Phe Ala Ala Phe Xaa Glu Phe
1               5                   10                  15

Ala Glu Glu Phe Leu Ala Arg Leu Lys Ser
            20                  25

<210> SEQ ID NO 43
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5594-3, ATI-5261 analog
<220> FEATURE:
<221> NAME/KEY: MOD_RES
<222> LOCATION: (3)...(14)
<223> OTHER INFORMATION: Xaa = citrulline (cit, Cit)

<400> SEQUENCE: 43

Glu Val Xaa Ser Lys Leu Glu Glu Val Phe Ala Ala Phe Xaa Glu Phe
1               5                   10                  15

Ala Glu Glu Phe Leu Ala Arg Leu Lys Ser
            20                  25

<210> SEQ ID NO 44
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5237-1, LeuATI-5261 analog
<220> FEATURE:
<221> NAME/KEY: MOD_RES
<222> LOCATION: (3)...(3)
<223> OTHER INFORMATION: Xaa = citrulline (cit, Cit)

<400> SEQUENCE: 44

Glu Val Xaa Ser Lys Leu Glu Glu Trp Leu Ala Ala Leu Arg Glu Leu

Ala Glu Glu Leu Leu Ala Arg Leu Lys Ser
            20                  25

<210> SEQ ID NO 45
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5237-2, LeuATI-5261 analog
<220> FEATURE:
<221> NAME/KEY: MOD_RES
<222> LOCATION: (14)...(14)
<223> OTHER INFORMATION: Xaa = citrulline (cit, Cit)

<400> SEQUENCE: 45

Glu Val Arg Ser Lys Leu Glu Glu Trp Leu Ala Ala Leu Xaa Glu Leu
1               5                   10                  15

Ala Glu Glu Leu Leu Ala Arg Leu Lys Ser
            20                  25

<210> SEQ ID NO 46
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5237-3, LeuATI-5261 analog
<220> FEATURE:
<221> NAME/KEY: MOD_RES
<222> LOCATION: (23)...(23)
<223> OTHER INFORMATION: Xaa = citrulline (cit, Cit)

<400> SEQUENCE: 46

Glu Val Arg Ser Lys Leu Glu Glu Trp Phe Ala Ala Phe Arg Glu Phe
1               5                   10                  15

Ala Glu Glu Phe Leu Ala Xaa Leu Lys Ser
            20                  25

<210> SEQ ID NO 47
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5237-4 (CS6253), LeuATI-5261 analog
<220> FEATURE:
<220> FEATURE:
<221> NAME/KEY: MOD_RES
<222> LOCATION: (3)...(14)
<223> OTHER INFORMATION: Xaa = citrulline (cit, Cit)

<400> SEQUENCE: 47

Glu Val Xaa Ser Lys Leu Glu Glu Trp Leu Ala Ala Leu Xaa Glu Leu
1               5                   10                  15

Ala Glu Glu Leu Leu Ala Arg Leu Lys Ser
            20                  25

<210> SEQ ID NO 48
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5237-5, LeuATI-5261 analog
<220> FEATURE:
<221> NAME/KEY: MOD_RES

```
<222> LOCATION: (3)...(23)
<223> OTHER INFORMATION: Xaa = citrulline (cit, Cit)

<400> SEQUENCE: 48

Glu Val Xaa Ser Lys Leu Glu Glu Trp Phe Ala Ala Phe Arg Glu Phe
1               5                   10                  15

Ala Glu Glu Phe Leu Ala Xaa Leu Lys Ser
            20                  25

<210> SEQ ID NO 49
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5237-6, LeuATI-5261 analog
<220> FEATURE:
<221> NAME/KEY: MOD_RES
<222> LOCATION: (14)...(23)
<223> OTHER INFORMATION: Xaa = citrulline (cit, Cit)

<400> SEQUENCE: 49

Glu Val Arg Ser Lys Leu Glu Glu Trp Phe Ala Ala Phe Xaa Glu Phe
1               5                   10                  15

Ala Glu Glu Phe Leu Ala Xaa Leu Lys Ser
            20                  25

<210> SEQ ID NO 50
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5237-7, LeuATI-5261 analog
<220> FEATURE:
<221> NAME/KEY: MOD_RES
<222> LOCATION: (3)...(23)
<223> OTHER INFORMATION: Xaa = citrulline (cit, Cit)

<400> SEQUENCE: 50

Glu Val Xaa Ser Lys Leu Glu Glu Trp Phe Ala Ala Phe Xaa Glu Phe
1               5                   10                  15

Ala Glu Glu Phe Leu Ala Xaa Leu Lys Ser
            20                  25

<210> SEQ ID NO 51
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5237-9, LeuATI-5261 analog
<220> FEATURE:
<221> NAME/KEY: MOD_RES
<222> LOCATION: (14)...(14)
<223> OTHER INFORMATION: Xaa = citrulline (cit, Cit)

<400> SEQUENCE: 51

Glu Val Arg Ser Lys Leu Glu Glu Leu Leu Ala Ala Leu Xaa Glu Leu
1               5                   10                  15

Ala Glu Glu Leu Leu Ala Arg Ala Lys Ser
            20                  25

<210> SEQ ID NO 52
<211> LENGTH: 26
<212> TYPE: PRT
<213> ORGANISM: Artificial Sequence
```

```
<220> FEATURE:
<223> OTHER INFORMATION: synthetic amphipathic alpha-helix cholesterol
      efflux peptide T5237-11, LeuATI-5261 analog
<220> FEATURE:
<221> NAME/KEY: MOD_RES
<222> LOCATION: (3)...(14)
<223> OTHER INFORMATION: Xaa = citrulline (cit, Cit)

<400> SEQUENCE: 52

Glu Val Xaa Ser Lys Leu Glu Glu Leu Leu Ala Ala Leu Xaa Glu Leu
1               5                   10                  15

Ala Glu Glu Leu Leu Ala Arg Ala Lys Ser
            20                  25

<210> SEQ ID NO 53
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5554-1, HDL mimetic peptide

<400> SEQUENCE: 53

Glu Val Arg Ser Lys Leu Gln Glu Trp Phe Ala Ala Phe Arg Glu Phe
1               5                   10                  15

Ala Gln Glu Phe Leu Ala Arg Leu Lys Ser
            20                  25

<210> SEQ ID NO 54
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5554-2, HDL mimetic peptide

<400> SEQUENCE: 54

Glu Val Arg Ser Lys Leu Gln Glu Trp Phe Ala Ala Phe Arg Glu Phe
1               5                   10                  15

Ala Glu Glu Phe Leu Ala Arg Leu Lys Ser
            20                  25

<210> SEQ ID NO 55
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5554-3, HDL mimetic peptide

<400> SEQUENCE: 55

Glu Val Arg Ser Lys Leu Glu Glu Trp Phe Ala Ala Phe Arg Glu Phe
1               5                   10                  15

Ala Gln Glu Phe Leu Ala Arg Leu Lys Ser
            20                  25

<210> SEQ ID NO 56
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5554-4, HDL mimetic peptide
<220> FEATURE:
<221> NAME/KEY: MOD_RES
<222> LOCATION: (3)...(3)
<223> OTHER INFORMATION: Xaa = citrulline (cit, Cit)
```

```
<400> SEQUENCE: 56

Glu Val Xaa Ser Lys Leu Gln Glu Trp Phe Ala Ala Phe Arg Glu Phe
1               5                   10                  15

Ala Glu Glu Phe Leu Ala Arg Leu Lys Ser
            20                  25

<210> SEQ ID NO 57
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5554-5, HDL mimetic peptide
<220> FEATURE:
<221> NAME/KEY: MOD_RES
<222> LOCATION: (3)...(14)
<223> OTHER INFORMATION: Xaa = citrulline (cit, Cit)

<400> SEQUENCE: 57

Glu Val Xaa Ser Lys Leu Gln Glu Trp Phe Ala Ala Phe Xaa Glu Phe
1               5                   10                  15

Ala Gln Glu Phe Leu Ala Arg Leu Lys Ser
            20                  25

<210> SEQ ID NO 58
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5554-6, HDL mimetic peptide
<220> FEATURE:
<221> NAME/KEY: MOD_RES
<222> LOCATION: (3)...(23)
<223> OTHER INFORMATION: Xaa = citrulline (cit, Cit)

<400> SEQUENCE: 58

Glu Val Xaa Ser Lys Leu Gln Glu Trp Phe Ala Ala Phe Xaa Glu Phe
1               5                   10                  15

Ala Gln Gln Phe Leu Ala Xaa Leu Lys Ser
            20                  25

<210> SEQ ID NO 59
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5554-7, HDL mimetic peptide
<220> FEATURE:
<221> NAME/KEY: MOD_RES
<222> LOCATION: (3)...(14)
<223> OTHER INFORMATION: Xaa = citrulline (cit, Cit)

<400> SEQUENCE: 59

Glu Val Xaa Ser Lys Leu Gln Glu Trp Phe Ala Ala Phe Xaa Glu Phe
1               5                   10                  15

Ala Glu Glu Phe Leu Ala Arg Leu Lys Ser
            20                  25

<210> SEQ ID NO 60
<211> LENGTH: 26
<212> TYPE: PRT
<213> ORGANISM: Artificial Sequence
<220> FEATURE:
<223> OTHER INFORMATION: synthetic amphipathic alpha-helix cholesterol
``` efflux peptide T5554-8, HDL mimetic peptide
<220> FEATURE:
<221> NAME/KEY: MOD_RES
<222> LOCATION: (3)...(14)
<223> OTHER INFORMATION: Xaa = citrulline (cit, Cit)

<400> SEQUENCE: 60

Glu Val Xaa Ser Lys Leu Glu Glu Trp Phe Ala Ala Phe Xaa Glu Phe
1               5                   10                  15

Ala Gln Glu Phe Leu Ala Arg Leu Lys Ser
            20                  25

<210> SEQ ID NO 61
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5554-9, HDL mimetic peptide

<400> SEQUENCE: 61

Glu Val Arg Ser Lys Leu Gln Glu Trp Leu Ala Ala Leu Arg Glu Leu
1               5                   10                  15

Ala Glu Glu Leu Leu Ala Arg Leu Lys Ser
            20                  25

<210> SEQ ID NO 62
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5554-10, HDL mimetic peptide
<220> FEATURE:
<221> NAME/KEY: MOD_RES
<222> LOCATION: (3)...(3)
<223> OTHER INFORMATION: Xaa = citrulline (cit, Cit)

<400> SEQUENCE: 62

Glu Val Xaa Ser Lys Leu Gln Glu Trp Leu Ala Ala Leu Arg Glu Leu
1               5                   10                  15

Ala Glu Glu Leu Leu Ala Arg Leu Lys Ser
            20                  25

<210> SEQ ID NO 63
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T5766-6, LeuATI-5261 analog

<400> SEQUENCE: 63

Glu Val Arg Ser Lys Leu Glu Glu Trp Leu Ala Ala Leu Arg Glu Leu
1               5                   10                  15

Ala Glu Glu Leu Leu Ala Arg Leu Lys Ser
            20                  25

<210> SEQ ID NO 64
<211> LENGTH: 24
<212> TYPE: PRT
<213> ORGANISM: Artificial Sequence
<220> FEATURE:
<223> OTHER INFORMATION: synthetic amphipathic alpha-helix cholesterol
      efflux peptide T6023-1, Cit.LeuATI-5261 analog
<220> FEATURE:
<221> NAME/KEY: MOD_RES

```
<222> LOCATION: (3)...(14)
<223> OTHER INFORMATION: Xaa = citrulline (cit, Cit)

<400> SEQUENCE: 64

Glu Val Xaa Ser Lys Leu Glu Glu Trp Leu Ala Ala Leu Xaa Glu Leu
1               5                   10                  15

Ala Glu Glu Leu Leu Ala Arg Leu
            20

<210> SEQ ID NO 65
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T6623-2, Cit.LeuATI-5261 analog, HDL mimetic
      peptide
<220> FEATURE:
<221> NAME/KEY: MOD_RES
<222> LOCATION: (14)...(14)
<223> OTHER INFORMATION: Xaa = citrulline (cit, Cit)

<400> SEQUENCE: 65

Glu Val Leu Ser Lys Leu Glu Glu Trp Leu Ala Ala Leu Xaa Glu Leu
1               5                   10                  15

Ala Glu Glu Leu Leu Ala Arg Leu Lys Ser
            20                  25

<210> SEQ ID NO 66
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T6275-3, Cit.LeuATI-5261 analog, HDL mimetic
      peptide
<220> FEATURE:
<221> NAME/KEY: MOD_RES
<222> LOCATION: (3)...(14)
<223> OTHER INFORMATION: Xaa = citrulline (cit, Cit)

<400> SEQUENCE: 66

Glu Leu Xaa Ser Lys Leu Glu Glu Trp Leu Ala Ala Leu Xaa Glu Leu
1               5                   10                  15

Ala Glu Glu Leu Leu Ala Arg Leu Lys Ser
            20                  25

<210> SEQ ID NO 67
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T6275-5, Cit.LeuATI-5261 analog
<220> FEATURE:
<221> NAME/KEY: MOD_RES
<222> LOCATION: (3)...(3)
<223> OTHER INFORMATION: Xaa = citrulline (cit, Cit)

<400> SEQUENCE: 67

Glu Val Xaa Ser Lys Leu Glu Glu Trp Leu Ala Ala Leu Leu Glu Leu
1               5                   10                  15

Ala Glu Glu Leu Leu Ala Arg Leu Lys Ser
            20                  25

<210> SEQ ID NO 68
<211> LENGTH: 26
```

```
<212> TYPE: PRT
<213> ORGANISM: Artificial Sequence
<220> FEATURE:
<223> OTHER INFORMATION: synthetic amphipathic alpha-helix cholesterol
      efflux peptide T6623-1, Cit.LeuATI-5261 analog
<220> FEATURE:
<221> NAME/KEY: MOD_RES
<222> LOCATION: (3)...(3)
<223> OTHER INFORMATION: Xaa = citrulline (cit, Cit)

<400> SEQUENCE: 68

Glu Leu Xaa Ser Lys Leu Glu Glu Trp Leu Ala Ala Leu Leu Glu Leu
1               5                   10                  15

Ala Glu Glu Leu Leu Ala Arg Leu Lys Ser
            20                  25

<210> SEQ ID NO 69
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T6623-3, Cit.LeuATI-5261 analog
<220> FEATURE:
<221> NAME/KEY: MOD_RES
<222> LOCATION: (14)...(14)
<223> OTHER INFORMATION: Xaa = citrulline (cit, Cit)

<400> SEQUENCE: 69

Glu Leu Leu Ser Lys Leu Glu Glu Trp Leu Ala Ala Leu Xaa Glu Leu
1               5                   10                  15

Ala Glu Glu Leu Leu Ala Arg Leu Lys Ser
            20                  25

<210> SEQ ID NO 70
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T6623-4, Cit.LeuATI-5261 analog

<400> SEQUENCE: 70

Glu Val Leu Ser Lys Leu Glu Glu Trp Leu Ala Ala Leu Leu Glu Leu
1               5                   10                  15

Ala Glu Glu Leu Leu Ala Arg Leu Lys Ser
            20                  25

<210> SEQ ID NO 71
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T6623-5, Cit.LeuATI-5261 analog

<400> SEQUENCE: 71

Glu Leu Leu Ser Lys Leu Glu Glu Trp Leu Ala Ala Leu Leu Glu Leu
1               5                   10                  15

Ala Glu Glu Leu Leu Ala Arg Leu Lys Ser
            20                  25

<210> SEQ ID NO 72
<211> LENGTH: 24
<212> TYPE: PRT
<213> ORGANISM: Artificial Sequence
<220> FEATURE:
```

```
<223> OTHER INFORMATION: synthetic amphipathic alpha-helix cholesterol
      efflux peptide T6623-6, Cit.LeuATI-5261 analog
<220> FEATURE:
<221> NAME/KEY: MOD_RES
<222> LOCATION: (3)...(3)
<223> OTHER INFORMATION: Xaa = citrulline (cit, Cit)

<400> SEQUENCE: 72

Glu Leu Xaa Ser Lys Leu Glu Glu Trp Leu Ala Ala Leu Leu Glu Leu
1               5                   10                  15

Ala Glu Glu Leu Leu Ala Arg Leu
            20

<210> SEQ ID NO 73
<211> LENGTH: 24
<212> TYPE: PRT
<213> ORGANISM: Artificial Sequence
<220> FEATURE:
<223> OTHER INFORMATION: synthetic amphipathic alpha-helix cholesterol
      efflux peptide T6623-7, Cit.LeuATI-5261 analog
<220> FEATURE:
<221> NAME/KEY: MOD_RES
<222> LOCATION: (14)...(14)
<223> OTHER INFORMATION: Xaa = citrulline (cit, Cit)

<400> SEQUENCE: 73

Glu Val Leu Ser Lys Leu Glu Glu Trp Leu Ala Ala Leu Xaa Glu Leu
1               5                   10                  15

Ala Glu Glu Leu Leu Ala Arg Leu
            20

<210> SEQ ID NO 74
<211> LENGTH: 24
<212> TYPE: PRT
<213> ORGANISM: Artificial Sequence
<220> FEATURE:
<223> OTHER INFORMATION: synthetic amphipathic alpha-helix cholesterol
      efflux peptide T6623-8, Cit.LeuATI-5261 analog
<220> FEATURE:
<221> NAME/KEY: MOD_RES
<222> LOCATION: (14)...(14)
<223> OTHER INFORMATION: Xaa = citrulline (cit, Cit)

<400> SEQUENCE: 74

Glu Leu Leu Ser Lys Leu Glu Glu Trp Leu Ala Ala Leu Xaa Glu Leu
1               5                   10                  15

Ala Glu Glu Leu Leu Ala Arg Leu
            20

<210> SEQ ID NO 75
<211> LENGTH: 24
<212> TYPE: PRT
<213> ORGANISM: Artificial Sequence
<220> FEATURE:
<223> OTHER INFORMATION: synthetic amphipathic alpha-helix cholesterol
      efflux peptide T6623-9, Cit.LeuATI-5261 analog

<400> SEQUENCE: 75

Glu Val Leu Ser Lys Leu Glu Glu Trp Leu Ala Ala Leu Leu Glu Leu
1               5                   10                  15

Ala Glu Glu Leu Leu Ala Arg Leu
            20

<210> SEQ ID NO 76
<211> LENGTH: 24
<212> TYPE: PRT
<213> ORGANISM: Artificial Sequence
```

```
<220> FEATURE:
<223> OTHER INFORMATION: synthetic amphipathic alpha-helix cholesterol
      efflux peptide T6623-10, Cit.LeuATI-5261 analog

<400> SEQUENCE: 76

Glu Leu Leu Ser Lys Leu Glu Glu Trp Leu Ala Ala Leu Leu Glu Leu
1               5                   10                  15

Ala Glu Glu Leu Leu Ala Arg Leu
            20

<210> SEQ ID NO 77
<211> LENGTH: 24
<212> TYPE: PRT
<213> ORGANISM: Artificial Sequence
<220> FEATURE:
<223> OTHER INFORMATION: synthetic amphipathic alpha-helix cholesterol
      efflux peptide T6623-11, Cit.LeuATI-5261 analog

<400> SEQUENCE: 77

Glu Leu Arg Ser Lys Leu Glu Glu Trp Leu Ala Ala Leu Leu Glu Leu
1               5                   10                  15

Ala Glu Glu Leu Leu Ala Arg Leu
            20

<210> SEQ ID NO 78
<211> LENGTH: 24
<212> TYPE: PRT
<213> ORGANISM: Artificial Sequence
<220> FEATURE:
<223> OTHER INFORMATION: synthetic amphipathic alpha-helix cholesterol
      efflux peptide T6623-12, Cit.LeuATI-5261 analog

<400> SEQUENCE: 78

Glu Leu Leu Ser Lys Leu Glu Glu Trp Leu Ala Ala Leu Arg Glu Leu
1               5                   10                  15

Ala Glu Glu Leu Leu Ala Arg Leu
            20

<210> SEQ ID NO 79
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T6991-1, ATI-5261 analog

<400> SEQUENCE: 79

Glu Val Arg Ser Lys Leu Glu Glu Trp Ile Ala Ala Ile Arg Glu Ile
1               5                   10                  15

Ala Glu Glu Ile Leu Ala Arg Leu Lys Ser
            20                  25

<210> SEQ ID NO 80
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T6991-2, ATI-5261 analog
<220> FEATURE:
<221> NAME/KEY: MOD_RES
<222> LOCATION: (3)...(14)
<223> OTHER INFORMATION: Xaa = citrulline (cit, Cit)

<400> SEQUENCE: 80

Glu Val Xaa Ser Lys Leu Glu Glu Trp Ile Ala Ala Ile Xaa Glu Ile
```

```
                1               5                   10                  15

Ala Glu Glu Ile Leu Ala Arg Leu Lys Ser
            20                  25

<210> SEQ ID NO 81
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T6991-3, ATI-5261 analog

<400> SEQUENCE: 81

Glu Val Arg Ala Lys Leu Glu Glu Trp Phe Ala Ala Phe Arg Glu Phe
1               5                   10                  15

Ser Glu Glu Phe Leu Ala Arg Leu Lys Ser
            20                  25

<210> SEQ ID NO 82
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T6991-4, ATI-5261 analog

<400> SEQUENCE: 82

Glu Val Arg Ser Lys Leu Glu Glu Trp Phe Ala Ala Phe Arg Glu Phe
1               5                   10                  15

Ser Glu Glu Phe Leu Ala Arg Leu Lys Ala
            20                  25

<210> SEQ ID NO 83
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T6991-5

<400> SEQUENCE: 83

Glu Val Arg Ser Lys Leu Glu Glu Trp Phe Ala Ala Phe Arg Glu Phe
1               5                   10                  15

Ser Glu Glu Phe Leu Ala Arg Leu Lys Ser
            20                  25

<210> SEQ ID NO 84
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T6991-6, ATI-5261 analog

<400> SEQUENCE: 84

Glu Val Arg Ser Lys Leu Glu Glu Trp Phe Ala Ala Phe Arg Glu Phe
1               5                   10                  15

Tyr Glu Glu Phe Leu Ala Arg Leu Lys Ser
            20                  25

<210> SEQ ID NO 85
<211> LENGTH: 26
<212> TYPE: PRT
<213> ORGANISM: Artificial Sequence
<220> FEATURE:
```

```
<223> OTHER INFORMATION: synthetic amphipathic alpha-helix cholesterol
      efflux peptide T6991-7, ATI-5261 analog

<400> SEQUENCE: 85

Glu Val Arg Ser Lys Leu Glu Tyr Phe Ala Ala Phe Arg Glu Phe
1               5                   10                  15

Ala Glu Glu Phe Leu Ala Arg Leu Lys Ser
            20                  25

<210> SEQ ID NO 86
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T6991-8, ATI-5261 analog

<400> SEQUENCE: 86

Glu Val Arg Ser Lys Leu Glu Glu Trp Phe Ala Ala Phe Arg Glu Phe
1               5                   10                  15

Ala Glu Glu Phe Leu Ala Arg Ser Lys Leu
            20                  25

<210> SEQ ID NO 87
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T6991-9, ATI-5261 analog

<400> SEQUENCE: 87

Glu Val Arg Ser Lys Leu Glu Glu Trp Phe Ala Ala Phe Arg Glu Phe
1               5                   10                  15

Tyr Glu Glu Phe Leu Ala Arg Ser Lys Leu
            20                  25

<210> SEQ ID NO 88
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T6275-1, LeuATI-5261 analog, CS6253 analog
<220> FEATURE:
<221> NAME/KEY: MOD_RES
<222> LOCATION: (3)...(14)
<223> OTHER INFORMATION: Xaa = citrulline (cit, Cit)

<400> SEQUENCE: 88

Glu Val Xaa Ser Lys Leu Glu Glu Trp Leu Ala Ala Leu Xaa Glu Leu
1               5                   10                  15

Ala Glu Glu Leu Leu Ala Arg Leu Lys Tyr
            20                  25

<210> SEQ ID NO 89
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide CS6257 (CS6257A), ATI-5261 analog, i, i+7 stapled
      peptide
<220> FEATURE:
<221> NAME/KEY: MOD_RES
<222> LOCATION: (14)...(14)
<223> OTHER INFORMATION: Xaa = S-alpha-methyl, alpha-n-pentenylglycine
```

(S5), R-4,11S(11) cyclized cross-link to R8 at position 21
<220> FEATURE:
<221> NAME/KEY: MOD_RES
<222> LOCATION: (21)...(21)
<223> OTHER INFORMATION: Xaa = R-alpha-methyl, alpha-n-octenylglycine
    (R8), R-4,11S(11) cyclized cross-link to S5 at position 14

<400> SEQUENCE: 89

Glu Val Ala Ser Lys Leu Glu Glu Trp Phe Ala Ala Phe Xaa Glu Phe
1               5                   10                  15

Ala Glu Glu Phe Xaa Ala Ala Leu Lys Ser
            20                  25

<210> SEQ ID NO 90
<211> LENGTH: 26
<212> TYPE: PRT
<213> ORGANISM: Artificial Sequence
<220> FEATURE:
<223> OTHER INFORMATION: synthetic amphipathic alpha-helix cholesterol
    efflux peptide CS6259, LeuATI-5261 analog, i, i+7 stapled peptide
<220> FEATURE:
<221> NAME/KEY: MOD_RES
<222> LOCATION: (14)...(14)
<223> OTHER INFORMATION: Xaa = R-alpha-methyl, alpha-n-octenylglycine
    (R8), R-4,11S(11) cyclized cross-link to S5 at position 21
<220> FEATURE:
<221> NAME/KEY: MOD_RES
<222> LOCATION: (21)...(21)
<223> OTHER INFORMATION: Xaa = S-alpha-methyl, alpha-n-pentenylglycine
    (S5), R-4,11S(11) cyclized cross-link to R8 at position 14

<400> SEQUENCE: 90

Glu Val Gln Ser Lys Leu Glu Glu Trp Leu Ala Ala Leu Xaa Glu Leu
1               5                   10                  15

Ala Glu Glu Leu Xaa Ala Gln Leu Lys Ser
            20                  25

<210> SEQ ID NO 91
<211> LENGTH: 26
<212> TYPE: PRT
<213> ORGANISM: Artificial Sequence
<220> FEATURE:
<223> OTHER INFORMATION: synthetic amphipathic alpha-helix cholesterol
    efflux peptide CS6256A, ATI-5261 analog, i, i+7 stapled peptide
<220> FEATURE:
<221> NAME/KEY: MOD_RES
<222> LOCATION: (14)...(14)
<223> OTHER INFORMATION: Xaa = S-alpha-methyl, alpha-n-pentenylglycine
    (S5), R-4,11S(11) cyclized cross-link to R8 at position 21
<220> FEATURE:
<221> NAME/KEY: MOD_RES
<222> LOCATION: (21)...(21)
<223> OTHER INFORMATION: Xaa = R-alpha-methyl, alpha-n-octenylglycine
    (R8), R-4,11S(11) cyclized cross-link to S5 at position 14

<400> SEQUENCE: 91

Glu Val Gln Ser Lys Leu Glu Glu Trp Phe Ala Ala Phe Xaa Glu Phe
1               5                   10                  15

Ala Glu Glu Phe Xaa Ala Gln Leu Lys Ser
            20                  25

<210> SEQ ID NO 92
<211> LENGTH: 24
<212> TYPE: PRT
<213> ORGANISM: Artificial Sequence
<220> FEATURE:
<223> OTHER INFORMATION: synthetic amphipathic alpha-helix cholesterol
    efflux peptide T7983-1, CitLeuATI-5261 (CS6253) analog

<400> SEQUENCE: 92

-continued

```
Glu Val Arg Ser Lys Leu Glu Glu Trp Ile Ala Ala Ile Arg Glu Ile
1               5                   10                  15

Ala Glu Glu Ile Leu Ala Arg Leu
            20

<210> SEQ ID NO 93
<211> LENGTH: 24
<212> TYPE: PRT
<213> ORGANISM: Artificial Sequence
<220> FEATURE:
<223> OTHER INFORMATION: synthetic amphipathic alpha-helix cholesterol
      efflux peptide T7983-2, CitLeuATI-5261 (CS6253) analog
<220> FEATURE:
<221> NAME/KEY: MOD_RES
<222> LOCATION: (3)...(14)
<223> OTHER INFORMATION: Xaa = citrulline (cit, Cit)

<400> SEQUENCE: 93

Glu Val Xaa Ser Lys Leu Glu Glu Trp Ile Ala Ala Ile Xaa Glu Ile
1               5                   10                  15

Ala Glu Glu Ile Leu Ala Arg Leu
            20

<210> SEQ ID NO 94
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T7983-3, CitLeuATI-5261 (CS6253) analog
<220> FEATURE:
<221> NAME/KEY: MOD_RES
<222> LOCATION: (3)...(14)
<223> OTHER INFORMATION: Xaa = citrulline (cit, Cit)

<400> SEQUENCE: 94

Glu Val Xaa Ser Lys Leu Glu Glu Trp Leu Ala Ala Leu Xaa Glu Leu
1               5                   10                  15

Ala Glu Glu Ile Leu Ala Arg Leu Lys Ser
            20                  25

<210> SEQ ID NO 95
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T7983-4, CitLeuATI-5261 (CS6253) analog
<220> FEATURE:
<221> NAME/KEY: MOD_RES
<222> LOCATION: (3)...(14)
<223> OTHER INFORMATION: Xaa = citrulline (cit, Cit)

<400> SEQUENCE: 95

Glu Val Xaa Ser Lys Leu Glu Glu Trp Ile Ala Ala Leu Xaa Glu Leu
1               5                   10                  15

Ala Glu Glu Ile Leu Ala Arg Leu Lys Ser
            20                  25

<210> SEQ ID NO 96
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T7983-5, CitLeuATI-5261 (CS6253) analog
<220> FEATURE:
```

```
<221> NAME/KEY: MOD_RES
<222> LOCATION: (3)...(14)
<223> OTHER INFORMATION: Xaa = citrulline (cit, Cit)

<400> SEQUENCE: 96

Glu Val Xaa Ser Lys Leu Glu Glu Trp Leu Ala Ala Ile Xaa Glu Ile
1               5                   10                  15

Ala Glu Glu Leu Leu Ala Arg Leu Lys Ser
            20                  25

<210> SEQ ID NO 97
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T7983-6, CitLeuATI-5261 (CS6253) analog
<220> FEATURE:
<221> NAME/KEY: MOD_RES
<222> LOCATION: (3)...(14)
<223> OTHER INFORMATION: Xaa = citrulline (cit, Cit)

<400> SEQUENCE: 97

Glu Val Xaa Ser Lys Leu Glu Glu Trp Ile Ala Ala Ile Xaa Glu Ile
1               5                   10                  15

Ala Glu Glu Leu Leu Ala Arg Leu Lys Ser
            20                  25

<210> SEQ ID NO 98
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T7983-7, CitLeuATI-5261 (CS6253) analog
<220> FEATURE:
<221> NAME/KEY: MOD_RES
<222> LOCATION: (3)...(14)
<223> OTHER INFORMATION: Xaa = citrulline (cit, Cit)

<400> SEQUENCE: 98

Glu Val Xaa Ser Lys Leu Glu Glu Trp Leu Ala Ala Ile Xaa Glu Ile
1               5                   10                  15

Ala Glu Glu Ile Leu Ala Arg Leu Lys Ser
            20                  25

<210> SEQ ID NO 99
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T7983-8, CitLeuATI-5261 (CS6253) analog
<220> FEATURE:
<221> NAME/KEY: MOD_RES
<222> LOCATION: (14)...(14)
<223> OTHER INFORMATION: Xaa = citrulline (cit, Cit)

<400> SEQUENCE: 99

Glu Val Ile Ser Lys Leu Glu Glu Trp Leu Ala Ala Leu Xaa Glu Leu
1               5                   10                  15

Ala Glu Glu Leu Leu Ala Arg Leu Lys Ser
            20                  25

<210> SEQ ID NO 100
<211> LENGTH: 26
<212> TYPE: PRT
```

<213> ORGANISM: Artificial Sequence
<220> FEATURE:
<223> OTHER INFORMATION: synthetic amphipathic alpha-helix cholesterol
      efflux peptide T7983-9, CitLeuATI-5261 (CS6253) analog
<220> FEATURE:
<221> NAME/KEY: MOD_RES
<222> LOCATION: (3)...(3)
<223> OTHER INFORMATION: Xaa = citrulline (cit, Cit)

<400> SEQUENCE: 100

Glu Val Xaa Ser Lys Leu Glu Glu Trp Leu Ala Ala Leu Ile Glu Leu
1               5                   10                  15

Ala Glu Glu Leu Leu Ala Arg Leu Lys Ser
            20                  25

<210> SEQ ID NO 101
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T7983-10, LeuATI-5261 analog

<400> SEQUENCE: 101

Glu Val Ile Ser Lys Leu Glu Glu Trp Leu Ala Ala Leu Ile Glu Leu
1               5                   10                  15

Ala Glu Glu Leu Leu Ala Arg Leu Lys Ser
            20                  25

<210> SEQ ID NO 102
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T8212-1, CitLeuATI-5261 (CS6253) analog
<220> FEATURE:
<221> NAME/KEY: MOD_RES
<222> LOCATION: (3)...(14)
<223> OTHER INFORMATION: Xaa = citrulline (cit, Cit)

<400> SEQUENCE: 102

Glu Val Xaa Ser Lys Leu Glu Glu Trp Ile Ala Ala Leu Xaa Glu Leu
1               5                   10                  15

Ala Glu Glu Leu Leu Ala Arg Leu Lys Ser
            20                  25

<210> SEQ ID NO 103
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T8212-2, CitLeuATI-5261 (CS6253) analog
<220> FEATURE:
<221> NAME/KEY: MOD_RES
<222> LOCATION: (3)...(14)
<223> OTHER INFORMATION: Xaa = citrulline (cit, Cit)

<400> SEQUENCE: 103

Glu Val Xaa Ser Lys Leu Glu Glu Trp Leu Ala Ala Ile Xaa Glu Leu
1               5                   10                  15

Ala Glu Glu Leu Leu Ala Arg Leu Lys Ser
            20                  25

<210> SEQ ID NO 104
<211> LENGTH: 26

```
<212> TYPE: PRT
<213> ORGANISM: Artificial Sequence
<220> FEATURE:
<223> OTHER INFORMATION: synthetic amphipathic alpha-helix cholesterol
      efflux peptide T8212-3, CitLeuATI-5261 (CS6253) analog
<220> FEATURE:
<221> NAME/KEY: MOD_RES
<222> LOCATION: (3)...(14)
<223> OTHER INFORMATION: Xaa = citrulline (cit, Cit)

<400> SEQUENCE: 104

Glu Val Xaa Ser Lys Leu Glu Glu Trp Leu Ala Ala Leu Xaa Glu Ile
1               5                   10                  15

Ala Glu Glu Leu Leu Ala Arg Leu Lys Ser
            20                  25

<210> SEQ ID NO 105
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T8212-4, CitLeuATI-5261 (CS6253) analog
<220> FEATURE:
<221> NAME/KEY: MOD_RES
<222> LOCATION: (3)...(14)
<223> OTHER INFORMATION: Xaa = citrulline (cit, Cit)

<400> SEQUENCE: 105

Glu Val Xaa Ser Lys Leu Glu Glu Trp Ile Ala Ala Leu Xaa Glu Leu
1               5                   10                  15

Ala Glu Glu Ile Leu Ala Arg Leu Lys Ser
            20                  25

<210> SEQ ID NO 106
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T8212-5, CitLeuATI-5261 (CS6253) analog
<220> FEATURE:
<221> NAME/KEY: MOD_RES
<222> LOCATION: (3)...(14)
<223> OTHER INFORMATION: Xaa = citrulline (cit, Cit)

<400> SEQUENCE: 106

Glu Val Xaa Ser Lys Ile Glu Glu Trp Ile Ala Ala Leu Xaa Glu Leu
1               5                   10                  15

Ala Glu Glu Ile Leu Ala Arg Leu Lys Ser
            20                  25

<210> SEQ ID NO 107
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T8212-6, CitLeuATI-5261 (CS6253) analog
<220> FEATURE:
<221> NAME/KEY: MOD_RES
<222> LOCATION: (3)...(14)
<223> OTHER INFORMATION: Xaa = citrulline (cit, Cit)

<400> SEQUENCE: 107

Glu Val Xaa Ser Lys Ile Glu Glu Trp Leu Ala Ala Ile Xaa Glu Ile
1               5                   10                  15

Ala Glu Glu Leu Leu Ala Arg Leu Lys Ser
```

```
            20                  25

<210> SEQ ID NO 108
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T8212-7, CitLeuATI-5261 (CS6253) analog
<220> FEATURE:
<221> NAME/KEY: MOD_RES
<222> LOCATION: (3)...(14)
<223> OTHER INFORMATION: Xaa = citrulline (cit, Ciit)

<400> SEQUENCE: 108

Glu Val Xaa Ser Lys Ile Glu Glu Trp Ile Ala Ala Ile Xaa Glu Ile
1               5                   10                  15

Ala Glu Glu Leu Leu Ala Arg Leu Lys Ser
            20                  25

<210> SEQ ID NO 109
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T8212-8, CitLeuATI-5261 (CS6253) analog
<220> FEATURE:
<221> NAME/KEY: MOD_RES
<222> LOCATION: (3)...(14)
<223> OTHER INFORMATION: Xaa = citrulline (cit, Cit)

<400> SEQUENCE: 109

Glu Val Xaa Ser Lys Ile Glu Glu Trp Ile Ala Ala Ile Xaa Glu Ile
1               5                   10                  15

Ala Glu Glu Ile Leu Ala Arg Leu Lys Ser
            20                  25

<210> SEQ ID NO 110
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T8212-9, CitLeuATI-5261 (CS6253) analog
<220> FEATURE:
<221> NAME/KEY: MOD_RES
<222> LOCATION: (3)...(14)
<223> OTHER INFORMATION: Xaa = citrulline (cit, Cit)

<400> SEQUENCE: 110

Glu Val Xaa Ser Lys Ile Glu Glu Trp Ile Ala Ala Ile Xaa Glu Ile
1               5                   10                  15

Ala Glu Glu Ile Ile Ala Arg Leu Lys Ser
            20                  25

<210> SEQ ID NO 111
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T8212-10, CitLeuATI-5261 (CS6253) analog
<220> FEATURE:
<221> NAME/KEY: MOD_RES
<222> LOCATION: (3)...(14)
<223> OTHER INFORMATION: Xaa = citrulline (cit, Cit)

<400> SEQUENCE: 111
```

```
Glu Val Xaa Ser Lys Ile Glu Trp Ile Ala Ala Ile Xaa Glu Ile
1               5                   10                  15

Ala Glu Glu Ile Ile Ala Arg Ile Lys Ser
            20                  25

<210> SEQ ID NO 112
<211> LENGTH: 26
<212> TYPE: PRT
<213> ORGANISM: Artificial Sequence
<220> FEATURE:
<223> OTHER INFORMATION: synthetic amphipathic alpha-helix cholesterol
      efflux peptide T7983-11, ATI-5261 analog
<220> FEATURE:
<221> NAME/KEY: MOD_RES
<222> LOCATION: (3)...(14)
<223> OTHER INFORMATION: Xaa = citrulline (cit, Cit)

<400> SEQUENCE: 112

Glu Val Xaa Ser Lys Leu Glu Glu Trp Ile Ala Ala Ile Xaa Glu Ile
1               5                   10                  15

Ala Glu Glu Ile Leu Ala Arg Leu Lys Tyr
            20                  25
```